United States Patent
Mata et al.

(10) Patent No.: US 11,851,673 B2
(45) Date of Patent: Dec. 26, 2023

(54) WPRE MUTANT CONSTRUCTS, COMPOSITIONS, AND METHODS THEREOF

(71) Applicant: Immatics US, Inc., Houston, TX (US)

(72) Inventors: Melinda Mata, Missouri City, TX (US); Mamta Kalra, Sugar Land, TX (US); Yannick Bulliard, Thousand Oaks, CA (US); Steffen Walter, Houston, TX (US); Ali Mohamed, Sugar Land, TX (US)

(73) Assignee: Immatics US, Inc., Houston, TX (US)

( * ) Notice: Subject to any disclaimer, the term of this patent is extended or adjusted under 35 U.S.C. 154(b) by 162 days.

(21) Appl. No.: 17/197,927

(22) Filed: Mar. 10, 2021

(65) Prior Publication Data
US 2021/0285011 A1    Sep. 16, 2021

Related U.S. Application Data

(60) Provisional application No. 62/988,202, filed on Mar. 11, 2020.

(51) Int. Cl.
| | | |
|---|---|---|
| *C12N 15/86* | (2006.01) | |
| *C07K 14/725* | (2006.01) | |
| *C12N 15/10* | (2006.01) | |
| *C12N 15/113* | (2010.01) | |

(52) U.S. Cl.
CPC .......... *C12N 15/86* (2013.01); *C07K 14/7051* (2013.01); *C12N 15/102* (2013.01); *C12N 15/113* (2013.01); *C12N 2830/48* (2013.01)

(58) Field of Classification Search
CPC .... C12N 15/86; C12N 15/102; C12N 15/113; C12N 2830/48; C12N 2500/10; C12N 2840/203; C07K 14/7051; C07K 14/525; C07K 14/57; C12P 21/02
See application file for complete search history.

(56) References Cited

U.S. PATENT DOCUMENTS

| | | |
|---|---|---|
| 6,136,597 A | 10/2000 | Hope et al. |
| 6,287,814 B1 | 9/2001 | Hope et al. |
| 7,419,829 B2 | 9/2008 | Mitrophanous et al. |

(Continued)

FOREIGN PATENT DOCUMENTS

| | | |
|---|---|---|
| WO | 2016/115177 A1 | 7/2016 |
| WO | 2019/161059 A1 | 8/2019 |

(Continued)

OTHER PUBLICATIONS

Biernacki MA, Brault M, Bleakley M. T-Cell Receptor-Based Immunotherapy for Hematologic Malignancies. Cancer J. May/Jun. 2019;25(3):179-190. (Year: 2019).*

(Continued)

*Primary Examiner* — Christopher M Babic
*Assistant Examiner* — Thomas R. Amick
(74) *Attorney, Agent, or Firm* — McBee Moore & Vanik IP, LLC

(57) ABSTRACT

The present invention provides a mutated woodchuck post-transcriptional regulatory element (WPRE). In particular, the present invention relates to a mutated WPRE sequence that can efficiently express nucleotides of interest in a retroviral vector system. The present invention also relates to methods of delivering and expressing nucleotides of interest to a target cell.

20 Claims, 29 Drawing Sheets

Specification includes a Sequence Listing.

(56) References Cited

U.S. PATENT DOCUMENTS

| | | | |
|---|---|---|---|
| 2005/0002907 A1 | 1/2005 | Mitrophanous et al. | |
| 2016/0199412 A1 | 7/2016 | Tareen | |
| 2018/0162922 A1* | 6/2018 | Bunk | A61P 31/00 |
| 2018/3053619 | 12/2018 | Michalakis et al. | |
| 2019/0135914 A1 | 5/2019 | Unverdorben et al. | |
| 2020/0376031 A1 | 12/2020 | Mata et al. | |

FOREIGN PATENT DOCUMENTS

| | | | |
|---|---|---|---|
| WO | 2020/042648 A1 | 3/2020 | |
| WO | WO-2020172332 A1 * | 8/2020 | A61K 35/17 |
| WO | 2020/243134 A1 | 12/2020 | |

OTHER PUBLICATIONS

International Preliminary Report on Patentability dated Sep. 6, 2022 in International Application No. PCT/US2021/021701 (9 pages).

Choi, et al., "A Generic Intron Increases Gene Expression in Transgenic Mice," Mol. Cell. Biol., (1991), vol. 11, No. 6: 3070-3074.

Huang, et al., "Role of the Hepatitis B Virus Posttranscriptional Regulatory Element in Export of Intronless Transcripts," Mol. Cell. Biol., (1995), vol. 15, No. 7: 3864-3869.

Zufferey, et al., "Woodchuck Hepatitis Virus Posttranscriptional Regulatory Element Enhances Expression of Transgenes Delivered by Retroviral Vectors," J. Virol., (1999), vol. 73, No. 4: 2886-2892.

Flajolet, et al., "Woodchuck Hepatitis Virus Enhancer I and Enhancer II Are Both Involved in N-myc2 Activation in Woodchuck Liver Tumors," J. Virol., (1998), vol. 72, No. 7: 6175-6180.

Donello, et al., "Woodchuck Hepatitis Virus Contains a Tripartite Posttranscriptional Regulatory Element," J. Virol., (1998), vol. 72, No. 6: 5085-5092.

Schambach, et al., "Woodchuck hepatitis virus post-transcriptional regulatory element deleted from X protein and promoter sequences enhances retroviral vector titer and expression," Gene Ther., (2006), vol. 13: 641-645.

Zanta-Boussif, et al., "Validation of a mutated PRE sequence allowing high and sustained transgene expression while abrogating WHV-X protein synthesis: application to the gene therapy of WAS," Gene Ther., (2009), vol. 16: 605-619.

Ou, et al., "Elements of lentiviral vector design toward gene therapy for treating mucopolysaccharidosis," Mol. Gen. Metab. Rep., (2016), vol. 8: 87-93.

Yang et al., "Development of optimal bicistronic lentiviral vectors facilitates high-level TCR gene expression and robust tumor cell recognition," Gene Therapy, (2008), vol. 15, No. 21: 1411-1423.

PCT International Search Report for PCT/US2021/021701, dated Jun. 29, 2021.

* cited by examiner

FIG 1

```
SEQ_ID_1
SEQ_ID_2
SEQ_ID_4
SEQ_ID_3    1 gagcatcttaccgccatttatacccatatttgttctgttttcttgatttgggtatacat 60

SEQ_ID_1    1 ttaaatgttaataaaacaaaatggtggggcaatcatttacattttatgggatatgtaatt 60
SEQ_ID_2
SEQ_ID_4
SEQ_ID_3   61 ttaaatgttaataaaacaaaatggtggggcaatcatttacattttatgggatatgtaatt 120

SEQ_ID_1   61 actagtcaggtgtattgccacaagacaaacatgttaagaaactttccgttatttacgc 120
SEQ_ID_2    1 ------------------cagtctgacgtacgcg-------------------------- 16
SEQ_ID_4    1 ------------------cagtctgacgtacgcg-------------------------- 16
SEQ_ID_3  121 actagttcaggtgtattgccacaagacaaacttgttaagaaactttccgttatttacgc 180

SEQ_ID_1  121 tctgttcctgttaatcaacctctggattacaaaatttgtgaaagattgactgatattctt 180
SEQ_ID_2   17 -----------taatcaacctctggattacaaaatttgtgaaagattgactggtattctt 65
SEQ_ID_4   17 -----------taatcaacctctggattacaaaatttgtgaaagattgactggtattctt 65
SEQ_ID_3  181 tctgttcctgttaatcaacctctggattacaaaatttgtgaaagattgactgatattctt 240

SEQ_ID_1  181 aactatgttgctcctttacgctgtgtggatatgctgcttaatgcctctgtatcatgct 240
SEQ_ID_2   66 aactatgttgctcctttacgctatgtggatacgctgcttaatgcctttgtatcatgct 125
SEQ_ID_4   66 aactatgttgctcctttacgctatgtggatacgctgcttaatgcctttgtatcatgct 125
SEQ_ID_3  241 aactttgttgctcctttacgctgtgtggatttgctgcttattgcctctgtatcttgct 300

SEQ_ID_1  241 attgcttcccgtacggctttcgttttctcctccttgtataaatccggttgctgtctctt 300
SEQ_ID_2  126 attgcttcccgtatggctttcattttctcctccttgtataaatccggttgctgtctctt 185
SEQ_ID_4  126 attgcttcccgtatggctttcattttctcctccttgtataaatccggttgctgtctctt 185
SEQ_ID_3  301 attgcttcccgtacggctttcgttttctcctccttgtataaatccggttgctgtctctt 360

SEQ_ID_1  301 tatgaggagttgtggcccgttgtccgtcaacgtggcgtggtgtgctctgtgtttgctgac 360
SEQ_ID_2  186 tatgaggagttgtggcccgttgtcaggcaacgtggcgtggtgtgcactgtgtttgctgac 245
SEQ_ID_4  186 tatgaggagttgtggcccgttgtcaggcaacgtggcgtggtgtgcactgtgtttgctgac 245
SEQ_ID_3  361 tttgaggagttgtggcccgttgtccgtcaacgtggcgtggtgtgctctgtgtttgctgac 420

SEQ_ID_1  361 gcaaccccactggctggggcattgccaccacctgtcaactccttctgggactttcgct 420
SEQ_ID_2  246 gcaaccccactggttggggcattgccaccacctgtcagctccttccgggactttcgct 305
SEQ_ID_4  246 gcaaccccactggttggggcattgccaccacctgtcagctccttccgggactttcgct 305
SEQ_ID_3  421 gcaaccccactggctggggcattgccaccacctgtcaactccttctgggactttcgct 480

SEQ_ID_1  421 ttccccctcccgatcgccacggcagaactcatcgccgcctgccttgcccgctgctggaca 480
SEQ_ID_2  306 ttccccctccctattgccacggcggaactcatcgccgcctgccttgcccgctgctggaca 365
SEQ_ID_4  306 ttccccctccctattgccacggcggaactcatcgccgcctgccttgcccgctgctggaca 365
SEQ_ID_3  481 ttccccctcccgatcgccacggcagaactcatcgccgcctgccttgcccgctgctggaca 540

SEQ_ID_1  481 gggctaggttgctgggcactgataattccgtggtgttgtcggggaagctgacgtcctt 540
SEQ_ID_2  366 gggctcggctgttgggcactgacaattccgtggtgttgtcggggaagctgacgtcctt 425
SEQ_ID_4  366 gggctcggctgttgggcactgacaattccgtggtgttgtcggggaaatcatcgtcctt 425
SEQ_ID_3  541 gggctaggttgctgggcactgataattccgtggtgttgtc-------------------- 581

SEQ_ID_1  541 ccatggctgctcgcctgtgttgccaactggatcctgcgcgggacgtccttctgctacgtc 600
SEQ_ID_2  426 ccatggctgctcgcctgtgttgccacctggattctgcgcgggacgtccttctgctacgtc 485
SEQ_ID_4  426 ccttggctgctcgcctgtgttgccacctggattctgcgcgggacgtccttctgctacgtc 485
SEQ_ID_3

SEQ_ID_1  601 ccttcggctctcaatccagcggacctcccttcccgaggccttctgccggttctgcggcct 660
SEQ_ID_2  486 ccttcggccctcaatccagcggaccttccttcccgcggcctgctgccggtctgcggcct 545
SEQ_ID_4  486 ccttcggccctcaatccagcggaccttccttcccgcggcctgctgccggtctgcggcct 545
SEQ_ID_3

SEQ_ID_1  661 ctccgcgtcttcgctttcggcctccgacgagtcggatctccctttgggccgcctcccg 720
SEQ_ID_2  546 cttccgcgtcttcgccttcgccctcagacgagtcggatctccctttgggccgcctcccg 605
SEQ_ID_4  546 cttccgcgtcttcgccttcgccctcagacgagtcggatctccctttgggccgcctcccg 605
SEQ_ID_3

SEQ_ID_1  721 cctg                                                         724
SEQ_ID_2  606 cc--                                                         607
SEQ_ID_4  606 cc--                                                         607
SEQ_ID_3
```

FIG 1

```
SEQ_1    1    GAGCATCTTACCGCCATTTATACCCATATTTGTTCTGTTTTTCTTGATTTGGGTATACAT    60
              ||||||||||||||||||||||||||||||||||||||||||||||||||||||||||||
SEQ_3    1    GAGCATCTTACCGCCATTTATACCCATATTTGTTCTGTTTTTCTTGATTTGGGTATACAT    60

SEQ_1   61    TTAAATGTTAATAAAACAAAATGGTGGGGCAATCATTTACATTTTATGGGATATGTAATT   120
              ||||||||||||||||||||||||||||||||||||||||||||| ||||||||||||||
SEQ_3   61    TTAAATGTTAATAAAACAAAATGGTGGGGCAATCATTTACATTTTTTGGGATATGTAATT   120

SEQ_1  121    ACTAGTTCAGGTGTATTGCCACAAGACAAACATGTTAAGAAACTTTCCCGTTATTTACGC   180
              |||||||||||||||||||||||||||||||| |||||||||||||||||||||||||||
SEQ_3  121    ACTAGTTCAGGTGTATTGCCACAAGACAAACTTGTTAAGAAACTTTCCCGTTATTTACGC   180

SEQ_1  181    TCTGTTCCTGTTAATCAACCTCTGGATTACAAAATTTGTGAAAGATTGACTGATATTCTT   240
              ||||||||||||||||||||||||||||||||||||||||||||||||||||||||||||
SEQ_3  181    TCTGTTCCTGTTAATCAACCTCTGGATTACAAAATTTGTGAAAGATTGACTGATATTCTT   240

SEQ_1  241    AACTATGTTGCTCCTTTTACGCTGTGTGGATATGCTGCTTTAATGCCTCTGTATCATGCT   300
              |||| ||||||||||||||||||||||||||| |||||||||| |||||||||||| |||
SEQ_3  241    AACTTGTTGCTCCTTTTACGCTGTGTGGATTTGCTGCTTTATTGCCTCTGTATCTTGCT   300

SEQ_1  301    ATTGCTTCCCGTACGGCTTTCGTTTTCTCCTCCTTGTATAAATCCTGGTTGCTGTCTCTT   360
              ||||||||||||||||||||||||||||||||||||||||||||||||||||||||||||
SEQ_3  301    ATTGCTTCCCGTACGGCTTTCGTTTTCTCCTCCTTGTATAAATCCTGGTTGCTGTCTCTT   360

SEQ_1  361    TATGAGGAGTTGTGGCCCGTTGTCCGTCAACGTGGCGTGGTGTGCTCTGTGTTTGCTGAC   420
              | ||||||||||||||||||||||||||||||||||||||||||||||||||||||||||
SEQ_3  361    TTTGAGGAGTTGTGGCCCGTTGTCCGTCAACGTGGCGTGGTGTGCTCTGTGTTTGCTGAC   420

SEQ_1  421    GCAACCCCCACTGGCTGGGGCATTGCCACCACCTGTCAACTCCTTTCTGGGACTTTCGCT   480
              ||||||||||||||||||||||||||||||||||||||||||||||||||||||||||||
SEQ_3  421    GCAACCCCCACTGGCTGGGGCATTGCCACCACCTGTCAACTCCTTTCTGGGACTTTCGCT   480
```

FIG 2

```
SEQ_1  481  TTCCCCCTCCCGATCGCCACGGCAGAACTCATCGCCGCCTGCCTTGCCCGCTGCTGGACA  540
            ||||||||||||||||||||||||||||||||||||||||||||||||||||||||||||
SEQ_3  481  TTCCCCCTCCCGATCGCCACGGCAGAACTCATCGCCGCCTGCCTTGCCCGCTGCTGGACA  540

SEQ_1  541  GGGGCTAGGTTGCTGGGCACTGATAATTCCGTGGTGTTGTCGGGGAAGCTGACGTCCTTT  600
            |||||||||||||||||||||||||||||||||||||||||
SEQ_3  541  GGGGCTAGGTTGCTGGGCACTGATAATTCCGTGGTGTTGTC                     581

SEQ_1  601  CCATGGCTGCTCGCCTGTGTTGCCAACTGGATCCTGCGCGGGACGTCCTTCTGCTACGTC  660

SEQ_1  661  CCTTCGGCTCTCAATCCAGCGGACCTCCCTTCCCGAGGCCTTCTGCCGGTTCTGCGGCCT  720

SEQ_1  721  CTCCCGCGTCTTCGCTTTCGGCCTCCGACGAGTCGGATCTCCCTTTGGGCCGCCTCCCCG  780
```

FIG 2 (cont)

| LV name | Abbreviated name | TCR-insert | | | | | |
|---|---|---|---|---|---|---|---|
| LV_R4P3F9_A | R4-A | R4P3F9 beta | Furin | SGSG | P2A | R4P3F9 alpha | WPRE |
| LV_R4P3F9_B | R4-B | R4P3F9 beta | Furin | SGSG | P2A | R4P3F9 alpha | WPRE |
| LV_R4P3F9_C | R4-C | R4P3F9 beta | Furin | SGSG | P2A | R4P3F9 alpha | WPRE |
| LV_R4P3F9_D | R4-D | R4P3F9 beta | Furin | SGSG | P2A | R4P3F9 alpha | WPRE |
| LV_R4P3F9_b4_A | R4-B4-A | R4P3F9 beta | Furin | SGSG | P2A | R4P3F9 alpha | WPRE |
| LV_R4P3F9_b4_B | R4-B4-B | R4P3F9 beta | Furin | SGSG | P2A | R4P3F9 alpha | WPRE |
| LV_R4P3F9_b4_C | R4-B4-C | R4P3F9 beta | Furin | SGSG | P2A | R4P3F9 alpha | WPRE |
| LV_R4P3F9_b4_D | R4-B4-D | R4P3F9 beta | Furin | SGSG | P2A | R4P3F9 alpha | WPRE |
| LV_R4P3F9_a1b4_A | R4-A1B4-A | R4P3F9 beta | Furin | SGSG | P2A | R4P3F9 alpha | WPRE |
| LV_R4P3F9_a1b4_B | R4-A1B4-B | R4P3F9 beta | Furin | SGSG | P2A | R4P3F9 alpha | WPRE |
| LV_R4P3F9_a1b4_C | R4-A1B4-C | R4P3F9 beta | Furin | SGSG | P2A | R4P3F9 alpha | WPRE |
| LV_R4P3F9_a1b4_D | R4-A1B4-D | R4P3F9 beta | Furin | SGSG | P2A | R4P3F9 alpha | WPRE |

FIG 4

SEQUENCE LISTING

<160> NUMBER OF SEQ ID NOS: 262

<210> SEQ ID NO 1
<211> LENGTH: 784
<212> TYPE: DNA
<213> ORGANISM: Woodchuck hepatitis virus
<220> FEATURE:
<221> NAME/KEY: misc_feature
<222> LOCATION: (1)..(784)
<223> OTHER INFORMATION: WT WPRE from GenBank Accession No. J02442.1

<400> SEQUENCE: 1

```
gagcatctta ccgccattta tacccatatt tgttctgttt ttcttgattt gggtatacat      60
ttaaatgtta ataaaacaaa atggtggggc aatcatttac attttatggg atatgtaatt     120
actagttcag gtgtattgcc acaagacaaa catgttaaga aactttcccg ttatttacgc     180
tctgttcctg ttaatcaacc tctggattac aaaatttgtg aaagattgac tgatattctt     240
aactatgttg ctccttttac gctgtgtgga tatgctgctt taatgcctct gtatcatgct     300
attgcttccc gtacggcttt cgttttctcc tccttgtata atcctggtt gctgtctctt     360 tatgaggagt tgtggcccgt tgtccgtcaa cgtggcgtgg tgtgctctgt gtttgctgac     420
gcaaccccca ctggctgggg cattgccacc acctgtcaac tcctttctgg gactttcgct     480
ttccccctcc cgatcgccac ggcagaactc atcgccgcct gccttgcccg ctgctggaca     540
ggggctaggt tgctgggcac tgataattcc gtggtgttgt cggggaagct gacgtccttt     600
ccatggctgc tcgcctgtgt tgccaactgg atcctgcgcg gacgtccctt ctgctacgtc     660
ccttcggctc tcaatccagc ggacctccct tcccgaggcc ttctgccggt tctgcggcct     720
ctcccgcgtc ttcgctttcg gcctccgacg agtcggatct cctttgggcc gcctccccg      780 cctg                                                                 784
```

<210> SEQ ID NO 2
<211> LENGTH: 590
<212> TYPE: DNA
<213> ORGANISM: Woodchuck hepatitis B virus
<220> FEATURE:
<221> NAME/KEY: misc_feature
<222> LOCATION: (1)..(590)
<223> OTHER INFORMATION: WT WPRE from Genbank Accession No. J04514.1

<400> SEQUENCE: 2

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aacccccact     240
ggttggggca ttgccaccac ctgtcagctc ctttccggga cttttcgctttt ccccctccct    300 attgccacgg cggaactcat cgccgcctgc cttgcccgct gctggacagg ggctcggctg     360
ttgggcactg acaattccgt ggtgttgtcg gggaagctga cgtcctttcc atggctgctc     420
gcctgtgttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgcc                590
```

<210> SEQ ID NO 3
<211> LENGTH: 581
<212> TYPE: DNA
<213> ORGANISM: Artificial Sequence -continued
<220> FEATURE:
<223> OTHER INFORMATION: mutant WPRE

<400> SEQUENCE: 3

| | | | | |
|---|---|---|---|---|
| gagcatctta ccgccattta tacccatatt tgttctgttt ttcttgattt gggtatacat | | | | 60 |
| ttaaatgtta ataaaacaaa atggtggggc aatcatttac attttttggg atatgtaatt | | | | 120 |
| actagttcag gtgtattgcc acaagacaaa cttgttaaga aactttcccg ttatttacgc | | | | 180 |
| tctgttcctg ttaatcaacc tctggattac aaaatttgtg aaagattgac tgatattctt | | | | 240 |
| aactttgttg ctccttttac gctgtgtgga tttgctgctt tattgcctct gtatcttgct | | | | 300 |
| attgcttccc gtacggcttt cgttttctcc tccttgtata aatcctggtt gctgtctctt | | | | 360 |
| tttgaggagt tgtggcccgt tgtccgtcaa cgtggcgtgg tgtgctctgt gtttgctgac | | | | 420 |
| gcaaccccca ctggctgggg cattgccacc acctgtcaac tcctttctgg gactttcgct | | | | 480 |
| ttccccctcc cgatcgccac ggcagaactc atcgccgcct gccttgcccg ctgctggaca | | | | 540 |
| ggggctaggt tgctgggcac tgataattcc gtggtgttgt c | | | | 581 |

<210> SEQ ID NO 4
<211> LENGTH: 607
<212> TYPE: DNA
<213> ORGANISM: Artificial Sequence
<220> FEATURE:
<223> OTHER INFORMATION: mutant WPRE

<400> SEQUENCE: 4

| | | | | |
|---|---|---|---|---|
| cagtctgacg tacgcgtaat caacctctgg attacaaaat tgtgaaaga ttgactggta | | | | 60 |
| ttcttaacta tgttgctcct tttacgctat gtggatacgc tgctttaatg cctttgtatc | | | | 120 |
| atgctattgc ttcccgtatg gctttcattt tctcctcctt gtataaatcc tggttgctgt | | | | 180 |
| ctctttatga ggagttgtgg cccgttgtca ggcaacgtgg cgtggtgtgc actgtgtttg | | | | 240 |
| ctgacgcaac ccccactggt tggggcattg ccaccacctg tcagctcctt ccgggactt | | | | 300 |
| tcgctttccc cctccctatt gccacggcgg aactcatcgc cgcctgcctt gcccgctgct | | | | 360 |
| ggacaggggc tcggctgttg gcactgaca attccgtggt gttgtcgggg aaatcatcgt | | | | 420 |
| cctttccttg gctgctcgcc tgtgttgcca cctggattct gcgcgggacg tccttctgct | | | | 480 |
| acgtcccttc ggccctcaat ccagcggacc ttccttcccg cggcctgctg ccggctctgc | | | | 540 |
| ggcctcttcc gcgtcttcgc cttcgccctc agacgagtcg atctccctt tgggccgcct | | | | 600 |
| ccccgcc | | | | 607 |

<210> SEQ ID NO 5
<211> LENGTH: 4
<212> TYPE: PRT
<213> ORGANISM: Artificial Sequence
<220> FEATURE:
<223> OTHER INFORMATION: linker sequence

<400> SEQUENCE: 5

Ser Gly Ser Gly
1

<210> SEQ ID NO 6
<211> LENGTH: 19
<212> TYPE: PRT
<213> ORGANISM: Artificial Sequence
<220> FEATURE:
<223> OTHER INFORMATION: P2A peptide

<400> SEQUENCE: 6

```
Ala Thr Asn Phe Ser Leu Leu Lys Gln Ala Gly Asp Val Glu Glu Asn
1               5                   10                  15

Pro Gly Pro

<210> SEQ ID NO 7
<211> LENGTH: 18
<212> TYPE: PRT
<213> ORGANISM: Artificial Sequence
<220> FEATURE:
<223> OTHER INFORMATION: T2A peptide

<400> SEQUENCE: 7

Glu Gly Arg Gly Ser Leu Leu Thr Cys Gly Asp Val Glu Glu Asn Pro
1               5                   10                  15

Gly Pro

<210> SEQ ID NO 8
<211> LENGTH: 20
<212> TYPE: PRT
<213> ORGANISM: Artificial Sequence
<220> FEATURE:
<223> OTHER INFORMATION: E2A peptide

<400> SEQUENCE: 8

Gln Cys Thr Asn Tyr Ala Leu Leu Lys Leu Ala Gly Asp Val Glu Ser
1               5                   10                  15

Asn Pro Gly Pro
            20

<210> SEQ ID NO 9
<211> LENGTH: 22
<212> TYPE: PRT
<213> ORGANISM: Artificial Sequence
<220> FEATURE:
<223> OTHER INFORMATION: F2A peptide

<400> SEQUENCE: 9

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 10
<211> LENGTH: 4
<212> TYPE: PRT
<213> ORGANISM: Artificial Sequence
<220> FEATURE:
<223> OTHER INFORMATION: Furin

<400> SEQUENCE: 10

Arg Ala Lys Arg
1

<210> SEQ ID NO 11
<211> LENGTH: 235
<212> TYPE: PRT
<213> ORGANISM: Homo sapiens

<400> SEQUENCE: 11

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30
```

```
Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
 50                  55                  60

Ala Ser Pro Thr Phe Leu Leu Tyr Leu Ser Gln Asn Lys Pro Lys Ala
 65                  70                  75                  80

Ala Glu Gly Leu Asp Thr Gln Arg Phe Ser Gly Lys Arg Leu Gly Asp
                    85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
        130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Leu Ser Leu Val Ile Thr Leu Tyr Cys Asn His
            195                 200                 205

Arg Asn Arg Arg Arg Val Cys Lys Cys Pro Arg Pro Val Val Lys Ser
        210                 215                 220

Gly Asp Lys Pro Ser Leu Ser Ala Arg Tyr Val
225                 230                 235

<210> SEQ ID NO 12
<211> LENGTH: 243
<212> TYPE: PRT
<213> ORGANISM: Homo sapiens

<400> SEQUENCE: 12

Met Arg Pro Arg Leu Trp Leu Leu Leu Ala Ala Gln Leu Thr Val Leu
 1               5                  10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
 50                  55                  60

Ser His His Glu Phe Leu Ala Leu Trp Asp Ser Ala Lys Gly Thr Ile
 65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
                100                 105                 110

Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
        130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
```

```
                    165                 170                 175
Val Ala Gly Val Leu Val Leu Val Ser Leu Gly Val Ala Ile His
            180                 185                 190

Leu Cys Cys Arg Arg Arg Ala Arg Leu Arg Phe Met Lys Gln Pro
        195                 200                 205

Gln Gly Glu Gly Ile Ser Gly Thr Phe Val Pro Gln Cys Leu His Gly
210             215                 220

Tyr Tyr Ser Asn Thr Thr Thr Ser Gln Lys Leu Leu Asn Pro Trp Ile
225                 230                 235                 240

Leu Lys Thr

<210> SEQ ID NO 13
<211> LENGTH: 273
<212> TYPE: PRT
<213> ORGANISM: Artificial Sequence
<220> FEATURE:
<223> OTHER INFORMATION: R11KEA alpha chain

<400> SEQUENCE: 13

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
            20                  25                  30

Leu His Val Gln Glu Gly Asp Ser Thr Asn Phe Thr Cys Ser Phe Pro
        35                  40                  45

Ser Ser Asn Phe Tyr Ala Leu His Trp Tyr Arg Lys Glu Thr Ala Lys
    50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Leu Tyr Asn Asn Asn Asp Met Arg Phe Gly Ala Gly Thr Arg Leu
        115                 120                 125

Thr Val Lys Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser
```

```
<210> SEQ ID NO 14
<211> LENGTH: 311
<212> TYPE: PRT
<213> ORGANISM: Artificial Sequence
<220> FEATURE:
<223> OTHER INFORMATION: R11KE beta chain

<400> SEQUENCE: 14

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Glu Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Pro Gly Ser Thr Asp Thr Gln Tyr Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 15
<211> LENGTH: 274
<212> TYPE: PRT
<213> ORGANISM: Artificial Sequence
<220> FEATURE:
<223> OTHER INFORMATION: R20P1H7 alpha chain

<400> SEQUENCE: 15
```

```
Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Leu Asn Cys Ser Tyr Thr Val
        35                  40                  45

Ser Gly Leu Arg Gly Leu Phe Trp Tyr Arg Gln Asp Pro Gly Lys Gly
50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val Gln
                100                 105                 110

Gly Glu Asn Ser Gly Tyr Ser Thr Leu Thr Phe Gly Lys Gly Thr Met
            115                 120                 125

Leu Leu Val Ser Pro Asp Ile Gln Asn Pro Asp Pro Ala Val Tyr Gln
        130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
                180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
        210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 16
<211> LENGTH: 314
<212> TYPE: PRT
<213> ORGANISM: Artificial Sequence
<220> FEATURE:
<223> OTHER INFORMATION: R20P1H7 beta chain

<400> SEQUENCE: 16

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80
```

```
Glu Gly Tyr Lys Val Ser Arg Lys Glu Lys Arg Asn Phe Pro Leu Ile
                85                  90                  95
Leu Glu Ser Pro Ser Pro Asn Gln Thr Ser Leu Tyr Phe Cys Ala Ser
            100                 105                 110
Ser Leu Gly Pro Gly Leu Ala Ala Tyr Asn Glu Gln Phe Phe Gly Pro
        115                 120                 125
Gly Thr Arg Leu Thr Val Leu Glu Asp Leu Lys Asn Val Phe Pro Pro
130                 135                 140
Glu Val Ala Val Phe Glu Pro Ser Glu Ala Glu Ile Ser His Thr Gln
145                 150                 155                 160
Lys Ala Thr Leu Val Cys Leu Ala Thr Gly Phe Tyr Pro Asp His Val
                165                 170                 175
Glu Leu Ser Trp Trp Val Asn Gly Lys Glu Val His Ser Gly Val Ser
            180                 185                 190
Thr Asp Pro Gln Pro Leu Lys Glu Gln Pro Ala Leu Asn Asp Ser Arg
        195                 200                 205
Tyr Cys Leu Ser Ser Arg Leu Arg Val Ser Ala Thr Phe Trp Gln Asn
210                 215                 220
Pro Arg Asn His Phe Arg Cys Gln Val Gln Phe Tyr Gly Leu Ser Glu
225                 230                 235                 240
Asn Asp Glu Trp Thr Gln Asp Arg Ala Lys Pro Val Thr Gln Ile Val
                245                 250                 255
Ser Ala Glu Ala Trp Gly Arg Ala Asp Cys Gly Phe Thr Ser Glu Ser
            260                 265                 270
Tyr Gln Gln Gly Val Leu Ser Ala Thr Ile Leu Tyr Glu Ile Leu Leu
        275                 280                 285
Gly Lys Ala Thr Leu Tyr Ala Val Leu Val Ser Ala Leu Val Leu Met
290                 295                 300
Ala Met Val Lys Arg Lys Asp Ser Arg Gly
305                 310

<210> SEQ ID NO 17
<211> LENGTH: 272
<212> TYPE: PRT
<213> ORGANISM: Artificial Sequence
<220> FEATURE:
<223> OTHER INFORMATION: R7P1D5 alpha chain

<400> SEQUENCE: 17

Met Lys Thr Phe Ala Gly Phe Ser Phe Leu Phe Leu Trp Leu Gln Leu
1               5                   10                  15
Asp Cys Met Ser Arg Gly Glu Asp Val Glu Gln Ser Leu Phe Leu Ser
            20                  25                  30
Val Arg Glu Gly Asp Ser Ser Val Ile Asn Cys Thr Tyr Thr Asp Ser
        35                  40                  45
Ser Ser Thr Tyr Leu Tyr Trp Tyr Lys Gln Glu Pro Gly Ala Gly Leu
    50                  55                  60
Gln Leu Leu Thr Tyr Ile Phe Ser Asn Met Asp Met Lys Gln Asp Gln
65                  70                  75                  80
Arg Leu Thr Val Leu Leu Asn Lys Lys Asp Lys His Leu Ser Leu Arg
                85                  90                  95
Ile Ala Asp Thr Gln Thr Gly Asp Ser Ala Ile Tyr Phe Cys Ala Glu
            100                 105                 110
Tyr Ser Ser Ala Ser Lys Ile Ile Phe Gly Ser Gly Thr Arg Leu Ser
        115                 120                 125
```

```
Ile Arg Pro Asn Ile Gln Asn Pro Asp Pro Ala Val Tyr Gln Leu Arg
    130                 135                 140
Asp Ser Lys Ser Ser Asp Lys Ser Val Cys Leu Phe Thr Asp Phe Asp
145                 150                 155                 160
Ser Gln Thr Asn Val Ser Gln Ser Lys Asp Ser Asp Val Tyr Ile Thr
                165                 170                 175
Asp Lys Thr Val Leu Asp Met Arg Ser Met Asp Phe Lys Ser Asn Ser
            180                 185                 190
Ala Val Ala Trp Ser Asn Lys Ser Asp Phe Ala Cys Ala Asn Ala Phe
        195                 200                 205
Asn Asn Ser Ile Ile Pro Glu Asp Thr Phe Phe Pro Ser Pro Glu Ser
    210                 215                 220
Ser Cys Asp Val Lys Leu Val Glu Lys Ser Phe Glu Thr Asp Thr Asn
225                 230                 235                 240
Leu Asn Phe Gln Asn Leu Ser Val Ile Gly Phe Arg Ile Leu Leu Leu
                245                 250                 255
Lys Val Ala Gly Phe Asn Leu Leu Met Thr Leu Arg Leu Trp Ser Ser
            260                 265                 270

<210> SEQ ID NO 18
<211> LENGTH: 310
<212> TYPE: PRT
<213> ORGANISM: Artificial Sequence
<220> FEATURE:
<223> OTHER INFORMATION: R7P1D5 beta chain

<400> SEQUENCE: 18

Met Gly Ser Trp Thr Leu Cys Cys Val Ser Leu Cys Ile Leu Val Ala
1               5                   10                  15
Lys His Thr Asp Ala Gly Val Ile Gln Ser Pro Arg His Glu Val Thr
            20                  25                  30
Glu Met Gly Gln Glu Val Thr Leu Arg Cys Lys Pro Ile Ser Gly His
        35                  40                  45
Asp Tyr Leu Phe Trp Tyr Arg Gln Thr Met Met Arg Gly Leu Glu Leu
    50                  55                  60
Leu Ile Tyr Phe Asn Asn Asn Val Pro Ile Asp Asp Ser Gly Met Pro
65                  70                  75                  80
Glu Asp Arg Phe Ser Ala Lys Met Pro Asn Ala Ser Phe Ser Thr Leu
                85                  90                  95
Lys Ile Gln Pro Ser Glu Pro Arg Asp Ser Ala Val Tyr Phe Cys Ala
            100                 105                 110
Ser Arg Ala Asn Thr Gly Glu Leu Phe Gly Glu Gly Ser Arg Leu
        115                 120                 125
Thr Val Leu Glu Asp Leu Lys Asn Val Phe Pro Pro Glu Val Ala Val
    130                 135                 140
Phe Glu Pro Ser Glu Ala Glu Ile Ser His Thr Gln Lys Ala Thr Leu
145                 150                 155                 160
Val Cys Leu Ala Thr Gly Phe Tyr Pro Asp His Val Glu Leu Ser Trp
                165                 170                 175
Trp Val Asn Gly Lys Glu Val His Ser Gly Val Ser Thr Asp Pro Gln
            180                 185                 190
Pro Leu Lys Glu Gln Pro Ala Leu Asn Asp Ser Arg Tyr Cys Leu Ser
        195                 200                 205
Ser Arg Leu Arg Val Ser Ala Thr Phe Trp Gln Asn Pro Arg Asn His
    210                 215                 220
```

```
Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
            245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
            290                 295                 300

Arg Lys Asp Ser Arg Gly
305                 310

<210> SEQ ID NO 19
<211> LENGTH: 277
<212> TYPE: PRT
<213> ORGANISM: Artificial Sequence
<220> FEATURE:
<223> OTHER INFORMATION: R10P2G12 alpha chain

<400> SEQUENCE: 19

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ser Glu Gly Asn Ser Gly Asn Thr Pro Leu Val Phe Gly Lys
        115                 120                 125

Gly Thr Arg Leu Ser Val Ile Ala Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270
```

-continued

```
Arg Leu Trp Ser Ser
        275

<210> SEQ ID NO 20
<211> LENGTH: 313
<212> TYPE: PRT
<213> ORGANISM: Artificial Sequence
<220> FEATURE:
<223> OTHER INFORMATION: R10P2G12 beta chain

<400> SEQUENCE: 20

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Ser Ser Gly Ser His Gln Glu Thr Gln Tyr Phe Gly Pro Gly
        115                 120                 125

Thr Arg Leu Leu Val Leu Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Ser Arg Gly
305                 310

<210> SEQ ID NO 21
<211> LENGTH: 271
<212> TYPE: PRT
<213> ORGANISM: Artificial Sequence
<220> FEATURE:
```

<223> OTHER INFORMATION: R10P1A7 alpha chain

<400> SEQUENCE: 21

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ser Lys Glu Thr Arg Leu Met Phe Gly Asp Gly Thr Gln Leu Val Val
        115                 120                 125

Lys Pro Asn Ile Gln Asn Pro Asp Pro Ala Val Tyr Gln Leu Arg Asp
130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 22
<211> LENGTH: 317
<212> TYPE: PRT
<213> ORGANISM: Artificial Sequence
<220> FEATURE:
<223> OTHER INFORMATION: R10P1A7 beta chain

<400> SEQUENCE: 22

Met Leu Leu Leu Leu Leu Leu Gly Pro Gly Ile Ser Leu Leu Leu
1               5                   10                  15

Pro Gly Ser Leu Ala Gly Ser Gly Leu Gly Ala Trp Ser Gln His Pro
            20                  25                  30

Ser Val Trp Ile Cys Lys Ser Gly Thr Ser Val Lys Ile Glu Cys Arg
        35                  40                  45

Ser Leu Asp Phe Gln Ala Thr Thr Met Phe Trp Tyr Arg Gln Phe Pro
50                  55                  60

Lys Gln Ser Leu Met Leu Met Ala Thr Ser Asn Glu Gly Ser Lys Ala
65                  70                  75                  80

```
Thr Tyr Glu Gln Gly Val Glu Lys Asp Lys Phe Leu Ile Asn His Ala
                85                  90                  95

Ser Leu Thr Leu Ser Thr Leu Thr Val Thr Ser Ala His Pro Glu Asp
            100                 105                 110

Ser Ser Phe Tyr Ile Cys Ser Ala Arg Ala Gly Gly His Glu Gln Phe
        115                 120                 125

Phe Gly Pro Gly Thr Arg Leu Thr Val Leu Glu Asp Leu Lys Asn Val
    130                 135                 140

Phe Pro Pro Glu Val Ala Val Phe Glu Pro Ser Glu Ala Glu Ile Ser
145                 150                 155                 160

His Thr Gln Lys Ala Thr Leu Val Cys Leu Ala Thr Gly Phe Tyr Pro
                165                 170                 175

Asp His Val Glu Leu Ser Trp Val Trp Asn Gly Lys Glu Val His Ser
            180                 185                 190

Gly Val Ser Thr Asp Pro Gln Pro Leu Lys Glu Gln Pro Ala Leu Asn
        195                 200                 205

Asp Ser Arg Tyr Cys Leu Ser Ser Arg Leu Arg Val Ser Ala Thr Phe
    210                 215                 220

Trp Gln Asn Pro Arg Asn His Phe Arg Cys Gln Val Gln Phe Tyr Gly
225                 230                 235                 240

Leu Ser Glu Asn Asp Glu Trp Thr Gln Asp Arg Ala Lys Pro Val Thr
                245                 250                 255

Gln Ile Val Ser Ala Glu Ala Trp Gly Arg Ala Asp Cys Gly Phe Thr
            260                 265                 270

Ser Glu Ser Tyr Gln Gln Gly Val Leu Ser Ala Thr Ile Leu Tyr Glu
        275                 280                 285

Ile Leu Leu Gly Lys Ala Thr Leu Tyr Ala Val Leu Val Ser Ala Leu
    290                 295                 300

Val Leu Met Ala Met Val Lys Arg Lys Asp Ser Arg Gly
305                 310                 315

<210> SEQ ID NO 23
<211> LENGTH: 271
<212> TYPE: PRT
<213> ORGANISM: Artificial Sequence
<220> FEATURE:
<223> OTHER INFORMATION: R4P1D10 alpha chain

<400> SEQUENCE: 23

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Phe His Asp Lys Ile Ile Phe Gly Lys Gly Thr Arg Leu His Ile
        115                 120                 125
```

-continued

```
Leu Pro Asn Ile Gln Asn Pro Asp Pro Ala Val Tyr Gln Leu Arg Asp
            130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 24
<211> LENGTH: 308
<212> TYPE: PRT
<213> ORGANISM: Artificial Sequence
<220> FEATURE:
<223> OTHER INFORMATION: R4P1D10 beta chain

<400> SEQUENCE: 24

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile His Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Ala Ser Ala Tyr Gly Tyr Thr Phe Gly Ser Gly Thr Arg Leu
        115                 120                 125

Thr Val Val Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220
```

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
            245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
        290                 295                 300

Arg Lys Asp Phe
305

<210> SEQ ID NO 25
<211> LENGTH: 274
<212> TYPE: PRT
<213> ORGANISM: Artificial Sequence
<220> FEATURE:
<223> OTHER INFORMATION: R4P3F9 alpha chain

<400> SEQUENCE: 25

Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
        50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ala
            100                 105                 110

Tyr Ser Gly Ala Gly Ser Tyr Gln Leu Thr Phe Gly Lys Gly Thr Lys
        115                 120                 125

Leu Ser Val Ile Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 26
<211> LENGTH: 308
<212> TYPE: PRT
<213> ORGANISM: Artificial Sequence
<220> FEATURE:
<223> OTHER INFORMATION: R4P3F9 beta chain

<400> SEQUENCE: 26

```
Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Glu Ser Ser Tyr Gly Tyr Thr Phe Gly Ser Gly Thr Arg Leu
        115                 120                 125

Thr Val Val Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe
305
```

<210> SEQ ID NO 27
<211> LENGTH: 271
<212> TYPE: PRT
<213> ORGANISM: Artificial Sequence
<220> FEATURE:

<223> OTHER INFORMATION: R4P3H3 alpha chain

<400> SEQUENCE: 27

Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Lys Ala Gly Asn Gln Phe Tyr Phe Gly Thr Gly Thr Ser Leu Thr Val
        115                 120                 125

Ile Pro Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 28
<211> LENGTH: 314
<212> TYPE: PRT
<213> ORGANISM: Artificial Sequence
<220> FEATURE:
<223> OTHER INFORMATION: R4P3H3 beta chain

<400> SEQUENCE: 28

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30

Lys Arg Gly Gln Asp Val Ala Leu Arg Cys Asp Pro Ile Ser Gly His
        35                  40                  45

Val Ser Leu Phe Trp Tyr Gln Gln Ala Leu Gly Gln Gly Pro Glu Phe
    50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
            85                  90                  95

Lys Ile Gln Arg Thr Gln Gln Glu Asp Ser Ala Val Tyr Leu Cys Ala
            100                 105                 110

Ser Ser Leu Leu Thr Ser Gly Gly Asp Asn Glu Gln Phe Phe Gly Pro
            115                 120                 125

Gly Thr Arg Leu Thr Val Leu Glu Asp Leu Lys Asn Val Phe Pro Pro
            130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
            165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
            195                 200                 205

Tyr Cys Leu Ser Ser Arg Leu Arg Val Ser Ala Thr Phe Trp Gln Asn
            210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
            245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
            275                 280                 285

Gly Lys Ala Thr Leu Tyr Ala Val Leu Val Ser Ala Leu Val Leu Met
            290                 295                 300

Ala Met Val Lys Arg Lys Asp Ser Arg Gly
305                 310

<210> SEQ ID NO 29
<211> LENGTH: 270
<212> TYPE: PRT
<213> ORGANISM: Artificial Sequence
<220> FEATURE:
<223> OTHER INFORMATION: R36P3F9 alpha chain

<400> SEQUENCE: 29

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
            35                  40                  45

Ile Asn Asn Leu Gln Trp Tyr Arg Gln Asn Ser Gly Arg Gly Leu Val
            50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
            85                  90                  95

Thr Ala Ser Arg Ala Ala Asp Thr Ala Ser Tyr Phe Cys Ala Thr Val
            100                 105                 110

Ser Asn Tyr Gln Leu Ile Trp Gly Ala Gly Thr Lys Leu Ile Ile Lys
            115                 120                 125

```
Pro Asp Ile Gln Asn Pro Asp Pro Ala Val Tyr Gln Leu Arg Asp Ser
        130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 30
<211> LENGTH: 314
<212> TYPE: PRT
<213> ORGANISM: Artificial Sequence
<220> FEATURE:
<223> OTHER INFORMATION: R36P3F9 beta chain

<400> SEQUENCE: 30

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Ser Thr Ser Gly Gly Leu Ser Gly Glu Thr Gln Tyr Phe Gly Pro
        115                 120                 125

Gly Thr Arg Leu Leu Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220
```

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
            245                 250                 255

Ser Ala Glu Ala Trp Gly Arg Ala Asp Cys Gly Phe Thr Ser Glu Ser
        260                 265                 270

Tyr Gln Gln Gly Val Leu Ser Ala Thr Ile Leu Tyr Glu Ile Leu Leu
    275                 280                 285

Gly Lys Ala Thr Leu Tyr Ala Val Leu Val Ser Ala Leu Val Leu Met
290                 295                 300

Ala Met Val Lys Arg Lys Asp Ser Arg Gly
305                 310

<210> SEQ ID NO 31
<211> LENGTH: 272
<212> TYPE: PRT
<213> ORGANISM: Artificial Sequence
<220> FEATURE:
<223> OTHER INFORMATION: R52P2G11 alpha chain

<400> SEQUENCE: 31

Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
            20                  25                  30

Ile Ile Leu Glu Gly Lys Asn Cys Thr Leu Gln Cys Asn Tyr Thr Val
        35                  40                  45

Ser Pro Phe Ser Asn Leu Arg Trp Tyr Lys Gln Asp Thr Gly Arg Gly
    50                  55                  60

Pro Val Ser Leu Thr Ile Met Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

Val Ser Ala Tyr Gly Lys Leu Gln Phe Gly Ala Gly Thr Gln Val Val
        115                 120                 125

Val Thr Pro Asp Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 32
<211> LENGTH: 312
<212> TYPE: PRT
<213> ORGANISM: Artificial Sequence
<220> FEATURE:
<223> OTHER INFORMATION: R52P2G11 beta chain

<400> SEQUENCE: 32

```
Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Leu Gly Ser Pro Asp Gly Asn Gln Pro Gln His Phe Gly Asp
        115                 120                 125

Gly Thr Arg Leu Ser Ile Leu Glu Asp Leu Asn Lys Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Phe
305                 310
```

<210> SEQ ID NO 33
<211> LENGTH: 279
<212> TYPE: PRT
<213> ORGANISM: Artificial Sequence
<220> FEATURE:
<223> OTHER INFORMATION: R53P2A9 alpha chain

<400> SEQUENCE: 33

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Asn Ser Tyr Ala Gly Gly Thr Ser Tyr Gly Lys Leu Thr Phe
        115                 120                 125

Gly Gln Gly Thr Ile Leu Thr Val His Pro Asn Ile Gln Asn Pro Asp
    130                 135                 140

Pro Ala Val Tyr Gln Leu Arg Asp Ser Lys Ser Ser Asp Lys Ser Val
145                 150                 155                 160

Cys Leu Phe Thr Asp Phe Asp Ser Gln Thr Asn Val Ser Gln Ser Lys
                165                 170                 175

Asp Ser Asp Val Tyr Ile Thr Asp Lys Thr Val Leu Asp Met Arg Ser
            180                 185                 190

Met Asp Phe Lys Ser Asn Ser Ala Val Ala Trp Ser Asn Lys Ser Asp
        195                 200                 205

Phe Ala Cys Ala Asn Ala Phe Asn Asn Ser Ile Ile Pro Glu Asp Thr
210                 215                 220

Phe Phe Pro Ser Pro Glu Ser Ser Cys Asp Val Lys Leu Val Glu Lys
225                 230                 235                 240

Ser Phe Glu Thr Asp Thr Asn Leu Asn Phe Gln Asn Leu Ser Val Ile
                245                 250                 255

Gly Phe Arg Ile Leu Leu Leu Lys Val Ala Gly Phe Asn Leu Leu Met
            260                 265                 270

Thr Leu Arg Leu Trp Ser Ser
        275

<210> SEQ ID NO 34
<211> LENGTH: 310
<212> TYPE: PRT
<213> ORGANISM: Artificial Sequence
<220> FEATURE:
<223> OTHER INFORMATION: R53P2A9 beta chain

<400> SEQUENCE: 34

Met Gly Pro Gly Leu Leu Cys Trp Val Leu Leu Cys Leu Leu Gly Ala
1               5                   10                  15

Gly Pro Val Asp Ala Gly Val Thr Gln Ser Pro Thr His Leu Ile Lys
            20                  25                  30

Thr Arg Gly Gln Gln Val Thr Leu Arg Cys Ser Pro Ile Ser Gly His
        35                  40                  45

Lys Ser Val Ser Trp Tyr Gln Gln Val Leu Gly Gln Gly Pro Gln Phe
    50                  55                  60

Ile Phe Gln Tyr Tyr Glu Lys Glu Glu Arg Gly Arg Gly Asn Phe Pro

```
            65                  70                  75                  80
Asp Arg Phe Ser Ala Arg Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Asp Gly Thr Ser Glu Gln Tyr Phe Gly Pro Gly Thr Arg Leu
            115                 120                 125

Thr Val Thr Glu Asp Leu Lys Asn Val Phe Pro Pro Glu Val Ala Val
        130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
        210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
        290                 295                 300

Arg Lys Asp Ser Arg Gly
305                 310

<210> SEQ ID NO 35
<211> LENGTH: 271
<212> TYPE: PRT
<213> ORGANISM: Artificial Sequence
<220> FEATURE:
<223> OTHER INFORMATION: R26P1A9 alpha chain

<400> SEQUENCE: 35

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Leu Ile Gly
            100                 105                 110

Ala Ser Gly Ser Arg Leu Thr Phe Gly Glu Gly Thr Gln Leu Thr Val
```

```
                115                 120                 125
Asn Pro Asp Ile Gln Asn Pro Asp Pro Ala Val Tyr Gln Leu Arg Asp
            130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
                180                 185                 190

Val Ala Trp Ser Asn Lys Ser Asp Phe Ala Cys Ala Asn Ala Phe Asn
                195                 200                 205

Asn Ser Ile Ile Pro Glu Asp Thr Phe Phe Pro Ser Pro Glu Ser Ser
            210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
                260                 265                 270

<210> SEQ ID NO 36
<211> LENGTH: 310
<212> TYPE: PRT
<213> ORGANISM: Artificial Sequence
<220> FEATURE:
<223> OTHER INFORMATION: R26P1A9 beta chain

<400> SEQUENCE: 36

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
            35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
                100                 105                 110

Ser Ser Tyr Phe Gly Trp Asn Glu Lys Leu Phe Phe Gly Ser Gly Thr
            115                 120                 125

Gln Leu Ser Val Leu Glu Asp Leu Asn Lys Val Phe Pro Pro Glu Val
            130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
```

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310

<210> SEQ ID NO 37
<211> LENGTH: 276
<212> TYPE: PRT
<213> ORGANISM: Artificial Sequence
<220> FEATURE:
<223> OTHER INFORMATION: R26P2A6 alpha chain

<400> SEQUENCE: 37

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65              70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Asp Val Ser Gly Gly Tyr Asn Lys Leu Ile Phe Gly Ala Gly
        115                 120                 125

Thr Arg Leu Ala Val His Pro Tyr Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg

Leu Trp Ser Ser
        275

<210> SEQ ID NO 38
<211> LENGTH: 311
<212> TYPE: PRT
<213> ORGANISM: Artificial Sequence
<220> FEATURE:
<223> OTHER INFORMATION: R26P2A6 beta chain

<400> SEQUENCE: 38

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Thr Thr Pro Asp Gly Thr Asp Glu Gln Phe Phe Gly Pro Gly Thr Arg
        115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 39
<211> LENGTH: 274
<212> TYPE: PRT

<213> ORGANISM: Artificial Sequence
<220> FEATURE:
<223> OTHER INFORMATION: R26P3H1 alpha chain

<400> SEQUENCE: 39

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Met Asn Arg Asp Asp Lys Ile Ile Phe Gly Lys Gly Thr Arg
        115                 120                 125

Leu His Ile Leu Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 40
<211> LENGTH: 310
<212> TYPE: PRT
<213> ORGANISM: Artificial Sequence
<220> FEATURE:
<223> OTHER INFORMATION: R26P3H1 beta chain

<400> SEQUENCE: 40

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu

```
                 50                  55                  60
Ile Tyr Tyr Ser Gln Ile Val Asn Asp Phe Gln Lys Gly Asp Ile Ala
 65                  70                  75                  80

Glu Gly Tyr Ser Val Ser Arg Glu Lys Lys Glu Ser Phe Pro Leu Thr
                 85                  90                  95

Val Thr Ser Ala Gln Lys Asn Pro Thr Ala Phe Tyr Leu Cys Ala Ser
                100                 105                 110

Ser Arg Ala Glu Gly Gly Glu Gln Tyr Phe Gly Pro Gly Thr Arg Leu
                115                 120                 125

Thr Val Thr Glu Asp Leu Lys Asn Val Phe Pro Pro Glu Val Ala Val
                130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
                195                 200                 205

Ser Arg Leu Arg Val Ser Ala Thr Phe Trp Gln Asn Pro Arg Asn His
                210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
                275                 280                 285

Leu Tyr Ala Val Leu Val Ser Ala Leu Val Leu Met Ala Met Val Lys
                290                 295                 300

Arg Lys Asp Ser Arg Gly
305                 310

<210> SEQ ID NO 41
<211> LENGTH: 273
<212> TYPE: PRT
<213> ORGANISM: Artificial Sequence
<220> FEATURE:
<223> OTHER INFORMATION: R35P3A4 alpha chain

<400> SEQUENCE: 41

Met Thr Ser Ile Arg Ala Val Phe Ile Phe Leu Trp Leu Gln Leu Asp
 1               5                  10                  15

Leu Val Asn Gly Glu Asn Val Glu Gln His Pro Ser Thr Leu Ser Val
                 20                  25                  30

Gln Glu Gly Asp Ser Ala Val Ile Lys Cys Thr Tyr Ser Asp Ser Ala
                 35                  40                  45

Ser Asn Tyr Phe Pro Trp Tyr Lys Gln Glu Leu Gly Lys Arg Pro Gln
                 50                  55                  60

Leu Ile Ile Asp Ile Arg Ser Asn Val Gly Glu Lys Lys Asp Gln Arg
 65                  70                  75                  80

Ile Ala Val Thr Leu Asn Lys Thr Ala Lys His Phe Ser Leu His Ile
                 85                  90                  95

Thr Glu Thr Gln Pro Glu Asp Ser Ala Val Tyr Phe Cys Ala Ala Ser
```

```
            100                 105                 110
Pro Thr Gly Gly Tyr Asn Lys Leu Ile Phe Gly Ala Gly Thr Arg Leu
            115                 120                 125

Ala Val His Pro Tyr Ile Gln Asn Pro Asp Pro Ala Val Tyr Gln Leu
            130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
            165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
            210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
            245                 250                 255

Leu Lys Val Ala Gly Phe Asn Leu Leu Met Thr Leu Arg Leu Trp Ser
            260                 265                 270

Ser

<210> SEQ ID NO 42
<211> LENGTH: 311
<212> TYPE: PRT
<213> ORGANISM: Artificial Sequence
<220> FEATURE:
<223> OTHER INFORMATION: R35P3A4 beta chain

<400> SEQUENCE: 42

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
            50                  55                  60

Ile His Tyr Ser Val Gly Ala Gly Ile Thr Asp Gln Gly Glu Val Pro
65              70                  75                  80

Asn Gly Tyr Asn Val Ser Arg Ser Thr Thr Glu Asp Phe Pro Leu Arg
            85                  90                  95

Leu Leu Ser Ala Ala Pro Ser Gln Thr Ser Val Tyr Phe Cys Ala Ser
            100                 105                 110

Ser Leu Gly Gly Ala Ser Gln Glu Gln Tyr Phe Gly Pro Gly Thr Arg
            115                 120                 125

Leu Thr Val Thr Glu Asp Leu Lys Asn Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
            165                 170                 175

Trp Trp Val Asn Gly Lys Glu Val His Ser Gly Val Ser Thr Asp Pro
            180                 185                 190
```

-continued

```
Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
                275                 280                 285

Thr Leu Tyr Ala Val Leu Val Ser Ala Leu Val Leu Met Ala Met Val
                290                 295                 300

Lys Arg Lys Asp Ser Arg Gly
305                 310

<210> SEQ ID NO 43
<211> LENGTH: 266
<212> TYPE: PRT
<213> ORGANISM: Artificial Sequence
<220> FEATURE:
<223> OTHER INFORMATION: R37P1C9 alpha chain

<400> SEQUENCE: 43

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
                20                  25                  30

Glu Pro Val His Leu Pro Cys Asn His Ser Thr Ile Ser Gly Thr Asp
            35                  40                  45

Tyr Ile His Trp Tyr Arg Gln Leu Pro Ser Gln Gly Pro Glu Tyr Val
    50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
                85                  90                  95

Leu Arg Asp Ala Ala Val Tyr Tyr Cys Ile Leu Phe Asn Phe Asn Lys
            100                 105                 110

Phe Tyr Phe Gly Ser Gly Thr Lys Leu Asn Val Lys Pro Asn Ile Gln
        115                 120                 125

Asn Pro Asp Pro Ala Val Tyr Gln Leu Arg Asp Ser Lys Ser Ser Asp
    130                 135                 140

Lys Ser Val Cys Leu Phe Thr Asp Phe Asp Ser Gln Thr Asn Val Ser
145                 150                 155                 160

Gln Ser Lys Asp Ser Asp Val Tyr Ile Thr Asp Lys Thr Val Leu Asp
                165                 170                 175

Met Arg Ser Met Asp Phe Lys Ser Asn Ser Ala Val Ala Trp Ser Asn
            180                 185                 190

Lys Ser Asp Phe Ala Cys Ala Asn Ala Phe Asn Asn Ser Ile Ile Pro
        195                 200                 205

Glu Asp Thr Phe Phe Pro Ser Pro Glu Ser Ser Cys Asp Val Lys Leu
    210                 215                 220

Val Glu Lys Ser Phe Glu Thr Asp Thr Asn Leu Asn Phe Gln Asn Leu
225                 230                 235                 240
```

```
Ser Val Ile Gly Phe Arg Ile Leu Leu Lys Val Ala Gly Phe Asn
                245                 250                 255

Leu Leu Met Thr Leu Arg Leu Trp Ser Ser
            260                 265

<210> SEQ ID NO 44
<211> LENGTH: 309
<212> TYPE: PRT
<213> ORGANISM: Artificial Sequence
<220> FEATURE:
<223> OTHER INFORMATION: R37P1C9 beta chain

<400> SEQUENCE: 44

Met Gly Pro Gly Leu Leu His Trp Met Ala Leu Cys Leu Leu Gly Thr
1               5                   10                  15

Gly His Gly Asp Ala Met Val Ile Gln Asn Pro Arg Tyr Gln Val Thr
            20                  25                  30

Gln Phe Gly Lys Pro Val Thr Leu Ser Cys Ser Gln Thr Leu Asn His
        35                  40                  45

Asn Val Met Tyr Trp Tyr Gln Gln Lys Ser Ser Gln Ala Pro Lys Leu
    50                  55                  60

Leu Phe His Tyr Tyr Asp Lys Asp Phe Asn Asn Glu Ala Asp Thr Pro
65                  70                  75                  80

Asp Asn Phe Gln Ser Arg Arg Pro Asn Thr Ser Phe Cys Phe Leu Asp
                85                  90                  95

Ile Arg Ser Pro Gly Leu Gly Asp Ala Ala Met Tyr Leu Cys Ala Thr
            100                 105                 110

Ser Ser Gly Glu Thr Asn Glu Lys Leu Phe Phe Gly Ser Gly Thr Gln
        115                 120                 125

Leu Ser Val Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 45
```

-continued

```
<211> LENGTH: 277
<212> TYPE: PRT
<213> ORGANISM: Artificial Sequence
<220> FEATURE:
<223> OTHER INFORMATION: R37P1H1 alpha chain

<400> SEQUENCE: 45

Met Thr Arg Val Ser Leu Leu Trp Ala Val Val Ser Thr Cys Leu
1               5                   10                  15

Glu Ser Gly Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Ser Asn Tyr Tyr Leu Phe Trp Tyr Lys Gln Pro Pro Ser Arg Gln
        50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Phe Gly Tyr Ser Gly Gly Ala Asp Gly Leu Thr Phe Gly Lys
        115                 120                 125

Gly Thr His Leu Ile Ile Gln Pro Tyr Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 46
<211> LENGTH: 311
<212> TYPE: PRT
<213> ORGANISM: Artificial Sequence
<220> FEATURE:
<223> OTHER INFORMATION: R37P1H1 beta chain

<400> SEQUENCE: 46

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
                20                  25                  30

Thr Arg Gly Gln Gln Val Thr Leu Arg Cys Ser Pro Lys Ser Gly His
```

```
                35                  40                  45
Asp Thr Val Ser Trp Tyr Gln Gln Ala Leu Gly Gln Gly Pro Gln Phe
 50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Glu Leu Asn
                85                  90                  95

Val Asn Ala Leu Leu Leu Gly Asp Ser Ala Leu Tyr Leu Cys Ala Ser
            100                 105                 110

Ser Asn Glu Gly Gln Gly Trp Glu Ala Glu Ala Phe Phe Gly Gln Gly
        115                 120                 125

Thr Arg Leu Thr Val Val Glu Asp Leu Asn Lys Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Phe
305                 310

<210> SEQ ID NO 47
<211> LENGTH: 268
<212> TYPE: PRT
<213> ORGANISM: Artificial Sequence
<220> FEATURE:
<223> OTHER INFORMATION: R42P3A9 alpha chain

<400> SEQUENCE: 47

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

Leu Gln Glu Gly Ala Asn Ser Thr Leu Arg Cys Asn Phe Ser Asp Ser
        35                  40                  45

Val Asn Asn Leu Gln Trp Phe His Gln Asn Pro Trp Gly Gln Leu Ile
    50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
```

```
            85                  90                  95
Ser Gln Thr Thr Asp Ser Gly Val Tyr Phe Cys Ala Val His Asn Phe
            100                 105                 110

Asn Lys Phe Tyr Phe Gly Ser Gly Thr Lys Leu Asn Val Lys Pro Asn
            115                 120                 125

Ile Gln Asn Pro Asp Pro Ala Val Tyr Gln Leu Arg Asp Ser Lys Ser
            130                 135                 140

Ser Asp Lys Ser Val Cys Leu Phe Thr Asp Phe Asp Ser Gln Thr Asn
145                 150                 155                 160

Val Ser Gln Ser Lys Asp Ser Asp Val Tyr Ile Thr Asp Lys Thr Val
            165                 170                 175

Leu Asp Met Arg Ser Met Asp Phe Lys Ser Asn Ser Ala Val Ala Trp
            180                 185                 190

Ser Asn Lys Ser Asp Phe Ala Cys Ala Asn Ala Phe Asn Asn Ser Ile
            195                 200                 205

Ile Pro Glu Asp Thr Phe Phe Pro Ser Pro Glu Ser Ser Cys Asp Val
            210                 215                 220

Lys Leu Val Glu Lys Ser Phe Glu Thr Asp Thr Asn Leu Asn Phe Gln
225                 230                 235                 240

Asn Leu Ser Val Ile Gly Phe Arg Ile Leu Leu Leu Lys Val Ala Gly
            245                 250                 255

Phe Asn Leu Leu Met Thr Leu Arg Leu Trp Ser Ser
            260                 265
```

<210> SEQ ID NO 48
<211> LENGTH: 322
<212> TYPE: PRT
<213> ORGANISM: Artificial Sequence
<220> FEATURE:
<223> OTHER INFORMATION: R42P3A9 beta chain

<400> SEQUENCE: 48

```
Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
            50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
            85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Leu Gly Gln Gly
            115                 120                 125

Tyr Asn Glu Gln Phe Phe Gly Pro Gly Thr Arg Leu Thr Val Leu Glu
            130                 135                 140

Asp Leu Lys Asn Val Phe Pro Pro Glu Val Ala Val Phe Glu Pro Ser
145                 150                 155                 160

Glu Ala Glu Ile Ser His Thr Gln Lys Ala Thr Leu Val Cys Leu Ala
            165                 170                 175

Thr Gly Phe Tyr Pro Asp His Val Glu Leu Ser Trp Trp Val Asn Gly
```

```
                180                 185                 190
Lys Glu Val His Ser Gly Val Ser Thr Asp Pro Gln Pro Leu Lys Glu
            195                 200                 205

Gln Pro Ala Leu Asn Asp Ser Arg Tyr Cys Leu Ser Arg Leu Arg
        210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg
            245                 250                 255

Ala Lys Pro Val Thr Gln Ile Val Ser Ala Glu Ala Trp Gly Arg Ala
        260                 265                 270

Asp Cys Gly Phe Thr Ser Glu Ser Tyr Gln Gln Gly Val Leu Ser Ala
            275                 280                 285

Thr Ile Leu Tyr Glu Ile Leu Leu Gly Lys Ala Thr Leu Tyr Ala Val
        290                 295                 300

Leu Val Ser Ala Leu Val Leu Met Ala Met Val Lys Arg Lys Asp Ser
305                 310                 315                 320

Arg Gly

<210> SEQ ID NO 49
<211> LENGTH: 276
<212> TYPE: PRT
<213> ORGANISM: Artificial Sequence
<220> FEATURE:
<223> OTHER INFORMATION: R43P3F2 alpha chain

<400> SEQUENCE: 49

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
            85                  90                  95

Phe Thr Ile Thr Ala Ser Gln Val Val Asp Ser Ala Val Tyr Phe Cys
        100                 105                 110

Ala Leu Ser Asn Asn Asn Ala Gly Asn Met Leu Thr Phe Gly Gly Gly
            115                 120                 125

Thr Arg Leu Met Val Lys Pro His Ile Gln Asn Pro Asp Pro Ala Val
        130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
            165                 170                 175

Val Tyr Ile Thr Asp Lys Thr Val Leu Asp Met Arg Ser Met Asp Phe
        180                 185                 190

Lys Ser Asn Ser Ala Val Ala Trp Ser Asn Lys Ser Asp Phe Ala Cys
            195                 200                 205

Ala Asn Ala Phe Asn Asn Ser Ile Ile Pro Glu Asp Thr Phe Phe Pro
        210                 215                 220
```

```
Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
            245                 250                 255

Ile Leu Leu Leu Lys Val Ala Gly Phe Asn Leu Leu Met Thr Leu Arg
        260                 265                 270

Leu Trp Ser Ser
        275

<210> SEQ ID NO 50
<211> LENGTH: 323
<212> TYPE: PRT
<213> ORGANISM: Artificial Sequence
<220> FEATURE:
<223> OTHER INFORMATION: R43P3F2 beta chain

<400> SEQUENCE: 50

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
            85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Pro Thr Gly Thr Ser
        115                 120                 125

Gly Tyr Asn Glu Gln Phe Phe Gly Pro Gly Thr Arg Leu Thr Val Leu
    130                 135                 140

Glu Asp Leu Lys Asn Val Phe Pro Pro Glu Val Ala Val Phe Glu Pro
145                 150                 155                 160

Ser Glu Ala Glu Ile Ser His Thr Gln Lys Ala Thr Leu Val Cys Leu
                165                 170                 175

Ala Thr Gly Phe Tyr Pro Asp His Val Glu Leu Ser Trp Trp Val Asn
            180                 185                 190

Gly Lys Glu Val His Ser Gly Val Ser Thr Asp Pro Gln Pro Leu Lys
        195                 200                 205

Glu Gln Pro Ala Leu Asn Asp Ser Arg Tyr Cys Leu Ser Ser Arg Leu
    210                 215                 220

Arg Val Ser Ala Thr Phe Trp Gln Asn Pro Arg Asn His Phe Arg Cys
225                 230                 235                 240

Gln Val Gln Phe Tyr Gly Leu Ser Glu Asn Asp Glu Trp Thr Gln Asp
            245                 250                 255

Arg Ala Lys Pro Val Thr Gln Ile Val Ser Ala Glu Ala Trp Gly Arg
        260                 265                 270

Ala Asp Cys Gly Phe Thr Ser Glu Ser Tyr Gln Gln Gly Val Leu Ser
    275                 280                 285

Ala Thr Ile Leu Tyr Glu Ile Leu Leu Gly Lys Ala Thr Leu Tyr Ala
    290                 295                 300
```

Val Leu Val Ser Ala Leu Val Leu Met Ala Met Val Lys Arg Lys Asp
305                 310                 315                 320

Ser Arg Gly

<210> SEQ ID NO 51
<211> LENGTH: 273
<212> TYPE: PRT
<213> ORGANISM: Artificial Sequence
<220> FEATURE:
<223> OTHER INFORMATION: R43P3G5 alpha chain

<400> SEQUENCE: 51

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
                20                  25                  30

Leu His Val Gln Glu Gly Asp Ser Thr Asn Phe Thr Cys Ser Phe Pro
            35                  40                  45

Ser Ser Asn Phe Tyr Ala Leu His Trp Tyr Arg Trp Glu Thr Ala Lys
    50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Leu Asn Arg Asp Asp Lys Ile Ile Phe Gly Lys Gly Thr Arg Leu
        115                 120                 125

His Ile Leu Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 52
<211> LENGTH: 311
<212> TYPE: PRT
<213> ORGANISM: Artificial Sequence
<220> FEATURE:
<223> OTHER INFORMATION: R43P3G5 beta chain

<400> SEQUENCE: 52

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
50                  55                  60

Ile Tyr Phe Ser Tyr Asp Val Lys Met Lys Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
                100                 105                 110

Arg Leu Pro Ser Arg Thr Tyr Glu Gln Tyr Phe Gly Pro Gly Thr Arg
            115                 120                 125

Leu Thr Val Thr Glu Asp Leu Lys Asn Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Ser Arg Gly
305                 310

<210> SEQ ID NO 53
<211> LENGTH: 270
<212> TYPE: PRT
<213> ORGANISM: Artificial Sequence
<220> FEATURE:
<223> OTHER INFORMATION: R59P2E7 alpha chain

<400> SEQUENCE: 53

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

```
Ile Tyr Asn Leu Gln Trp Phe Arg Gln Asp Pro Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Asn
            100                 105                 110

Ser Asp Tyr Lys Leu Ser Phe Gly Ala Gly Thr Thr Val Thr Val Arg
        115                 120                 125

Ala Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 54
<211> LENGTH: 321
<212> TYPE: PRT
<213> ORGANISM: Artificial Sequence
<220> FEATURE:
<223> OTHER INFORMATION: R59P2E7 beta chain

<400> SEQUENCE: 54

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
                20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Gly Leu Gly Thr
        115                 120                 125

Gly Asp Tyr Gly Tyr Thr Phe Gly Ser Gly Thr Arg Leu Thr Val Val
    130                 135                 140
```

Glu Asp Leu Asn Lys Val Phe Pro Pro Glu Val Ala Val Phe Glu Pro
145                 150                 155                 160

Ser Glu Ala Glu Ile Ser His Thr Gln Lys Ala Thr Leu Val Cys Leu
            165                 170                 175

Ala Thr Gly Phe Phe Pro Asp His Val Glu Leu Ser Trp Trp Val Asn
            180                 185                 190

Gly Lys Glu Val His Ser Gly Val Ser Thr Asp Pro Gln Pro Leu Lys
            195                 200                 205

Glu Gln Pro Ala Leu Asn Asp Ser Arg Tyr Cys Leu Ser Ser Arg Leu
        210                 215                 220

Arg Val Ser Ala Thr Phe Trp Gln Asn Pro Arg Asn His Phe Arg Cys
225                 230                 235                 240

Gln Val Gln Phe Tyr Gly Leu Ser Glu Asn Asp Glu Trp Thr Gln Asp
                245                 250                 255

Arg Ala Lys Pro Val Thr Gln Ile Val Ser Ala Glu Ala Trp Gly Arg
            260                 265                 270

Ala Asp Cys Gly Phe Thr Ser Val Ser Tyr Gln Gln Gly Val Leu Ser
            275                 280                 285

Ala Thr Ile Leu Tyr Glu Ile Leu Leu Gly Lys Ala Thr Leu Tyr Ala
            290                 295                 300

Val Leu Val Ser Ala Leu Val Leu Met Ala Met Val Lys Arg Lys Asp
305                 310                 315                 320

Phe

<210> SEQ ID NO 55
<211> LENGTH: 273
<212> TYPE: PRT
<213> ORGANISM: Artificial Sequence
<220> FEATURE:
<223> OTHER INFORMATION: R11P3D3 alpha chain

<400> SEQUENCE: 55

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
            20                  25                  30

Leu His Val Gln Glu Gly Asp Ser Thr Asn Phe Thr Cys Ser Phe Pro
        35                  40                  45

Ser Ser Asn Phe Tyr Ala Leu His Trp Tyr Arg Trp Glu Thr Ala Lys
    50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Leu Tyr Asn Asn Asn Asp Met Arg Phe Gly Ala Gly Thr Arg Leu
        115                 120                 125

Thr Val Lys Pro Asn Ile Gln Asn Pro Asp Pro Ala Val Tyr Gln Leu
130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn

```
                180              185                 190
Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
            210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
            245                 250                 255

Leu Lys Val Ala Gly Phe Asn Leu Leu Met Thr Leu Arg Leu Trp Ser
            260                 265                 270

Ser

<210> SEQ ID NO 56
<211> LENGTH: 311
<212> TYPE: PRT
<213> ORGANISM: Artificial Sequence
<220> FEATURE:
<223> OTHER INFORMATION: R11P3D3 beta chain

<400> SEQUENCE: 56

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
            35                  40                  45

Asn Ser Leu Phe Trp Tyr Arg Gln Thr Met Met Arg Gly Leu Glu Leu
50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
            85                  90                  95

Lys Ile Gln Pro Ser Glu Pro Arg Asp Ser Ala Val Tyr Phe Cys Ala
            100                 105                 110

Ser Ser Pro Gly Ser Thr Asp Thr Gln Tyr Phe Gly Pro Gly Thr Arg
            115                 120                 125

Leu Thr Val Leu Glu Asp Leu Lys Asn Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
            165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
            210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Glu Ser Tyr Gln Gln
            260                 265                 270
```

```
Gly Val Leu Ser Ala Thr Leu Tyr Glu Ile Leu Leu Gly Lys Ala
            275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 57
<211> LENGTH: 275
<212> TYPE: PRT
<213> ORGANISM: Artificial Sequence
<220> FEATURE:
<223> OTHER INFORMATION: R16P1C10 alpha chain

<400> SEQUENCE: 57

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ala
            100                 105                 110

Val Ile Ser Asn Phe Gly Asn Glu Lys Leu Thr Phe Gly Thr Gly Thr
        115                 120                 125

Arg Leu Thr Ile Ile Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 58
<211> LENGTH: 311
<212> TYPE: PRT
<213> ORGANISM: Artificial Sequence
```

<220> FEATURE:
<223> OTHER INFORMATION: R16P1C10 beta chain

<400> SEQUENCE: 58

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Pro Trp Asp Ser Pro Asn Glu Gln Tyr Phe Gly Pro Gly Thr Arg
        115                 120                 125

Leu Thr Val Thr Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 59
<211> LENGTH: 274
<212> TYPE: PRT
<213> ORGANISM: Artificial Sequence
<220> FEATURE:
<223> OTHER INFORMATION: R16P1E8 alpha chain

<400> SEQUENCE: 59

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro

```
                    20                  25                  30
Leu Ser Val Pro Glu Gly Ala Ile Val Ser Leu Asn Cys Thr Tyr Ser
                35                  40                  45

Asn Ser Ala Phe Gln Tyr Phe Met Trp Tyr Arg Gln Tyr Ser Arg Lys
            50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Glu Ala Ala Gly Asn Lys Leu Thr Phe Gly Gly Gly Thr Arg
            115                 120                 125

Val Leu Val Lys Pro Asn Ile Gln Asn Pro Asp Pro Ala Val Tyr Gln
        130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
        210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 60
<211> LENGTH: 309
<212> TYPE: PRT
<213> ORGANISM: Artificial Sequence
<220> FEATURE:
<223> OTHER INFORMATION: R16P1E8 beta chain

<400> SEQUENCE: 60

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110
```

Ser Ser Tyr Thr Asn Gln Gly Glu Ala Phe Phe Gly Gln Gly Thr Arg
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 61
<211> LENGTH: 273
<212> TYPE: PRT
<213> ORGANISM: Artificial Sequence
<220> FEATURE:
<223> OTHER INFORMATION: R17P1A9 alpha chain

<400> SEQUENCE: 61

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Ser Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Leu Asn Gln Ala Gly Thr Ala Leu Ile Phe Gly Lys Gly Thr Thr Leu
        115                 120                 125

Ser Val Ser Ser Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

```
Asp Ser Gln Thr Asn Val Ser Gln Ser Lys Asp Ser Asp Val Tyr Ile
                165                 170                 175
Thr Asp Lys Thr Val Leu Asp Met Arg Ser Met Asp Phe Lys Ser Asn
            180                 185                 190
Ser Ala Val Ala Trp Ser Asn Lys Ser Asp Phe Ala Cys Ala Asn Ala
        195                 200                 205
Phe Asn Asn Ser Ile Ile Pro Glu Asp Thr Phe Phe Pro Ser Pro Glu
    210                 215                 220
Ser Ser Cys Asp Val Lys Leu Val Glu Lys Ser Phe Glu Thr Asp Thr
225                 230                 235                 240
Asn Leu Asn Phe Gln Asn Leu Ser Val Ile Gly Phe Arg Ile Leu Leu
                245                 250                 255
Leu Lys Val Ala Gly Phe Asn Leu Leu Met Thr Leu Arg Leu Trp Ser
            260                 265                 270
Ser

<210> SEQ ID NO 62
<211> LENGTH: 314
<212> TYPE: PRT
<213> ORGANISM: Artificial Sequence
<220> FEATURE:
<223> OTHER INFORMATION: R17P1A9 beta chain

<400> SEQUENCE: 62

Met Gly Phe Arg Leu Leu Cys Cys Val Ala Phe Cys Leu Leu Gly Ala
1               5                   10                  15
Gly Pro Val Asp Ser Gly Val Thr Gln Thr Pro Lys His Leu Ile Thr
            20                  25                  30
Ala Thr Gly Gln Arg Val Thr Leu Arg Cys Ser Pro Arg Ser Gly Asp
        35                  40                  45
Leu Ser Val Tyr Trp Tyr Gln Gln Ser Leu Asp Gln Gly Leu Gln Phe
    50                  55                  60
Leu Ile Gln Tyr Tyr Asn Gly Glu Glu Arg Ala Lys Gly Asn Ile Leu
65                  70                  75                  80
Glu Arg Phe Ser Ala Gln Gln Phe Pro Asp Leu His Ser Glu Leu Asn
                85                  90                  95
Leu Ser Ser Leu Glu Leu Gly Asp Ser Ala Leu Tyr Phe Cys Ala Ser
            100                 105                 110
Ser Ala Glu Thr Gly Pro Trp Leu Gly Asn Glu Gln Phe Phe Gly Pro
        115                 120                 125
Gly Thr Arg Leu Thr Val Leu Glu Asp Leu Lys Asn Val Phe Pro Pro
    130                 135                 140
Glu Val Ala Val Phe Glu Pro Ser Glu Ala Glu Ile Ser His Thr Gln
145                 150                 155                 160
Lys Ala Thr Leu Val Cys Leu Ala Thr Gly Phe Tyr Pro Asp His Val
                165                 170                 175
Glu Leu Ser Trp Trp Val Asn Gly Lys Glu Val His Ser Gly Val Ser
            180                 185                 190
Thr Asp Pro Gln Pro Leu Lys Glu Gln Pro Ala Leu Asn Asp Ser Arg
        195                 200                 205
Tyr Cys Leu Ser Ser Arg Leu Arg Val Ser Ala Thr Phe Trp Gln Asn
    210                 215                 220
Pro Arg Asn His Phe Arg Cys Gln Val Gln Phe Tyr Gly Leu Ser Glu
225                 230                 235                 240
```

```
Asn Asp Glu Trp Thr Gln Asp Arg Ala Lys Pro Val Thr Gln Ile Val
            245                 250                 255

Ser Ala Glu Ala Trp Gly Arg Ala Asp Cys Gly Phe Thr Ser Glu Ser
    260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

<210> SEQ ID NO 63
<211> LENGTH: 277
<212> TYPE: PRT
<213> ORGANISM: Artificial Sequence
<220> FEATURE:
<223> OTHER INFORMATION: R17P1D7 alpha chain

<400> SEQUENCE: 63

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Arg Trp Ala Gln Gly Gly Ser Glu Lys Leu Val Phe Gly Lys
        115                 120                 125

Gly Thr Lys Leu Thr Val Asn Pro Tyr Ile Gln Lys Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275
```

<210> SEQ ID NO 64
<211> LENGTH: 313
<212> TYPE: PRT
<213> ORGANISM: Artificial Sequence
<220> FEATURE:
<223> OTHER INFORMATION: R17P1D7 beta chain

<400> SEQUENCE: 64

| Met | Thr | Ile | Arg | Leu | Leu | Cys | Tyr | Met | Gly | Phe | Tyr | Phe | Leu | Gly | Ala |
|---|---|---|---|---|---|---|---|---|---|---|---|---|---|---|---|
| 1 | | | | 5 | | | | | 10 | | | | | 15 | |

| Gly | Leu | Met | Glu | Ala | Asp | Ile | Tyr | Gln | Thr | Pro | Arg | Tyr | Leu | Val | Ile |
| | | | 20 | | | | | 25 | | | | | 30 | | |

| Gly | Thr | Gly | Lys | Lys | Ile | Thr | Leu | Glu | Cys | Ser | Gln | Thr | Met | Gly | His |
| | | | 35 | | | | | 40 | | | | | 45 | | |

| Asp | Lys | Met | Tyr | Trp | Tyr | Gln | Gln | Asp | Pro | Gly | Met | Glu | Leu | His | Leu |
| | 50 | | | | | 55 | | | | | 60 | | | | |

| Ile | His | Tyr | Ser | Tyr | Gly | Val | Asn | Ser | Thr | Glu | Lys | Gly | Asp | Leu | Ser |
| 65 | | | | | 70 | | | | | 75 | | | | | 80 |

| Ser | Glu | Ser | Thr | Val | Ser | Arg | Ile | Arg | Thr | Glu | His | Phe | Pro | Leu | Thr |
| | | | | 85 | | | | | 90 | | | | | 95 | |

| Leu | Glu | Ser | Ala | Arg | Pro | Ser | His | Thr | Ser | Gln | Tyr | Leu | Cys | Ala | Thr |
| | | | 100 | | | | | 105 | | | | | 110 | | |

| Glu | Leu | Trp | Ser | Ser | Gly | Gly | Thr | Gly | Glu | Leu | Phe | Phe | Gly | Glu | Gly |
| | | | 115 | | | | | 120 | | | | | 125 | | |

| Ser | Arg | Leu | Thr | Val | Leu | Glu | Asp | Leu | Lys | Asn | Val | Phe | Pro | Pro | Glu |
| | 130 | | | | | 135 | | | | | 140 | | | | |

| Val | Ala | Val | Phe | Glu | Pro | Ser | Glu | Ala | Glu | Ile | Ser | His | Thr | Gln | Lys |
| 145 | | | | | 150 | | | | | 155 | | | | | 160 |

| Ala | Thr | Leu | Val | Cys | Leu | Ala | Thr | Gly | Phe | Tyr | Pro | Asp | His | Val | Glu |
| | | | | 165 | | | | | 170 | | | | | 175 | |

| Leu | Ser | Trp | Trp | Val | Asn | Gly | Lys | Glu | Val | His | Ser | Gly | Val | Ser | Thr |
| | | | 180 | | | | | 185 | | | | | 190 | | |

| Asp | Pro | Gln | Pro | Leu | Lys | Glu | Gln | Pro | Ala | Leu | Asn | Asp | Ser | Arg | Tyr |
| | | | 195 | | | | | 200 | | | | | 205 | | |

| Cys | Leu | Ser | Ser | Arg | Leu | Arg | Val | Ser | Ala | Thr | Phe | Trp | Gln | Asn | Pro |
| 210 | | | | | 215 | | | | | 220 | | | | | |

| Arg | Asn | His | Phe | Arg | Cys | Gln | Val | Gln | Phe | Tyr | Gly | Leu | Ser | Glu | Asn |
| 225 | | | | | 230 | | | | | 235 | | | | | 240 |

| Asp | Glu | Trp | Thr | Gln | Asp | Arg | Ala | Lys | Pro | Val | Thr | Gln | Ile | Val | Ser |
| | | | 245 | | | | | 250 | | | | | 255 | | |

| Ala | Glu | Ala | Trp | Gly | Arg | Ala | Asp | Cys | Gly | Phe | Thr | Ser | Glu | Ser | Tyr |
| | | | 260 | | | | | 265 | | | | | 270 | | |

| Gln | Gln | Gly | Val | Leu | Ser | Ala | Thr | Ile | Leu | Tyr | Glu | Ile | Leu | Leu | Gly |
| | | | 275 | | | | | 280 | | | | | 285 | | |

| Lys | Ala | Thr | Leu | Tyr | Ala | Val | Leu | Val | Ser | Ala | Leu | Val | Leu | Met | Ala |
| | | | 290 | | | | | 295 | | | | | 300 | | |

| Met | Val | Lys | Arg | Lys | Asp | Ser | Arg | Gly |
|---|---|---|---|---|---|---|---|---|
| 305 | | | | | 310 | | | |

<210> SEQ ID NO 65
<211> LENGTH: 206
<212> TYPE: PRT
<213> ORGANISM: Artificial Sequence
<220> FEATURE:
<223> OTHER INFORMATION: R17P1G3 alpha chain

<400> SEQUENCE: 65

```
Ile Met Ser Ile Tyr Ser Asn Gly Asp Lys Glu Asp Gly Arg Phe Thr
1               5                   10                  15

Ala Gln Leu Asn Lys Ala Ser Gln Tyr Val Ser Leu Leu Ile Arg Asp
            20                  25                  30

Ser Gln Pro Ser Asp Ser Ala Thr Tyr Leu Cys Ala Val Gly Pro Ser
        35                  40                  45

Gly Thr Tyr Lys Tyr Ile Phe Gly Thr Gly Thr Arg Leu Lys Val Leu
    50                  55                  60

Ala Asn Ile Gln Asn Pro Asp Pro Ala Val Tyr Gln Leu Arg Asp Ser
65                  70                  75                  80

Lys Ser Ser Asp Lys Ser Val Cys Leu Phe Thr Asp Phe Asp Ser Gln
                85                  90                  95

Thr Asn Val Ser Gln Ser Lys Asp Ser Asp Val Tyr Ile Thr Asp Lys
            100                 105                 110

Thr Val Leu Asp Met Arg Ser Met Asp Phe Lys Ser Asn Ser Ala Val
        115                 120                 125

Ala Trp Ser Asn Lys Ser Asp Phe Ala Cys Ala Asn Ala Phe Asn Asn
    130                 135                 140

Ser Ile Ile Pro Glu Asp Thr Phe Phe Pro Ser Pro Glu Ser Ser Cys
145                 150                 155                 160

Asp Val Lys Leu Val Glu Lys Ser Phe Glu Thr Asp Thr Asn Leu Asn
                165                 170                 175

Phe Gln Asn Leu Ser Val Ile Gly Phe Arg Ile Leu Leu Leu Lys Val
            180                 185                 190

Ala Gly Phe Asn Leu Leu Met Thr Leu Arg Leu Trp Ser Ser
        195                 200                 205

<210> SEQ ID NO 66
<211> LENGTH: 311
<212> TYPE: PRT
<213> ORGANISM: Artificial Sequence
<220> FEATURE:
<223> OTHER INFORMATION: R17P1G3 beta chain

<400> SEQUENCE: 66

Met Gly Pro Gln Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Pro Gly Gly Ser Gly Asn Glu Gln Phe Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160
```

-continued

```
Leu Val Cys Leu Ala Thr Gly Phe Tyr Pro Asp His Val Glu Leu Ser
                165                 170                 175
Trp Trp Val Asn Gly Lys Glu Val His Ser Gly Val Ser Thr Asp Pro
            180                 185                 190
Gln Pro Leu Lys Glu Gln Pro Ala Leu Asn Asp Ser Arg Tyr Cys Leu
        195                 200                 205
Ser Ser Arg Leu Arg Val Ser Ala Thr Phe Trp Gln Asn Pro Arg Asn
    210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Glu Ser Tyr Gln Gln
            260                 265                 270
Gly Val Leu Ser Ala Thr Ile Leu Tyr Glu Ile Leu Leu Gly Lys Ala
        275                 280                 285
Thr Leu Tyr Ala Val Leu Val Ser Ala Leu Val Leu Met Ala Met Val
    290                 295                 300
Lys Arg Lys Asp Ser Arg Gly
305                 310
```

<210> SEQ ID NO 67
<211> LENGTH: 274
<212> TYPE: PRT
<213> ORGANISM: Artificial Sequence
<220> FEATURE:
<223> OTHER INFORMATION: R17P2B6 alpha chain

<400> SEQUENCE: 67

```
Met Lys Ser Leu Arg Val Leu Leu Val Ile Leu Trp Leu Gln Leu Ser
1               5                   10                  15
Trp Val Trp Ser Gln Gln Lys Glu Val Glu Gln Asn Ser Gly Pro Leu
            20                  25                  30
Ser Val Pro Glu Gly Ala Ile Ala Ser Leu Asn Cys Thr Tyr Ser Asp
        35                  40                  45
Arg Gly Ser Gln Ser Phe Phe Trp Tyr Arg Gln Tyr Ser Gly Lys Ser
    50                  55                  60
Pro Glu Leu Ile Met Phe Ile Tyr Ser Asn Gly Asp Lys Glu Asp Gly
65                  70                  75                  80
Arg Phe Thr Ala Gln Leu Asn Lys Ala Ser Gln Tyr Val Ser Leu Leu
                85                  90                  95
Ile Arg Asp Ser Gln Pro Ser Asp Ser Ala Thr Tyr Leu Cys Ala Val
            100                 105                 110
Val Ser Gly Gly Gly Ala Asp Gly Leu Thr Phe Gly Lys Gly Thr His
        115                 120                 125
Leu Ile Ile Gln Pro Tyr Ile Gln Lys Pro Asp Pro Ala Val Tyr Gln
    130                 135                 140
Leu Arg Asp Ser Lys Ser Ser Asp Lys Ser Val Cys Leu Phe Thr Asp
145                 150                 155                 160
Phe Asp Ser Gln Thr Asn Val Ser Gln Ser Lys Asp Ser Asp Val Tyr
                165                 170                 175
Ile Thr Asp Lys Thr Val Leu Asp Met Arg Ser Met Asp Phe Lys Ser
            180                 185                 190
Asn Ser Ala Val Ala Trp Ser Asn Lys Ser Asp Phe Ala Cys Ala Asn
        195                 200                 205
```

```
Ala Phe Asn Asn Ser Ile Ile Pro Glu Asp Thr Phe Phe Pro Ser Pro
        210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
            245                 250                 255

Leu Leu Lys Val Ala Gly Phe Asn Leu Leu Met Thr Leu Arg Leu Trp
        260                 265                 270

Ser Ser

<210> SEQ ID NO 68
<211> LENGTH: 319
<212> TYPE: PRT
<213> ORGANISM: Artificial Sequence
<220> FEATURE:
<223> OTHER INFORMATION: R17P2B6 beta chain

<400> SEQUENCE: 68

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Gly Arg Gly Gly
        115                 120                 125

Gln Pro Gln His Phe Gly Asp Gly Thr Arg Leu Ser Ile Leu Glu Asp
    130                 135                 140

Leu Asn Lys Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
                165                 170                 175

Gly Phe Phe Pro Asp His Val Glu Leu Ser Trp Trp Val Asn Gly Lys
            180                 185                 190

Glu Val His Ser Gly Val Ser Thr Asp Pro Gln Pro Leu Lys Glu Gln
        195                 200                 205

Pro Ala Leu Asn Asp Ser Arg Tyr Cys Leu Ser Ser Arg Leu Arg Val
    210                 215                 220

Ser Ala Thr Phe Trp Gln Asn Pro Arg Asn His Phe Arg Cys Gln Val
225                 230                 235                 240

Gln Phe Tyr Gly Leu Ser Glu Asn Asp Glu Trp Thr Gln Asp Arg Ala
                245                 250                 255

Lys Pro Val Thr Gln Ile Val Ser Ala Glu Ala Trp Gly Arg Ala Asp
            260                 265                 270

Cys Gly Phe Thr Ser Val Ser Tyr Gln Gln Gly Val Leu Ser Ala Thr
        275                 280                 285
```

```
Ile Leu Tyr Glu Ile Leu Gly Lys Ala Thr Leu Tyr Ala Val Leu
    290                 295                 300

Val Ser Ala Leu Val Leu Met Ala Met Val Lys Arg Lys Asp Phe
305                 310                 315
```

<210> SEQ ID NO 69
<211> LENGTH: 273
<212> TYPE: PRT
<213> ORGANISM: Artificial Sequence
<220> FEATURE:
<223> OTHER INFORMATION: R11P3D3KE alpha chain

<400> SEQUENCE: 69

```
Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
                20                  25                  30

Leu His Val Gln Glu Gly Asp Ser Thr Asn Phe Thr Cys Ser Phe Pro
            35                  40                  45

Ser Ser Asn Phe Tyr Ala Leu His Trp Tyr Arg Lys Glu Thr Ala Lys
    50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Leu Tyr Asn Asn Asn Asp Met Arg Phe Gly Ala Gly Thr Arg Leu
        115                 120                 125

Thr Val Lys Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser
```

<210> SEQ ID NO 70
<211> LENGTH: 243
<212> TYPE: PRT
<213> ORGANISM: Artificial Sequence
<220> FEATURE:
<223> OTHER INFORMATION: R11P3D3KE beta chain

<400> SEQUENCE: 70

```
Asn Asn Asn Val Pro Ile Asp Asp Ser Gly Met Pro Glu Asp Arg Phe
1               5                   10                  15

Ser Ala Lys Met Pro Asn Ala Ser Phe Ser Thr Leu Lys Ile Gln Pro
            20                  25                  30

Ser Glu Pro Arg Asp Ser Ala Val Tyr Phe Cys Ala Ser Ser Pro Gly
        35                  40                  45

Ser Thr Asp Thr Gln Tyr Phe Gly Pro Gly Thr Arg Leu Thr Val Leu
    50                  55                  60

Glu Asp Leu Lys Asn Val Phe Pro Pro Glu Val Ala Val Phe Glu Pro
65                  70                  75                  80

Ser Glu Ala Glu Ile Ser His Thr Gln Lys Ala Thr Leu Val Cys Leu
                85                  90                  95

Ala Thr Gly Phe Tyr Pro Asp His Val Glu Leu Ser Trp Trp Val Asn
                100                 105                 110

Gly Lys Glu Val His Ser Gly Val Ser Thr Asp Pro Gln Pro Leu Lys
            115                 120                 125

Glu Gln Pro Ala Leu Asn Asp Ser Arg Tyr Cys Leu Ser Ser Arg Leu
        130                 135                 140

Arg Val Ser Ala Thr Phe Trp Gln Asn Pro Arg Asn His Phe Arg Cys
145                 150                 155                 160

Gln Val Gln Phe Tyr Gly Leu Ser Glu Asn Asp Glu Trp Thr Gln Asp
                165                 170                 175

Arg Ala Lys Pro Val Thr Gln Ile Val Ser Ala Glu Ala Trp Gly Arg
            180                 185                 190

Ala Asp Cys Gly Phe Thr Ser Glu Ser Tyr Gln Gln Gly Val Leu Ser
        195                 200                 205

Ala Thr Leu Leu Tyr Glu Ile Leu Leu Gly Lys Ala Thr Leu Tyr Ala
    210                 215                 220

Val Leu Val Ser Ala Leu Val Leu Met Ala Met Val Lys Arg Lys Asp
225                 230                 235                 240

Ser Arg Gly

<210> SEQ ID NO 71
<211> LENGTH: 223
<212> TYPE: PRT
<213> ORGANISM: Artificial Sequence
<220> FEATURE:
<223> OTHER INFORMATION: R39P1C12 alpha chain

<400> SEQUENCE: 71

Thr Tyr Leu Tyr Trp Tyr Lys Gln Glu Pro Gly Ala Gly Leu Gln Leu
1               5                   10                  15

Leu Thr Tyr Ile Phe Ser Asn Met Asp Met Lys Gln Asp Gln Arg Leu
            20                  25                  30

Thr Val Leu Leu Asn Lys Lys Asp Lys His Leu Ser Leu Arg Ile Ala
        35                  40                  45

Asp Thr Gln Thr Gly Asp Ser Ala Ile Tyr Phe Cys Ala Glu Ile Asp
    50                  55                  60

Asn Gln Gly Gly Lys Leu Ile Phe Gly Gln Gly Thr Glu Leu Ser Val
65                  70                  75                  80

Lys Pro Asn Ile Gln Asn Pro Asp Pro Ala Val Tyr Gln Leu Arg Asp
                85                  90                  95

Ser Lys Ser Ser Asp Lys Ser Val Cys Leu Phe Thr Asp Phe Asp Ser
            100                 105                 110

Gln Thr Asn Val Ser Gln Ser Lys Asp Ser Asp Val Tyr Ile Thr Asp
```

```
              115                 120                 125
Lys Thr Val Leu Asp Met Arg Ser Met Asp Phe Lys Ser Asn Ser Ala
    130                 135                 140

Val Ala Trp Ser Asn Lys Ser Asp Phe Ala Cys Ala Asn Ala Phe Asn
145                 150                 155                 160

Asn Ser Ile Ile Pro Glu Asp Thr Phe Phe Pro Ser Pro Glu Ser Ser
                165                 170                 175

Cys Asp Val Lys Leu Val Glu Lys Ser Phe Glu Thr Asp Thr Asn Leu
                180                 185                 190

Asn Phe Gln Asn Leu Ser Val Ile Gly Phe Arg Ile Leu Leu Leu Lys
                195                 200                 205

Val Ala Gly Phe Asn Leu Leu Met Thr Leu Arg Leu Trp Ser Ser
    210                 215                 220

<210> SEQ ID NO 72
<211> LENGTH: 307
<212> TYPE: PRT
<213> ORGANISM: Artificial Sequence
<220> FEATURE:
<223> OTHER INFORMATION: R39P1C12 beta chain

<400> SEQUENCE: 72

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
                20                  25                  30

Thr Arg Gly Gln Gln Val Thr Leu Arg Cys Ser Pro Lys Ser Gly His
            35                  40                  45

Asp Thr Val Ser Trp Tyr Gln Gln Ala Leu Gly Gln Gly Pro Gln Phe
        50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
                100                 105                 110

Ser Gln Leu Asn Thr Glu Ala Phe Phe Gly Gln Gly Thr Arg Leu Thr
            115                 120                 125

Val Val Glu Asp Leu Asn Lys Val Phe Pro Pro Glu Val Ala Val Phe
        130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
                180                 185                 190

Leu Lys Glu Gln Pro Ala Leu Asn Asp Ser Arg Tyr Cys Leu Ser Ser
            195                 200                 205

Arg Leu Arg Val Ser Ala Thr Phe Trp Gln Asn Pro Arg Asn His Phe
        210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
```

```
              260                 265                 270
Leu Ser Ala Thr Ile Leu Tyr Glu Ile Leu Gly Lys Ala Thr Leu
            275                 280                 285

Tyr Ala Val Leu Val Ser Ala Leu Val Leu Met Ala Met Val Lys Arg
            290                 295                 300

Lys Asp Phe
305

<210> SEQ ID NO 73
<211> LENGTH: 270
<212> TYPE: PRT
<213> ORGANISM: Artificial Sequence
<220> FEATURE:
<223> OTHER INFORMATION: R39P1F5 alpha chain

<400> SEQUENCE: 73

Met Lys Ser Leu Arg Val Leu Leu Val Ile Leu Trp Leu Gln Leu Ser
1               5                  10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Asn Ala Arg Leu Met Phe Gly Asp Gly Thr Gln Leu Val Val Lys
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 74
<211> LENGTH: 311
<212> TYPE: PRT
<213> ORGANISM: Artificial Sequence
<220> FEATURE:
<223> OTHER INFORMATION: R39P1F5 beta chain
```

<400> SEQUENCE: 74

```
Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gly Gln Gly Ala Asn Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310
```

<210> SEQ ID NO 75
<211> LENGTH: 272
<212> TYPE: PRT
<213> ORGANISM: Artificial Sequence
<220> FEATURE:
<223> OTHER INFORMATION: R40P1C2 alpha chain

<400> SEQUENCE: 75

```
Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30
```

-continued

Val Gln Glu Ala Glu Thr Val Thr Leu Ser Cys Thr Tyr Asp Thr Ser
                35                  40                  45

Glu Ser Asp Tyr Tyr Leu Phe Trp Tyr Lys Gln Pro Pro Ser Arg Gln
 50                  55                  60

Met Ile Leu Val Ile Arg Gln Glu Ala Tyr Lys Gln Gln Asn Ala Thr
 65                  70                  75                  80

Glu Asn Arg Phe Ser Val Asn Phe Gln Lys Ala Ala Lys Ser Phe Ser
                 85                  90                  95

Leu Lys Ile Ser Asp Ser Gln Leu Gly Asp Ala Ala Met Tyr Phe Cys
                100                 105                 110

Ala Tyr Leu Asn Tyr Gln Leu Ile Trp Gly Ala Gly Thr Lys Leu Ile
                115                 120                 125

Ile Lys Pro Asp Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
                180                 185                 190

Ala Val Ala Trp Ser Asn Lys Ser Asp Phe Ala Cys Ala Asn Ala Phe
                195                 200                 205

Asn Asn Ser Ile Ile Pro Glu Asp Thr Phe Phe Pro Ser Pro Glu Ser
                210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
                260                 265                 270

<210> SEQ ID NO 76
<211> LENGTH: 311
<212> TYPE: PRT
<213> ORGANISM: Artificial Sequence
<220> FEATURE:
<223> OTHER INFORMATION: R40P1C2 beta chain

<400> SEQUENCE: 76

Met Asp Thr Trp Leu Val Cys Trp Ala Ile Phe Ser Leu Leu Lys Ala
 1               5                  10                  15

Gly Leu Thr Glu Pro Glu Val Thr Gln Thr Pro Ser His Gln Val Thr
                20                  25                  30

Gln Met Gly Gln Glu Val Ile Leu Arg Cys Val Pro Ile Ser Asn His
                35                  40                  45

Leu Tyr Phe Tyr Trp Tyr Arg Gln Ile Leu Gly Gln Lys Val Glu Phe
 50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                 85                  90                  95

Lys Ile Arg Ser Thr Lys Leu Glu Asp Ser Ala Met Tyr Phe Cys Ala
                100                 105                 110

Ser Ser Glu Met Thr Ala Val Gly Gln Tyr Phe Gly Pro Gly Thr Arg
                115                 120                 125

Leu Thr Val Thr Glu Asp Leu Lys Asn Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
        290                 295                 300

Lys Arg Lys Asp Ser Arg Gly
305                 310

<210> SEQ ID NO 77
<211> LENGTH: 271
<212> TYPE: PRT
<213> ORGANISM: Artificial Sequence
<220> FEATURE:
<223> OTHER INFORMATION: R41P3E6 alpha chain

<400> SEQUENCE: 77

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ala
            100                 105                 110

Phe Ser Gly Tyr Ala Leu Asn Phe Gly Lys Gly Thr Ser Leu Leu Val
        115                 120                 125

Thr Pro His Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

```
Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
            245                 250                 255

Val Ala Gly Phe Asn Leu Leu Met Thr Leu Arg Leu Trp Ser Ser
        260                 265                 270
```

<210> SEQ ID NO 78
<211> LENGTH: 310
<212> TYPE: PRT
<213> ORGANISM: Artificial Sequence
<220> FEATURE:
<223> OTHER INFORMATION: R41P3E6 beta chain

<400> SEQUENCE: 78

```
Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gln Tyr Thr Gly Glu Leu Phe Phe Gly Glu Gly Ser Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270
```

```
Val Leu Ser Ala Thr Ile Leu Tyr Glu Ile Leu Gly Lys Ala Thr
            275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 79
<211> LENGTH: 270
<212> TYPE: PRT
<213> ORGANISM: Artificial Sequence
<220> FEATURE:
<223> OTHER INFORMATION: R43P3G4 alpha chain

<400> SEQUENCE: 79

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Gly Gly Asp Met Arg Phe Gly Ala Gly Thr Arg Leu Thr Val Lys
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 80
<211> LENGTH: 311
<212> TYPE: PRT
<213> ORGANISM: Artificial Sequence
<220> FEATURE:
<223> OTHER INFORMATION: R43P3G4 beta chain

<400> SEQUENCE: 80
```

-continued

```
Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gly Gln Gly Ala Leu Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 81
<211> LENGTH: 281
<212> TYPE: PRT
<213> ORGANISM: Artificial Sequence
<220> FEATURE:
<223> OTHER INFORMATION: R44P3B3 alpha chain

<400> SEQUENCE: 81

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45
```

Cys Asp Tyr Thr Asn Ser Met Phe Asp Tyr Phe Leu Trp Tyr Lys Lys
            50                  55                  60

Tyr Pro Ala Glu Gly Pro Thr Phe Leu Ile Ser Ile Ser Ser Ile Lys
 65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Gly Leu Tyr Asn Gln Gly Gly Lys Leu
        115                 120                 125

Ile Phe Gly Gln Gly Thr Glu Leu Ser Val Lys Pro Asn Ile Gln Asn
    130                 135                 140

Pro Asp Pro Ala Val Tyr Gln Leu Arg Asp Ser Lys Ser Ser Asp Lys
145                 150                 155                 160

Ser Val Cys Leu Phe Thr Asp Phe Asp Ser Gln Thr Asn Val Ser Gln
                165                 170                 175

Ser Lys Asp Ser Asp Val Tyr Ile Thr Asp Lys Thr Val Leu Asp Met
            180                 185                 190

Arg Ser Met Asp Phe Lys Ser Asn Ser Ala Val Ala Trp Ser Asn Lys
        195                 200                 205

Ser Asp Phe Ala Cys Ala Asn Ala Phe Asn Asn Ser Ile Ile Pro Glu
    210                 215                 220

Asp Thr Phe Phe Pro Ser Pro Glu Ser Ser Cys Asp Val Lys Leu Val
225                 230                 235                 240

Glu Lys Ser Phe Glu Thr Asp Thr Asn Leu Asn Phe Gln Asn Leu Ser
                245                 250                 255

Val Ile Gly Phe Arg Ile Leu Leu Leu Lys Val Ala Gly Phe Asn Leu
            260                 265                 270

Leu Met Thr Leu Arg Leu Trp Ser Ser
        275                 280

<210> SEQ ID NO 82
<211> LENGTH: 311
<212> TYPE: PRT
<213> ORGANISM: Artificial Sequence
<220> FEATURE:
<223> OTHER INFORMATION: R44P3B3 beta chain

<400> SEQUENCE: 82

Met Gly Cys Arg Leu Leu Cys Cys Val Phe Cys Leu Leu Gln Ala
 1               5                  10                  15

Gly Pro Leu Asp Thr Ala Val Ser Gln Thr Pro Lys Tyr Leu Val Thr
                20                  25                  30

Gln Met Gly Asn Asp Lys Ser Ile Lys Cys Glu Gln Asn Leu Gly His
            35                  40                  45

Asp Thr Met Tyr Trp Tyr Lys Gln Asp Ser Lys Lys Phe Leu Lys Ile
        50                  55                  60

Met Phe Ser Tyr Asn Asn Lys Glu Leu Ile Ile Asn Glu Thr Val Pro
 65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Leu Gly Asp Arg Gly Tyr Glu Gln Tyr Phe Gly Pro Gly Thr Arg
        115                 120                 125

```
Leu Thr Val Thr Glu Asp Leu Lys Asn Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Ser Arg Gly
305                 310

<210> SEQ ID NO 83
<211> LENGTH: 272
<212> TYPE: PRT
<213> ORGANISM: Artificial Sequence
<220> FEATURE:
<223> OTHER INFORMATION: R44P3E7 alpha chain

<400> SEQUENCE: 83

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
        50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ile Asn Asn Asn Ala Arg Leu Met Phe Gly Asp Gly Thr Gln Leu Val
        115                 120                 125

Val Lys Pro Asn Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175
```

```
Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270
```

<210> SEQ ID NO 84
<211> LENGTH: 320
<212> TYPE: PRT
<213> ORGANISM: Artificial Sequence
<220> FEATURE:
<223> OTHER INFORMATION: R44P3E7 beta chain

<400> SEQUENCE: 84

```
Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Pro Pro Asp Gln Asn
            115                 120                 125

Thr Gln Tyr Phe Gly Pro Gly Thr Arg Leu Thr Val Leu Glu Asp Leu
        130                 135                 140

Lys Asn Val Phe Pro Pro Glu Val Ala Val Phe Glu Pro Ser Glu Ala
145                 150                 155                 160

Glu Ile Ser His Thr Gln Lys Ala Thr Leu Val Cys Leu Ala Thr Gly
                165                 170                 175

Phe Tyr Pro Asp His Val Glu Leu Ser Trp Trp Val Asn Gly Lys Glu
            180                 185                 190

Val His Ser Gly Val Ser Thr Asp Pro Gln Pro Leu Lys Glu Gln Pro
            195                 200                 205

Ala Leu Asn Asp Ser Arg Tyr Cys Leu Ser Ser Arg Leu Arg Val Ser
        210                 215                 220

Ala Thr Phe Trp Gln Asn Pro Arg Asn His Phe Arg Cys Gln Val Gln
225                 230                 235                 240

Phe Tyr Gly Leu Ser Glu Asn Asp Glu Trp Thr Gln Asp Arg Ala Lys
                245                 250                 255

Pro Val Thr Gln Ile Val Ser Ala Glu Ala Trp Gly Arg Ala Asp Cys
            260                 265                 270
```

```
Gly Phe Thr Ser Glu Ser Tyr Gln Gln Gly Val Leu Ser Ala Thr Ile
        275                 280                 285

Leu Tyr Glu Ile Leu Leu Gly Lys Ala Thr Leu Tyr Ala Val Leu Val
    290                 295                 300

Ser Ala Leu Val Leu Met Ala Met Val Lys Arg Lys Asp Ser Arg Gly
305                 310                 315                 320

<210> SEQ ID NO 85
<211> LENGTH: 273
<212> TYPE: PRT
<213> ORGANISM: Artificial Sequence
<220> FEATURE:
<223> OTHER INFORMATION: R49P2B7 alpha chain

<400> SEQUENCE: 85

Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
            20                  25                  30

Ser Glu Gly Ala Leu Val Leu Leu Arg Cys Asn Tyr Ser Ser Ser Val
        35                  40                  45

Pro Pro Tyr Leu Phe Trp Tyr Val Gln Tyr Pro Asn Gln Gly Leu Gln
    50                  55                  60

Leu Leu Leu Lys Tyr Thr Thr Gly Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
            100                 105                 110

Arg Ile Phe Gly Asn Glu Lys Leu Thr Phe Gly Thr Gly Thr Arg Leu
        115                 120                 125

Thr Ile Ile Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 86
<211> LENGTH: 312
<212> TYPE: PRT
<213> ORGANISM: Artificial Sequence
<220> FEATURE:
```

<223> OTHER INFORMATION: R49P2B7 beta chain

<400> SEQUENCE: 86

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Met Gly Glu Leu Thr Gly Glu Leu Phe Phe Gly Glu Gly Ser
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 87
<211> LENGTH: 276
<212> TYPE: PRT
<213> ORGANISM: Artificial Sequence
<220> FEATURE:
<223> OTHER INFORMATION: R55P1G7 alpha chain

<400> SEQUENCE: 87

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

```
Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
        50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Met Gly Asp Thr Gly Thr Ala Ser Lys Leu Thr Phe Gly Thr Gly
        115                 120                 125

Thr Arg Leu Gln Val Thr Leu Asp Ile Gln Asn Pro Asp Pro Ala Val
        130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
        210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 88
<211> LENGTH: 309
<212> TYPE: PRT
<213> ORGANISM: Artificial Sequence
<220> FEATURE:
<223> OTHER INFORMATION: R55P1G7 beta chain

<400> SEQUENCE: 88

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110
```

Ser Phe Gly Gly Tyr Glu Gln Tyr Phe Gly Pro Gly Thr Arg Leu Thr
    115                 120                 125

Val Thr Glu Asp Leu Lys Asn Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
                180                 185                 190

Leu Lys Glu Gln Pro Ala Leu Asn Asp Ser Arg Tyr Cys Leu Ser Ser
            195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
                260                 265                 270

Leu Ser Ala Thr Ile Leu Tyr Glu Ile Leu Leu Gly Lys Ala Thr Leu
            275                 280                 285

Tyr Ala Val Leu Val Ser Ala Leu Val Leu Met Ala Met Val Lys Arg
        290                 295                 300

Lys Asp Ser Arg Gly
305

<210> SEQ ID NO 89
<211> LENGTH: 144
<212> TYPE: PRT
<213> ORGANISM: Artificial Sequence
<220> FEATURE:
<223> OTHER INFORMATION: R59P2A7 alpha chain

<400> SEQUENCE: 89

Val Lys Pro Asn Ile Gln Asn Pro Asp Pro Ala Val Tyr Gln Leu Arg
1               5                   10                  15

Asp Ser Lys Ser Ser Asp Lys Ser Val Cys Leu Phe Thr Asp Phe Asp
                20                  25                  30

Ser Gln Thr Asn Val Ser Gln Ser Lys Asp Ser Asp Val Tyr Ile Thr
            35                  40                  45

Asp Lys Thr Val Leu Asp Met Arg Ser Met Asp Phe Lys Ser Asn Ser
50                  55                  60

Ala Val Ala Trp Ser Asn Lys Ser Asp Phe Ala Cys Ala Asn Ala Phe
65                  70                  75                  80

Asn Asn Ser Ile Ile Pro Glu Asp Thr Phe Phe Pro Ser Pro Glu Ser
                85                  90                  95

Ser Cys Asp Val Lys Leu Val Glu Lys Ser Phe Glu Thr Asp Thr Asn
            100                 105                 110

Leu Asn Phe Gln Asn Leu Ser Val Ile Gly Phe Arg Ile Leu Leu Leu
        115                 120                 125

Lys Val Ala Gly Phe Asn Leu Leu Met Thr Leu Arg Leu Trp Ser Ser
    130                 135                 140

<210> SEQ ID NO 90

<211> LENGTH: 307
<212> TYPE: PRT
<213> ORGANISM: Artificial Sequence
<220> FEATURE:
<223> OTHER INFORMATION: R59P2A7 beta chain

<400> SEQUENCE: 90

Met Leu Cys Ser Leu Leu Ala Leu Leu Gly Thr Phe Phe Gly Val
1               5                   10                  15

Arg Ser Gln Thr Ile His Gln Trp Pro Ala Thr Leu Val Gln Pro Val
            20                  25                  30

Gly Ser Pro Leu Ser Leu Glu Cys Thr Val Glu Gly Thr Ser Asn Pro
        35                  40                  45

Asn Leu Tyr Trp Tyr Arg Gln Ala Ala Gly Arg Gly Leu Gln Leu Leu
    50                  55                  60

Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ser Gly
            100                 105                 110

Leu Val Ala Glu Gln Phe Phe Gly Pro Gly Thr Arg Leu Thr Val Leu
        115                 120                 125

Glu Asp Leu Lys Asn Val Phe Pro Pro Glu Val Ala Val Phe Glu Pro
    130                 135                 140

Ser Glu Ala Glu Ile Ser His Thr Gln Lys Ala Thr Leu Val Cys Leu
145                 150                 155                 160

Ala Thr Gly Phe Tyr Pro Asp His Val Glu Leu Ser Trp Trp Val Asn
                165                 170                 175

Gly Lys Glu Val His Ser Gly Val Ser Thr Asp Pro Gln Pro Leu Lys
            180                 185                 190

Glu Gln Pro Ala Leu Asn Asp Ser Arg Tyr Cys Leu Ser Ser Arg Leu
        195                 200                 205

Arg Val Ser Ala Thr Phe Trp Gln Asn Pro Arg Asn His Phe Arg Cys
    210                 215                 220

Gln Val Gln Phe Tyr Gly Leu Ser Glu Asn Asp Glu Trp Thr Gln Asp
225                 230                 235                 240

Arg Ala Lys Pro Val Thr Gln Ile Val Ser Ala Glu Ala Trp Gly Arg
                245                 250                 255

Ala Asp Cys Gly Phe Thr Ser Glu Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Ala Leu Val Leu Met Ala Met Val Lys Arg Lys Asp
    290                 295                 300

Ser Arg Gly
305

<210> SEQ ID NO 91
<211> LENGTH: 274
<212> TYPE: PRT
<213> ORGANISM: Artificial Sequence
<220> FEATURE:
<223> OTHER INFORMATION: Variant R4P3F9 alpha chain

<400> SEQUENCE: 91

Met Lys Ser Leu Arg Val Leu Leu Val Ile Leu Trp Leu Gln Leu Ser

```
                1               5                   10                  15
            Trp Val Trp Ser Gln Gln Lys Glu Val Glu Gln Asn Ser Gly Pro Leu
                            20                  25                  30

Ser Val Pro Glu Gly Ala Ile Ala Ser Leu Asn Cys Thr Tyr Ser Asp
                            35                  40                  45

Arg Arg Ser Gln Ser Phe Phe Trp Tyr Arg Gln Tyr Ser Gly Lys Ser
                        50                  55                  60

Pro Glu Leu Ile Met Phe Ile Tyr Ser Asn Gly Asp Lys Glu Asp Gly
            65                  70                  75                  80

Arg Phe Thr Ala Gln Leu Asn Lys Ala Ser Gln Tyr Val Ser Leu Leu
                            85                  90                  95

Ile Arg Asp Ser Gln Pro Ser Asp Ser Ala Thr Tyr Leu Cys Ala Ala
                            100                 105                 110

Tyr Ser Gly Ala Gly Ser Tyr Gln Leu Thr Phe Gly Lys Gly Thr Lys
                        115                 120                 125

Leu Ser Val Ile Pro Asn Ile Gln Asn Pro Asp Pro Ala Val Tyr Gln
            130                 135                 140

Leu Arg Asp Ser Lys Ser Ser Asp Lys Ser Val Cys Leu Phe Thr Asp
            145                 150                 155                 160

Phe Asp Ser Gln Thr Asn Val Ser Gln Ser Lys Asp Ser Asp Val Tyr
                            165                 170                 175

Ile Thr Asp Lys Thr Val Leu Asp Met Arg Ser Met Asp Phe Lys Ser
                            180                 185                 190

Asn Ser Ala Val Ala Trp Ser Asn Lys Ser Asp Phe Ala Cys Ala Asn
                        195                 200                 205

Ala Phe Asn Asn Ser Ile Ile Pro Glu Asp Thr Phe Phe Pro Ser Pro
                    210                 215                 220

Glu Ser Ser Cys Asp Val Lys Leu Val Glu Lys Ser Phe Glu Thr Asp
            225                 230                 235                 240

Thr Asn Leu Asn Phe Gln Asn Leu Ser Val Ile Gly Phe Arg Ile Leu
                            245                 250                 255

Leu Leu Lys Val Ala Gly Phe Asn Leu Leu Met Thr Leu Arg Leu Trp
                        260                 265                 270

Ser Ser

<210> SEQ ID NO 92
<211> LENGTH: 308
<212> TYPE: PRT
<213> ORGANISM: Artificial Sequence
<220> FEATURE:
<223> OTHER INFORMATION: Variant R4P3F9 beta chain

<400> SEQUENCE: 92

Met Gly Phe Arg Leu Leu Cys Cys Val Ala Phe Cys Leu Leu Gly Ala
            1               5                   10                  15

Gly Pro Val Asp Ser Gly Val Thr Gln Thr Pro Lys His Leu Ile Thr
                            20                  25                  30

Ala Thr Gly Gln Arg Val Thr Leu Arg Cys Ser Pro Ala Met Asp His
                        35                  40                  45

Pro Tyr Val Tyr Trp Tyr Gln Gln Ser Leu Asp Gln Gly Leu Gln Phe
                    50                  55                  60

Leu Ile Gln Tyr Tyr Asn Gly Glu Glu Arg Ala Lys Gly Asn Ile Leu
            65                  70                  75                  80

Glu Arg Phe Ser Ala Gln Gln Phe Pro Asp Leu His Ser Glu Leu Asn
                            85                  90                  95
```

Leu Ser Ser Leu Glu Leu Gly Asp Ser Ala Leu Tyr Phe Cys Ala Ser
            100                 105                 110

Ser Val Glu Ser Ser Tyr Gly Tyr Thr Phe Gly Ser Gly Thr Arg Leu
        115                 120                 125

Thr Val Val Glu Asp Leu Asn Lys Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe
305

<210> SEQ ID NO 93
<211> LENGTH: 4
<212> TYPE: PRT
<213> ORGANISM: Artificial Sequence
<220> FEATURE:
<223> OTHER INFORMATION: Furin consensus sequence
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 93

Arg Xaa Xaa Arg
1

<210> SEQ ID NO 94
<211> LENGTH: 367
<212> TYPE: DNA
<213> ORGANISM: Artificial Sequence
<220> FEATURE:
<223> OTHER INFORMATION: murine stem cell virus promoter

<400> SEQUENCE: 94
tgaaagaccc cacctgtagg tttggcaagc tagcttaagt aacgccattt tgcaaggcat     60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300

```
cgcttctcgc ttctgttcgc gcgcttctgc tccccgagct caataaaaga gcccacaacc    360
cctcact                                                              367
```

<210> SEQ ID NO 95
<211> LENGTH: 559
<212> TYPE: PRT
<213> ORGANISM: Artificial Sequence
<220> FEATURE:
<223> OTHER INFORMATION: RD114TR

<400> SEQUENCE: 95

```
Met Lys Leu Pro Thr Gly Met Val Ile Leu Cys Ser Leu Ile Ile Val
 1               5                  10                  15

Arg Ala Gly Phe Asp Asp Pro Arg Lys Ala Ile Ala Leu Val Gln Lys
             20                  25                  30

Gln His Gly Lys Pro Cys Glu Cys Ser Gly Gly Gln Val Ser Glu Ala
         35                  40                  45

Pro Pro Asn Ser Ile Gln Gln Val Thr Cys Pro Gly Lys Thr Ala Tyr
     50                  55                  60

Leu Met Thr Asn Gln Lys Trp Lys Cys Arg Val Thr Pro Lys Ile Ser
 65                  70                  75                  80

Pro Ser Gly Gly Glu Leu Gln Asn Cys Pro Cys Asn Thr Phe Gln Asp
                 85                  90                  95

Ser Met His Ser Ser Cys Tyr Thr Glu Tyr Arg Gln Cys Arg Arg Ile
            100                 105                 110

Asn Lys Thr Tyr Tyr Thr Ala Thr Leu Leu Lys Ile Arg Ser Gly Ser
        115                 120                 125

Leu Asn Glu Val Gln Ile Leu Gln Asn Pro Asn Gln Leu Leu Gln Ser
130                 135                 140

Pro Cys Arg Gly Ser Ile Asn Gln Pro Val Cys Trp Ser Ala Thr Ala
145                 150                 155                 160

Pro Ile His Ile Ser Asp Gly Gly Gly Pro Leu Asp Thr Lys Arg Val
                165                 170                 175

Trp Thr Val Gln Lys Arg Leu Glu Gln Ile His Lys Ala Met Thr Pro
            180                 185                 190

Glu Leu Gln Tyr His Pro Leu Ala Leu Pro Lys Val Arg Asp Asp Leu
        195                 200                 205

Ser Leu Asp Ala Arg Thr Phe Asp Ile Leu Asn Thr Thr Phe Arg Leu
    210                 215                 220

Leu Gln Met Ser Asn Phe Ser Leu Ala Gln Asp Cys Trp Leu Cys Leu
225                 230                 235                 240

Lys Leu Gly Thr Pro Thr Pro Leu Ala Ile Pro Thr Pro Ser Leu Thr
                245                 250                 255

Tyr Ser Leu Ala Asp Ser Leu Ala Asn Ala Ser Cys Gln Ile Ile Pro
            260                 265                 270

Pro Leu Leu Val Gln Pro Met Gln Phe Ser Asn Ser Cys Leu Ser
        275                 280                 285

Ser Pro Phe Ile Asn Asp Thr Glu Gln Ile Asp Leu Gly Ala Val Thr
    290                 295                 300

Phe Thr Asn Cys Thr Ser Val Ala Asn Val Ser Ser Pro Leu Cys Ala
305                 310                 315                 320

Leu Asn Gly Ser Val Phe Leu Cys Gly Asn Asn Met Ala Tyr Thr Tyr
                325                 330                 335

Leu Pro Gln Asn Trp Thr Arg Leu Cys Val Gln Ala Ser Leu Leu Pro
```

```
              340                 345                 350
Asp Ile Asp Ile Asn Pro Gly Asp Glu Pro Val Pro Ile Pro Ala Ile
            355                 360                 365

Asp His Tyr Ile His Arg Pro Lys Arg Ala Val Gln Phe Ile Pro Leu
        370                 375                 380

Leu Ala Gly Leu Gly Ile Thr Ala Ala Phe Thr Gly Ala Thr Gly
385                 390                 395                 400

Leu Gly Val Ser Val Thr Gln Tyr Thr Lys Leu Ser His Gln Leu Ile
                405                 410                 415

Ser Asp Val Gln Val Leu Ser Gly Thr Ile Gln Asp Leu Gln Asp Gln
            420                 425                 430

Val Asp Ser Leu Ala Glu Val Val Leu Gln Asn Arg Arg Gly Leu Asp
        435                 440                 445

Leu Leu Thr Ala Glu Gln Gly Gly Ile Cys Leu Ala Leu Gln Glu Lys
    450                 455                 460

Cys Cys Phe Tyr Ala Asn Lys Ser Gly Ile Val Arg Asn Lys Ile Arg
465                 470                 475                 480

Thr Leu Gln Glu Glu Leu Gln Lys Arg Arg Glu Ser Leu Ala Ser Asn
                485                 490                 495

Pro Leu Trp Thr Gly Leu Gln Gly Phe Leu Pro Tyr Leu Leu Pro Leu
            500                 505                 510

Leu Gly Pro Leu Leu Thr Leu Leu Ile Leu Thr Ile Gly Pro Cys
        515                 520                 525

Val Phe Asn Arg Leu Val Gln Phe Val Lys Asp Arg Ile Ser Val Val
    530                 535                 540

Gln Ala Leu Val Leu Thr Gln Gln Tyr His Gln Leu Lys Pro Leu
545                 550                 555

<210> SEQ ID NO 96
<211> LENGTH: 9
<212> TYPE: PRT
<213> ORGANISM: Artificial Sequence
<220> FEATURE:
<223> OTHER INFORMATION: Viral antigenic peptide

<400> SEQUENCE: 96

Ser Leu Tyr Asn Thr Val Ala Thr Leu
1               5

<210> SEQ ID NO 97
<211> LENGTH: 9
<212> TYPE: PRT
<213> ORGANISM: Artificial Sequence
<220> FEATURE:
<223> OTHER INFORMATION: Viral antigenic peptide

<400> SEQUENCE: 97

Gly Ile Leu Gly Phe Val Phe Thr Leu
1               5

<210> SEQ ID NO 98
<211> LENGTH: 9
<212> TYPE: PRT
<213> ORGANISM: Artificial Sequence
<220> FEATURE:
<223> OTHER INFORMATION: Viral antigenic peptide

<400> SEQUENCE: 98

Asn Leu Val Pro Met Val Ala Thr Val
1               5
```

<210> SEQ ID NO 99
<211> LENGTH: 10
<212> TYPE: PRT
<213> ORGANISM: Homo sapiens

<400> SEQUENCE: 99

Tyr Leu Tyr Asp Ser Glu Thr Lys Asn Ala
1               5                   10

<210> SEQ ID NO 100
<211> LENGTH: 9
<212> TYPE: PRT
<213> ORGANISM: Homo sapiens

<400> SEQUENCE: 100

His Leu Met Asp Gln Pro Leu Ser Val
1               5

<210> SEQ ID NO 101
<211> LENGTH: 9
<212> TYPE: PRT
<213> ORGANISM: Homo sapiens

<400> SEQUENCE: 101

Gly Leu Leu Lys Lys Ile Asn Ser Val
1               5

<210> SEQ ID NO 102
<211> LENGTH: 9
<212> TYPE: PRT
<213> ORGANISM: Homo sapiens

<400> SEQUENCE: 102

Phe Leu Val Asp Gly Ser Ser Ala Leu
1               5

<210> SEQ ID NO 103
<211> LENGTH: 10
<212> TYPE: PRT
<213> ORGANISM: Homo sapiens

<400> SEQUENCE: 103

Phe Leu Phe Asp Gly Ser Ala Asn Leu Val
1               5                   10

<210> SEQ ID NO 104
<211> LENGTH: 9
<212> TYPE: PRT
<213> ORGANISM: Homo sapiens

<400> SEQUENCE: 104

Phe Leu Tyr Lys Ile Ile Asp Glu Leu
1               5

<210> SEQ ID NO 105
<211> LENGTH: 11
<212> TYPE: PRT
<213> ORGANISM: Homo sapiens

<400> SEQUENCE: 105

Phe Ile Leu Asp Ser Ala Glu Thr Thr Thr Leu
1               5                   10

```
<210> SEQ ID NO 106
<211> LENGTH: 9
<212> TYPE: PRT
<213> ORGANISM: Homo sapiens

<400> SEQUENCE: 106

Ser Val Asp Val Ser Pro Pro Lys Val
1               5

<210> SEQ ID NO 107
<211> LENGTH: 8
<212> TYPE: PRT
<213> ORGANISM: Homo sapiens

<400> SEQUENCE: 107

Val Ala Asp Lys Ile His Ser Val
1               5

<210> SEQ ID NO 108
<211> LENGTH: 9
<212> TYPE: PRT
<213> ORGANISM: Homo sapiens

<400> SEQUENCE: 108

Ile Val Asp Asp Leu Thr Ile Asn Leu
1               5

<210> SEQ ID NO 109
<211> LENGTH: 9
<212> TYPE: PRT
<213> ORGANISM: Homo sapiens

<400> SEQUENCE: 109

Gly Leu Leu Glu Glu Leu Val Thr Val
1               5

<210> SEQ ID NO 110
<211> LENGTH: 10
<212> TYPE: PRT
<213> ORGANISM: Homo sapiens

<400> SEQUENCE: 110

Thr Leu Asp Gly Ala Ala Val Asn Gln Val
1               5                   10

<210> SEQ ID NO 111
<211> LENGTH: 10
<212> TYPE: PRT
<213> ORGANISM: Homo sapiens

<400> SEQUENCE: 111

Ser Val Leu Glu Lys Glu Ile Tyr Ser Ile
1               5                   10

<210> SEQ ID NO 112
<211> LENGTH: 9
<212> TYPE: PRT
<213> ORGANISM: Homo sapiens

<400> SEQUENCE: 112

Leu Leu Asp Pro Lys Thr Ile Phe Leu
1               5

<210> SEQ ID NO 113
<211> LENGTH: 9
```

```
<212> TYPE: PRT
<213> ORGANISM: Homo sapiens

<400> SEQUENCE: 113

Tyr Thr Phe Ser Gly Asp Val Gln Leu
1               5

<210> SEQ ID NO 114
<211> LENGTH: 9
<212> TYPE: PRT
<213> ORGANISM: Homo sapiens

<400> SEQUENCE: 114

Tyr Leu Met Asp Asp Phe Ser Ser Leu
1               5

<210> SEQ ID NO 115
<211> LENGTH: 9
<212> TYPE: PRT
<213> ORGANISM: Homo sapiens

<400> SEQUENCE: 115

Lys Val Trp Ser Asp Val Thr Pro Leu
1               5

<210> SEQ ID NO 116
<211> LENGTH: 11
<212> TYPE: PRT
<213> ORGANISM: Homo sapiens

<400> SEQUENCE: 116

Leu Leu Trp Gly His Pro Arg Val Ala Leu Ala
1               5                   10

<210> SEQ ID NO 117
<211> LENGTH: 11
<212> TYPE: PRT
<213> ORGANISM: Homo sapiens

<400> SEQUENCE: 117

Lys Ile Trp Glu Glu Leu Ser Val Leu Glu Val
1               5                   10

<210> SEQ ID NO 118
<211> LENGTH: 9
<212> TYPE: PRT
<213> ORGANISM: Homo sapiens

<400> SEQUENCE: 118

Leu Leu Ile Pro Phe Thr Ile Phe Met
1               5

<210> SEQ ID NO 119
<211> LENGTH: 9
<212> TYPE: PRT
<213> ORGANISM: Homo sapiens

<400> SEQUENCE: 119

Phe Leu Ile Glu Asn Leu Leu Ala Ala
1               5

<210> SEQ ID NO 120
<211> LENGTH: 11
<212> TYPE: PRT
<213> ORGANISM: Homo sapiens
```

<400> SEQUENCE: 120

Leu Leu Trp Gly His Pro Arg Val Ala Leu Ala
1               5                   10

<210> SEQ ID NO 121
<211> LENGTH: 9
<212> TYPE: PRT
<213> ORGANISM: Homo sapiens

<400> SEQUENCE: 121

Phe Leu Leu Glu Arg Glu Gln Leu Leu
1               5

<210> SEQ ID NO 122
<211> LENGTH: 9
<212> TYPE: PRT
<213> ORGANISM: Homo sapiens

<400> SEQUENCE: 122

Ser Leu Ala Glu Thr Ile Phe Ile Val
1               5

<210> SEQ ID NO 123
<211> LENGTH: 9
<212> TYPE: PRT
<213> ORGANISM: Homo sapiens

<400> SEQUENCE: 123

Thr Leu Leu Glu Gly Ile Ser Arg Ala
1               5

<210> SEQ ID NO 124
<211> LENGTH: 9
<212> TYPE: PRT
<213> ORGANISM: Homo sapiens

<400> SEQUENCE: 124

Lys Ile Gln Glu Ile Leu Thr Gln Val
1               5

<210> SEQ ID NO 125
<211> LENGTH: 10
<212> TYPE: PRT
<213> ORGANISM: Homo sapiens

<400> SEQUENCE: 125

Val Ile Phe Glu Gly Glu Pro Met Tyr Leu
1               5                   10

<210> SEQ ID NO 126
<211> LENGTH: 9
<212> TYPE: PRT
<213> ORGANISM: Homo sapiens

<400> SEQUENCE: 126

Ser Leu Phe Glu Ser Leu Glu Tyr Leu
1               5

<210> SEQ ID NO 127
<211> LENGTH: 9
<212> TYPE: PRT
<213> ORGANISM: Homo sapiens

<400> SEQUENCE: 127

Ser Leu Leu Asn Gln Pro Lys Ala Val
1               5

<210> SEQ ID NO 128
<211> LENGTH: 9
<212> TYPE: PRT
<213> ORGANISM: Homo sapiens

<400> SEQUENCE: 128

Gly Leu Ala Glu Phe Gln Glu Asn Val
1               5

<210> SEQ ID NO 129
<211> LENGTH: 9
<212> TYPE: PRT
<213> ORGANISM: Homo sapiens

<400> SEQUENCE: 129

Lys Leu Leu Ala Val Ile His Glu Leu
1               5

<210> SEQ ID NO 130
<211> LENGTH: 9
<212> TYPE: PRT
<213> ORGANISM: Homo sapiens

<400> SEQUENCE: 130

Thr Leu His Asp Gln Val His Leu Leu
1               5

<210> SEQ ID NO 131
<211> LENGTH: 11
<212> TYPE: PRT
<213> ORGANISM: Homo sapiens

<400> SEQUENCE: 131

Thr Leu Tyr Asn Pro Glu Arg Thr Ile Thr Val
1               5                   10

<210> SEQ ID NO 132
<211> LENGTH: 9
<212> TYPE: PRT
<213> ORGANISM: Homo sapiens

<400> SEQUENCE: 132

Lys Leu Gln Glu Lys Ile Gln Glu Leu
1               5

<210> SEQ ID NO 133
<211> LENGTH: 10
<212> TYPE: PRT
<213> ORGANISM: Homo sapiens

<400> SEQUENCE: 133

Ser Val Leu Glu Lys Glu Ile Tyr Ser Ile
1               5                   10

<210> SEQ ID NO 134
<211> LENGTH: 11
<212> TYPE: PRT
<213> ORGANISM: Homo sapiens

<400> SEQUENCE: 134

Arg Val Ile Asp Asp Ser Leu Val Val Gly Val

<210> SEQ ID NO 135
<211> LENGTH: 9
<212> TYPE: PRT
<213> ORGANISM: Homo sapiens

<400> SEQUENCE: 135

Val Leu Phe Gly Glu Leu Pro Ala Leu
1               5

<210> SEQ ID NO 136
<211> LENGTH: 9
<212> TYPE: PRT
<213> ORGANISM: Homo sapiens

<400> SEQUENCE: 136

Gly Leu Val Asp Ile Met Val His Leu
1               5

<210> SEQ ID NO 137
<211> LENGTH: 9
<212> TYPE: PRT
<213> ORGANISM: Homo sapiens

<400> SEQUENCE: 137

Phe Leu Asn Ala Ile Glu Thr Ala Leu
1               5

<210> SEQ ID NO 138
<211> LENGTH: 9
<212> TYPE: PRT
<213> ORGANISM: Homo sapiens

<400> SEQUENCE: 138

Ala Leu Leu Gln Ala Leu Met Glu Leu
1               5

<210> SEQ ID NO 139
<211> LENGTH: 9
<212> TYPE: PRT
<213> ORGANISM: Homo sapiens

<400> SEQUENCE: 139

Ala Leu Ser Ser Ser Gln Ala Glu Val
1               5

<210> SEQ ID NO 140
<211> LENGTH: 11
<212> TYPE: PRT
<213> ORGANISM: Homo sapiens

<400> SEQUENCE: 140

Ser Leu Ile Thr Gly Gln Asp Leu Leu Ser Val
1               5                   10

<210> SEQ ID NO 141
<211> LENGTH: 9
<212> TYPE: PRT
<213> ORGANISM: Homo sapiens

<400> SEQUENCE: 141

Gln Leu Ile Glu Lys Asn Trp Leu Leu
1               5

<210> SEQ ID NO 142
<211> LENGTH: 9
<212> TYPE: PRT
<213> ORGANISM: Homo sapiens

<400> SEQUENCE: 142

Leu Leu Asp Pro Lys Thr Ile Phe Leu
1               5

<210> SEQ ID NO 143
<211> LENGTH: 9
<212> TYPE: PRT
<213> ORGANISM: Homo sapiens

<400> SEQUENCE: 143

Arg Leu His Asp Glu Asn Ile Leu Leu
1               5

<210> SEQ ID NO 144
<211> LENGTH: 9
<212> TYPE: PRT
<213> ORGANISM: Homo sapiens

<400> SEQUENCE: 144

Tyr Thr Phe Ser Gly Asp Val Gln Leu
1               5

<210> SEQ ID NO 145
<211> LENGTH: 9
<212> TYPE: PRT
<213> ORGANISM: Homo sapiens

<400> SEQUENCE: 145

Gly Leu Pro Ser Ala Thr Thr Thr Val
1               5

<210> SEQ ID NO 146
<211> LENGTH: 11
<212> TYPE: PRT
<213> ORGANISM: Homo sapiens

<400> SEQUENCE: 146

Gly Leu Leu Pro Ser Ala Glu Ser Ile Lys Leu
1               5                   10

<210> SEQ ID NO 147
<211> LENGTH: 9
<212> TYPE: PRT
<213> ORGANISM: Homo sapiens

<400> SEQUENCE: 147

Lys Thr Ala Ser Ile Asn Gln Asn Val
1               5

<210> SEQ ID NO 148
<211> LENGTH: 9
<212> TYPE: PRT
<213> ORGANISM: Homo sapiens

<400> SEQUENCE: 148

Ser Leu Leu Gln His Leu Ile Gly Leu
1               5

<210> SEQ ID NO 149

```
<211> LENGTH: 9
<212> TYPE: PRT
<213> ORGANISM: Homo sapiens

<400> SEQUENCE: 149

Tyr Leu Met Asp Asp Phe Ser Ser Leu
1               5

<210> SEQ ID NO 150
<211> LENGTH: 9
<212> TYPE: PRT
<213> ORGANISM: Homo sapiens

<400> SEQUENCE: 150

Leu Met Tyr Pro Tyr Ile Tyr His Val
1               5

<210> SEQ ID NO 151
<211> LENGTH: 9
<212> TYPE: PRT
<213> ORGANISM: Homo sapiens

<400> SEQUENCE: 151

Lys Val Trp Ser Asp Val Thr Pro Leu
1               5

<210> SEQ ID NO 152
<211> LENGTH: 11
<212> TYPE: PRT
<213> ORGANISM: Homo sapiens

<400> SEQUENCE: 152

Leu Leu Trp Gly His Pro Arg Val Ala Leu Ala
1               5                   10

<210> SEQ ID NO 153
<211> LENGTH: 9
<212> TYPE: PRT
<213> ORGANISM: Homo sapiens

<400> SEQUENCE: 153

Val Leu Asp Gly Lys Val Ala Val Val
1               5

<210> SEQ ID NO 154
<211> LENGTH: 9
<212> TYPE: PRT
<213> ORGANISM: Homo sapiens

<400> SEQUENCE: 154

Gly Leu Leu Gly Lys Val Thr Ser Val
1               5

<210> SEQ ID NO 155
<211> LENGTH: 9
<212> TYPE: PRT
<213> ORGANISM: Homo sapiens

<400> SEQUENCE: 155

Lys Met Ile Ser Ala Ile Pro Thr Leu
1               5

<210> SEQ ID NO 156
<211> LENGTH: 11
<212> TYPE: PRT
```

<213> ORGANISM: Homo sapiens

<400> SEQUENCE: 156

Gly Leu Leu Glu Thr Thr Gly Leu Leu Ala Thr
1               5                   10

<210> SEQ ID NO 157
<211> LENGTH: 9
<212> TYPE: PRT
<213> ORGANISM: Homo sapiens

<400> SEQUENCE: 157

Thr Leu Asn Thr Leu Asp Ile Asn Leu
1               5

<210> SEQ ID NO 158
<211> LENGTH: 9
<212> TYPE: PRT
<213> ORGANISM: Homo sapiens

<400> SEQUENCE: 158

Val Ile Ile Lys Gly Leu Glu Glu Ile
1               5

<210> SEQ ID NO 159
<211> LENGTH: 9
<212> TYPE: PRT
<213> ORGANISM: Homo sapiens

<400> SEQUENCE: 159

Tyr Leu Glu Asp Gly Phe Ala Tyr Val
1               5

<210> SEQ ID NO 160
<211> LENGTH: 11
<212> TYPE: PRT
<213> ORGANISM: Homo sapiens

<400> SEQUENCE: 160

Lys Ile Trp Glu Glu Leu Ser Val Leu Glu Val
1               5                   10

<210> SEQ ID NO 161
<211> LENGTH: 9
<212> TYPE: PRT
<213> ORGANISM: Homo sapiens

<400> SEQUENCE: 161

Leu Leu Ile Pro Phe Thr Ile Phe Met
1               5

<210> SEQ ID NO 162
<211> LENGTH: 10
<212> TYPE: PRT
<213> ORGANISM: Homo sapiens

<400> SEQUENCE: 162

Ile Ser Leu Asp Glu Val Ala Val Ser Leu
1               5                   10

<210> SEQ ID NO 163
<211> LENGTH: 10
<212> TYPE: PRT
<213> ORGANISM: Homo sapiens

<400> SEQUENCE: 163

Lys Ile Ser Asp Phe Gly Leu Ala Thr Val
1               5                   10

<210> SEQ ID NO 164
<211> LENGTH: 11
<212> TYPE: PRT
<213> ORGANISM: Homo sapiens

<400> SEQUENCE: 164

Lys Leu Ile Gly Asn Ile His Gly Asn Glu Val
1               5                   10

<210> SEQ ID NO 165
<211> LENGTH: 9
<212> TYPE: PRT
<213> ORGANISM: Homo sapiens

<400> SEQUENCE: 165

Ile Leu Leu Ser Val Leu His Gln Leu
1               5

<210> SEQ ID NO 166
<211> LENGTH: 9
<212> TYPE: PRT
<213> ORGANISM: Homo sapiens

<400> SEQUENCE: 166

Leu Asp Ser Glu Ala Leu Leu Thr Leu
1               5

<210> SEQ ID NO 167
<211> LENGTH: 13
<212> TYPE: PRT
<213> ORGANISM: Homo sapiens

<400> SEQUENCE: 167

Val Leu Gln Glu Asn Ser Ser Asp Tyr Gln Ser Asn Leu
1               5                   10

<210> SEQ ID NO 168
<211> LENGTH: 11
<212> TYPE: PRT
<213> ORGANISM: Homo sapiens

<400> SEQUENCE: 168

His Leu Leu Gly Glu Gly Ala Phe Ala Gln Val
1               5                   10

<210> SEQ ID NO 169
<211> LENGTH: 9
<212> TYPE: PRT
<213> ORGANISM: Homo sapiens

<400> SEQUENCE: 169

Ser Leu Val Glu Asn Ile His Val Leu
1               5

<210> SEQ ID NO 170
<211> LENGTH: 9
<212> TYPE: PRT
<213> ORGANISM: Homo sapiens

<400> SEQUENCE: 170

Tyr Thr Phe Ser Gly Asp Val Gln Leu
1               5

<210> SEQ ID NO 171
<211> LENGTH: 9
<212> TYPE: PRT
<213> ORGANISM: Homo sapiens

<400> SEQUENCE: 171

Ser Leu Ser Glu Lys Ser Pro Glu Val
1               5

<210> SEQ ID NO 172
<211> LENGTH: 10
<212> TYPE: PRT
<213> ORGANISM: Homo sapiens

<400> SEQUENCE: 172

Ala Met Phe Pro Asp Thr Ile Pro Arg Val
1               5                   10

<210> SEQ ID NO 173
<211> LENGTH: 9
<212> TYPE: PRT
<213> ORGANISM: Homo sapiens

<400> SEQUENCE: 173

Phe Leu Ile Glu Asn Leu Leu Ala Ala
1               5

<210> SEQ ID NO 174
<211> LENGTH: 9
<212> TYPE: PRT
<213> ORGANISM: Homo sapiens

<400> SEQUENCE: 174

Phe Thr Ala Glu Phe Leu Glu Lys Val
1               5

<210> SEQ ID NO 175
<211> LENGTH: 9
<212> TYPE: PRT
<213> ORGANISM: Homo sapiens

<400> SEQUENCE: 175

Ala Leu Tyr Gly Asn Val Gln Gln Val
1               5

<210> SEQ ID NO 176
<211> LENGTH: 9
<212> TYPE: PRT
<213> ORGANISM: Homo sapiens

<400> SEQUENCE: 176

Leu Phe Gln Ser Arg Ile Ala Gly Val
1               5

<210> SEQ ID NO 177
<211> LENGTH: 11
<212> TYPE: PRT
<213> ORGANISM: Homo sapiens

<400> SEQUENCE: 177

Ile Leu Ala Glu Glu Pro Ile Tyr Ile Arg Val
1               5                   10

```
<210> SEQ ID NO 178
<211> LENGTH: 9
<212> TYPE: PRT
<213> ORGANISM: Homo sapiens

<400> SEQUENCE: 178

Phe Leu Leu Glu Arg Glu Gln Leu Leu
1               5

<210> SEQ ID NO 179
<211> LENGTH: 10
<212> TYPE: PRT
<213> ORGANISM: Homo sapiens

<400> SEQUENCE: 179

Leu Leu Leu Pro Leu Glu Leu Ser Leu Ala
1               5                   10

<210> SEQ ID NO 180
<211> LENGTH: 9
<212> TYPE: PRT
<213> ORGANISM: Homo sapiens

<400> SEQUENCE: 180

Ser Leu Ala Glu Thr Ile Phe Ile Val
1               5

<210> SEQ ID NO 181
<211> LENGTH: 11
<212> TYPE: PRT
<213> ORGANISM: Homo sapiens

<400> SEQUENCE: 181

Ala Ile Leu Asn Val Asp Glu Lys Asn Gln Val
1               5                   10

<210> SEQ ID NO 182
<211> LENGTH: 9
<212> TYPE: PRT
<213> ORGANISM: Homo sapiens

<400> SEQUENCE: 182

Arg Leu Phe Glu Glu Val Leu Gly Val
1               5

<210> SEQ ID NO 183
<211> LENGTH: 9
<212> TYPE: PRT
<213> ORGANISM: Homo sapiens

<400> SEQUENCE: 183

Tyr Leu Asp Glu Val Ala Phe Met Leu
1               5

<210> SEQ ID NO 184
<211> LENGTH: 11
<212> TYPE: PRT
<213> ORGANISM: Homo sapiens

<400> SEQUENCE: 184

Lys Leu Ile Asp Glu Asp Glu Pro Leu Phe Leu
1               5                   10
```

```
<210> SEQ ID NO 185
<211> LENGTH: 9
<212> TYPE: PRT
<213> ORGANISM: Homo sapiens

<400> SEQUENCE: 185

Lys Leu Phe Glu Lys Ser Thr Gly Leu
1               5

<210> SEQ ID NO 186
<211> LENGTH: 11
<212> TYPE: PRT
<213> ORGANISM: Homo sapiens

<400> SEQUENCE: 186

Ser Leu Leu Glu Val Asn Glu Ala Ser Ser Val
1               5                   10

<210> SEQ ID NO 187
<211> LENGTH: 10
<212> TYPE: PRT
<213> ORGANISM: Homo sapiens

<400> SEQUENCE: 187

Gly Val Tyr Asp Gly Arg Glu His Thr Val
1               5                   10

<210> SEQ ID NO 188
<211> LENGTH: 10
<212> TYPE: PRT
<213> ORGANISM: Homo sapiens

<400> SEQUENCE: 188

Gly Leu Tyr Pro Val Thr Leu Val Gly Val
1               5                   10

<210> SEQ ID NO 189
<211> LENGTH: 9
<212> TYPE: PRT
<213> ORGANISM: Homo sapiens

<400> SEQUENCE: 189

Ala Leu Leu Ser Ser Val Ala Glu Ala
1               5

<210> SEQ ID NO 190
<211> LENGTH: 9
<212> TYPE: PRT
<213> ORGANISM: Homo sapiens

<400> SEQUENCE: 190

Thr Leu Leu Glu Gly Ile Ser Arg Ala
1               5

<210> SEQ ID NO 191
<211> LENGTH: 9
<212> TYPE: PRT
<213> ORGANISM: Homo sapiens

<400> SEQUENCE: 191

Ser Leu Ile Glu Glu Ser Glu Glu Leu
1               5

<210> SEQ ID NO 192
<211> LENGTH: 9
```

<212> TYPE: PRT
<213> ORGANISM: Homo sapiens

<400> SEQUENCE: 192

Ala Leu Tyr Val Gln Ala Pro Thr Val
1               5

<210> SEQ ID NO 193
<211> LENGTH: 10
<212> TYPE: PRT
<213> ORGANISM: Homo sapiens

<400> SEQUENCE: 193

Lys Leu Ile Tyr Lys Asp Leu Val Ser Val
1               5                   10

<210> SEQ ID NO 194
<211> LENGTH: 9
<212> TYPE: PRT
<213> ORGANISM: Homo sapiens

<400> SEQUENCE: 194

Ile Leu Gln Asp Gly Gln Phe Leu Val
1               5

<210> SEQ ID NO 195
<211> LENGTH: 9
<212> TYPE: PRT
<213> ORGANISM: Homo sapiens

<400> SEQUENCE: 195

Ser Leu Leu Asp Tyr Glu Val Ser Ile
1               5

<210> SEQ ID NO 196
<211> LENGTH: 9
<212> TYPE: PRT
<213> ORGANISM: Homo sapiens

<400> SEQUENCE: 196

Leu Leu Gly Asp Ser Ser Phe Phe Leu
1               5

<210> SEQ ID NO 197
<211> LENGTH: 10
<212> TYPE: PRT
<213> ORGANISM: Homo sapiens

<400> SEQUENCE: 197

Val Ile Phe Glu Gly Glu Pro Met Tyr Leu
1               5                   10

<210> SEQ ID NO 198
<211> LENGTH: 9
<212> TYPE: PRT
<213> ORGANISM: Homo sapiens

<400> SEQUENCE: 198

Ala Leu Ser Tyr Ile Leu Pro Tyr Leu
1               5

<210> SEQ ID NO 199
<211> LENGTH: 9
<212> TYPE: PRT
<213> ORGANISM: Homo sapiens -continued

```
<400> SEQUENCE: 199

Phe Leu Phe Val Asp Pro Glu Leu Val
1               5

<210> SEQ ID NO 200
<211> LENGTH: 11
<212> TYPE: PRT
<213> ORGANISM: Homo sapiens

<400> SEQUENCE: 200

Ser Glu Trp Gly Ser Pro His Ala Ala Val Pro
1               5                   10

<210> SEQ ID NO 201
<211> LENGTH: 9
<212> TYPE: PRT
<213> ORGANISM: Homo sapiens

<400> SEQUENCE: 201

Ala Leu Ser Glu Leu Glu Arg Val Leu
1               5

<210> SEQ ID NO 202
<211> LENGTH: 9
<212> TYPE: PRT
<213> ORGANISM: Homo sapiens

<400> SEQUENCE: 202

Ser Leu Phe Glu Ser Leu Glu Tyr Leu
1               5

<210> SEQ ID NO 203
<211> LENGTH: 9
<212> TYPE: PRT
<213> ORGANISM: Homo sapiens

<400> SEQUENCE: 203

Lys Val Leu Glu Tyr Val Ile Lys Val
1               5

<210> SEQ ID NO 204
<211> LENGTH: 10
<212> TYPE: PRT
<213> ORGANISM: Homo sapiens

<400> SEQUENCE: 204

Val Leu Leu Asn Glu Ile Leu Glu Gln Val
1               5                   10

<210> SEQ ID NO 205
<211> LENGTH: 9
<212> TYPE: PRT
<213> ORGANISM: Homo sapiens

<400> SEQUENCE: 205

Ser Leu Leu Asn Gln Pro Lys Ala Val
1               5

<210> SEQ ID NO 206
<211> LENGTH: 9
<212> TYPE: PRT
<213> ORGANISM: Homo sapiens

<400> SEQUENCE: 206
```

Lys Met Ser Glu Leu Gln Thr Tyr Val
1               5

<210> SEQ ID NO 207
<211> LENGTH: 11
<212> TYPE: PRT
<213> ORGANISM: Homo sapiens

<400> SEQUENCE: 207

Ala Leu Leu Glu Gln Thr Gly Asp Met Ser Leu
1               5                   10

<210> SEQ ID NO 208
<211> LENGTH: 11
<212> TYPE: PRT
<213> ORGANISM: Homo sapiens

<400> SEQUENCE: 208

Val Ile Ile Lys Gly Leu Glu Glu Ile Thr Val
1               5                   10

<210> SEQ ID NO 209
<211> LENGTH: 9
<212> TYPE: PRT
<213> ORGANISM: Homo sapiens

<400> SEQUENCE: 209

Lys Gln Phe Glu Gly Thr Val Glu Ile
1               5

<210> SEQ ID NO 210
<211> LENGTH: 9
<212> TYPE: PRT
<213> ORGANISM: Homo sapiens

<400> SEQUENCE: 210

Lys Leu Gln Glu Glu Ile Pro Val Leu
1               5

<210> SEQ ID NO 211
<211> LENGTH: 9
<212> TYPE: PRT
<213> ORGANISM: Homo sapiens

<400> SEQUENCE: 211

Gly Leu Ala Glu Phe Gln Glu Asn Val
1               5

<210> SEQ ID NO 212
<211> LENGTH: 9
<212> TYPE: PRT
<213> ORGANISM: Homo sapiens

<400> SEQUENCE: 212

Asn Val Ala Glu Ile Val Ile His Ile
1               5

<210> SEQ ID NO 213
<211> LENGTH: 9
<212> TYPE: PRT
<213> ORGANISM: Homo sapiens

<400> SEQUENCE: 213

Ala Leu Ala Gly Ile Val Thr Asn Val

```
<210> SEQ ID NO 214
<211> LENGTH: 12
<212> TYPE: PRT
<213> ORGANISM: Homo sapiens

<400> SEQUENCE: 214

Asn Leu Leu Ile Asp Asp Lys Gly Thr Ile Lys Leu
1               5                   10

<210> SEQ ID NO 215
<211> LENGTH: 10
<212> TYPE: PRT
<213> ORGANISM: Homo sapiens

<400> SEQUENCE: 215

Val Leu Met Gln Asp Ser Arg Leu Tyr Leu
1               5                   10

<210> SEQ ID NO 216
<211> LENGTH: 9
<212> TYPE: PRT
<213> ORGANISM: Homo sapiens

<400> SEQUENCE: 216

Lys Val Leu Glu His Val Val Arg Val
1               5

<210> SEQ ID NO 217
<211> LENGTH: 9
<212> TYPE: PRT
<213> ORGANISM: Homo sapiens

<400> SEQUENCE: 217

Leu Leu Trp Gly Asn Leu Pro Glu Ile
1               5

<210> SEQ ID NO 218
<211> LENGTH: 9
<212> TYPE: PRT
<213> ORGANISM: Homo sapiens

<400> SEQUENCE: 218

Ser Leu Met Glu Lys Asn Gln Ser Leu
1               5

<210> SEQ ID NO 219
<211> LENGTH: 9
<212> TYPE: PRT
<213> ORGANISM: Homo sapiens

<400> SEQUENCE: 219

Lys Leu Leu Ala Val Ile His Glu Leu
1               5

<210> SEQ ID NO 220
<211> LENGTH: 10
<212> TYPE: PRT
<213> ORGANISM: Homo sapiens

<400> SEQUENCE: 220

Ala Leu Gly Asp Lys Phe Leu Leu Arg Val
1               5                   10
```

-continued

```
<210> SEQ ID NO 221
<211> LENGTH: 11
<212> TYPE: PRT
<213> ORGANISM: Homo sapiens

<400> SEQUENCE: 221

Phe Leu Met Lys Asn Ser Asp Leu Tyr Gly Ala
1               5                   10

<210> SEQ ID NO 222
<211> LENGTH: 10
<212> TYPE: PRT
<213> ORGANISM: Homo sapiens

<400> SEQUENCE: 222

Lys Leu Ile Asp His Gln Gly Leu Tyr Leu
1               5                   10

<210> SEQ ID NO 223
<211> LENGTH: 12
<212> TYPE: PRT
<213> ORGANISM: Homo sapiens

<400> SEQUENCE: 223

Gly Pro Gly Ile Phe Pro Pro Pro Pro Gln Pro
1               5                   10

<210> SEQ ID NO 224
<211> LENGTH: 9
<212> TYPE: PRT
<213> ORGANISM: Homo sapiens

<400> SEQUENCE: 224

Ala Leu Asn Glu Ser Leu Val Glu Cys
1               5

<210> SEQ ID NO 225
<211> LENGTH: 9
<212> TYPE: PRT
<213> ORGANISM: Homo sapiens

<400> SEQUENCE: 225

Gly Leu Ala Ala Leu Ala Val His Leu
1               5

<210> SEQ ID NO 226
<211> LENGTH: 9
<212> TYPE: PRT
<213> ORGANISM: Homo sapiens

<400> SEQUENCE: 226

Leu Leu Leu Glu Ala Val Trp His Leu
1               5

<210> SEQ ID NO 227
<211> LENGTH: 9
<212> TYPE: PRT
<213> ORGANISM: Homo sapiens

<400> SEQUENCE: 227

Ser Ile Ile Glu Tyr Leu Pro Thr Leu
1               5

<210> SEQ ID NO 228
```

```
<211> LENGTH: 9
<212> TYPE: PRT
<213> ORGANISM: Homo sapiens

<400> SEQUENCE: 228

Thr Leu His Asp Gln Val His Leu Leu
1               5

<210> SEQ ID NO 229
<211> LENGTH: 9
<212> TYPE: PRT
<213> ORGANISM: Homo sapiens

<400> SEQUENCE: 229

Ser Leu Leu Met Trp Ile Thr Gln Cys
1               5

<210> SEQ ID NO 230
<211> LENGTH: 11
<212> TYPE: PRT
<213> ORGANISM: Homo sapiens

<400> SEQUENCE: 230

Phe Leu Leu Asp Lys Pro Gln Asp Leu Ser Ile
1               5                   10

<210> SEQ ID NO 231
<211> LENGTH: 10
<212> TYPE: PRT
<213> ORGANISM: Homo sapiens

<400> SEQUENCE: 231

Tyr Leu Leu Asp Met Pro Leu Trp Tyr Leu
1               5                   10

<210> SEQ ID NO 232
<211> LENGTH: 9
<212> TYPE: PRT
<213> ORGANISM: Homo sapiens

<400> SEQUENCE: 232

Gly Leu Leu Asp Cys Pro Ile Phe Leu
1               5

<210> SEQ ID NO 233
<211> LENGTH: 9
<212> TYPE: PRT
<213> ORGANISM: Homo sapiens

<400> SEQUENCE: 233

Val Leu Ile Glu Tyr Asn Phe Ser Ile
1               5

<210> SEQ ID NO 234
<211> LENGTH: 11
<212> TYPE: PRT
<213> ORGANISM: Homo sapiens

<400> SEQUENCE: 234

Thr Leu Tyr Asn Pro Glu Arg Thr Ile Thr Val
1               5                   10

<210> SEQ ID NO 235
<211> LENGTH: 9
<212> TYPE: PRT
```

```
<213> ORGANISM: Homo sapiens

<400> SEQUENCE: 235

Ala Val Pro Pro Pro Ser Ser Val
1               5

<210> SEQ ID NO 236
<211> LENGTH: 9
<212> TYPE: PRT
<213> ORGANISM: Homo sapiens

<400> SEQUENCE: 236

Lys Leu Gln Glu Glu Leu Asn Lys Val
1               5

<210> SEQ ID NO 237
<211> LENGTH: 11
<212> TYPE: PRT
<213> ORGANISM: Homo sapiens

<400> SEQUENCE: 237

Lys Leu Met Asp Pro Gly Ser Leu Pro Pro Leu
1               5                   10

<210> SEQ ID NO 238
<211> LENGTH: 9
<212> TYPE: PRT
<213> ORGANISM: Homo sapiens

<400> SEQUENCE: 238

Ala Leu Ile Val Ser Leu Pro Tyr Leu
1               5

<210> SEQ ID NO 239
<211> LENGTH: 9
<212> TYPE: PRT
<213> ORGANISM: Homo sapiens

<400> SEQUENCE: 239

Phe Leu Leu Asp Gly Ser Ala Asn Val
1               5

<210> SEQ ID NO 240
<211> LENGTH: 10
<212> TYPE: PRT
<213> ORGANISM: Homo sapiens

<400> SEQUENCE: 240

Ala Leu Asp Pro Ser Gly Asn Gln Leu Ile
1               5                   10

<210> SEQ ID NO 241
<211> LENGTH: 9
<212> TYPE: PRT
<213> ORGANISM: Homo sapiens

<400> SEQUENCE: 241

Ile Leu Ile Lys His Leu Val Lys Val
1               5

<210> SEQ ID NO 242
<211> LENGTH: 9
<212> TYPE: PRT
<213> ORGANISM: Homo sapiens
```

```
<400> SEQUENCE: 242

Val Leu Leu Asp Thr Ile Leu Gln Leu
1               5

<210> SEQ ID NO 243
<211> LENGTH: 9
<212> TYPE: PRT
<213> ORGANISM: Homo sapiens

<400> SEQUENCE: 243

His Leu Ile Ala Glu Ile His Thr Ala
1               5

<210> SEQ ID NO 244
<211> LENGTH: 9
<212> TYPE: PRT
<213> ORGANISM: Homo sapiens

<400> SEQUENCE: 244

Ser Met Asn Gly Gly Val Phe Ala Val
1               5

<210> SEQ ID NO 245
<211> LENGTH: 9
<212> TYPE: PRT
<213> ORGANISM: Homo sapiens

<400> SEQUENCE: 245

Met Leu Ala Glu Lys Leu Leu Gln Ala
1               5

<210> SEQ ID NO 246
<211> LENGTH: 9
<212> TYPE: PRT
<213> ORGANISM: Homo sapiens

<400> SEQUENCE: 246

Tyr Met Leu Asp Ile Phe His Glu Val
1               5

<210> SEQ ID NO 247
<211> LENGTH: 11
<212> TYPE: PRT
<213> ORGANISM: Homo sapiens

<400> SEQUENCE: 247

Ala Leu Trp Leu Pro Thr Asp Ser Ala Thr Val
1               5                   10

<210> SEQ ID NO 248
<211> LENGTH: 9
<212> TYPE: PRT
<213> ORGANISM: Homo sapiens

<400> SEQUENCE: 248

Gly Leu Ala Ser Arg Ile Leu Asp Ala
1               5

<210> SEQ ID NO 249
<211> LENGTH: 9
<212> TYPE: PRT
<213> ORGANISM: Homo sapiens

<400> SEQUENCE: 249
```

```
Ala Leu Ser Val Leu Arg Leu Ala Leu
1               5

<210> SEQ ID NO 250
<211> LENGTH: 9
<212> TYPE: PRT
<213> ORGANISM: Homo sapiens

<400> SEQUENCE: 250

Ser Tyr Val Lys Val Leu His His Leu
1               5

<210> SEQ ID NO 251
<211> LENGTH: 9
<212> TYPE: PRT
<213> ORGANISM: Homo sapiens

<400> SEQUENCE: 251

Val Tyr Leu Pro Lys Ile Pro Ser Trp
1               5

<210> SEQ ID NO 252
<211> LENGTH: 9
<212> TYPE: PRT
<213> ORGANISM: Homo sapiens

<400> SEQUENCE: 252

Asn Tyr Glu Asp His Phe Pro Leu Leu
1               5

<210> SEQ ID NO 253
<211> LENGTH: 9
<212> TYPE: PRT
<213> ORGANISM: Homo sapiens

<400> SEQUENCE: 253

Val Tyr Ile Ala Glu Leu Glu Lys Ile
1               5

<210> SEQ ID NO 254
<211> LENGTH: 12
<212> TYPE: PRT
<213> ORGANISM: Homo sapiens

<400> SEQUENCE: 254

Val His Phe Glu Asp Thr Gly Lys Thr Leu Leu Phe
1               5                   10

<210> SEQ ID NO 255
<211> LENGTH: 9
<212> TYPE: PRT
<213> ORGANISM: Homo sapiens

<400> SEQUENCE: 255

Val Leu Ser Pro Phe Ile Leu Thr Leu
1               5

<210> SEQ ID NO 256
<211> LENGTH: 9
<212> TYPE: PRT
<213> ORGANISM: Homo sapiens

<400> SEQUENCE: 256

His Leu Leu Glu Gly Ser Val Gly Val
1               5
```

```
<210> SEQ ID NO 257
<211> LENGTH: 4
<212> TYPE: PRT
<213> ORGANISM: Artificial Sequence
<220> FEATURE:
<223> OTHER INFORMATION: Linker peptide

<400> SEQUENCE: 257

Gly Gly Gly Ser
1

<210> SEQ ID NO 258
<211> LENGTH: 5
<212> TYPE: PRT
<213> ORGANISM: Artificial Sequence
<220> FEATURE:
<223> OTHER INFORMATION: Linker peptide

<400> SEQUENCE: 258

Gly Gly Gly Gly Ser
1               5

<210> SEQ ID NO 259
<211> LENGTH: 5
<212> TYPE: PRT
<213> ORGANISM: Artificial Sequence
<220> FEATURE:
<223> OTHER INFORMATION: Linker peptide

<400> SEQUENCE: 259

Gly Gly Ser Gly Gly
1               5

<210> SEQ ID NO 260
<211> LENGTH: 5
<212> TYPE: PRT
<213> ORGANISM: Artificial Sequence
<220> FEATURE:
<223> OTHER INFORMATION: Linker peptide

<400> SEQUENCE: 260

Thr Val Ala Ala Pro
1               5

<210> SEQ ID NO 261
<211> LENGTH: 5
<212> TYPE: PRT
<213> ORGANISM: Artificial Sequence
<220> FEATURE:
<223> OTHER INFORMATION: Linker peptide

<400> SEQUENCE: 261

Thr Val Leu Arg Thr
1               5

<210> SEQ ID NO 262
<211> LENGTH: 6
<212> TYPE: PRT
<213> ORGANISM: Artificial Sequence
<220> FEATURE:
<223> OTHER INFORMATION: Linker peptide

<400> SEQUENCE: 262

Thr Val Ser Ser Ala Ser
1               5
```

WPRE MUTANT CONSTRUCTS, COMPOSITIONS, AND METHODS THEREOF

CROSS-REFERENCE TO RELATED APPLICATIONS

This Non-Provisional patent application claims priority to U.S. Provisional Patent Application No. 62/988,202, filed 11 Mar. 2020. This application is incorporated by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "3000011-017001_Sequence_Listing_ST25.txt" created on 10 Mar. 2021, and 247,701 bytes in size) is submitted concurrently with the instant application, and the entire contents of the Sequence Listing are incorporated herein by reference.

BACKGROUND

1. Field

The present disclosure relates to a vector comprising a mutated post-transcriptional regulatory element. In particular, the present invention relates to mutated WPRE sequences that can efficiently express nucleotides of interest in a retroviral vector system. The present invention also relates to methods of delivering and expressing nucleotides of interest in a target cell.

2. Background

Retroviral vectors, such as lentiviral vectors, have been proposed as a delivery system for, inter alia, the transfer of a nucleotide of interest to one or more sites of interest.

One shortcoming of retroviral vectors, whether based on retroviruses or lentiviruses, is their frequent inability to generate high levels of gene expression, particularly in vivo. Many steps, both transcriptional and post-transcriptional, are involved in regulating gene expression. Therefore, it is possible to enhance expression of transgenes delivered by retroviral vectors through the addition of elements known to post-transcriptionally increase gene expression. An example is the inclusion of introns within the expression cassette (Choi, T. et al, (1991) Mol. Cell. Biol. 9:3070-3074). Many gene transfer experiments, performed both in vitro and in vivo, have demonstrated that the presence of an intron can facilitate gene expression.

Other types of elements can also be used to stimulate heterologous gene expression post-transcriptionally. These elements, unlike introns, are advantageous in that they do not require splicing events. For instance, previous studies have suggested that the hepatitis B virus (HBV) post-transcriptional regulatory element (PRE) and an intron are functionally equivalent (Huang, Z. M. and Yen, T. S. (1995) Mol. Cell. Biol. 15: 3864-3869). Woodchuck hepatitis virus (WHV), a close relative of HBV, also harbors a PRE (hereinafter referred to as WPRE; see U.S. Pat. Nos. 6,136,597 and 6,287,814). The WPRE has been shown to be more active than its HBV counterpart, correlating to the presence of additional cis-acting sequences not found in the HBV PRE. Insertion of the WPRE in lentiviral vectors resulted in significant stimulation of expression of reporter genes such as luciferase and green fluorescent protein (GFP) in a variety of cells spanning different species (Zufferey, R. et al. (1999) J. Virol 73: 2886-2892). Stimulation was irrespective of the cycling status of transduced cells.

The WPRE contains three cis-acting sequences important for its function in enhancing expression levels. However, it also contains a fragment of approximately 180 base pairs (bp) comprising the 5' end of the WHV X protein open reading frame, together with its associated promoter. The full-length X protein has been implicated in tumorigenesis (Flajolet, M. et al. (1998) J. Virol. 72: 6175-6180). Cis-activation of myc family oncogenes due to the insertion of viral DNA into the host genome is known to be a key mechanism of WHV-mediated carcinogenesis (Buendia, M. A. (1994) In C. Brechot (ed.), Primary liver cancer: etiological and progression factors, p. 211-224: CRC Press, Boca Raton, Fla.; Fourel, G. (1994) In F. Tronche and M. Yaniv (ed.), Liver gene expression, p. 297-343; R. G. Landes Company, Austin, Tex.). The tumorigenic potential of the WHV X protein has raised concerns regarding inclusion of the WPRE in retroviral vectors, in particular for in vivo applications.

Previous studies have suggested that mutation of the X protein open reading frame (ORF) within the WPRE reduces tumorigenic activity of the X protein, thereby improving its safety profile for inclusion in retroviral vectors (see, e.g., U.S. Pat. No. 7,419,829; Donello, J. E. et al. (1998) J. Virol. 72(6): 5085-5092; Schambach, A. et al. (2006) Gene Ther. 13: 641-645; Zanta-Boussif, M. A. et al. (2009) Gene Ther. 16: 605-619; Ou L. et al. (2016) Mol. Gen. Metab. Rep. 8: 87-93). However, inconsistent effects on post-transcriptional stimulation of heterologous gene expression have been seen in the various mutant WPREs. Generally, the greater the extent of mutations introduced into the WPRE, the less effective the mutant WPRE is in stimulating post-transcriptional heterologous gene expression.

Thus, there remains a need for safe and effective WPREs for use in retroviral vectors.

BRIEF SUMMARY

In an aspect, the present application relates to mutated WPRE sequences for use in, for example, retroviral vectors in which WHV X protein expression is attenuated or absent. In some embodiments, start codons of any open reading frame (ORF) within WPRE are mutated, the WHV X protein promoter is deleted, and the WHV X protein OFR is deleted. In some embodiments, the WHV X protein promoter and WHV X protein start codon is mutated.

In some embodiments, the mutated WPRE sequence contains a mutation at one or more of the start codons corresponding to nucleotide positions 106-108, 152-154, 245-247, 272-274, 283-285, 362-364, and 603-605 within the WT WPRE nucleotide sequence according to SEQ ID NO: 1. In some embodiments, the mutated WPRE sequence contains a mutation at one or more of the start codons corresponding to nucleotide positions 70-72, 108-110, 121-123, 138-140, 187-189, and 428-430 within the WT WPRE nucleotide sequence according to SEQ ID NO: 2.

The start codon(s) may be mutated at one, two, or all three positions within the one or more start codons. If more than one start codon is mutated, each start codon mutation may be independent of the others. In other words, each start codon mutated within the WPRE need not be mutated in an identical manner. In some embodiments, each of the one or more start codon(s) is mutated at one position within the start codon(s). For example, the first nucleotide of the start codon may be mutated from "A" to "C", "G", or "T"; or the second nucleotide of the start codon may be mutated from "T" to "A", "C", or "G", or the third nucleotide of the start codon may be mutated from "G" to "A", "C", or "T". In some embodiments, one or more of the start codon(s) is mutated from "ATG" to "TTG". In some embodiments, each of the one or more start codon(s) is mutated from "ATG" to "TTG".

In some embodiments, the mutant WPRE sequence is selected from SEQ ID NO: 3 and SEQ ID NO: 4.

The present application also provides vectors, such as retroviral or lentiviral vectors, comprising the mutant WPREs of the invention. Such vectors can be used in functional genomics, drug discovery, target validation, protein production (e.g., therapeutic proteins, vaccines, monoclonal antibodies), gene therapy, and therapeutic treatments, such as in gene delivery systems for adaptive cellular therapy.

In some aspects, lentiviral transduction vectors, and constructs for their manufacture, are provided which can be used to introduce expressible nucleotide sequences of interest (NOI) into host cells. A lentiviral transduction vector is an enveloped virion particle that contains an expressible nucleotide sequence, and which is capable of penetrating a target host cell, thereby carrying the expressible sequence into the cell. The enveloped particle is preferably pseudotyped with an engineered or native viral envelope protein from another viral species, including non-lentiviruses, which alters the host range and infectivity of the native lentivirus. As described in more detail below, the transduction vectors can be utilized in a wide range of applications, including, e.g., for protein production (including vaccine production), for gene therapy, to deliver therapeutic polypeptides, to deliver siRNA, ribozymes, anti-sense, and other functional polynucleotides, etc. Such transduction vectors have the ability to carry single or multiple genes, and to include inhibitory sequences (e.g., RNAi or antisense).

In some aspects, the vector comprises more than one NOI. Such vectors can be used, for example, to produce multimeric proteins in a host cell. In some aspects, the vector comprises a first nucleotide sequence S1 encoding a protein Z1 and a second nucleotide sequence S2 encoding a protein Z2, in which Z1 and Z2 form a dimer. The vector may further comprise a third nucleotide sequence S3 encoding a protein Y1, and a fourth nucleotide sequence S4 encoding a protein Y2, in which Y1 and Y2 form a second dimer.

In another aspect, the vector may further include a fifth nucleotide sequence S5 encoding a 2A peptide and a sixth nucleotide sequence S6 encoding a linker peptide, wherein S5 and S6 are positioned between 51 and S2, 51 and S3, 51 and S4, S2 and S3, S2 and S4, and/or S3 and S4.

In some aspects, the 2A peptide may be selected from P2A (SEQ ID NO: 6), T2A (SEQ ID NO: 7), E2A (SEQ ID NO: 8), or F2A (SEQ ID NO: 9).

In some aspects, the linker peptide is any peptide having a length of 3 to 10 amino acid length. In some aspects, the linker peptide may be GSG or SGSG (SEQ ID NO: 5).

In another aspect, the vector may further include a seventh nucleotide sequence S7 encoding a furin peptide (SEQ ID NO: 10) positioned between 51 and S2, 51 and S3, 51 and S4, S2 and S3, S2 and S4, and/or S3 and S4.

In another aspect, the vector may further include a promoter sequence that controls the transcription of 51, S2, S3, S4, S5, S6 and/or S7, wherein the promoter sequence is selected from cytomegalovirus (CMV) promoter, phosphoglycerate kinase (PGK) promoter, myelin basic protein (MBP) promoter, glial fibrillary acidic protein (GFAP) promoter, modified MoMuLV LTR containing myeloproliferative sarcoma virus enhancer (MNDU3), Ubiqitin C promoter, EF-1 alpha promoter, or Murine Stem Cell Virus (MSCV) promoter.

In some aspects, the first dimer Z1Z2 may be selected from SEQ ID NO: 13 and 14, 15 and 16, 17 and 18, 19 and 20, 21 and 22, 23 and 24, 25 and 26, 25 and 92, 91 and 92, 27 and 28, 29 and 30, 31 and 32, 33 and 34, 35 and 36, 37 and 38, 39 and 40, 41 and 42, 43 and 44, 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, or 89 and 90.

In some aspects, the second dimer Y1Y2 is set forth in SEQ ID NO: 11 and 12.

In another aspect, the viral vector is selected from adenoviruses, poxviruses, alphaviruses, arenaviruses, flaviruses, rhabdoviruses, retroviruses, lentiviruses, herpesviruses, paramyxoviruses, or picornaviruses.

In another aspect, the vector is pseudotyped with an envelope protein of a virus selected from the native feline endogenous virus (RD114), a chimeric version of RD114 (RD114TR), gibbon ape leukemia virus (GALV), a chimeric version of GALV (GALV-TR), amphotropic murine leukemia virus (MLV 4070A), baculovirus (GP64), vesicular stomatitis virus (VSV-G), fowl plague virus (FPV), Ebola virus (EboV), baboon retroviral envelope glycoprotein (BaEV), or lymphocytic choriomeningitis virus (LCMV).

In one aspect, the present disclosure relates to a method of preparing T cells for immunotherapy including isolating T cells from a blood sample of a human subject, activating the isolated T cells in the presence of an aminobisphosphonate, transducing the activated T cells with the vector described herein, and expanding the transduced T cells.

In another aspect, the T cells may be isolated from a leukapheresis human sample.

In another aspect, the aminobisphosphonate may be selected from pamidronic acid, alendronic acid, zoledronic acid, risedronic acid, ibandronic acid, incadronic acid, a salt thereof and/or a hydrate thereof.

In another aspect, the T cells can be activated with OKT3 and anti-CD28.

In another aspect, the activating may be further in the presence of human recombinant interleukin 2 (IL-2), human recombinant interleukin 15 (IL-15), human recombinant interleukin 7 (IL-7).

In another aspect, the expanding may be in the presence of IL-2 and IL-15 or IL-15 and IL-7.

In another aspect, the T cells may be γδ T cells or αβ cells.

In another aspect, the first dimer Z1Z2 and the second dimer Y1Y2 are co-expressed on the surface of the expanded T cells.

In another aspect, the present disclosure relates to a population of expanded T cells prepared by the method of the above aspects.

In some aspects, the composition further includes an adjuvant.

In some aspects, the adjuvant is selected from one or more of anti-CD40 antibody, imiquimod, resiquimod, GM-CSF, cyclophosphamide, sunitinib, bevacizumab, atezolizuma, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

In one aspect, the present disclosure relates to a method of treating a patient who has cancer, comprising administering to the patient a composition comprising the population of expanded T cells described herein, in which the T cells kill cancer cells that present a peptide in a complex with an MHC molecule on the surface, wherein the peptide is selected from any of SEQ ID NO: 99-256, in which the cancer is selected from the group consisting of non-small cell lung cancer, small cell lung cancer, melanoma, liver cancer, breast cancer, uterine cancer, Merkel cell carcinoma, pancreatic cancer, gallbladder cancer, bile duct cancer, colorectal cancer, urinary bladder cancer, kidney cancer, leukemia, ovarian cancer, esophageal cancer, brain cancer, gastric cancer, and prostate cancer.

In one aspect, the present disclosure relates to T cells described herein or compositions comprising the population of expanded T cells described herein for use in the treatment of cancer, in which the cancer is selected from the group consisting of non-small cell lung cancer, small cell lung cancer, melanoma, liver cancer, breast cancer, uterine cancer, Merkel cell carcinoma, pancreatic cancer, gallbladder cancer, bile duct cancer, colorectal cancer, urinary bladder cancer, kidney cancer, leukemia, ovarian cancer, esophageal cancer, brain cancer, gastric cancer, and prostate cancer.

In a further aspect, the present disclosure refers to the use of T cells described herein or compositions comprising T cells described herein for the manufacture of a medicament.

In a further aspect, the present disclosure refers to the use of T cells described herein or compositions comprising T cells described herein for the manufacture of a medicament for the treatment of cancer, in particular for the herein above-mentioned cancers.

In one aspect, the present disclosure relates to a method of eliciting an immune response in a patient who has cancer, comprising administering to the patient a composition comprising the population of expanded T cells described herein, in which the T cells kill cancer cells that present a peptide in a complex with an MHC molecule on the surface, wherein the peptide is selected from any of SEQ ID NO: 99-256, and in which the cancer is selected from the group consisting of non-small cell lung cancer, small cell lung cancer, melanoma, liver cancer, breast cancer, uterine cancer, Merkel cell carcinoma, pancreatic cancer, gallbladder cancer, bile duct cancer, colorectal cancer, urinary bladder cancer, kidney cancer, leukemia, ovarian cancer, esophageal cancer, brain cancer, gastric cancer, and prostate cancer.

In another aspect, the immune response comprises a cytotoxic T cell response.

Finally, the invention also provides kits comprising at least one vector of the invention. In one embodiment, the kit comprises at least one vector of the invention, optionally packaging material, and optionally a label or packaging insert contained within the packaging material.

In an aspect, the present disclosure relates to a method of preparing T cells for immunotherapy, including isolating T cells from a blood sample of a human subject, activating the isolated T cells in the presence of a statin, transducing the activated T cells with the vector of the present disclosure, in which the vector may be pseudotyped with any envelope protein described herein including vesicular stomatitis virus (VSV-G) and RD114TR, and expanding the transduced T cells.

In another aspect, the T cells may include CD4+ T cells, CD8+ T cells, γδ T cells, and/or natural killer T cells.

In another aspect, statin may be selected from atorvastatin, cerivastatin, dalvastatin, fluindostatin, fluvastatin, mevastatin, pravastatin, simvastatin, velostatin, and rosuvastatin.

BRIEF DESCRIPTION OF THE DRAWINGS

FIG. 1 shows an alignment of a wild-type (WT) WPRE derived from the woodchuck hepatitis virus genome provided in GenBank Accession No. J02440.1 (SEQ ID NO: 1), a WT WPRE derived from the woodchuck hepatitis B virus (strain WHV8) provided in GenBank Accession No. J04514.1 (SEQ ID NO: 2), a mutant WPRE in which the X protein promoter and start codon is mutated (SEQ ID NO: 4), and a mutant WPRE in which multiple start codons within the WPRE are mutated and both the X protein promoter and ORF are deleted (SEQ ID NO: 3).

FIG. 2 shows an alignment of a wild-type (WT) WPRE derived from the woodchuck hepatitis virus genome provided in GenBank Accession No. J02440.1 (SEQ ID NO: 1) and a mutant WPRE in which multiple start codons within the WPRE are mutated and both the X protein promoter and ORF are deleted (SEQ ID NO: 3). The X protein promoter is underlined and the X protein start codon is italicized.

FIG. 4 shows exemplary lentiviral constructs in accordance with some embodiments of the present disclosure.

DETAILED DESCRIPTION

Figure 3:
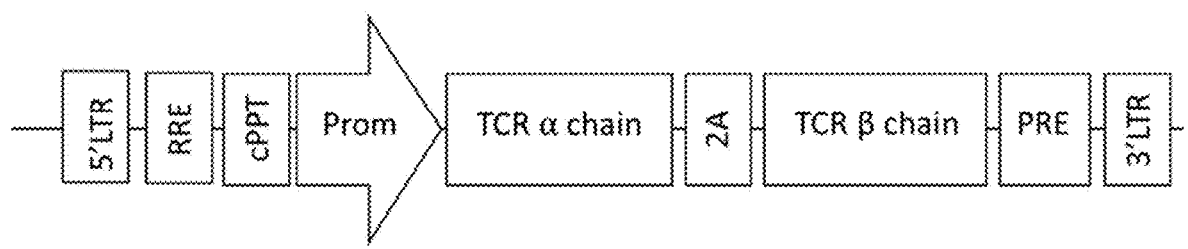
FIG. 3 shows a schematic diagram of vector constructs in accordance with some embodiments of the present disclosure.

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

As used herein, the term "operably linked" means that the components described are in a relationship permitting them to function in their intended manner.

As used herein, the term "self-cleaving 2A peptide" refers to relatively short peptides (of the order of 20 amino acids long, depending on the virus of origin) acting co-translationally, by preventing the formation of a normal peptide bond between the glycine and last proline, resulting in the ribosome skipping to the next codon, and the nascent peptide cleaving between the Gly and Pro. After cleavage, the short 2A peptide remains fused to the C-terminus of the 'upstream' protein, while the proline is added to the N-terminus of the 'downstream' protein. Self-cleaving 2A peptide may be selected from porcine teschovirus-1 (P2A), equine rhinitis A virus (E2A), Thosea asigna virus (T2A), foot-and-mouth disease virus (F2A), or any combination thereof (see, e.g., Kim et al., PLOS One 6:e18556, 2011, the content of which including 2A nucleic acid and amino acid sequences are incorporated herein by reference in their entireties). By adding the linker sequences (such as GSG or SGSG (SEQ ID NO: 5)) before the self-cleaving 2A sequence, this may enable efficient synthesis of biologically active proteins, e.g., TCRs.

As used herein, the term "promoter" refers to a regulatory region of DNA generally located upstream (towards the 5' region of the sense strand) of a gene that allows transcription of the gene. The promoter contains specific DNA sequences and response elements that are recognized by proteins known as transcription factors. These factors bind to the promoter sequences, recruiting RNA polymerase, the enzyme that synthesizes the RNA from the coding region of the gene. For example, the promoter sequence used herein may be selected from cytomegalovirus (CMV) promoter, phosphoglycerate kinase (PGK) promoter, myelin basic protein (MBP) promoter, glial fibrillary acidic protein (GFAP) promoter, modified MoMuLV LTR containing myeloproliferative sarcoma virus enhancer (MNDU3), Ubiqitin C promoter, EF-1 alpha promoter, or Murine Stem Cell Virus (MSCV) promoter.

As used herein, the term "cistron" refers to a section of the DNA molecule that specifies the formation of one polypeptide chain, i.e. coding for one polypeptide chain. For example, "bi-cistron" refers to two sections of the DNA molecule that specify the formation of two polypeptide chains, i.e. coding for two polypeptide chains; "tri-cistron" refers to three sections of the DNA molecule that specify the formation of three polypeptide chains, i.e. coding for three polypeptide chains; etc.

As used herein, the term "multi-cistronic RNA" or "multi-cistronic mRNA" refers to an RNA that contains the genetic information to translate to several proteins. In contrast, a mono-cistronic RNA contains the genetic information to translate only a single protein. In the context of the present disclosure, the multi-cistronic RNA transcribed from the lentivirus may be translated into translated to two proteins, for example, a TCRα chain and TCRβ chain.

As used herein, the term "arranged in tandem" refers to the arrangement of the genes contiguously, one following or behind the other, in a single file on a nucleic acid sequence. The genes are ligated together contiguously on a nucleic acid sequence, with the coding strands (sense strands) of each gene ligated together on a nucleic acid sequence.

As used herein, the term "sense strand" refers to the DNA strand of a gene that is translated or translatable into protein. When a gene is oriented in the "sense direction" with respect to the promoter in a nucleic acid sequence, the "sense strand" is located at the 5' end downstream of the promoter, wherein the first codon of the nucleic acid encoding the protein is proximal to the promoter and the last codon is distal from the promoter.

As used herein, the term "viral vector" refers to a nucleic acid vector construct that includes at least one element of viral origin and has the capacity to be packaged into a viral vector particle, and encodes at least an exogenous nucleic acid. The vector and/or particle can be utilized for the purpose of transferring any nucleic acids into cells either in vitro or in vivo. Numerous forms of viral vectors are known in the art. The term "virion" is used to refer to a single infective viral particle. "Viral vector", "viral vector particle" and "viral particle" also refer to a complete virus particle with its DNA or RNA core and protein coat as it exists outside the cell. For example, a viral vector may be selected from adenoviruses, poxviruses, alphaviruses, arenaviruses, flaviruses, rhabdoviruses, retroviruses, lentiviruses, herpesviruses, paramyxoviruses, or picornaviruses.

The terms "T cell" or "T lymphocyte" are art-recognized and are intended to include thymocytes, naïve T lymphocytes, immature T lymphocytes, mature T lymphocytes, resting T lymphocytes, or activated T lymphocytes. Illustrative populations of T cells suitable for use in particular embodiments include, but are not limited to, helper T cells (HTL; CD4+ T cell), a cytotoxic T cell (CTL; CD8+ T cell), CD4+CD8+ T cell, CD4−CD8− T cell, natural killer T cell, γδ T cells, or any other subset of T cells. Other illustrative populations of T cells suitable for use in particular embodiments include, but are not limited to, T cells expressing one or more of the following markers: CD3, CD4, CD8, CD27, CD28, CD45RA, CD45RO, CD62L, CD127, CD197, and HLA-DR and if desired, can be further isolated by positive or negative selection techniques.

The term "statin," "vastatin," or as used interchangeably herein "3-hydroxy-3-methylglutaryl coenzyme A (HMG-CoA) reductase inhibitor" refers to a pharmaceutical agent which inhibits the enzyme 3-hydroxy-3-methylglutaryl-coenzyme A (HMG-CoA) reductase. This enzyme is involved in the conversion of HMG-CoA to mevalonate, which is one of the steps in cholesterol biosynthesis. Such inhibition is readily determined according to standard assays well known to those skilled in the art.

Preferred statins which may be used in accordance with this present disclosure include atorvastatin, disclosed in U.S. Pat. No. 4,681,893; atorvastatin calcium, disclosed in U.S. Pat. No. 5,273,995; cerivastatin, disclosed in U.S. Pat. No. 5,502,199; dalvastatin, disclosed in U.S. Pat. No. 5,316,765; fluindostatin, disclosed in U.S. Pat. No. 4,915,954; fluvastatin, disclosed in U.S. Pat. No. 4,739,073; lovastatin, disclosed in U.S. Pat. No. 4,231,938; mevastatin, disclosed in U.S. Pat. No. 3,983,140; pravastatin, disclosed in U.S. Pat. No. 4,346,227; simvastatin, disclosed in U.S. Pat. No. 4,444,784; velostatin, disclosed in U.S. Pat. Nos. 4,448,784 and 4,450,171; and rosuvastatin, disclosed in U.S. Pat. Nos. 6,858,618 and 7,511,140. The contents of each of these patents are hereby incorporated by reference in their entireties. Preferred 3-hydroxy-3-methylglutaryl coenzyme A reductase inhibitors may include atorvastatin, atorvastatin calcium, also known as Liptor®, lovastatin, also known as Mevacor®, pravastatin, also known as Pravachol®, simvastatin, also known as Zocor®, and rosuvastatin.

Post-Transcriptional Regulatory Elements

The Woodchuck hepatitis virus (WHV) post-transcriptional regulatory element (WPRE) can enhance expression from a number of different vector types including lentiviral vectors (U.S. Pat. Nos. 6,136,597; 6,287,814; Zufferey, R., et al. (1999). J. Virol. 73:2886-92). Without wishing to be bound by theory, this enhancement is thought to be due to improved RNA processing at the post-transcriptional level, resulting in increased levels of nuclear transcripts. A two-fold increase in mRNA stability also contributes to this enhancement (Zufferey, R., et al. ibid). The level of enhancement of protein expression from transcripts containing the WPRE versus those without the WPRE has been reported to be around 2-to-5 fold, and correlates well with the increase in transcript levels. This has been demonstrated with a number of different transgenes (Zufferey, R., et al. ibid).

The WPRE contains three cis-acting sequences important for its function in enhancing expression levels. In addition, it contains a fragment of approximately 180 bp comprising the 5'-end of the WHVX protein ORF (full length ORF is 425 bp), together with its associated promoter. Translation from transcripts initiated from the X promoter results in formation of a protein representing the $NH_2$-terminal 60 amino acids of the X protein. This truncated X protein can promote tumorigenesis, particularly if the truncated X protein sequence is integrated into the host cell genome at specific loci (Balsano, C. et al., (1991) Biochem. Biophys Res. Commun. 176:985-92; Flajolet, M. et al. (1998) J. Virol. 72: 6175-80; Zheng, Y. W., et al. (1994) J. Biol. Chem. 269: 22593-8: Runkel, L., et al. (1993) Virology 197: 529-36). Therefore, expression of the truncated X protein could promote tumorigenesis if delivered to cells of interest, precluding safe use of wild-type WPRE sequences.

As used herein, the "X region" of the WPRE is defined as comprising at least the first 60-amino acids of the X protein ORF, including the translation initiation codon, and its associated promoter. An "X protein" is defined herein as a truncated X protein encoded by an X protein ORF as described herein.

The present inventors have introduced mutations into the WPRE sequence to prevent expression of an X protein. In some aspects, these mutations are introduced into one or more start codons occurring with the WPRE sequence. In some aspects, the X protein promoter and ORF are deleted from the WPRE sequence, resulting in a truncated WPRE sequence. In another aspect, the X protein promoter and X protein start codon is mutated.

As used herein, a "mutation" can comprise one or more nucleotide deletions, additions, or substitutions.

In some aspects, the mutated WPRE sequence contains a mutation at one or more of the start codons corresponding to nucleotide positions 106-108, 152-154, 245-247, 272-274, 283-285, 362-364, and 603-605 within the WT WPRE nucleotide sequence according to SEQ ID NO: 1. In some aspects, the mutated WPRE sequence contains a mutation at one, at two, at three, at four, at five, at six, or at all seven of the start codons corresponding to nucleotide positions 106-108, 152-154, 245-247, 272-274, 283-285, 362-364, and 603-605 within the WT WPRE nucleotide sequence according to SEQ ID NO: 1. In some aspects, the mutated WPRE sequence contains a mutation at each of the start codons corresponding to nucleotide positions 106-108, 152-154, 245-247, 272-274, 283-285, 362-364, and 603-605 within the WT WPRE nucleotide sequence according to SEQ ID NO: 1.

In another aspect, the mutated WPRE sequence contains a mutation at one or more of the start codons corresponding to nucleotide positions 70-72, 108-110, 121-123, 138-140, 187-189, and 428-430 within the WT WPRE nucleotide sequence according to SEQ ID NO: 2. In some aspects, the mutated WPRE sequence contains a mutation at one, at two, at three, at four, at five, or at all six of the start codons corresponding to nucleotide positions 70-72, 108-110, 121-123, 138-140, 187-189, and 428-430 within the WT WPRE nucleotide sequence according to SEQ ID NO: 2. In some aspects, the mutated WPRE sequence contains a mutation at each of the start codons corresponding to nucleotide positions 70-72, 108-110, 121-123, 138-140, 187-189, and 428-430 within the WT WPRE nucleotide sequence according to SEQ ID NO: 2.

The one or more start codon(s) may be mutated at one, two, or all three positions within the start codon. If more than one start codon is mutated, each start codon mutation may be independent of the others. In other words, each start codon mutated within the WPRE need not be mutated in an identical manner. In some embodiments, each of the one or more start codon(s) is mutated at one position within the start codon(s). For example, the first nucleotide of the start codon may be mutated from "A" to "C", "G", or "T"; or the second nucleotide of the start codon may be mutated from "T" to "A", "C", or "G", or the third nucleotide of the start codon may be mutated from "G" to "A", "C", or "T".

In some embodiments, each of the one or more start codon(s) is mutated at two or at all three positions within the start codon(s). For example, the first nucleotide of the start codon may be mutated from "A" to "C", "G", or "T"; and/or the second nucleotide of the start codon may be mutated from "T" to "A", "C", or "G", and/or the third nucleotide of the start codon may be mutated from "G" to "A", "C", or "T".

In some embodiments, one or more of the start codon(s) is mutated from "ATG" to "TTG". In some embodiments, each of the one or more start codon(s) is mutated from "ATG" to "TTG".

In an aspect, the mutant WPRE sequence is selected from SEQ ID NO: 3 and SEQ ID NO: 4. In another aspect, the mutant WPRE sequence is at least about 80%, at least about 85%, at least about 90%, at least about 95%, at least about 96%, at least about 97%, at least about 98%, or at least about 99% identical to SEQ ID NO: 3 or 4. In some aspects, the mutant WPRE sequence is 95% or more, 96% or more, 97% or more, 98% or more, 98% or more, 99% or more, or 100% identical to SEQ ID NO: 3, wherein the mutant WPRE sequence does not comprise "ATG". In some aspects, the mutant WPRE sequence is 95% or more, 96% or more, 97% or more, 98% or more, 98% or more, 99% or more, or 100% identical to SEQ ID NO: 3, wherein the mutant WPRE sequence does not comprise "ATG" except at nucleotide positions 65-67.

In some aspects, the WPRE sequence is 95% or more, 96% or more, 97% or more, 98% or more, 98% or more, 99% or more, or 100% identical to SEQ ID NO: 4, wherein nucleotide positions 413-417 are "ATCAT" and nucleotide positions 428-430 are not "ATG".

Retroviruses

The concept of using viral vectors for gene or cell therapy is recognized in, for example, Verma and Somia (1997) Nature 389:239-242, the content of which is incorporated by its entirety.

In an aspect, viruses refer to natural occurring viruses as well as artificial viruses. Viruses in accordance to some embodiments of the present disclosure may be either an enveloped or non-enveloped virus. Parvoviruses (such as AAVs) are examples of non-enveloped viruses. In a preferred embodiment, the viruses may be enveloped viruses. In preferred embodiments, the viruses may be retroviruses and in particular lentiviruses. Viral envelope proteins that can promote viral infection of eukaryotic cells may include HIV-1 derived lentiviral vectors (LVs) pseudotyped with envelope glycoproteins (GPs) from the vesicular stomatitis virus (VSV-G), the modified feline endogenous retrovirus (RD114TR) (SEQ ID NO: 95), and the modified gibbon ape leukemia virus (GALVTR). These envelope proteins can efficiently promote entry of other viruses, such as parvoviruses, including adeno-associated viruses (AAV), thereby demonstrating their broad efficiency. For example, other viral envelope proteins may be used including Moloney murine leukemia virus (MLV) 4070 env (such as described in Merten et al., *J. Virol.* 79:834-840, 2005; the content of which is incorporated herein by reference), RD114 env, chimeric envelope protein RD114pro or RDpro (which is an RD114-HIV chimera that was constructed by replacing the R peptide cleavage sequence of RD114 with the HIV-1 matrix/capsid (MA/CA) cleavage sequence, such as described in Bell et al. *Experimental Biology and Medicine* 2010; 235: 1269-1276; the content of which is incorporated herein by reference), baculovirus GP64 env (such as described in Wang et al. *J. Virol.* 81:10869-10878, 2007; the content of which is incorporated herein by reference), or GALV env (such as described in Merten et al., *J. Virol.* 79:834-840, 2005; the content of which is incorporated herein by reference), or derivatives thereof.

As used herein, the term "retrovirus" includes, but is not limited to, murine leukemia virus (MLV), human immunodeficiency virus (HIV), equine infectious anemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al. ("Retroviruses" 1997 Cold Spring Harbour Laboratory Press Eds: J M Coffin, S M Hughes, H E Varmus pp 758-763).

Lentiviruses also belong to the retrovirus family, but they can infect both dividing and non-dividing cells.

The lentivirus group can be split into "primate" and "non-primate". Examples of primate lentiviruses include the human immunodeficiency virus (HIV). The non-primate lentiviral group includes the prototype "slow virus" visna/maedi virus (VMV), as well as the related caprine arthritis encephalitis virus (CAEV), equine infectious anemia virus (EIAV) and the more recently described feline immunodeficiency virus (FIV) and bovine immunodeficiency virus (BIV).

Details on the genomic structure of some lentiviruses may be found, for example, in the NCBI Genbank database (i.e. GenBank Accession Nos. AF033819 and AF033820 respectively). Details of HIV variants may also be found in the HIV databases maintained by Los Alamos National Laboratory.

During the process of infection, a retrovirus initially attaches to a specific cell surface receptor. On entry into the susceptible host cell, the retroviral RNA genome is then copied to DNA by the virally encoded reverse transcriptase, which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular genes. The provirus encodes the proteins and other factors required to make more virus, which can leave the cell by a process sometimes called "budding".

Each retroviral genome comprises genes called gag, pol and env, which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome.

The LTRs themselves are identical sequences that can be divided into three elements, which are called U3, R, and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

For the viral genome, the site of transcription initiation is at the boundary between U3 and R in the left hand side LTR and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

With regard to the structural genes gag, pol and env themselves; gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome. The env gene encodes the surface (SU) glycoprotein and the transmembrane (TM) protein of the virion, which form a complex that interacts specifically with cellular receptor proteins. This interaction leads ultimately to infection by fusion of the viral membrane with the cell membrane.

Retroviruses may also contain "additional" genes, which code for proteins other than gag, pol and env. Examples of additional genes include, in HIV, one or more of vif, vpr, vpx, vpu, tat, rev, and nef. EIAV contains, for example, the additional genes S2 and dUTPase.

Proteins encoded by additional genes serve various functions, some of which may be duplicative of a function provided by a cellular protein. In EIAV, for example, tat acts as a transcriptional activator of the viral LTR. It binds to a stable, stem-loop RNA secondary structure referred to as TAR. Rev regulates and co-ordinates the expression of viral genes through rev-response elements (RRE). The mechanisms of action of these two proteins are thought to be broadly similar to the analogous mechanisms in the primate viruses. The function of S2 is unknown but it does not appear to be essential. In addition, an EIAV protein, Ttm, has been identified that is encoded by the first exon of tat spliced to the env coding sequence at the start of the transmembrane protein.

Delivery Systems

Retroviral vector systems have been proposed as a delivery system for, inter alia, the transfer of a nucleotide of interest (NOI) to one or more sites of interest. The transfer can occur in vitro, ex vivo, in vivo, or combinations thereof. Retroviral vector systems have even been exploited to study various aspects of the retrovirus life cycle, including receptor usage, reverse transcription and RNA packaging (reviewed by Miller, 1992 Curr Top Microbiol Immunol 158: 1-24, the content which is incorporated herein by reference).

A recombinant retroviral vector particle is capable of transducing a recipient cell with an NOI. Once within the cell, the RNA genome from the vector particle is reverse transcribed into DNA and integrated into the DNA of the recipient cell.

As used herein, the term "vector genome" refers to the RNA construct present in the retroviral vector particle and/or the integrated DNA construct. The term also embraces a separate or isolated DNA construct capable of encoding such an RNA genome. A retroviral or lentiviral genome should comprise at least one component part derivable from a retrovirus or a lentivirus. The term "derivable" is used in its normal sense as meaning a nucleotide sequence or a part thereof, which need not necessarily be obtained from a virus such as a lentivirus but instead could be derived therefrom. By way of example, the sequence may be prepared synthetically or by use of recombinant DNA techniques. Preferably, the genome comprises a psi region (or an analogous component that is capable of causing encapsidation).

The viral vector genome is preferably "replication defective", by which we mean that the genome does not comprise sufficient genetic information alone to enable independent replication to produce infectious viral particles within the recipient cell. In a preferred embodiment, the genome lacks a functional env, gag or pol gene.

The viral vector genome may comprise some or all of the long terminal repeats (LTRs). Preferably, the genome comprises at least part of the LTRs or an analogous sequence, which is capable of mediating proviral integration, and transcription. The sequence may also comprise or act as an enhancer-promoter sequence.

The viral vector genome according to some aspects of the invention may be provided as a kit of parts. For example, the kit may comprise (i) a plasmid or plasm ids containing the NOIs and internal regulatory sequences, such as, for example, a promoter or an IRES sequence(s); and (ii) a retroviral genome construct with suitable restriction enzyme recognition sites for cloning the NOIs and internal regulatory sequence(s) into the viral genome.

It is recognized that the separate expression of the components required to produce a retroviral vector particle on separate DNA sequences co-introduced into the same cell will yield retroviral particles carrying defective retroviral genomes that carry therapeutic genes. This cell is referred to as the producer cell.

There are two common procedures for generating producer cells. In one, the sequences encoding retroviral Gag, Pol and Env proteins are introduced into the cell and stably integrated into the cell genome; a stable cell line is produced which is referred to as the packaging cell line. The packaging cell line produces the proteins required for packaging retroviral RNA but it cannot bring about encapsidation due to the lack of a psi region. However, when a vector genome having a psi region is introduced into the packaging cell line, the helper proteins can package the psi-positive recombinant vector RNA to produce the recombinant virus stock. This can be used to transduce the NOI into recipient cells. The recombinant virus whose genome lacks all genes required to make viral proteins can infect only once and cannot propagate. Hence, the NOI is introduced into the host cell genome without the generation of potentially harmful retrovirus. A summary of the available packaging lines is presented in "Retroviruses" (1997 Cold Spring Harbour Laboratory Press Eds: J M Coffin, S M Hughes, H E Varmus pp 449, the content which is incorporated by reference in its entirety).

The present invention also provides a packaging cell line comprising a viral vector genome of the present invention. For example, the packaging cell line may be transduced with a viral vector system comprising the genome or transfected with a plasmid carrying a DNA construct capable of encoding the RNA genome. The present invention also provides a retroviral (or lentiviral) vector particle produced by such a cell.

The second approach is to introduce the three different DNA sequences that are required to produce a retroviral vector particle, i.e. the env coding sequences, the gag-pol coding sequence and the defective retroviral genome containing one or more NOIs into the cell at the same time by transient transfection and the procedure is referred to as transient triple transfection (Landau & Littman 1992; Pear et al. 1993). The triple transfection procedure has been optimized (Soneoka et al. 1995; Finer et al. 1994). WO 94/29438 describes the production of producer cells in vitro using this multiple DNA transient transfection method.

The components of the viral system, which are required to complement the vector genome, may be present on one or more "producer plasmids" for transfecting into cells.

The present invention also provides a vector system for producing a retrovirus-derived particle, comprising (i) a retroviral genome according to some aspects of the invention; (ii) a nucleotide sequence coding for retroviral gag and pol proteins; (iii) nucleotide sequences encoding other essential viral packaging components not encoded by the nucleotide sequence of (ii).

In an aspect, the nucleic acid sequence(s) encoding at least one of Vpr, Vif, Tat, Nef, or analogous auxiliary genes, from the retrovirus from which the particles are derived, are disrupted such as said nucleic acid sequence(s) are incapable of encoding functional Vpr, Vif, Tat, Nef, or analogous auxiliary proteins, or are removed from the system.

The present invention also provides a cell transfected with such a vector system and a retroviral vector particle produced by such a cell. Preferably, the gag-pol sequence is codon optimized for use in the particular producer cell (see below).

The env protein encoded by the nucleotide sequence of iii) may be a homologous retroviral or lentiviral env protein. Alternatively, it may be a heterologous env, or an env from a non-retro or lentivirus (see below under "pseudotyping").

The term "viral vector system" is used generally to mean a kit of parts that can be used when combined with other necessary components for viral particle production to produce viral particles in host cells. For example, the retroviral vector genome may lack one or more of the genes needed for viral replication. This may be combined in a kit with a further complementary nucleotide sequence or sequences, for example on one or more producer plasm ids. By co-transfection of the genome together with the producer plasm id(s), the necessary components should be provided for the production of infectious viral particles.

Alternatively, the complementary nucleotide sequence(s) may be stably present within a packaging cell line that is included in the kit.

The present invention also relates to a retroviral vector system, which is capable of delivering an RNA genome to a recipient cell, wherein the genome is longer than the wild type genome of the lentivirus.

In some aspects, the RNA genome of the vector system has up to 5%, preferably, up to 10% or even up to 30% more bases than the wild-type genome. Preferably, the RNA genome is about 10% longer than the wild-type genome. For example, wild type EIAV comprises an RNA genome of approximately 8 kb. An EIAV vector system of the present invention may have an RNA genome of up to (preferably about) 8.8 kb.

In some aspects, the retroviral vector system of the present invention is a self-inactivating (SIN) vector system. For example, self-inactivating retroviral vector systems have been constructed by deleting the transcriptional enhancers or the enhancers and promoter in the U3 region of the 3' LTR. After a round of vector reverse transcription and integration, these changes are copied into both the 5' and the 3' LTRs, producing a transcriptionally inactive provirus. However, any promoter(s) internal to the LTRs in such vectors will still be transcriptionally active. This strategy has been employed to eliminate effects of the enhancers and promoters in the viral LTRs on transcription from internally placed genes. Such effects include increased transcription or suppression of transcription. This strategy can also be used to eliminate downstream transcription from the 3' LTR into genomic DNA. This is of particular concern in human gene therapy where it may be important to prevent the adventitious activation of an endogenous oncogene.

In some aspects, a recombinase-assisted mechanism is used, which facilitates the production of high titer regulated lentiviral vectors from the producer cells of the present invention.

In some aspects, the present disclosure comprises a method of transducing T cells comprising: obtaining T cells from at least one donor, patient, or individual; activating the T cells with an anti-CD3 antibody and/or an anti-CD28 antibody; transducing the activated T cells with a viral vector; and optionally expanding the transduced T cells; optionally measuring a quantity of the expanded T cells that express the transgene and/or a copy number of integrated transgene in each of the T cells at the plurality of volumetric concentrations; and optionally identifying the volumetric concentration that yields a maximum average of the quantity of the expanded T cells that express the transgene and/or a maximum average of the copy number of the integrated transgene without exceeding five copies of the integrated transgene in each of the expanded T cells from the plurality of healthy donors, and transducing T cells obtained from a patient with the viral vector at the identified volumetric concentration for the immunotherapy, as described in US20190216852 (the content of which is hereby incorporated by reference in its entirety).

In some aspects, the plurality of volumetric concentrations are from about 0.01 µl per about $10^6$ cells to about 1 ml per about $10^6$ cells; from about 0.01 µl per about $2 \times 10^6$ cells to about 1 ml per about $2 \times 10^6$ cells; from about 0.01 µl per about $5 \times 10^6$ cells to about 1 ml per about $5 \times 10^6$ cells; from about 0.01 µl per about $10^7$ cells to about 1 ml per about $10^7$ cells; from about 1 µl per about $10^7$ cells to about 500 µl per about $10^7$ cells; from about 5 µl per about $10^7$ cells to about 150 µl per about $10^7$ cells; or from about 8 µl per about $10^7$ cells to about 12 µl per about $10^7$ cells.

As used herein, the term "recombinase assisted system" includes, but is not limited to, a system using the Cre recombinase/loxP recognition sites of bacteriophage P1 or the site-specific FLP recombinase of S. cerevisiae, which catalyzes recombination events between 34 bp FLP recognition targets (FRTs).

The site-specific FLP recombinase of S. cerevisiae, which catalyzes recombination events between 34 bp FLP recognition targets (FRTs), has been configured into DNA constructs to generate high level producer cell lines using recombinase-assisted recombination events (Karreman et al. (1996) NAR 24:1616-1624). A similar system has been developed using the Cre recombinase/loxP recognition sites of bacteriophage P1 (Vanin et al. (1997) J. Virol 71:7820-7826). This was configured into a lentiviral genome such that high titer lentiviral producer cell lines were generated.

By using producer/packaging cell lines, it is possible to propagate and isolate quantities of retroviral vector particles (e.g. to prepare suitable titers of the retroviral vector particles) for subsequent transduction of, for example, a site of interest (such as a specific organ or tissue) or in a cell of interest (such as a T cell). Producer cell lines are usually better for large-scale production of vector particles.

Transient transfection has certain advantages over the packaging cell method. In this regard, transient transfection avoids the longer time required to generate stable vector-producing cell lines and is used if the vector genome or retroviral packaging components are toxic to cells. If the vector genome encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient transfection that produce vector titer levels that are comparable to the levels obtained from stable vector-producing cell lines (Pear et al. 1993, PNAS 90:8392-8396).

Producer cells/packaging cells can be of any suitable cell type. Producer cells are generally mammalian cells, but can be, for example, insect cells.

As used herein, the term "producer cell" or "vector producing cell" refers to a cell that contains all the elements necessary for production of retroviral vector particles.

In some aspects, the producer cell is obtainable from a stable producer cell line, from a derived stable producer cell line, or from a derived producer cell line.

As used herein, the term "derived producer cell line" is a transduced producer cell line that has been screened and selected for high expression of a marker gene. Such cell lines support high-level expression from the retroviral genome. The term "derived producer cell line" is used interchangeably with the term "derived stable producer cell line" and the term "stable producer cell line".

In some aspects, the derived producer cell line includes, but is not limited to, a retroviral and/or a lentiviral producer cell.

In some aspects, the envelope protein sequences, and nucleocapsid sequences are all stably integrated in the producer and/or packaging cell. However, one or more of these sequences could also exist in episomal form and gene expression could occur from the episome.

As used herein, the term "packaging cell" refers to a cell that contains those elements necessary for production of infectious recombinant virus that are lacking in the RNA genome. Typically, such packaging cells contain one or more producer plasmids, which are capable of expressing viral structural proteins (such as codon optimized gag-pol and env) but they do not contain a packaging signal.

The term "packaging signal" which is referred to interchangeably as "packaging sequence" or "psi" is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon.

Packaging cell lines suitable for use with the above-described vector constructs may be readily prepared (see also WO 92/05266, the content of which is incorporated by reference), and utilized to create producer cell lines for the production of retroviral vector particles. As mentioned above, a summary of the available packaging lines is presented in "Retroviruses".

Also, as discussed above, simple packaging cell lines, comprising a provirus in which the packaging signal has been deleted, have been found to lead to the rapid production of undesirable replication competent viruses through recombination. In order to improve safety, second-generation cell lines have been produced, wherein the 3' LTR of the provirus is deleted. In such cells, two recombinations would be necessary to produce a wild type virus. A further improvement involves the introduction of the gag-pol genes and the env gene on separate constructs, so-called third generation packaging cell lines. These constructs are introduced sequentially to prevent recombination during transfection.

In some aspects, the packaging cell lines are second-generation packaging cell lines or third generation packaging cell lines.

In these split-construct, third generation cell lines, a further reduction in recombination may be achieved by changing the codons. This technique, based on the redundancy of the genetic code, aims to reduce homology between the separate constructs, for example, between the regions of overlap in the gag-pol and env open reading frames.

The packaging cell lines are useful for providing the gene products necessary to encapsulate and provide a membrane protein for a high titer vector particle production. The packaging cell may be a cell cultured in vitro, such as a tissue culture cell line. Suitable cell lines include, but are not limited to, mammalian cells, such as murine fibroblast derived cell lines or human cell lines. In some aspects, the packaging cell line is a primate or human cell line, such as for example: HEK293, 293-T, TE671, HT1080.

It is desirable to use high-titer virus preparations in both experimental and practical applications. Techniques for increasing viral titer include using a psi plus packaging signal as discussed above and concentration of viral stocks.

As used herein, the term "high titer" means an effective amount of a retroviral vector or particle that is capable of transducing a target site such as a cell.

As used herein, the term "effective amount" means an amount of a retroviral or lentiviral vector or vector particle that is sufficient to induce expression of the NOIs at a target site.

A high-titer viral preparation for a producer/packaging cell is usually on the order of $10^5$ to $10^7$ retrovirus particles per mL. In another aspect, the preparation has at least $10^8$ TU/mL, preferably from $10^8$ to $10^9$ TU/mL, more preferably at least $10^9$ TU/mL (titer is expressed in transducing units per mL (TU/mL) as titred on a standard D17 cell line). Other methods of concentration such as ultrafiltration or binding to and elution from a matrix may be used.

The expression products encoded by the NOIs may be proteins that are secreted from the cell. Alternatively, the NOI expression products are not secreted and are active within the cell. For some applications, it is preferred for the NOI expression product to demonstrate a bystander effect or a distant bystander effect; that is the production of the expression product in one cell leading to the modulation of additional, related cells, either neighboring or distant (e.g. metastatic), which possess a common phenotype (Zennou et al., (2000) Cell 101: 173; Folleuzi et al., (2000) Nat. Genetics 25: 217; Zennou et al., (2001) Nat. Biotechnol. 19: 446), the content of each which is incorporated by reference in their entireties.

The presence of a sequence termed the central polypurine tract (cPPT) may improve the efficiency of gene delivery to non-dividing cells. This cis-acting element is located, for example, in the viral polymerase coding region element. In some aspects, the viral genome of the present invention comprises a cPPT sequence.

In addition, the viral genome may comprise a translational enhancer.

The NOIs may be operatively linked to one or more promoter/enhancer elements. Transcription of one or more NOIs may be under the control of viral LTRs or alternatively promoter-enhancer elements. In some aspects, the promoter is a strong viral promoter such as CMV, or is a cellular constitutive promoter such as PGK, beta-actin or EFlalpha. The promoter may be regulated or tissue-specific. The control of expression can also be achieved by using such systems as the tetracycline system that switches gene expression on or off in response to outside agents (for example, tetracycline or its analogues).

Pseudotyping

In the design of retroviral vector systems, it is desirable to engineer particles with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector particle to replace or add to the native envelope protein of the virus.

The term pseudotyping means incorporating in at least a part of, or substituting a part of, or replacing all of an env gene of a viral genome with a heterologous env gene, for example, an env gene from another virus. Pseudotyping is not a new phenomenon and examples may be found in WO 99/61639, WO-A-98/05759, WO-A-98/05754, WO-A-97/17457, WO-A-96/09400, WO-A-91/00047 and Mebatsion et al. (1997) Cell 90: 841-847, the content of each which is herein in incorporated by reference in their entireties.

In some aspects, the vector system is pseudotyped with a gene encoding at least part of the rabies G protein. Examples of rabies G pseudotyped retroviral vectors may be found in WO99/61639. In a further aspect, the vector system is pseudotyped with a gene encoding at least part of the VSV-G protein. Examples of VSV-G pseudotyped retroviral vectors may be found in U.S. Pat. No. 5,817,491, the content of which is herein incorporated by reference in its entirety. In another aspect, the vector is pseudotyped with an envelope protein of a virus selected from the native feline endogenous virus (RD114), a chimeric version of RD114 (RD114TR; SEQ ID NO: 95), gibbon ape leukemia virus (GALV), a chimeric version of GALV (GALV-TR), amphotropic murine leukemia virus (MLV 4070A), baculovirus (GP64), vesicular stomatitis virus (VSV-G), fowl plague virus (FPV), Ebola virus (EboV), baboon retroviral envelope glycoprotein (BaEV), or lymphocytic choriomeningitis virus (LCMV).

It has been demonstrated that a retrovirus or lentivirus minimal system can be constructed from HIV, SIV, FIV, and EIAV viruses. Such a system requires none of the additional genes vif, vpr, vpx, Vpu, tat, rev and nef for either vector production or for transduction of dividing and non-dividing cells. It has also been demonstrated that an EIAV minimal vector system can be constructed which does not require S2 for either vector production or for transduction of dividing and non-dividing cells. The deletion of additional genes is advantageous. Firstly, it permits vectors to be produced without the genes associated with disease in lentiviral (e.g. HIV) infections. In particular, tat is associated with disease. Secondly, the deletion of additional genes permits the vector to package more heterologous DNA. Thirdly, genes whose function is unknown, such as S2, may be omitted, thus reducing the risk of causing undesired effects. Examples of minimal lentiviral vectors are disclosed in WO-A-99732646 and in WO-A-98/17815, the content of which is herein incorporated by reference in its entirety.

The absence of functional auxiliary genes from the retroviral vector production system means that those functional genes will also be absent from retroviral vector particles produced by the system. Also, any auxiliary proteins that would otherwise be encoded by those genes and incorporated into the vector particles will be absent from the vector particles. In known retroviral vector production systems, the auxiliary genes may be present as part of the vector genome encoding DNA, or together with the packaging components. The location of an auxiliary gene in a vector production system depends in part on its relationship with other retroviral components. For example, vif is often part of a gag-pol packaging cassette in a packaging cell. Thus, to remove a functional auxiliary gene for the purposes of the invention may involve its removal from the packaging components, or from the vector genome, or perhaps both.

To remove a functional auxiliary gene may not require removal of the gene in its entirety. Usually removal of part of the gene, or disruption of the gene in some other way will be sufficient. The absence of a functional auxiliary gene is understood herein to mean that the gene is not present in a form in which it is capable of encoding the functional auxiliary protein.

In some aspects, functional vpr and tat genes or analogous genes normally present in the lentivirus on which the vector particles are based are both absent. These two auxiliary genes are associated with characteristics of lentiviruses that are particularly undesirable for a gene or cell therapy vector. However, other than by the proviso given above, the invention is not limited with regard to the combination of auxiliary genes that are absent in a system according to the invention for producing HIV-1-based vector particles, any combination of three, or more preferably four, of the genes may be absent in their functional form. Most preferably, all five of the auxiliary genes vpr, vif, tat, nef, and vpu are absent in their functional form. Similarly, for systems concerned with other lentiviruses, it is most preferable that all of the auxiliary genes are absent in their functional form (except rev which is preferably present unless replaced by a system analogous to the rev/RRE system).

Thus, in some aspects, the delivery system according to the invention is devoid of at least tat and S2 (if it is an EIAV vector system), and possibly also vif, vpr, vpx, vpu and nef. Preferably, the systems of the present invention are also devoid of rev. Rev was previously thought to be essential in some retroviral genomes for efficient virus production. For example, in the case of HIV, it was thought that rev and RRE sequence should be included. However, it has been found that the requirement for rev and RRE can be reduced or eliminated by codon optimization (see below) or by replacement with other functional equivalent systems such as the MPMV system. As expression of the codon-optimized gag-pol is rev-independent, RRE can be removed from the gag-pol expression cassette, thus removing any potential for recombination with any RRE contained on the vector genome.

In some aspects, the viral genome of the present invention lacks the Rev response element (RRE). In another aspect, a nucleic acid sequence encoding Rev, or a functional equivalent thereof, is disrupted such that the nucleic acid sequence is incapable of encoding the functional Rev or is removed from the vector genome.

In some aspects, the system used in the present invention is based on a so-called "minimal system in which some or all of the additional genes have been removed. Preferably, the viral vector of the present invention has a minimal viral genome.

As used herein, the term "minimal viral genome" means that the viral vector has been manipulated so as to remove the non-essential elements and to retain the essential elements to provide the required functionality to infect, transduce and deliver a NOI to a target host cell. Preferably, the viral vector with the minimal viral genome is a minimal lentiviral vector.

Codon Optimization

Codon optimization has previously been described in WO 99/41397, the content of which is herein incorporated by reference in its entirety. Different cells differ in their usage of particular codons. This codon bias corresponds to a bias in the relative abundance of particular tRNAs in the cell type. By altering the codons in the sequence to match with the relative abundance of corresponding tRNAS, it is possible to increase expression. By the same token, it is possible to decrease expression by deliberately choosing codons for which the corresponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimization has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. Codon optimization also overcomes the Rev/RRE requirement for export, rendering optimized sequences Rev-independent. Codon optimization also reduces homologous recombination between different constructs within the vector system (for example, between the regions of overlap in the gag-pol and env open reading frames). The overall effect of codon optimization is therefore a notable increase in viral titer and improved safety.

In one aspect, only codons relating to INS are codon optimized. However, in a more preferred and practical embodiment, the sequences are codon optimized in their entirety, with the exception of the sequence encompassing the frameshift site.

The gag-pol gene comprises two overlapping reading frames encoding gag and pol proteins respectively. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. For HIV, the region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is preferably not codon optimized. Retaining this fragment will enable more efficient expression of the gag-pol proteins.

Derivations from optimal codon usage may be made, for example, to accommodate convenient restriction sites, and conservative amino acid changes may be introduced into the gag-pol proteins.

In some aspects, codon optimization is based on highly expressed mammalian genes. The third and sometimes the second and third base may be changed.

Due to the degenerate nature of the genetic code, it will be appreciated that a skilled worker can achieve numerous gag-pol sequences. Also, there are many retroviral variants described that can be used as a starting point for generating a codon optimized gag-pol sequence. Lentiviral genomes can be quite variable. For example, there are many quasi-species of HIV-1 that are still functional. This is also the case for EIAV. These variants may be used to enhance particular parts of the transduction process. Details of HIV variants may also be found in the HIV databases maintained by Los Alamos National Laboratory. Details of EIAV clones may be found at the NCBI database maintained by the National Institutes of Health.

The strategy for codon optimized gag-pol sequences can be used in relation to any retrovirus. This would apply to all lentiviruses, including EIAV, FIV, BIV, CAEV, VMR, SIV, HIV-1, and HIV-2. In addition, this method could be used to increase expression of genes from HTLV-1, HTLV-2, HFV, HSRV and human endogenous retroviruses (HERV), MLV, and other retroviruses.

Codon optimization can render gag-pol expression Rev independent. To enable the use of anti-rev or RRE factors in the retroviral vector, however, it would be necessary to render the viral vector generation system totally Rev/RRE independent. Thus, the genome also should be modified. This can be achieved by optimizing vector genome components. Advantageously, these modifications can also lead to the production of a safer system absent of all additional proteins both in the producer and in the transduced cell.

As described above, the packaging components for a retroviral vector include expression products of gag, pol, and env genes. In addition, efficient packaging depends on a short sequence of 4 stem loops followed by a partial sequence from gag and env (the "packaging signal"). Thus, inclusion of a deleted gag sequence in the retroviral vector genome (in addition to the full gag sequence on the packaging construct) will optimize vector titer. To date, efficient packaging has been reported to require from 255 to 360 nucleotides of gag in vectors that still retain env sequences, or about 40 nucleotides of gag in a particular combination of splice donor mutation, gag and env deletions. It has been found that a deletion of all but the N-terminal 360 nucleotides or so in gag leads to an increase in vector titer. Thus, preferably, the retroviral vector genome includes a gag sequence that comprises one or more deletions, more preferably the gag sequence comprises about 360 nucleotides derivable from the N-terminus.

NOIs

In the present invention, the term NOI (nucleotide sequence of interest) includes any suitable nucleotide sequence, which need not necessarily be a complete naturally occurring DNA or RNA sequence. Thus, the NOI can be, for example, a synthetic RNA/DNA sequence, a codon optimized RNA/DNA sequence, a recombinant RNA/DNA sequence (i.e. prepared by use of recombinant DNA techniques), a cDNA sequence or a partial genomic DNA sequence, including combinations thereof. The sequence need not be a coding region. If it is a coding region, it need not be an entire coding region. In addition, the RNA/DNA sequence can be in a sense orientation or in an anti-sense orientation. Preferably, it is in a sense orientation. Preferably, the sequence is, comprises, or is transcribed from cDNA.

The NOI(s), also referred to as heterologous sequence(s), heterologous gene(s) or transgene(s), may be any heterologous sequence of interest without limitation, including, for example, sequences coding for therapeutic proteins, enzymes, and antibodies, etc.; siRNA; anti-sense; microRNAs, aptamers; ribozymes, any gene inhibitory or silencing sequence; and any sequence which is to be delivered to a host cell via a lentiviral transducing vector, such as any one or more of a selection gene(s), marker gene(s) and therapeutic gene(s).

The NOI may be a candidate gene that is of potential significance in a disease process. Thus, the vector system of the present invention may, for example, be used for target validation purposes.

The NOI may have a therapeutic or diagnostic application. Suitable NOIs include, but are not limited to: sequences encoding enzymes, cytokines, chemokines, hormones, antibodies, anti-oxidant molecules, engineered immunoglobulin-like molecules, a single chain antibody, fusion proteins, immune co-stimulatory molecules, immunomodulatory molecules, anti-sense RNA, small interfering RNA (siRNA), a trans dominant negative mutant of a target protein, a toxin, a conditional toxin, an antigen, an antigen receptor, a chimeric antigen receptor, a T-cell receptor, a tumor suppressor protein, and growth factors, membrane proteins, pro- and anti-angiogenic proteins and peptides, vasoactive proteins and peptides, antiviral proteins and ribozymes, and derivatives thereof (such as with an associated reporter group). The NOIs may also encode pro-drug activating enzymes. When used in a research context, the NOIs may also encode reporter genes such as, but not limited to, green fluorescent protein (GFP), luciferase, β-galactosidase, or resistance genes to antibiotics such as, for example, ampicillin, neomycin, bleomycin, Zeocin, chloramphenicol, hygromycin, kanamycin, among others.

The NOI may encode all or part of the protein of interest ("POI"), or a mutant, homologue or variant thereof. For example, the NOI may encode a fragment of the POI that is capable of functioning in vivo in an analogous manner to the wild-type protein.

The term "mutant" includes POIs that include one or more amino acid variations from the wild-type sequence. For example, a mutant may comprise one or more amino acid additions, deletions or substitutions.

Here, the term "homologue" means an entity having a certain homology with the NOI, or which encodes a protein having a degree of homology with the POI. Here, the term "homology" can be equated with "identity".

In an aspect, vectors, constructs, or sequences described herein may comprise at least about 80%, at least about 85%, at least about 90%, at least about 95%, at least about 96%, at least about 97%, at least about 98%, or at least about 99% to a reference sequence. A sequence "at least 85% identical to a reference sequence" is a sequence having, on its entire length, 85%, or more, in particular 90%, 91%, 92%, 93%, 94%, 95%, 96%, 97%, 98% or 99% sequence identity with the entire length of the reference sequence. In an aspect, vectors, constructs, or sequences described herein may comprise at least about 80%, at least about 85%, at least about 90%, at least about 95%, at least about 96%, at least about 97%, at least about 98%, or at least about 99% to any of SEQ ID NO: 1-95.

In the context of the present application, the "percentage of identity" or "percent identity" is calculated using a global pairwise alignment (i.e. the two sequences are compared over their entire length). Methods for comparing the identity of two or more sequences are well known in the art. The «needle» program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk World Wide Web site and is further described in the following publication (*EMBOSS: The European Molecular Biology Open Software Suite* (2000) Rice, P. Longden, I. and Bleasby, A. Trends in Genetics 16, (6) pp. 276-277). The percentage of identity between two polypeptides, in accordance with the invention, is calculated using the EMBOSS: needle (global) program with a "Gap Open" parameter equal to 10.0, a "Gap Extend" parameter equal to 0.5, and a Blosum62 matrix.

Proteins consisting of an amino acid sequence "at least 80%, 85%, 90%, 95%, 96%, 97%, 98% or 99% identical" to a reference sequence may comprise mutations such as deletions, insertions and/or substitutions compared to the reference sequence. In case of substitutions, the protein consisting of an amino acid sequence at least 80%, 85%, 90%, 95%, 96%, 97%, 98% or 99% A identical to a reference sequence may correspond to a homologous sequence derived from another species than the reference sequence.

"Amino acid substitutions" may be conservative or non-conservative. Preferably, substitutions are conservative substitutions, in which one amino acid is substituted for another amino acid with similar structural and/or chemical properties.

In an embodiment, conservative substitutions may include those, which are described by Dayhoff in "The Atlas of Protein Sequence and Structure. Vol. 5", Natl. Biomedical Research, the contents of which are incorporated by reference in their entirety. For example, in an aspect, amino acids, which belong to one of the following groups, can be exchanged for one another, thus, constituting a conservative exchange: Group 1: alanine (A), proline (P), glycine (G), asparagine (N), serine (S), threonine (T); Group 2: cysteine (C), serine (S), tyrosine (Y), threonine (T); Group 3: valine (V), isoleucine (I), leucine (L), methionine (M), alanine (A), phenylalanine (F); Group 4: lysine (K), arginine (R), histidine (H); Group 5: phenylalanine (F), tyrosine (Y), tryptophan (W), histidine (H); and Group 6: aspartic acid (D), glutamic acid (E). In an aspect, a conservative amino acid substitution may be selected from the following of T→A, G→A, A→I, T→V, A→M, T→I, A→V, T→G, and/or T→S.

In a further embodiment, a conservative amino acid substitution may include the substitution of an amino acid by another amino acid of the same class, for example, (1) nonpolar: Ala, Val, Leu, Ile, Pro, Met, Phe, Trp; (2) uncharged polar: Gly, Ser, Thr, Cys, Tyr, Asn, Gln; (3) acidic: Asp, Glu; and (4) basic: Lys, Arg, His. Other conservative amino acid substitutions may also be made as follows: (1) aromatic: Phe, Tyr, His; (2) proton donor: Asn, Gln, Lys, Arg, His, Trp; and (3) proton acceptor: Glu, Asp, Thr, Ser, Tyr, Asn, Gln (see, for example, U.S. Pat. No. 10,106,805, the contents of which are incorporated by reference in their entirety).

In another embodiment, conservative substitutions may be made in accordance with Table A. Methods for predicting tolerance to protein modification may be found in, for example, Guo et al., Proc. Natl. Acad. Sci., USA, 101(25): 9205-9210 (2004), the contents of which are incorporated by reference in their entirety.

TABLE A

Conservative Amino Acid substitution
Conservative Amino Acid Substitutions

| Amino Acid | Substitutions (others are known in the art) |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

In an aspect, sequences described herein may include 1, 2, 3, 4, 5, 10, 15, 20, 25, or 30 amino acid or nucleotide mutations, substitutions, deletions. In an aspect, any one of SEQ ID NO: 1-95 may include 1, 2, 3, 4, 5, 10, 15, 20, 25, or 30 mutations, substitutions, or deletions. In yet another aspect, the mutations or substitutions are conservative amino acid substitutions.

In another embodiment, conservative substitutions may be those shown in Table B under the heading of "conservative substitutions." If such substitutions result in a change in biological activity, then more substantial changes, denominated "exemplary substitutions" in Table B, may be introduced and the products screened if needed.

TABLE B

Amino Acid substitution
Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Len | Leu; Phe; Ile |
| Phe (F) | Tyr | Leu; Val; Ile; Ala; Tyr |
| Pro (P) | Ala | Ala |
| Ser (S) | Thr | Thr |

TABLE B-continued

Amino Acid substitution
Amino Acid Substitutions

| Original Residue (naturally occurring amino acid) | Conservative Substitutions | Exemplary Substitutions |
|---|---|---|
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Internal Ribosome Entry Site (IRES)

The viral genome of the present invention comprises at least one, but can optionally comprise two or more NOIs. In order for two or more NOIs to be expressed, there may be two or more transcription units within the vector genome, one for each NOI. However, it is clear from the literature that retroviral vectors achieve the highest titers and most potent gene expression properties if they are kept genetically simple (PCT/GB96/01230; Bowtell et al., 1988 J. Virol. 62, 2464; Correll et al., 1994 Blood 84, 1812; Emerman and Temin 1984 Cell 39, 459; Ghattas et al., 1991 Mol. Cell. Biol. 11, 5848; Hantzopoulos et al., 1989 PNAS 86, 3519; Hatzoglou et al., 1991 J. Biol. Chem 266, 8416; Hatzoglou et al., 1988. J. Biol. Chem 263, 17798; Li et al., 1992 Hum. Gen. Ther. 3, 381; McLachlin et al., 1993 Virol. 195, 1; Overell et al., 1988 Mol. Cell Biol. 8, 1803; Scharfman et al., 1991 PNAS 88, 4626; Vile et al., 1994 Gene Ther 1,307; Xu et al., 1989 Virol. 171, 331; Yee et al., 1987 PNAS 84, 5197). Thus, it is preferable to use an internal ribosome entry site (IRES) to initiate translation of the second (and subsequent) coding sequence(s) in a poly-cistronic (or as used herein, "multi-cistronic") message (Adam et al. 1991 J. Virol. 65, 4985).

Insertion of IRES elements into retroviral vectors is compatible with the retroviral replication cycle and allows expression of multiple coding regions from a single promoter (Adam et al. (as above); Koo et al. (1992) Virology 186:669-675; Chen et al. 1993 J. Virol 67:2142-2148). IRES elements were first found in the non-translated 5' ends of picornaviruses where they promote cap-independent translation of viral proteins (Jang et al. (1990) Enzyme 44; 292-309). When located between open reading frames in an RNA, IRES elements allow efficient translation of the downstream open reading frame by promoting entry of the ribosome at the IRES element followed by downstream initiation of translation.

The term "cistron" refers to a section of the DNA molecule that specifies the formation of one polypeptide chain, i.e. coding for one polypeptide chain. For example, "bi-cistron" refers to two sections of the DNA molecule that specify the formation of two polypeptide chains, i.e. coding for two polypeptide chains; "tri-cistron" refers to three sections of the DNA molecule that specify the formation of three polypeptide chains, i.e. coding for three polypeptide chains; etc. The term "multi-cistronic RNA" refers to an RNA that contains the genetic information to translate to several proteins. In contrast, a mono-cistronic RNA contains the genetic information to translate only a single protein. In the context of the present disclosure, the multi-cistronic RNA transcribed from the lentivirus may be translated into translated to two proteins, for example, a TCRα chain and TCRβ chain.

A review on IRES is presented by Mountford and Smith (TIG May 1995 vol 11, No 5:179-184). A number of different IRES sequences are known including those from encephalomyocarditis virus (EMCV) (Ghattas, I. R., et al., Mol. Cell. Biol., 11:5848-5859 (1991); BiP protein Macejak and Sarnow, Nature 353:91 (1991); the Antennapedia gene of *Drosophila* (exons d and e) Oh, et al., Genes & Development, 6:1643-1653 (1992) as well as those in poliovirus (PV) Pelletier and Sonenberg, Nature 334: 320-325 (1988); see also Mountford and Smith, TIG 11, 179-184 (1985).

According to WO-A-97/14809, IRES sequences are typically found in the 5' non-coding region of genes. In addition to those in the literature they can be found empirically by looking for genetic sequences that affect expression and then determining whether that sequence affects the DNA (i.e. acts as a promoter or enhancer) or only the RNA (acts as an IRES sequence).

IRES elements from PV, EMCV and swine vesicular disease virus have previously been used in retroviral vectors (Coffin et al, as above).

The term "IRES" includes any sequence or combination of sequences which work as or improve the function of an IRES. The IRES(s) may be of viral origin (such as EMCV IRES, PV IRES, or FMDV 2A-like sequences) or cellular origin (such as FGF2 IRES, NRF IRES, Notch 2 IRES or EIF4 IRES).

For the IRES to be capable of initiating translation of each NOI, it should be located between or prior to NOIs in the vector genome. For example, for a multi-cistronic sequence containing in NOIs, the genome may be as follows:

[NOI$_1$-IRES$_1$] . . . NOI$_n$, n=any integer

For bi- and tri-cistronic sequences, the order may be as follows:

NOI$_1$-IRES$_1$-NOI$_2$

NOI$_1$-IRES$_1$-NOI$_2$-IRES$_2$-NOI$_3$

Alternative configurations of IRESs and NOIs can also be utilized. For example transcripts containing the IRESs and NOIs need not be driven from the same promoter.

An example of this arrangement may be:

IRES$_1$-NOI$_1$-promoter-NOI$_2$-IRES$_2$-NOI$_3$.

In some aspects, in any construct utilizing an internal cassette having more than one IRES and NOI, the IRESs may be of different origins, that is, heterologous to one another. For example, one IRES may be from EMCV and the other IRES may be from poliovirus.

Other Methods of Expressing Multiple Genes from One Vector

Although IRESs are an efficient way to co-express multiple genes from one vector, other methods are also useful, and may be used alone or in conjunction with IRESs. These include the use of multiple internal promoters in the vector (Overell et al., Mol Cell Biol. 8: 1803-8 (1988)), or the use of alternate splicing patterns leading to multiple RNA species derived from the single viral genome that expresses the different genes. This strategy has previously been used by itself for two genes (Cepko et al. Cell 37: 1053 (1984)).

For example, multiple cloning sites (MCS) can further be incorporated into the vector that facilitate the insertion of NOIs. This MCS facilitates the introduction of any promoter, a single gene, two genes and optionally a gene inhibitory sequence, such as an antisense, ribozyme, shRNA, RNAi, microRNA, aptamer, transdominant mutant protein or the like. A preferable embodiment is the expression of a gene of interest that has been modified so that its nucleotide sequence is codon degenerated with respect to the endogenous gene in a cell, and additionally, the same vector expresses a gene inhibitory or silencing sequences capable of inhibiting or silencing the native gene of interest. This approach has enormous utility in the understanding the function of various protein domains by expressing the protein of interest that has been modified in these domains, and at the same time expressing a gene inhibitory or silencing sequence that represses or silences expression of the native non-modified gene of interest. This application can also be used in gene therapeutic approaches for the treatment of disease. For example, a lentiviral vector expressing an RNAi targeted to beta-hemoglobin can repress or silence sickle-hemoglobin in patients with sickle cell anemia. The same lentiviral vector can also express a normal hemoglobin molecule that has been codon-degenerated at the site targeted by the RNAi. In this way, erythroid cells expressing sickle globin can repress sickle globin expression, while expressing native hemoglobin and correct the genetic abnormality. The lentiviral vector could be delivered into a stem cell population that would give rise to erythroid cells expressing hemoglobin that would eventually become red cells. This approach can be used to treat a wide variety of diseases, including cancer, genetic disease and infectious diseases.

Transduced Cells

The present invention also relates to a cell that has been transduced with a vector system comprising a viral genome according to the invention.

The cell may be transduced in vivo, in vitro or ex vivo by any suitable means. For example, if the cell is a cell from a mammalian subject, the cell may be removed from the subject and transduced ready for reimplantation into the subject (ex vivo transduction). Alternatively, the cell may be transduced by direct gene transfer in vivo, using the vector system of the present invention in accordance with standard techniques (such as via injection of vector stocks expressing the NOIs). If the cell is part of a cell line that is stable in culture (i.e. which can survive numerous passages and can multiple in vitro) then it may be transduced in vitro by standard techniques, for example, by exposure of the cell to viral supernatants comprising vectors expressing the NOIs.

The cell may be any cell that is susceptible to transduction. If the vector system is capable of transducing non-dividing cells (for example if it is a lentiviral system) then the cell may be a non-dividing cell.

In one aspect, the present disclosure relates to activation, transduction, and/or expansion of immune cells, such as lymphocytes, neutrophils, and/or monocytes. In some aspects, the immune cells are lymphocytes, such as T cells (e.g., tumor-infiltrating lymphocytes, CD8+ T cells, CD4+ T cells, and γδ T cells), B cells, and/or NK cells, that may be used for transgene expression. In another aspect, the disclosure relates to activation, transduction, and expansion of γδ T cells while depleting α- and/or β-TCR positive cells.

In an aspect, whole PBMC population, without prior depletion of specific cell populations, such as monocytes, αβ T-cells, B-cells, and NK cells, can be activated and expanded. In another aspect, γδ T cells may be isolated from a complex sample that is cultured in vitro. In another aspect, enriched γδ T cell populations can be generated prior to their specific activation and expansion. In another aspect, activation and expansion of T cells may be performed without the presence of native or engineered APCs. In another aspect, isolation and expansion of T cells from tumor specimens can be performed using immobilized T cell mitogens, including antibodies specific to TCR, and other TCR activating agents, including lectins. In another aspect, isolation and expansion of T cells from tumor specimens can be performed in the absence of T cell mitogens, including antibodies specific to TCR, and other TCR activating agents, including lectins.

In an aspect, T cells are isolated from leukapheresis of a subject, for example, a human subject. In another aspect, T cells are not isolated from peripheral blood mononuclear cells (PBMC).

T cell preparation may be performed by using methods disclosed in US20190247433, the content of which is hereby incorporated by reference in its entirety.

In an aspect, the disclosure provides for methods of transducing a T cell including thawing frozen PBMC, resting the thawed PBMC, activating the T cell in the cultured PBMC with an anti-CD3 antibody and an anti-CD28 antibody, transducing the activated T cell with a viral vector, expanding the transduced T cell, and obtaining the expanded T cells.

In another aspect, the present disclosure relates to a method of preparing a T cell population, including obtaining fresh PBMC, i.e., PBMC is not obtained by thawing cryo-preserved PBMC, activating the T cell in the fresh PBMC with an anti-CD3 antibody and an anti-CD28 antibody, transducing the activated T cell with a viral vector, expanding the transduced T cell, and harvesting the expanded T cell.

In another embodiment of the present disclosure, for fresh PBMC, i.e., not frozen, resting may not be needed. Thus, fresh PBMC, without resting, may be activated by anti-CD3 antibody and anti-CD28 antibody, followed by viral vector transduction to obtain transduced T cells.

In another aspect, the thawing, the resting, the activating, the transducing, the expanding, and/or the obtaining may be performed in a closed system.

In another aspect, the activating, the transducing, the expanding, and the harvesting may be performed in a closed or semi-closed system.

In another aspect, the closed system may be CliniMACS, Prodigy™, WAVE (XURI™) Bioreactor, WAVE (XURI™) Bioreactor in combination with BioSafe Sepax™ II, G-Rex/GatheRex™ closed system, or G-Rex/GatheRex™ closed system in combination with BioSafe Sepax™ II.

To produce T cells with improved efficacy for adoptive immunotherapy, T cell may be prepared by using methods disclosed in US20190292520, the content of which is hereby incorporated by reference in its entirety.

In an aspect, methods for producing T cells with improved efficacy for adoptive immunotherapy may include obtaining T cells from at least one healthy donor, patient, or individual, activating the T cells, transducing the activated T cells with a viral vector, expanding the transduced T cells for about 3 days to about 5 days after activation, collecting the expanded transduced T cells for infusing into the at least one healthy donor, patient, or individual, in which the efficacy for adoptive immunotherapy of the T cells expanded for about 3 to about 5 days is improved relative to activated and transduced T cells expanded for about 7 days or more after activation.

In another aspect, the expanded T cells exhibit a naïve T cells ($T_N$) and/or stem memory T cells ($T_{scm}$)/T central memory ($T_{cm}$) phenotype.

In another aspect, methods for producing T cells with improved efficacy for adoptive immunotherapy may include obtaining a population of CD8+ T cells from a patient or a donor, determining the percent of CD28+ CD8+ T cells in the obtained population, activating the determined population with anti-CD3 antibody and anti-CD28 antibody, in which the determined population comprises at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% of CD28+ CD8+ T cells, transducing the activated T cell population with a viral vector, and expanding the transduced T cell population.

In another aspect, the disclosure relates to ex vivo methods for producing T cells with improved efficacy for immunotherapy including: determining in an isolated CD8+ T cell population a percent of CD28+ CD8+ T cells, activating the determined population with anti-CD3 antibody and anti-CD28 antibody, and provided that the determined population comprises at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of CD28+ CD8+ T cells, transducing the activated T cell population with a viral vector, and expanding the transduced T cell population.

In another aspect, the disclosure relates to methods for producing T cells with improved efficacy for immunotherapy including: obtaining a population of CD8+ T cells from a patient or a donor, determining the percent of CD28+ CD8+ T cells in the obtained population, activating the determined TCR population with anti-CD3 antibody in the absence of anti-CD28 antibody, provided that the determined population comprises less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1% of CD28+ CD8+ T cells, transducing the activated T cell population with a viral vector, and expanding the transduced T cell population.

In another aspect, the disclosure relates to ex vivo methods for producing T cells with improved efficacy for immunotherapy including: determining in an isolated CD8+ T cell population the percent of CD28+ CD8+ T cells, activating the determined TCR population with anti-CD3 antibody in the absence of anti-CD28 antibody, provided that the determined population comprises less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1% of CD28+ CD8+ T cells, transducing the activated T cell population with a viral vector, and expanding the transduced T cell population.

In another aspect, the transducing and the expanding may be carried out in the presence of at least one cytokine.

In an aspect, the isolated γδ T cells can rapidly expand in response to contact with one or more antigens. Some γδ T cells, such as Vγ9Vδ2+ T cells, can rapidly expand in vitro in response to contact with some antigens, like prenyl-pyrophosphates, alkyl amines, and metabolites or microbial extracts during tissue culture. Stimulated γδ T-cells can exhibit numerous antigen-presentation, co-stimulation, and adhesion molecules that can facilitate the isolation of γδ T-cells from a complex sample. γδ T cells within a complex sample can be stimulated in vitro with at least one antigen for 1 day, 2 days, 3 days, 4 days, 5 days, 6 days, 7 days, or another suitable period of time. Stimulation of γδ T cells with a suitable antigen can expand γδ T cell population in vitro.

Non-limiting examples of antigens that may be used to stimulate the expansion of γδ T cells from a complex sample in vitro may include, prenyl-pyrophosphates, such as isopentenyl pyrophosphate (IPP), alkyl-amines, metabolites of human microbial pathogens, metabolites of commensal bacteria, methyl-3-butenyl-1-pyrophosphate (2M3B1PP), (E)-4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyrophosphate (MEPP), 3-formyl-1-butyl-pyrophosphate (TUBAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-γ-uridine triphosphate, crotoyl-γ-uridine triphosphate, allyl-γ-uridine triphosphate, ethylamine, isobutylamine, sec-butylamine, iso-amylamine and nitrogen containing bisphosphonates.

Activation and expansion of γδ T cells can be performed using activation and co-stimulatory agents described herein to trigger specific γδ T cell proliferation and persistence populations. In an aspect, activation and expansion of γδ T-cells from different cultures can achieve distinct clonal or mixed polyclonal population subsets. In another aspect, different agonist agents can be used to identify agents that provide specific γδ activating signals. In another aspect, agents that provide specific γδ activating signals can be different monoclonal antibodies (MAbs) directed against the γδ TCRs. In another aspect, companion co-stimulatory agents to assist in triggering specific γδ T cell proliferation without induction of cell energy and apoptosis can be used. These co-stimulatory agents can include ligands binding to receptors expressed on γδ cells, such as NKG2D, CD161, CD70, JAML, DNAX accessory molecule-1 (DNAM-1), ICOS, CD27, CD137, CD30, HVEM, SLAM, CD122, DAP, and CD28. In another aspect, co-stimulatory agents can be antibodies specific to unique epitopes on CD2 and CD3 molecules. CD2 and CD3 can have different conformation structures when expressed on αβ or γδ T-cells. In another aspect, specific antibodies to CD3 and CD2 can lead to distinct activation of γδ T cells.

A population of γδ T-cells may be expanded ex vivo prior to engineering of the γδ T-cells. Non-limiting example of reagents that can be used to facilitate the expansion of a γδ T-cell population in vitro may include anti-CD3 or anti-CD2, anti-CD27, anti-CD30, anti-CD70, anti-OX40 antibodies, IL-2, IL-15, IL-12, IL-9, IL-33, IL-18, or IL-21, CD70 (CD27 ligand), phytohaemagglutinin (PHA), concavalin A (ConA), pokeweed (PWM), protein peanut agglutinin (PNA), soybean agglutinin (SBA), Les *Culinaris* Agglutinin (LCA), *Pisum Sativum* Agglutinin (PSA), *Helix pomatia* agglutinin (HPA), *Vicia graminea* Lectin (VGA), or another suitable mitogen capable of stimulating T-cell proliferation.

In an aspect, engineered (or transduced) γδ T cells can be expanded ex vivo without stimulation by an antigen presenting cell or aminobisphosphonate. Antigen reactive engineered T cells of the present disclosure may be expanded ex vivo and in vivo. In another aspect, an active population of engineered γδ T cells of the present disclosure may be expanded ex vivo without antigen stimulation by an antigen presenting cell, an antigenic peptide, a non-peptide molecule, or a small molecule compound, such as an aminobisphosphonate but using certain antibodies, cytokines, mitogens, or fusion proteins, such as IL-17 Fc fusion, MICA Fc fusion, and CD70 Fc fusion. Examples of antibodies that can be used in the expansion of a γδ T-cell population include anti-CD3, anti-CD27, anti-CD30, anti-CD70, anti-OX40, anti-NKG2D, or anti-CD2 antibodies, examples of cytokines may include IL-2, IL-15, IL-12, IL-21, IL-18, IL-9, IL-7, and/or IL-33, and examples of mitogens may include CD70 the ligand for human CD27, phytohaemagglutinin (PHA), concavalin A (ConA), pokeweed mitogen (PWM), protein peanut agglutinin (PNA), soybean agglutinin (SBA), les culinaris agglutinin (LCA), Pisum sativum agglutinin (PSA), Helix pomatia agglutinin (HPA), Vicia graminea Lectin (VGA) or another suitable mitogen capable of stimulating T-cell proliferation. In another aspect, a population of engineered γδ T cells can be expanded in less than 60 days, less than 48 days, less than 36 days, less than 24 days, less than 12 days, or less than 6 days. In another aspect, a population of engineered γδ T cells can be expanded from about 7 days to about 49 days, about 7 days to about 42 days, from about 7 days to about 35 days, from about 7 days to about 28 days, from about 7 days to about 21 days, or from about 7 days to about 14 days.

In another aspect, the present disclosure provides methods for the ex vivo expansion of a population of engineered T-cells for adoptive transfer therapy. Engineered T cells of the disclosure may be expanded ex vivo. Engineered T cells of the disclosure can be expanded in vitro without activation by APCs, or without co-culture with APCs, and aminophosphates.

The ability of T cells to recognize a broad spectrum of antigens can be enhanced by genetic engineering of the T cells. In an aspect, T cells can be engineered to provide a universal allogeneic therapy that recognizes an antigen of choice in vivo. Genetic engineering of the T-cells may include stably integrating a construct expressing a tumor recognition moiety, such as αβ TCR, γδ TCR, chimeric antigen receptor (CAR), which combines both antigen-binding and T-cell activating functions into a single receptor, an antigen binding fragment thereof, or a lymphocyte activation domain into the genome of the isolated T-cell(s), a cytokine (for example, IL-15, IL-12, IL-2. IL-7. IL-21, IL-18, IL-19, IL-33, IL-4, IL-9, IL-23, or IL1β) to enhance T-cell proliferation, survival, and function ex vivo and in vivo. Genetic engineering of the isolated T-cell may also include deleting or disrupting gene expression from one or more endogenous genes in the genome of the isolated T-cells, such as the MHC locus (loci).

Chimeric Antigen Receptors (CARs)

Embodiments of the present disclosure may include introducing nucleic acids that encode one or more CARs into T cells. T cells may be αβ T cells, γδ T cells, or natural killer T cells. In various embodiments, the present disclosure provides T cells genetically engineered with vectors designed to express CARs that redirect cytotoxicity toward tumor cells. CARs are molecules that combine antibody-based specificity for a target antigen, e.g., tumor antigen, with a T cell receptor-activating intracellular domain to generate a chimeric protein that exhibits a specific anti-tumor cellular immune activity. As used herein, the term, "chimeric," describes being composed of parts of different proteins or DNAs from different origins.

CARs may contain an extracellular domain that binds to a specific target antigen (also referred to as a binding domain or antigen-specific binding domain), a transmembrane domain and an intracellular signaling domain. The main characteristic of CARs may be their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific coreceptors.

In particular embodiments, CARs may contain an extracellular binding domain including but not limited to an antibody or antigen binding fragment thereof, a tethered ligand, or the extracellular domain of a coreceptor, that specifically binds a target antigen that is a tumor-associated antigen (TAA) or a tumor-specific antigen (TSA). In certain embodiments, the TAA or TSA may be expressed on a blood cancer cell. In another embodiment, the TAA or TSA may be expressed on a cell of a solid tumor. In particular embodiments, the solid tumor may be a glioblastoma, a non-small cell lung cancer, a lung cancer other than a non-small cell lung cancer, breast cancer, prostate cancer, pancreatic cancer, liver cancer, colon cancer, stomach cancer, a cancer of the spleen, skin cancer, a brain cancer other than a glioblastoma, a kidney cancer, a thyroid cancer, or the like.

In particular embodiments, the TAA or TSA may be selected from the group consisting of alpha folate receptor, 5T4, αvβ6 integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, *Glypican-3 (GPC3), HLA-A1+MAGE1, HLA-A2+MAGE1, HLA-A3+MAGE1, HLA-A1+NY-ESO-1, HLA-A2+NY-ESO-1 HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, and VEGFR2.

Binding Domains of CARs

In particular embodiments, CARs contemplated herein comprise an extracellular binding domain that specifically binds to a target polypeptide, e.g., target antigen, expressed on tumor cell. As used herein, the terms, "binding domain," "extracellular domain,"
"extracellular binding domain," "antigen-specific binding domain," and "extracellular antigen specific binding domain," may be used interchangeably and provide a CAR with the ability to specifically bind to the target antigen of interest. A binding domain may include any protein, polypeptide, oligopeptide, or peptide that possesses the ability to specifically recognize and bind to a biological molecule (e.g., a cell surface receptor or tumor protein, lipid, polysaccharide, or other cell surface target molecule, or component thereof). A binding domain may include any naturally occurring, synthetic, semi-synthetic, or recombinantly produced binding partner for a biological molecule of interest.

In particular embodiments, the extracellular binding domain of a CAR may include an antibody or antigen binding fragment thereof. An "antibody" refers to a binding agent that is a polypeptide containing at least a light chain or heavy chain immunoglobulin variable region, which specifically recognizes and binds an epitope of a target antigen, such as a peptide, lipid, polysaccharide, or nucleic acid containing an antigenic determinant, such as those recognized by an immune cell. Antibodies may include antigen binding fragments thereof. The term may also include genetically engineered forms, such as chimeric antibodies (for example, humanized murine antibodies), hetero-conjugate antibodies, e.g., bispecific antibodies, and antigen binding fragments thereof. See also, Pierce Catalog and Handbook, 1994-1995 (Pierce Chemical Co., Rockford, Ill.); Kuby, J., Immunology, 3rd Ed., W. H. Freeman & Co., New York, 1997.

In particular embodiments, the target antigen may be an epitope of an alpha folate receptor, 5T4, αvβ6 integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, *Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, or VEGFR2 polypeptide.

Light and heavy chain variable regions may contain a "framework" region interrupted by three hypervariable regions, also called "complementarity-determining regions" or "CDRs." The CDRs can be defined or identified by conventional methods, such as by sequence according to Kabat et al (Wu, T T and Kabat, E. A., J Exp Med. 132(2):211-50, (1970); Borden, P. and Kabat E. A., PNAS, 84: 2440-2443 (1987); (see, Kabat et al, Sequences of Proteins of Immunological Interest, U.S. Department of Health and Human Services, 1991, which is hereby incorporated by reference), or by structure according to Chothia et al (Choithia, C. and Lesk, A. M., J Mol. Biol, 196(4): 901-917 (1987), Choithia, C. et al, Nature, 342: 877-883 (1989)). The contents of the afore-mentioned references are hereby incorporated by reference in their entireties. The sequences of the framework regions of different light or heavy chains may be relatively conserved within a species, such as humans. The framework region of an antibody that is the combined framework regions of the constituent light and heavy chains may serve to position and align the CDRs in three-dimensional space. The CDRs may be primarily responsible for binding to an epitope of an antigen. The CDRs of each chain may be typically referred to as CDR1, CDR2, and CDR3, numbered sequentially starting from the N-terminus, and may be also typically identified by the chain, in which the particular CDR is located. Thus, the CDRs located in the variable domain of the heavy chain of the antibody may be referred to as CDRH1, CDRH2, and CDRH3, whereas the CDRs located in the variable domain of the light chain of the antibody are referred to as CDRL1, CDRL2, and CDRL3. Antibodies with different specificities (i.e., different combining sites for different antigens) may have different CDRs. Although it is the CDRs that vary from antibody to antibody, only a limited number of amino acid positions within the CDRs are directly involved in antigen binding. These positions within the CDRs are called specificity determining residues (SDRs).

References to "VH" or "VH" refers to the variable region of an immunoglobulin heavy chain, including that of an antibody, Fv, scFv, dsFv, Fab, or other antibody fragment. References to "VL" or "VL" refers to the variable region of an immunoglobulin light chain, including that of an antibody, Fv, scFv, dsFv, Fab, or other antibody fragment.

A "monoclonal antibody" is an antibody produced by a single clone of B lymphocytes or by a cell into which the light and heavy chain genes of a single antibody have been transfected. Monoclonal antibodies may be produced by methods known to those of skill in the art, for example, by making hybrid antibody-forming cells from a fusion of myeloma cells with immune spleen cells. Monoclonal antibodies may include humanized monoclonal antibodies.

A "chimeric antibody" has framework residues from one species, such as human, and CDRs (which generally confer antigen binding) from another species, such as a mouse. In particular preferred embodiments, a CAR disclosed herein may contain antigen-specific binding domain that is a chimeric antibody or antigen binding fragment thereof.

In certain embodiments, the antibody may be a humanized antibody (such as a humanized monoclonal antibody) that specifically binds to a surface protein on a tumor cell. A "humanized" antibody is an immunoglobulin including a human framework region and one or more CDRs from a non-human (for example a mouse, rat, or synthetic) immunoglobulin. Humanized antibodies can be constructed by means of genetic engineering (see for example, U.S. Pat. No. 5,585,089, the content of which is hereby incorporated by reference in its entirety).

In embodiments, the extracellular binding domain of a CAR may contain an antibody or antigen binding fragment thereof, including but not limited to a Camel Ig (a camelid antibody (VHH)), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody).

"Camel Ig" or "camelid VHH" as used herein refers to the smallest known antigen-binding unit of a heavy chain antibody (Koch-Nolte, et al, FASEB J., 21:3490-3498 (2007), the content of which is hereby incorporated by reference in its entirety). A "heavy chain antibody" or a "camelid antibody" refers to an antibody that contains two VH domains and no light chains (Riechmann L. et al, J. Immunol. Methods 231:25-38 (1999); WO94/04678; WO94/25591; U.S. Pat. No. 6,005,079; the contents of which are hereby incorporated by reference in its entirety).

"IgNAR" of "immunoglobulin new antigen receptor" refers to class of antibodies from the shark immune repertoire that consist of homodimers of one variable new antigen receptor (VNAR) domain and five constant new antigen receptor (CNAR) domains.

Papain digestion of antibodies produces two identical antigen-binding fragments, called "Fab" fragments, each with a single antigen-binding site, and a residual "Fc" fragment, whose name reflects its ability to crystallize readily. The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue (s) of the constant domains bear a free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-binding site. In a single-chain Fv (scFv) species, one heavy- and one light-chain variable domain can be covalently linked by a flexible peptide linker such that the light and heavy chains can associate in a "dimeric" structure analogous to that in a two-chain Fv species.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al, Nat. Med. 9:129-134 (2003); and Hollinger et al, PNAS USA 90: 6444-6448 (1993). Triabodies and tetrabodies are also described in Hudson et al, Nat. Med. 9:129-134 (2003). The contents of the afore-mentioned references are hereby incorporated by reference in their entireties.

"Single domain antibody" or "sdAb" or "nanobody" refers to an antibody fragment that consists of the variable region of an antibody heavy chain (VH domain) or the variable region of an antibody light chain (VL domain) (Holt, L., et al, Trends in Biotechnology, 21(11): 484-490, the content of which is hereby incorporated by reference in its entirety).

"Single-chain Fv" or "scFv" antibody fragments comprise the VH and VL domains of antibody, wherein these domains are present in a single polypeptide chain and in either orientation {e.g., VL-VH or VH-VL). Generally, the scFv polypeptide further comprises a polypeptide linker between the VH and VL domains which enables the scFv to form the desired structure for antigen binding. For a review of scFv, see, e.g., Pluckthun, in The Pharmacology of Monoclonal Antibodies, vol. 113, Rosenburg and Moore eds., (Springer-Verlag, New York, 1994), pp. 269-315, the content of which is hereby incorporated by reference in its entirety.

In a certain embodiment, the scFv binds an alpha folate receptor, 5T4, αvβ6 integrin, BCMA, B7-H3, B7-H6, CALX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, *Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, or VEGFR2 polypeptide.

Linkers of CARs

In certain embodiments, the CARs may contain linker residues between the various domains, e.g., between VH and VL domains, added for appropriate spacing and conformation of the molecule. CARs may contain one, two, three, four, or five or more linkers. In particular embodiments, the length of a linker may be about 1 to about 25 amino acids, about 5 to about 20 amino acids, or about 10 to about 20 amino acids, or any intervening length of amino acids. In some embodiments, the linker may be 1, 2, 3, 4, 5, 6, 7, 8, 9, 10, 11, 12, 13, 14, 15, 16, 17, 18, 19, 20, 21, 22, 23, 24, 25, or more amino acids long. Illustrative examples of linkers include glycine polymers (G)n; glycine-serine polymers (Gi_sSi_5)n, where n is an integer of at least one, two, three, four, or five; glycine-alanine polymers; alanine-serine polymers; and other flexible linkers known in the art. Glycine and glycine-serine polymers are relatively unstructured, and therefore may be able to serve as a neutral tether between domains of fusion proteins, such as CARs. Glycine may access significantly more phi-psi space than even alanine, and may be much less restricted than residues with longer side chains (see Scheraga, Rev. Computational Chem. 11173-142 (1992), the content of which is hereby incorporated by reference in its entirety). The ordinarily skilled artisan may recognize that design of a CAR in particular embodiments can include linkers that may be all or partially flexible, such that the linker can include a flexible linker as well as one or more portions that confer less flexible structure to provide for a desired CAR structure.

In particular embodiments a CAR may include a scFV that may further contain a variable region linking sequence. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that may contain the same light and heavy chain variable regions. In one embodiment, the variable region linking sequence may be 1, 2, 3, 4, 5, 6, 7, 8, 9, 10, 11, 12, 13, 14, 15, 16, 17, 18, 19, 20, 21, 22, 23, 24, 25, or more amino acids long. In a particular embodiment, the variable region linking sequence may contain a glycine-serine polymer (Gi_sSi_5)n, where n is an integer of at least 1, 2, 3, 4, or 5. In another embodiment, the variable region linking sequence comprises a $(G_4S)_3$ amino acid linker.

Spacer Domains of CARs

In particular embodiments, the binding domain of the CAR may be followed by one or more "spacer domains," which refers to the region that moves the antigen binding domain away from the effector cell surface to enable proper cell/cell contact, antigen binding and activation (Patel et al, Gene Therapy, 1999; 6: 412-419, the content of which is hereby incorporated by reference in its entirety). The spacer domain may be derived either from a natural, synthetic, semi-synthetic, or recombinant source. In certain embodiments, a spacer domain may be a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region. In one embodiment, the spacer domain may include the CH2 and CH3 of IgG1.

Hinge Domains of CARs

The binding domain of CAR may be generally followed by one or more "hinge domains," which may play a role in positioning the antigen binding domain away from the effector cell surface to enable proper cell/cell contact, antigen binding and activation. CAR generally may include one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the CARs may include the hinge region derived from the extracellular regions of type 1 membrane proteins, such as CD8a, CD4, CD28 and CD7, which may be wild-type hinge regions from these molecules or may be altered. In another embodiment, the hinge domain may include a CD8a hinge region.

Transmembrane (TM) Domains of CARs

The "transmembrane domain" may be the portion of CAR that can fuse the extracellular binding portion and intracellular signaling domain and anchors CAR to the plasma membrane of the immune effector cell. The TM domain may be derived either from a natural, synthetic, semi-synthetic, or recombinant source. Illustrative TM domains may be derived from (including at least the transmembrane region(s) of) the α, β, or ζ chain of the T-cell receptor, CD3ε, CD3ϑ, CD4, CD5, CD9, CD16, CD22, CD27, CD28, CD33, CD37, CD45, CD64, CD80, CD86, CD 134, CD137, and CD154. In one embodiment, CARs may contain a TM domain derived from CD8a. In another embodiment, a CAR contemplated herein comprises a TM domain derived from CD8a and a short oligo- or polypeptide linker, preferably between 1, 2, 3, 4, 5, 6, 7, 8, 9, or 10 amino acids in length that links the TM domain and the intracellular signaling domain of CAR. A glycine-serine linker provides a particularly suitable linker.

Intracellular Signaling Domains of CARs

In particular embodiments, CARs may contain an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of the cell. Effector function of the T cell, for example, may be cytolytic activity or help or activity including the secretion of a cytokine. Thus, the term "intracellular signaling domain" refers to the portion of a protein, which can transduce the effector function signal and that direct the cell to perform a specialized function. While usually the entire intracellular signaling domain can be employed, in many cases it is not necessary to use the entire domain. To the extent that a truncated portion of an intracellular signaling domain may be used, such truncated portion may be used in place of the entire domain as long as it can transduce the effector function signal. The term intracellular signaling domain may be meant to include any truncated portion of the intracellular signaling domain sufficient to transducing effector function signal.

It is known that signals generated through TCR alone are insufficient for full activation of the T cell and that a secondary or costimulatory signal may be also required. Thus, T cell activation can be said to be mediated by two distinct classes of intracellular signaling domains: primary signaling domains that initiate antigen-dependent primary activation through the TCR (e.g., a TCR/CD3 complex) and costimulatory signaling domains that act in an antigen-independent manner to provide a secondary or costimulatory signal. In preferred embodiments, CAR may include an intracellular signaling domain that may contain one or more "costimulatory signaling domain" and a "primary signaling domain." Primary signaling domains can regulate primary activation of the TCR complex either in a stimulatory way, or in an inhibitory way. Primary signaling domains that act in a stimulatory manner may contain signaling motifs, which are known as immunoreceptor tyrosine-based activation motifs or ITAMs. Illustrative examples of ITAM containing primary signaling domains that are of particular use in the invention may include those derived from TCRζ, FcRγ, FcRβ, CD3γ, CD3δ, CD3ε, CD3ζ CD22, CD79a, CD79b, and CD66d. In particular preferred embodiments, CAR may include a CD3ζ primary signaling domain and one or more costimulatory signaling domains. The intracellular primary signaling and costimulatory signaling domains may be linked in any order in tandem to the carboxyl terminus of the transmembrane domain.

CARs may contain one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule. Illustrative examples of such costimulatory molecules may include CD27, CD28, 4-1BB (CD137), OX40 (CD134), CD30, CD40, PD-1, ICOS (CD278), CTLA4, LFA-1, CD2, CD7, LIGHT, TRIM, LCK3, SLAM, DAP10, LAG3, HVEM and NKD2C, and CD83. In one embodiment, CAR may contain one or more costimulatory signaling domains selected from the group consisting of CD28, CD137, and CD134, and a CD3ζ primary signaling domain.

In one embodiment, CAR may contain an scFv that binds an alpha folate receptor, 5T4, αvβ6 integrin, BCMA, B7-H3, B7-H6, CALX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, *Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, or VEGFR2 polypeptide; a transmembrane domain derived from a polypeptide selected from the group consisting of: CD8α; CD4, CD45, PD1, and CD152; and one or more intracellular costimulatory signaling domains selected from the group consisting of: CD28, CD54, CD134, CD137, CD152, CD273, CD274, and CD278; and a CD3ζ primary signaling domain.

In another embodiment, CAR may contain an scFv that binds an alpha folate receptor, 5T4, αvβ6 integrin, BCMA, B7-H3, B7-H6, CALX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, *Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, or VEGFR2 polypeptide; a hinge domain selected from the group consisting of: IgG1 hinge/CH2/CH3 and CD8α, and CD8α; a transmembrane domain derived from a polypeptide selected from the group consisting of: CD8α; CD4, CD45, PD1, and CD152; and one or more intracellular costimulatory signaling domains selected from the group consisting of: CD28, CD 134, and CD 137; and a CD3ζ primary signaling domain.

In yet another embodiment, CAR may contain an scFv, further including a linker, that binds an alpha folate receptor, 5T4, αvβ6 integrin, BCMA, B7-H3, B7-H6, CAIX, CD 19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, *Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY- ESO-1, PRAME, PSCA, PSMA, ROR1, SSX, Survivin, TAG72, TEMs, or VEGFR2 polypeptide; a hinge domain selected from the group consisting of: IgG1 hinge/CH2/CH3 and CD8α, and CD8α; a transmembrane domain comprising a TM domain derived from a polypeptide selected from the group consisting of: CD8α; CD4, CD45, PD1, and CD 152, and a short oligo- or polypeptide linker, preferably between 1, 2, 3, 4, 5, 6, 7, 8, 9, or 10 amino acids in length that links the TM domain to the intracellular signaling domain of the CAR; and one or more intracellular costimulatory signaling domains selected from the group consisting of: CD28, CD 134, and CD137; and a CD3ζ primary signaling domain.

In a particular embodiment, CAR may contain an scFv that binds an alpha folate receptor, 5T4, αvβ6 integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, *Glypican-3 (GPC3), HLA-A1+MAGE1, HLA-A2+M AGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, or VEGFR2 polypeptide; a hinge domain containing a CD8a polypeptide; a CD8a transmembrane domain containing a polypeptide linker of about 3 amino acids; one or more intracellular costimulatory signaling domains selected from the group consisting of: CD28, CD134, and CD137; and a CD3ζ primary signaling domain.

Engineered T-cells may be generated with various methods. For example, a polynucleotide encoding an expression cassette that comprises a tumor recognition, or another type of recognition moiety, can be stably introduced into the T-cell by a transposon/transposase system or a viral-based gene transfer system, such as a lentiviral or a retroviral system, or another suitable method, such as transfection, electroporation, transduction, lipofection, calcium phosphate ($CaPO_4$), nanoengineered substances, such as Ormosil, viral delivery methods, including adenoviruses, retroviruses, lentiviruses, adeno-associated viruses, or another suitable method. A number of viral methods have been used for human gene therapy, such as the methods described in WO 1993020221, the content of which is incorporated herein in its entirety. Non-limiting examples of viral methods that can be used to engineer T cells may include γ-retroviral, adenoviral, lentiviral, herpes simplex virus, vaccinia virus, pox virus, or adeno-virus associated viral methods.

In an aspect, constructs and vectors described herein are used with the methodology described in U.S. Ser. No. 16/200,308, filed on Nov. 26, 2018, the contents of which are incorporated by reference in their entirety.

Cassettes

The present invention can employ cassettes comprising one or more NOIs, which, in the case of two or more NOIs, can be operably linked by an IRES. These cassettes may be used in a method for producing the vector genome in a producer cell.

The present invention also provides an expression vector comprising such a cassette. Transfection of a suitable cell with such an expression vector should result in a cell that expresses each POI encoded by the NOI in the cassette. The present invention also provides such a transfected cell.

Cloning of the cassette into an expression vector and transfection of cells with the vector (to give expression of the cassette) can be carried out by techniques well known in the art (such as those described in Sambrook et al. (Molecular Cloning: A Laboratory Manual, 2nd Edition, Cold Spring Harbor Laboratory Press (1989)), and other laboratory textbooks).

In some aspects, the cassette comprises a promoter.

In some aspects, the cassette comprises one NOI. The NOI can be any NOI as described in detail above. For example, the NOI may have a therapeutic or diagnostic application. Suitable NOIs include, but are not limited to: sequences encoding enzymes, cytokines, chemokines, hormones, antibodies, anti-oxidant molecules, engineered immunoglobulin-like molecules, a single chain antibody, fusion proteins, immune co-stimulatory molecules, immunomodulatory molecules, anti-sense RNA, small interfering RNA (siRNA), a trans dominant negative mutant of a target protein, a toxin, a conditional toxin, an antigen, an antigen receptor, a chimeric antigen receptor, a T-cell receptor, a tumor suppressor protein, and growth factors, membrane proteins, pro- and anti-angiogenic proteins and peptides, vasoactive proteins and peptides, antiviral proteins and ribozymes, and derivatives thereof (such as with an associated reporter group).

In some aspects, the cassette comprises two or more NOIs. A cassette comprising two or more NOIs can be bi-cistronic or tri-cistronic, and can comprise the following elements:

Promoter-($NOI_1$)-($IRES_1$)-($NOI_2$)
Promoter-($NOI_1$)-($IRES_1$)-($NOI_2$)-($IRES_2$)-($NOI_3$)

In some embodiments, a single lentiviral cassette can be used to create a single lentiviral vector, expressing one or more proteins. In particular, a single lentiviral cassette can be used to create a single lentiviral vector expressing at least four individual monomer proteins of two distinct dimers from a single multi-cistronic mRNA so as to co-express the dimers on the cell surface. For example, the integration of a single copy of the lentiviral vector has been shown to be sufficient to transform γδ T cells to co-express TCRαβ and CD8αβ.

In one aspect, the present disclosure relates to vectors containing a multi-cistronic cassette within a single vector capable of expressing more than one, more than two, more than three, more than four genes, more than five genes, or more than six genes, in which the polypeptides encoded by these genes may interact with one another, or may form dimers. The dimers may be homodimers, i.e., two identical proteins forming a dimer, or heterodimers, i.e., two structurally different proteins forming a dimer.

In one aspect, a lentiviral vector may contain a first nucleotide sequence S1 encoding a protein Z1, a second nucleotide sequence S2 encoding a protein Z2, a third nucleotide sequence S3 encoding a protein Y1, and a fourth nucleotide sequence S4 encoding a protein Y2, in which Z1 and Z2 form a first dimer and Y1 and Y2 form a second dimer, in which the first dimer Z1Z2 is different from the second dimer Y1Y2.

In one aspect, a first lentiviral vector may contain a bi-cistronic cassette (2-in-1) encoding a dimer Z1Z2, and a second lentiviral vector may contain a bi-cistronic cassette (2-in-1) encoding a dimer Y1Y2. In the 2-in-1 vectors, S1 and S2 may be arranged in tandem in a 5' to 3' orientation of S1-S2 or S2-S1. Likewise, in the 2-in-1 vectors, S3 and S4 may be arranged in tandem in a 5' to 3' orientation of S3-S4 or S4-S3. Z1 and Z2 or Y1 and Y2 may be separated by one or more self-cleaving 2A peptides.

In another aspect, a single lentiviral vector (4-in-1) may encode both distinct dimers Z1Z2 and Y1Y2, in which Z1, Z2, Y1, and Y2 may be separated by one or more self-cleaving 2A peptides. For example, the S1, S2, S3, and S4 may be arranged in tandem in a 5' to 3' orientation selected from S1-S2-S3-S4, S1-S2-S4-S3, S1-S3-S2-S4, S1-S3-S4-S2, S1-S4-S3-S2, S1-S4-S2-S3, S2-S1-S3-S4, S2-S1-S4-S3, S2-S3-S1-S4, S2-S3-S4-S1, S2-S4-S3-S1, S2-S4-S1-S3, S3-S1-S2-S4, S3-S1-S4-S2, S3-S2-S1-S4, S3-S2-S4-S1, S3-S4-S1-S2, S3-S4-S2-S1, S4-S1-S2-S3, S4-S1-S3-S2, S4-S2-S1-S3, S4-S2-S3-S1, S4-S3-S1-S2, or S4-S3-S2-S1.

In an aspect, the dimer Z1Z2 and/or the dimer Y1Y2 may be TCRs having a TCRα chain and a TCR chain or TCRs having a TCRγ chain and a TCRδ chain.

In an aspect, TCRs and antigen binding proteins that are capable of use with the constructs, methods and embodiments described herein include, for example, those listed in Table 3 (SEQ ID NOs: 13-92) and those TCRs and antigen binding proteins described in U.S. Publication 20170267738, U.S. Publication 20170312350, U.S. Publication 20180051080, U.S. Publication 20180164315, U.S. Publication 20180161396, U.S. Publication 20180162922, U.S. Publication 20180273602, U.S. Publication 20190016801, U.S. Publication 20190002556, and U.S. Publication 20190135914, the contents of each of these publications and sequence listings described therein are herein incorporated by reference in their entireties.

In an aspect, TCRs and antigen binding proteins that are capable of use with the constructs, methods and embodiments described herein include, for example, TCRs and antigen binding proteins that bind to binds to a "target antigenic (TA) peptide".

The "target antigenic (TA) peptide" as used in context of the present invention refers to peptides which have been isolated and identified from infected or tumorous material, such as material isolated from individuals suffering from tuberculosis, or from an infection of the Epstein-Barr virus or from cancer. The protein from which the TA peptide is derived is subject to antigen processing in an infected cell or a tumor cell, ten presented at the cell surface by the MHC molecule and the cell, in particular the TA peptide/MHC complex can thus be recognized by immune effector cells of the host, such as T-cells or NKT cells. The TA peptide in context of the present invention comprises or consists of 10, 12 or 14, such as 8 to 14, 8 to 12, for example 9 to 11 amino acids. In context of the present invention, when it is referred to a specific TA peptide, it is referred to TA-C. Examples of TA antigenic peptides, such as TA-C peptides are viral antigenic peptides, bacterial antigenic peptides or tumour associated antigen (TAA) antigenic peptides, preferably TAA antigenic peptides. Accordingly, in one embodiment, the TA antigenic peptide, in particular the TA-C, is a viral peptide, a bacterial peptide or a tumour associated antigen (TAA) antigenic peptide, preferably a TAA antigenic peptide.

A "viral antigenic peptide" in context of the present invention is an antigenic peptide that is presented by the MHC molecule on the surface of a diseased cell and is of a viral origin, i.e. the cell is typically infected by said virus. Such viral antigenic peptides have been discovered in context of infections from, for example, human immunodeficiency viruses (HIV), Human Cytomegalovirus (HCMV), cytomegalovirus (CMV), human papillomavirus (HPV), Hepatitis B virus (HBV), Hepatitis C virus (HCV), human papillomavirus infection (HPV), Epstein-Barr virus (EBV), Influenza virus. Accordingly, the viral antigenic peptide in context of the present invention may be an antigenic peptide selected from the group consisting of HIV antigenic peptides, HCMV antigenic peptide, CMV antigenic peptides, HPV antigenic peptides, HBV antigenic peptides; HCV antigenic peptides; EBV antigenic peptides, Influenza antigenic peptides, preferably HIV, HBV, Influenza and HCMV antigenic peptides.

Viral antigenic peptides that are capable of use with methods and embodiments described herein include, for example, those viral antigenic peptides described in in the table herein below. In an aspect, viral antigenic peptides that are capable of use with the methods and embodiments described herein include at least one viral antigenic peptide comprising or consisting of an amino acid sequence selected from the amino acid sequences of SEQ ID NO: 96 to SEQ ID NO: 98, as depicted herein below in table 1.

TABLE 1

List of viral antigenic peptides

| SEQ ID NO: | Peptide | Virus | MHC |
|---|---|---|---|
| 96 | SLYNTVATL | HIV | HLA-A*02:01 |
| 97 | GILGFVFTL | Influenza A | HLA-A*02:01 |
| 98 | NLVPMVATV | HCMV | HLA-A*02:01 |

A "bacterial antigenic peptide" in context of the present invention is an antigenic peptide that is presented by the MHC molecule on the surface of a diseased cell and is of a bacterial origin, i.e. the cell is typically infected by said bacteria. Such bacterial antigenic peptides have been discovered in context of infections from, for example, *Mycobacterium tuberculosis*. Accordingly, the bacterial antigenic peptide in context of the present invention may be a *Mycobacterium tuberculosis* antigenic peptide.

"Tumor-associated antigens (TAA) peptides" also referred to as "TAA peptides" herein denotes peptides which have been isolated and identified from tumorous material and which underwent antigen processing in a tumor cell and can thus be recognized by immune effector cells of the host. The TAA peptides comprises or consists of 10, 12 or 14, such as 8 to 14, 8 to 12, for example 9 to 11 amino acids. The TAA peptides in context of the present invention may be for example a cancer/testis (CT) antigenic peptide. Examples of cancer/testis (CT) antigenic peptides are the MAGE-A antigenic peptide of the amino acid sequence of SEQ ID NO: 216 and the PRAME antigenic peptide of the amino acid sequence of SEQ ID NO: 148. The TAA peptide in context of the present invention comprises a T-cell epitope and may also be referred to as TAA peptide, in a general context, and as TAA peptide C in context of the present invention when it is referred to one specific TAA peptide.

In an aspect, tumor associated antigen (TAA) peptides that are capable of use with methods and embodiments described herein include, for example, those TAA peptides described in U.S. Publication 20160187351, U.S. Publication 20170165335, U.S. Publication 20170035807, U.S. Publication 20160280759, U.S. Publication 20160287687, U.S. Publication 20160346371, U.S. Publication 20160368965, U.S. Publication 20170022251, U.S. Publication 20170002055, U.S. Publication 20170029486, U.S. Publication 20170037089, U.S. Publication 20170136108, U.S. Publication 20170101473, U.S. Publication 20170096461, U.S. Publication 20170165337, U.S. Publication 20170189505, U.S. Publication 20170173132, U.S. Publication 20170296640, U.S. Publication 20170253633, U.S. Publication 20170260249, U.S. Publication 20180051080, and U.S. Publication No. 20180164315, the contents of each of these publications and sequence listings described therein are herein incorporated by reference in their entireties.

In an aspect, the bispecific antigen binding proteins described herein, in particular the antigen binding site B in context of the present invention, selectively recognize cells which present a TAA peptide described in one of more of the patents and publications described above. In another aspect, TAA that are capable of use with the methods and embodiments described herein include at least one TAA consisting of an amino acid sequence selected from the amino acid sequences of SEQ ID NO: 99 to 256, preferably SEQ ID NO: 148 and 216. In an aspect, the bispecific antigen binding proteins, in particular the antigen binding site B of the bispecific antigen binding proteins, selectively recognize cells which present a TAA peptide/MHC complex, wherein the TAA peptide comprises or consist of an amino acid sequence of SEQ ID NO: 99 to 256, or any of the amino acid sequences described in the patents or applications described herein, preferably SEQ ID NO: 148 and 216.

Furthermore, the TA antigenic peptide in context of the present invention is a specific ligand of MHC-class-1-molecules or MHC-class-II-molecules, preferably MHC-class-I-molecules.

In context of the present invention, the TAA antigenic peptide C is preferably selected from the group of TAA antigenic peptides consisting of the amino acids sequence of SEQ ID NO: 99 to 256, preferably the PRAME antigenic peptide comprising or consisting of the amino acid sequence 'SLLQHLIGL' of SEQ ID NO: 148 or the MAGE-A antigenic peptide comprising or consisting of the amino acid sequence 'KVLEHVVRV' of SEQ ID NO: 216, more preferably SEQ ID NO: 216, wherein the MHC is preferably a HLA-A*02.

In another aspect, the dimer Z1Z2 and/or the dimer Y1Y2 may be TCRα chain and TCRβ chain selected from R11KEA (SEQ ID NO: 13 and 14), R20P1H7 (SEQ ID NO: 15 and 16), R7P1D5 (SEQ ID NO: 17 and 18), R10P2G12 (SEQ ID NO: 19 and 20), R10P1A7 (SEQ ID NO: 21 and 22), R4P1D10 (SEQ ID NO: 23 and 24), R4P3F9 (SEQ ID NO: 25 and 26), R4P3F9-B4 (SEQ ID NO: 25 and 92), R4P3F9-A1B4 (SEQ ID NO: 91 and 92), R4P3H3 (SEQ ID NO: 27 and 28), R36P3F9 (SEQ ID NO: 29 and 30), R52P2G11 (SEQ ID NO: 31 and 32), R53P2A9 (SEQ ID NO: 33 and 34), R26P1A9 (SEQ ID NO: 35 and 36), R26P2A6 (SEQ ID NO: 37 and 38), R26P3H1 (SEQ ID NO: 39 and 40), R35P3A4 (SEQ ID NO: 41 and 42), R37P1C9 (SEQ ID NO: 43 and 44), R37P1H1 (SEQ ID NO: 45 and 46), R42P3A9 (SEQ ID NO: 47 and 48), R43P3F2 (SEQ ID NO: 49 and 50), R43P3G5 (SEQ ID NO: 51 and 52), R59P2E7 (SEQ ID NO: 53 and 54), R11P3D3 (SEQ ID NO: 55 and 56), R16P1C10 (SEQ ID NO: 57 and 58), R16P1E8 (SEQ ID NO: 59 and 60), R17P1A9 (SEQ ID NO: 61 and 62), R17P1D7 (SEQ ID NO: 63 and 64), R17P1G3 (SEQ ID NO: 65 and 66), R17P2B6 (SEQ ID NO: 67 and 68), R11P3D3KE (SEQ ID NO: 69 and 70), R39P1C12 (SEQ ID NO: 71 and 72), R39P1F5 (SEQ ID NO: 73 and 74), R40P1C2 (SEQ ID NO: 75 and 76), R41P3E6 (SEQ ID NO: 77 and 78), R43P3G4 (SEQ ID NO: 79 and 80), R44P3B3 (SEQ ID NO: 81 and 82), R44P3E7 (SEQ ID NO: 83 and 84), R49P2B7 (SEQ ID NO: 85 and 86), R55P1G7 (SEQ ID NO: 87 and 88), or R59P2A7 (SEQ ID NO: 89 and 90).

Table 2 shows examples of the peptides to which TCRs bind when the peptide is in a complex with an MHC molecule.

TABLE 2

| TCR name | Peptide (SEQ ID NO:) |
|---|---|
| R20P1H7, R7P1D5, R10P2G12 | KVLEHVVRV (SEQ ID NO: 216) |
| R10P1A7 | KIQEILTQV (SEQ ID NO: 124) |
| R4P1D10, R4P3F9, R4P3H3 | FLLDGSANV (SEQ ID NO: 239) |
| R36P3F9, R52P2G11, R53P2A9 | ILQDGQFLV (SEQ ID NO: 194) |
| R26P1A9, R26P2A6, R26P3H1, R35P3A4, R37P1C9, R37P1H1, R42P3A9, R43P3F2, R43P3G5, R59P2E7 | KVLEYVIKV (SEQ ID NO: 203) |
| R11KEA, R11P3D3, R16P1C10, R16P1E8, R17P1A9, R17P1D7, R17P1G3, R17P2B6, R11P3D3KE | SLLQHLIGL (SEQ ID NO: 148) |
| R39P1C12, R39P1F5, R40P1C2, R41P3E6, R43P3G4, R44P3B3, R44P3E7, R49P2B7, R55P1G7, R59P2A7 | ALSVLRLAL (SEQ ID NO: 249) |

In an aspect, tumor associated antigen (TAA) peptides that are capable of use with the methods and embodiments described herein include, for example, those listed in Table 4 and those TAA peptides described in U.S. Publication 20160187351, U.S. Publication 20170165335, U.S. Publication 20170035807, U.S. Publication 20160280759, U.S. Publication 20160287687, U.S. Publication 20160346371, U.S. Publication 20160368965, U.S. Publication 20170022251, U.S. Publication 20170002055, U.S. Publication 20170029486, U.S. Publication 20170037089, U.S. Publication 20170136108, U.S. Publication 20170101473, U.S. Publication 20170096461, U.S. Publication 20170165337, U.S. Publication 20170189505, U.S. Publication 20170173132, U.S. Publication 20170296640, U.S. Publication 20170253633, U.S. Publication 20170260249, U.S. Publication 20180051080, and U.S. Publication No. 20180164315, the contents of each of these publications and sequence listings described therein are herein incorporated by reference in their entireties.

In another aspect, the dimer Z1Z2 and/or the dimer Y1Y2 may be T cell dimeric signaling modules, such as CD3δ/ε, CD3γ/ε, and CD247 ζ/ζ or ζ/η, a dimer of a TCRα variable region (Vα) and a TCRβ variable region (Vβ), a dimer of immunoglobulin heavy chain variable region (VH) and immunoglobulin light chain variable region (VL), a dimer of Vα and VH, a dimer of Vα and VL, a dimer of Vβ and VH, or a dimer of Vβ and VL.

In another aspect, the dimer Z1Z2 and/or the dimer Y1Y2 may be a TCR coreceptor, such as a CD8a chain and CD8β chain, a CD4a chain and a CD4β chain, or any other suitable dimeric membrane receptors, preferably those expressed in the CD8+ T cells and/or in the CD4+ T cells.

In some aspects, the dimer Z1Z2 is a TCR and the dimer Y1Y2 is a TCR coreceptor.

Furin is a ubiquitous subtilisin-like proprotein convertase, whose natural substrates include certain serum proteins and growth factor receptors, such as the insulin-like growth factor receptor. The consensus sequence for furin cleavage is RXXR (SEQ ID NO: 93) but the potential for actual cleavage is dependent on substrate tertiary structure and the amino acids immediately surrounding the recognition site.

Addition of a furin cleavage site plus the linker sequences (such as GSG or SGSG (SEQ ID NO: 5)) may enable highly efficient gene expression.

In one aspect, a nucleotide sequence of furin-linker-2A peptide arranged in tandem may be positioned between Z1 and Z2, between Z1 and Y1, between Z1 and Y2, between Z2 and Y1, between Z2 and Y2, and/or between Y1 and Y2. The furin may have a consensus sequence of RXXR (SEQ ID NO: 93), e.g., RAKR (SEQ ID NO: 10). The linker sequence may be from 3 to 10 amino acids long, such as from 3 to 8 amino acids long, from 3 to 5 amino acids long, or from 3 to 4 amino acids long. In some aspects, the linker sequence may be SGS, GGGS (SEQ ID NO: 257), GGGGS (SEQ ID NO: 258), GGSGG (SEQ ID NO: 259), TVAAP (SEQ ID NO: 260), TVLRT (SEQ ID NO: 261), TVSSAS (SEQ ID NO: 262). In some aspects, the linker sequence may be GSG or SGSG (SEQ ID NO: 5). The 2A peptide may be selected from P2A (SEQ ID NO: 3), T2A (SEQ ID NO: 4), E2A (SEQ ID NO: 5), F2A (SEQ ID NO: 6), or any combination thereof.

In another aspect, a nucleotide sequence of linker-2A peptide arranged in tandem may be positioned between Z1 and Z2, between Z1 and Y1, between Z1 and Y2, between Z2 and Y1, between Z2 and Y2, and/or between Y1 and Y2. The linker sequence may be GSG or SGSG (SEQ ID NO: 5). The 2A peptide may be selected from P2A (SEQ ID NO: 6), T2A (SEQ ID NO: 7), E2A (SEQ ID NO: 8), F2A (SEQ ID NO: 9), or any combination thereof.

Therapeutic Compositions

The invention also provides a therapeutic composition comprising a population of transduced cells, such as transduced T cells, described herein.

The composition of the present disclosure may also include one or more adjuvants. Adjuvants are substances that non-specifically enhance or potentiate the immune response (e.g., immune responses mediated by CD8-positive T cells and helper-T (TH) cells to an antigen and would thus be considered useful in the medicament of the present invention. Suitable adjuvants include, but are not limited to, 1018 ISS, aluminum salts, AMPLIVAX®, AS15, BCG, CP-870,893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, Juvlmmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactide co-glycolide) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, immune checkpoint inhibitors including ipilimumab, nivolumab, pembrolizumab, atezolizumab, avelumab, durvalumab, and cemiplimab, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, atezolizumab, interferon-alpha, interferon-beta, CpG oligonucleotides and derivatives, poly-(I:C) and derivatives, RNA, sildenafil, and particulate formulations with poly(lactide co-glycolide) (PLG), virosomes, and/or interleukin (IL)-1, IL-2, IL-4, IL-7, IL-12, IL-13, IL-15, IL-21, and IL-23.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

Methods of Manufacturing Polypeptides

The present invention also relates to a method of producing a recombinant host cell expressing a protein, such as a therapeutic protein, said method comprising the steps consisting of: (i) introducing in vitro or ex vivo a vector of the invention into a competent host cell, (ii) culturing in vitro or ex vivo the recombinant host cell obtained and (iii), optionally, selecting the cells which express and/or secrete said protein.

The present invention also provides methods of manufacturing polypeptides using vectors, such as the lentiviral transduction vectors disclosed herein, and the products of such methods. The methods can comprise one or more of the following steps, e.g., transducing a host cell with a lentivirus transduction vector to form a transduced host cell, wherein said vector comprises an expressible heterologous polynucleotide coding for a heterologous polypeptide of interest; culturing said transduced host cell under conditions effective to produce said polypeptide of interest; isolating polypeptide from said host, e.g., from the culture medium when a polypeptide is secreted into the culture medium. The heterologous polynucleotide sequence coding for the polypeptide can comprise any further sequences necessary for transcription, translation, and/or secretion into the medium (e.g., secretory sequences). Any cells lines can be transduced in accordance with the present invention, including, for example, CHO (such as CHO DG44) and HEK 293 (such as HEK293F).

Transduction vectors can be prepared routinely, including according to the methods described herein. For example, a producer cell line can be transformed with a helper plasmid (containing a suitable envelope and gag/pol precursor) and a transfer vector containing the heterologous NOI under conditions effective to produce functional transduction vectors. The envelope protein can be selected for its ability to transduce a target host cell in which the polypeptide is to be manufactured.

Examples of host cells, include, e.g., mammalian cell lines (e.g., Vero cells, CHO cells, 3T3 cells, COS cells, etc.) as well as primary or established cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. The YB2/0 cell may be preferred for some therapeutic antibodies, since ADCC activity of chimeric or humanized antibodies is enhanced when expressed in this cell.

In an aspect, host cells may include T cells, such as CD4+ T cells, CD8+ T cells, γδ T cells, and/or natural killer T cells.

In another aspect, host cells may include natural killer (NK) cells, dendritic cells, macrophages, and/or cancer cells.

In another aspect, host cells may not include NK cells.

In another aspect, host cells may not include cancer cells.

In particular, for expression of a therapeutic protein, such as a dimeric therapeutic protein, the expression vector may be either of a type in which a gene encoding one polypeptide (chain) and a gene encoding the other polypeptide (chain) exists on separate vectors or of a type in which both genes exist on the same vector (tandem type). In respect of easiness of construction of antibodies or TCR expression vector, easiness of introduction into animal cells, and balance between the expression levels of antibody H and L chains or alpha and beta chains in animal cells, expression vector of the tandem type is preferred (Shitara K et al. J Immunol Methods. 1994 Jan. 3; 167(1-2):271-8).

For manufacturing flu vaccines, the following cell lines and corresponding envelope proteins are preferred, e.g., HEK293 or CHO; VSV-G, ampho, Mokola, and Paramyxoviridae (for example, see ncbi.nlm.nih.gov/ICTVdb/Ictv/fs_param.htm).

Any suitable or desired heterologous sequence can be expressed, including, e.g., vaccines, interferons (alpha, beta, gamma, epsilon), erythropoietin, Factor VIII, clotting factors, antibodies and fragments thereof (e.g., including single chain, Fab, and humanized), insulin, chemokines, cytokines, growth factors, angiogenesis modulatory factors, apoptosis modulatory factors, etc. Single-chain antibodies (e.g., single chain variable fragments or "scFv") can be made routinely.

In certain embodiments of the present invention, lentiviral transduction vectors can be used to prepare antigenic preparations that be used as vaccines. Any suitable antigen(s) can be prepared in accordance with the present invention, including antigens obtained from prions, viruses, *mycobacterium*, protozoa (e.g., *Plasmodium falciparum* (malaria)), trypanosomes, bacteria (e.g., *Streptococcus, Neisseria*, etc.), etc.

Host cells can be transduced with a single lentiviral vector containing one or more heterologous NOI(s), or with a plurality of lentiviral vectors, where each vector comprises the same or different heterologous NOI(s). For example, a multi-subunit antigen (including intracellular and cell-surface multi-subunit components) can be prepared by expressing the individual subunits on separate vectors, but infecting the same host cell with all the vectors, such that assembly occurs within the host cell.

Vaccines often contain a plurality of antigen components, e.g., derived from different proteins, and/or from different epitopic regions of the same protein. For example, a vaccine against a viral disease can comprise one or more polypeptide sequences obtained from the virus which, when administered to a host, elicit an immunogenic or protective response to viral challenge.

As mentioned, the present invention can also be used to prepare polypeptide multimers, e.g., where an antigenic preparation is produced which is comprised of more than one polypeptide. For instance, virus capsids can be made up of more than one polypeptide subunit. By transducing a host cell with vectors carrying different viral envelope sequences, the proteins, when expressed in the cell, can self-assemble into three-dimensional structures containing more than one protein subunit (e.g., in their native configuration). The structures can possess functional activity, including antigenic activity, enzyme activity, cell binding activity, etc. Moreover, when expressed in a suitable cell line, they can be secreted into the cell culture medium, facilitating purification. For instance, when influenza N and H capsid proteins, and optionally M protein (see below), are introduced into a production cell line using lentiviral transduction vectors, empty capsids or viral-like particles (VLP) can be formed in the cell, and then secreted into the culture media. Such VLP can be routinely isolated and purified, and then administered as an influenza vaccine. A VLP is, e.g., a self-assembled capsid which does not contain substantial amounts (e.g., is empty) of viral RNA. A VLP is preferably able to elicit an immune response that is effective to provide at least some degree of protection against a challenge of the native infectious virus particle, or at least elicit antibodies to it.

Currently, there are many available viral vaccines, including vaccines to such diseases as measles, mumps, hepatitis (A and B), rubella, influenza, polio, smallpox, varicella, adenovirus, Japanese encephalitis, rabies, ebola, etc. The present invention can be used to prepare vaccines against any of the above-mentioned diseases.

Examples of viruses to which vaccines can be produced in accordance with the present invention include, e.g., orthomyxoviruses, influenza virus A (including all strains varying in their HA and NA proteins, such as (non-limiting examples) H1N1, H1N2, H2N2, H3N2, H7N7, and H3N8); influenza B, influenza C, thogoto virus (including Dhori, Batken virus, SiAR 126 virus), and isavirus (e.g., infectious salmon anemia virus). These include influenza isolated or transmitted from all species types, including isolates from invertebrates, vertebrates, mammals, humans, non-human primates, monkeys, pigs, cows, and other livestock, birds, domestic poultry such as turkeys, chickens, quail, and ducks, wild birds (including aquatic and terrestrial birds), reptiles, etc. These also include existing strains which have changed, e.g., through mutation, antigenic drift, antigenic shift, recombination, etc., especially strains which have increased virulence and/or interspecies transmission (e.g., human-to-human).

Of particular interest are influenza viruses which are panzootic and/or which cross species either because they have a broad host range, or because of recombination in the infected host, and/or because of naturally-occurring or directed mutation. For example, H5N1 (in reference to the subtypes of surface antigens present on the virus, hemagglutinin type 5 and neuraminadase type 1) is a subtype of avian influenza A, which caused an outbreak of flu in domestic birds in Asia. As of November 2005, more 120 million birds died from infection or were killed to prevent further infection from spreading. This virus has also spread into human hosts ("bird flu") where it is associated with high lethality.

An influenza antigenic preparation (such as a vaccine) can comprise one or more polypeptides that occur naturally in an influenza virion. However, it preferably does not comprise all the polypeptide genes that would give rise to the native pathogenic virus. These include, e.g., hemagglutinin (encoded by HA gene), neuraminidase (encoded by NA gene), nucleoprotein (encoded by NA gene), matrix (M1) proteins (encoded by M gene), M2 (encoded by M gene), non-structural proteins (encoded by NS gene), and polymerases. The naturally-occurring virion is sheathed in a lipid bilayer which is "studded" with integral proteins H and N ("capsid layer"). Matrix proteins (M1) form a protein layer ("matrix layer") underneath the viral membrane, and are involved in viral assembly, stability and integrity. See, e.g., Harris et al., Virol. 289:34-44, 2001. M2 protein is a membrane protein ion channel. A VLP of the present invention can comprise H, N, and optionally M1 and M2 proteins. Sequences for said proteins are known in the art and/or can be identified in GenBank. See, e.g., Widjaja et al. J. Virol., 78:8771-8779, 2004 for M1 and M2 sequences.

These can be cloned into transfer vectors, either individually or on the same plasmid, and utilized to produce transduction vectors. In one embodiment of the present invention, a plurality of transduction vectors can be prepared, each which contains a unique influenza gene sequence (e.g., coding for H, for N, and for M1 to result in a three different transduction vectors). When such vectors are co-expressed in the same host cell (e.g., CHO or HEK293), a self-assembling VLP is produced which can be secreted into the medium, harvested by centrifugation, and then administered as a vaccine.

Transduction vectors of the present invention can result in high levels of heterologous protein production, e.g., from about 0.1 to 0.3 mg/ml to about 5-10 mg/ml, or more, of recombinant heterologous protein per ml of unprocessed culture media, when such proteins are secreted into the culture media.

The present application also provides methods of producing antibodies. For example, methods are provided to produce monoclonal antibodies (e.g., human, mouse, and other mammalian types) without the need for hybridomas or animal models. In one non-limiting example, lentiviral vectors expressing oncogenic proteins are transduced in peripheral blood B cells from mice previously stimulated with antigen. These vectors efficiently transduce the mouse cells to make them into antibody producing cells. In a second non-limiting example, two lentiviral vectors are engineered, one expressing the heavy antibody chain and the second vector the light antibody chain. The constant areas of the genes are derived from the human (or other species if desired) immunoglobulin gene (e.g., IgG, IgM or other type of Ig). The variable areas of the genes are modified or degenerated to create diversity. The degenerate sequence can be obtained by any suitable techniques that is known in the art and cloned into the lentiviral vector to create a library of lentiviral vectors that express either the heavy or light immunoglobulin molecules. The antibodies can be produced by transducing cells with both vectors to produce functional antibodies that contain both heavy and light chains. Transduced and expressing cells can be selected and screened for binding to antigen, and then positive clones can be isolated and subjected to multiple rounds of affinity maturation.

An advantage of this method is that antibodies are produced in a non-biased method. Other methods, such as traditional hybridoma and Xenomouse technologies rely on B cells that have undergone clonal selection and deletion of particular antibody clones since they are reactive to endogenous, for example, mouse tissue. Some of these deleted clones may be valuable as antibodies as they could cross react with human antigens. The advantage of the described method is that there is no deletion of molecular antibody clones and they are all analyzed in a non-biased method and yet are fully humanized (if humanization is desired) antibody molecules. Another advantage of lentiviral vectors is that the genes can be transduced into cells at high multiplicity to produce a variety of antibody type in one cell. This reduces the number of cells that need to be produced to create a library that contains a very diverse antigenic binding sites. A second advantage is placing the heavy and light genes in different lentiviral vectors so that additional diversity can be generated by transducing cells with a higher multiplicity of infection than 1. For example, if a MOI of 10 is used for the transduction of cells with each heavy and light chain expressing Lentiviral vector, then the number of combinations of antibodies produced in each cell is 100. Therefore in a 96-well plate, where there are about 10,000 cells in a single well, the number of possible variants that can be generated with this method is 1,000,000 in a single well of a 96-well plate. Therefore, with scale, a large number of antibody variants can be generated with this method. The method does not limit to using a MOI of 10 for each construct per cell, higher MOIs can also be used, as needed. For example, if a MOI of 100 is used then each cell can produce 10,000 variant antibodies and each well of a 96 well plate can produce 10,000,000,000 variants. Therefore, each 96 well plate can produce $1 \times 10^{12}$ variant antibody molecules that can be used for screening against a target antigen, for which there are many methods known in the art (e.g., ELISA). Once a particular well has been identified that produces the desired antibody reaction, then the cells can be cloned by limiting dilution to find the cell clone that expresses the correct antibody. Once this clone has been identified, then PCR can be used to clone out the vectors that express the heavy and light antibody chains. The vector DNA can then be transfected with helper construct(s) to produce vector. Alternatively, this clone of cells can be transfected directly with the helper construct(s) (PEI, calcium phosphate, lipotransfection, or other transfection method known in the art), to produce the variant lentiviral vectors. The vectors that are produced can then tittered and then transduced onto cells at a lower MOI, but a larger number of cells, to isolate a clone that produces the antibody of interest. Once the clone of cell is isolated, then the antibody can be produced to higher titers by transducing cells with higher multiplicity of infection, the same method is not limited to whole antibody molecules but can also be applied to single chain antibodies, antibody fragments, phage display and other antibody-like molecules, all known in the art. In addition to expressing the antibody, the vector can express other genes to increase the production of the monoclonal antibody, or to increase their yield. Such genes can be oncogenes such as ras and myc, but other genes can also be used, such as anti-apoptotic genes such as Bcl-2. Furthermore, such vectors can be used to create monoclonal antibodies from B cells in the blood of animals that have been exposed to antigen. For example, B cells from mice exposed to antigen can be transformed into myeloma cells by using a combination of oncogenes or gene silencing RNA. Such genes include, e.g., Growth Factors, including, e.g., Amphiregulin, B-lymphocyte stimulator, Interleukin 16 (IL16), Thymopoietin, TRAIL, Apo-2, Pre B cell colony enhancing factor, Endothelial differentiation-related factor 1 (EDF1), Endothelial monocyte activating polypeptide II, Macrophage migration inhibitory factor MIF, Natural killer cell enhancing factor (NKEFA), Bone morphogenetic protein 8 (osteogenic protein 2), Bone morphogenic protein 6, Connective tissue growth factor (CTGF), CGI-149 protein (neuroendocrine differentiation factor), Cytokine A3 (macrophage inflammatory protein 1-alpha), Glialblastoma cell differentiation-related protein (GBDR1), Hepatoma-derived growth factor, Neuromedin U-25 precursor, any tumor gene, oncogene, proto-oncogene or cell modulating gene (which can be found at condor.bcm.tmc.edu/oncogene), Vascular endothelial growth factor (VEGF), Vascular endothelial growth factor B (VEGF-B), T-cell specific RANTES precursor, Thymic dendritic cell-derived factor 1; Receptors, such as Activin A receptor, type II (ACVR2), β-signal sequence receptor (SSR2), CD14 monocyte LPS receptor, CD36 (collagen type 1/thrombospondin receptor)-like 2, CD44R (Hermes antigen gp90 homing receptor), G protein coupled receptor 9, Chemokine C×C receptor 4, Colony stimulating factor 2 receptor β(CSF2RB), FLT-3 receptor tyrosine kinase, Similar to transient receptor potential C precursor, Killer cell lectin-like receptor subfamily B, Low density lipoprotein receptor gene, low-affinity Fc-gamma receptor IIC, MCP-1 receptor, Monocyte chemoattractant protein 1 receptor (CCR2), Nuclear receptor subfamily 4, group A, member 1, Orphan G protein-coupled receptor GPRC5D, Peroxisome proliferative activated receptor gamma, Pheromore related-receptor (rat), Vasopressin-activated calcium mobilizing putative receptor, Retinoic x receptor, Toll-like receptor 6, Transmembrane activator and CAML interactor (TACI), B cell maturation peptide (BCMA), CSF-1 receptor, Interferon (α, β and gamma) receptor 1 (IFNAR1).

Methods of Treatment

The vectors provided herein can be used in a wide variety of therapeutic methods.

In some aspects, a lentiviral vector for therapeutic use is provided which expresses a native or fusion polypeptide comprising of any individual or combination of a human chemokine and a viral or bacterial antigen (e.g. HIV, diphtheria toxin antigen), a chemokine (e.g. IP-10, MCP-1, MCP-2, MCP-3, MCP-4, MIP 1, RANTES, SDF-1, MIG and/or MDC) or a pro-apoptotic protein, a suicide gene protein or a protein that promotes the inflammatory response.

In addition, the present invention provides a method of producing an immune response in a subject, comprising administering to the subject any of the individual or fusion polypeptides of this invention, such as a chemokine and a human immunodeficiency virus (HIV) antigen, or a chemokine, a pro-apoptotic gene, a suicide gene and a tumor antigen, either as a protein or a nucleic acid encoding the individual or fusion polypeptide expressed from a lentiviral vector. Also provided is a method of treating a cancer in a subject comprising administering to the subject a lentiviral vector expressing any of the individual or fusion polypeptides of this invention, such as a chemokine and a tumor antigen, either as a protein or a nucleic acid encoding the fusion polypeptide.

Further provided is a method of treating or preventing HIV infection in a subject, comprising administering to the subject any combination of the following peptides derived from the following proteins: chemokine, suicide gene, HIV protein, cytokine, cell surface protein, tumor antigen, or any cellular gene that affects the production of HIV from the cell (either by overexpressing the cellular gene or inhibiting its expression by RNAi, or the like), all provided and expressed from a lentiviral vector.

In some aspects, compositions containing engineered immune cells, such as T cells (e.g., γδ T cells), described herein may be administered for prophylactic and/or therapeutic treatments. In therapeutic applications, pharmaceutical compositions can be administered to a subject already suffering from a disease or condition in an amount sufficient to cure or at least partially arrest the symptoms of the disease or condition. An engineered immune cell can also be administered to lessen a likelihood of developing, contracting, or worsening a condition. Effective amounts of a population of engineered immune cells for therapeutic use can vary based on the severity and course of the disease or condition, previous therapy, the subject's health status, weight, and/or response to the drugs, and/or the judgment of the treating physician.

Engineered immune cells, such as T cells, of the present disclosure can be used to treat a subject in need of treatment for a condition, for example, a cancer described herein.

A method of treating a condition (e.g., ailment) in a subject with engineered immune cells, such as engineered T cells, may include administering to the subject a therapeutically effective amount of engineered immune cells, such as engineered T cells. Engineered immune cells, such as engineered T cells, of the present disclosure may be administered at various regimens (e.g., timing, concentration, dosage, spacing between treatment, and/or formulation). A subject can also be preconditioned with, for example, chemotherapy, radiation, or a combination of both, prior to receiving engineered immune cells, such as engineered T cells, of the present disclosure. A population of engineered immune cells, such as engineered T cells, may also be frozen or cryopreserved prior to being administered to a subject. A population of engineered immune cells, such as engineered T cells, can include two or more cells that express identical, different, or a combination of identical and different tumor recognition moieties. For instance, a population of engineered immune cells, such as engineered T-cells, can include several distinct engineered immune cells, such as engineered T cells, that are designed to recognize different antigens, or different epitopes of the same antigen.

Engineered immune cells, such as engineered T cells, of the present disclosure may be used to treat various conditions. In an aspect, engineered immune cells, such as engineered T cells, of the present disclosure may be used to treat a cancer, including solid tumors and hematologic malignancies. Non-limiting examples of cancers include: acute lymphoblastic leukemia, acute myeloid leukemia, adrenocortical carcinoma, AIDS-related cancers, AIDS-related lymphoma, anal cancer, appendix cancer, astrocytomas, neuroblastoma, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrm macroglobulinemia, and Wilms tumor.

In an aspect, engineered immune cells, such as engineered T cells, of the present disclosure may be used to treat an infectious disease. In another aspect, engineered immune cells, such as engineered T cells, of the present disclosure may be used to treat an infectious disease, an infectious disease may be caused a virus. In yet another aspect, engineered immune cells, such as engineered T cells, of the present disclosure may be used to treat an immune disease, such as an autoimmune disease.

Treatment with engineered immune cells, such as engineered T cells, of the present disclosure may be provided to the subject before, during, and after the clinical onset of the condition. Treatment may be provided to the subject after 1 day, 1 week, 6 months, 12 months, or 2 years after clinical onset of the disease. Treatment may be provided to the subject for more than 1 day, 1 week, 1 month, 6 months, 12 months, 2 years, 3 years, 4 years, 5 years, 6 years, 7 years, 8 years, 9 years, 10 years or more after clinical onset of disease. Treatment may be provided to the subject for less than 1 day, 1 week, 1 month, 6 months, 12 months, or 2 years after clinical onset of the disease. Treatment may also include treating a human in a clinical trial. A treatment can include administering to a subject a pharmaceutical composition comprising engineered immune cells, such as engineered T cells, of the present disclosure.

In another aspect, administration of engineered immune cells, such as engineered T cells, of the present disclosure to a subject may modulate the activity of endogenous lymphocytes in a subject's body. In another aspect, administration of engineered immune cells, such as engineered T cells, to a subject may provide an antigen to an endogenous T-cell and may boost an immune response. In another aspect, the memory T cell may be a CD4+ T-cell. In another aspect, the memory T cell may be a CD8+ T-cell. In another aspect, administration of engineered immune cells, such as engineered T cells, of the present disclosure to a subject may activate the cytotoxicity of another immune cell. In another aspect, the other immune cell may be a CD8+ T-cell. In another aspect, the other immune cell may be a Natural Killer T-cell. In another aspect, administration of engineered immune cells, such as engineered T-cells, of the present disclosure to a subject may suppress a regulatory T-cell. In another aspect, the regulatory T-cell may be a FOX3+ Treg cell. In another aspect, the regulatory T-cell may be a FOX3-Treg cell. Non-limiting examples of cells whose activity can be modulated by engineered immune cells, such as engineered T cells of the disclosure may include: hematopioietic stem cells; B cells; CD4; CD8; red blood cells; white blood cells; dendritic cells, including dendritic antigen presenting cells; leukocytes; macrophages; memory B cells; memory T-cells; monocytes; natural killer cells; neutrophil granulocytes; T-helper cells; and T-killer cells.

During most bone marrow transplants, a combination of cyclophosphamide with total body irradiation may be conventionally employed to prevent rejection of the hematopietic stem cells (HSC) in the transplant by the subject's immune system. In an aspect, incubation of donor bone marrow with interleukin-2 (IL-2) ex vivo may be performed to enhance the generation of killer lymphocytes in the donor marrow. Interleukin-2 (IL-2) is a cytokine that may be necessary for the growth, proliferation, and differentiation of wild-type lymphocytes. Current studies of the adoptive transfer of γδ T-cells into humans may require the co-administration of γδ T-cells and interleukin-2. However, both low- and high-dosages of IL-2 can have highly toxic side effects. IL-2 toxicity can manifest in multiple organs/systems, most significantly the heart, lungs, kidneys, and central nervous system. In another aspect, the disclosure provides a method for administrating engineered γδ T cells to a subject without the co-administration of a native cytokine or modified versions thereof, such as IL-2, IL-15, IL-12, IL-21. In another aspect, engineered γδ T cells can be administered to a subject without co-administration with IL-2. In another aspect, engineered γδ T cells may be administered to a subject during a procedure, such as a bone marrow transplant without the co-administration of IL-2.

Methods of Administration

One or multiple engineered immune cell, such as engineered T cell, populations may be administered to a subject in any order or simultaneously. If simultaneously, the multiple engineered immune cell, such as T cell, can be provided in a single, unified form, such as an intravenous injection, or in multiple forms, for example, as multiple intravenous infusions, s.c, injections or pills. Engineered immune cells, such as engineered T-cells, can be packed together or separately, in a single package or in a plurality of packages. One or all of the engineered immune cells, such as engineered T cells, can be given in multiple doses. If not simultaneous, the timing between the multiple doses may vary to as much as about a week, a month, two months, three months, four months, five months, six months, or about a year. In another aspect, engineered immune cells, such as engineered T cells, can expand within a subject's body, in vivo, after administration to a subject. Engineered immune cells, such as engineered T cells, can be frozen to provide cells for multiple treatments with the same cell preparation. Engineered immune cells, such as engineered T cells, of the present disclosure, and pharmaceutical compositions comprising the same, can be packaged as a kit. A kit may include instructions (e.g., written instructions) on the use of engineered immune cells, such as engineered T cells, and compositions comprising the same.

In another aspect, a method of treating a cancer comprises administering to a subject a therapeutically-effective amount of engineered immune cells, such as engineered T cells, in which the administration treats the cancer. In another embodiments, the therapeutically-effective amount of engineered immune cells, such as engineered T cells, may be administered for at least about 10 seconds, 30 seconds, 1 minute, 10 minutes, 30 minutes, 1 hour, 2 hours, 3 hours, 4 hours, 5 hours, 6 hours, 12 hours, 24 hours, 2 days, 3 days, 4 days, 5 days, 6 days, 1 week, 2 weeks, 3 weeks, 1 month, 2 months, 3 months, 4 months, 5 months, 6 months, or 1 year. In another aspect, the therapeutically-effective amount of the engineered immune cells, such as engineered T cells, may be administered for at least one week. In another aspect, the therapeutically-effective amount of engineered immune cells, such as engineered T cells, may be administered for at least two weeks.

Engineered immune cells, such as engineered T-cells, described herein can be administered before, during, or after the occurrence of a disease or condition, and the timing of administering a pharmaceutical composition containing an engineered immune cells, such as engineered T-cell, can vary. For example, engineered immune cells, such as engineered T cells, can be used as a prophylactic and can be administered continuously to subjects with a propensity to conditions or diseases in order to lessen the likelihood of occurrence of the disease or condition. Engineered immune cells, such as engineered T-cells, can be administered to a subject during or as soon as possible after the onset of the symptoms. The administration of engineered immune cells, such as engineered T cells, can be initiated immediately within the onset of symptoms, within the first 3 hours of the onset of the symptoms, within the first 6 hours of the onset of the symptoms, within the first 24 hours of the onset of the symptoms, within 48 hours of the onset of the symptoms, or within any period of time from the onset of symptoms. The initial administration can be via any route practical, such as by any route described herein using any formulation described herein. In another aspect, the administration of engineered immune cells, such as engineered T cells, of the present disclosure may be an intravenous administration. One or multiple dosages of engineered immune cells, such as engineered T cells, can be administered as soon as is practicable after the onset of a cancer, an infectious disease, an immune disease, sepsis, or with a bone marrow transplant, and for a length of time necessary for the treatment of the immune disease, such as, for example, from about 24 hours to about 48 hours, from about 48 hours to about 1 week, from about 1 week to about 2 weeks, from about 2 weeks to about 1 month, from about 1 month to about 3 months. For the treatment of cancer, one or multiple dosages of engineered immune cells, such as engineered T cells, can be administered years after onset of the cancer and before or after other treatments. In another aspect, engineered immune cells, such as engineered T cells, can be administered for at least about 10 minutes, 30 minutes, 1 hour, 2 hours, 3 hours, 4 hours, 5 hours, 6 hours, 12 hours, 24 hours, at least 48 hours, at least 72 hours, at least 96 hours, at least 1 week, at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years at least 3 years, at least 4 years, or at least 5 years. The length of treatment can vary for each subject.

Preservation

In an aspect, immune cells, such as T cells, may be formulated in freezing media and placed in cryogenic storage units such as liquid nitrogen freezers (−196° C.) or ultra-low temperature freezers (−65° C., −80° C., −120° C., or −150° C.) for long-term storage of at least about 1 month, 2 months, 3 months, 4 months, 5 months, 6 months, 1 year, 2 years, 3 years, or at least 5 years. The freeze media can contain dimethyl sulfoxide (DMSO), and/or sodium chloride (NaCl), and/or dextrose, and/or dextran sulfate and/or hydroyethyl starch (HES) with physiological pH buffering agents to maintain pH between about 6.0 to about 6.5, about 6.5 to about 7.0, about 7.0 to about 7.5, about 7.5 to about 8.0 or about 6.5 to about 7.5. The cryopreserved immune cells, such as T cells, can be thawed and further processed by stimulation with antibodies, proteins, peptides, and/or cytokines as described herein. The cryopreserved immune cells, such as T-cells, can be thawed and genetically modified with viral vectors (including retroviral, adeno-associated virus (AAV), and lentiviral vectors) or non-viral means (including RNA, DNA, e.g., transposons, and proteins) as described herein. The modified immune cells, such as modified T cells, can be further cryopreserved to generate cell banks in quantities of at least about 1, 5, 10, 100, 150, 200, 500 vials at about at least $10^1$, $10^2$, $10^3$, $10^4$, $10^5$, $10^6$, $10^7$, $10^8$, $10^9$, or at least about $10^{10}$ cells per mL in freeze media. The cryopreserved cell banks may retain their functionality and can be thawed and further stimulated and expanded. In another aspect, thawed cells can be stimulated and expanded in suitable closed vessels, such as cell culture bags and/or bioreactors, to generate quantities of cells as allogeneic cell product. Cryopreserved immune cells, such as T cells, can maintain their biological functions for at least about 6 months, 7 months, 8 months, 9 months, 10 months, 11 months, 12 months, 13 months, 15 months, 18 months, 20 months, 24 months, 30 months, 36 months, 40 months, 50 months, or at least about 60 months under cryogenic storage condition. In another aspect, no preservatives may be used in the formulation. Cryopreserved immune cells, such as T-cells, can be thawed and infused into multiple patients as allogeneic off-the-shelf cell product.

In an aspect, engineered immune cells, such as engineered T-cells, described herein may be present in a composition in an amount of at least $1\times10^3$ cells/ml, at least $2\times10^3$ cells/ml, at least $3\times10^3$ cells/ml, at least $4\times10^3$ cells/ml, at least $5\times10^3$ cells/ml, at least $6\times10^3$ cells/ml, at least $7\times10^3$ cells/ml, at least $8\times10^3$ cells/ml, at least $9\times10^3$ cells/ml, at least $1\times10^4$ cells/ml, at least $2\times10^4$ cells/ml, at least $3\times10^4$ cells/ml, at least $4\times10^4$ cells/ml, at least $5\times10^4$ cells/ml, at least $6\times10^4$ cells/ml, at least $7\times10^4$ cells/ml, at least $8\times10^4$ cells/ml, at least $9\times10^4$ cells/ml, at least $1\times10^5$ cells/ml, at least $2\times10^5$ cells/ml, at least $3\times10^5$ cells/ml, at least $4\times10^5$ cells/ml, at least $5\times10^5$ cells/ml, at least $6\times10^5$ cells/ml, at least $7\times10^5$ cells/ml, at least $8\times10^5$ cells/ml, at least $9\times10^5$ cells/ml, at least $1\times10^6$ cells/ml, at least $2\times10^6$ cells/ml, at least $3\times10^6$ cells/ml, at least $4\times10^6$ cells/ml, at least $5\times10^6$ cells/ml, at least $6\times10^6$ cells/ml, at least $7\times10^6$ cells/ml, at least $8\times10^6$ cells/ml, at least $9\times10^6$ cells/ml, at least $1\times10^7$ cells/ml, at least $2\times10^7$ cells/ml, at least $3\times10^7$ cells/ml, at least $4\times10^7$ cells/ml, at least $5\times10^7$ cells/ml, at least $6\times10^7$ cells/ml, at least $7\times10^7$ cells/ml, at least $8\times10^7$ cells/ml, at least $9\times10^7$ cells/ml, at least $1\times10^8$ cells/ml, at least $2\times10^8$ cells/ml, at least $3\times10^8$ cells/ml, at least $4\times10^8$ cells/ml, at least $5\times10^8$ cells/ml, at least $6\times10^8$ cells/ml, at least $7\times10^8$ cells/ml, at least $8\times10^8$ cells/ml, at least $9\times10^8$ cells/ml, at least $1\times10^9$ cells/ml, or more, from about $1\times10^3$ cells/ml to about at least $1\times10^8$ cells/ml, from about $1\times10^5$ cells/ml to about at least $1\times10^8$ cells/ml, or from about $1\times10^6$ cells/ml to about at least $1\times10^8$ cells/ml.

In an aspect, methods described herein may be used to produce autologous or allogenic products according to an aspect of the disclosure.

EXAMPLES

Example 1

TABLE 3

DNA and protein sequences

| SEQ ID NO: | Description | Sequence |
|---|---|---|
| 1 | WT WPRE derived from GenBank Accession No. J02440.1 | gagcatcttaccgccatttatacccatatt tgttctgttttcttgatttgggtatacat ttaaatgttaataaaacaaaatggtggggc aatcatttacattttatgggatatgtaatt actagttcaggtgtattgccacaagacaaa catgttaagaaactttcccgttatttacgc tctgttcctgttaatcaacctctggattac aaaatttgtgaaagattgactgatattctt aactatgttgctccttttacgctgtgtgga tatgctgctttaatgcctctgtatcatgct attgcttcccgtacggctttcgttttctcc tccttgtataaatcctggttgctgtctctt tatgaggagttgtggcccgttgtccgtcaa cgtggcgtggtgtgctctgtgtttgctgac gcaaccccactggctggggcattgccacc acctgtcaactcctttctgggactttcgct ttccccctcccgatcgccacggcagaactc atcgccgcctgccttgcccgctgctggaca ggggctaggttgctgggcactgataattcc gtggtgttgtcggggaagctgacgtcctttt ccatgctgctcgcctgtgttgccaactgg atcctgcgcgggacgtccttctgctacgtc ccttcggctctcaatccagcggacctccct tcccgaggccttctgccggttctgcggcct ctcccgcgtcttcgctttcggcctccgacg agtcggatctccctttgggccgcctccccg cctg |
| 2 | WT WPRE derived from GenBank Accession No. J04514.1 | cagtctgacgtacgcgtaatcaacctctgg attacaaaatttgtgaaagattgactggta ttcttaactatgttgctccttttacgctat gtggatacgctgctttaatgcctttgtatc atgctattgcttcccgtatggctttcattt tctcctccttgtataaatcctggttgctgt ctctttatgaggagttgtggcccgttgtca ggcaacgtggcgtggtgtgcactgtgtttg ctgacgcaaccccactggttggggcattg ccaccacctgtcagctcctttccgggactt tcgctttccccctccctattgccacggcgg aactcatcgccgcctgccttgcccgctgct ggacaggggctcggctgttgggcactgaca attccgtggtgttgtcggggaagctgacgt ccttttccatgctgctcgcctgtgttgcca cctggattctgcgcgggacgtccttctgct agtccccttcggccctcaatccagcggacc ttccttcccgcggcctgctgccggctctgc ggcctcttccgcgtcttcgcctttcgcctc agacgagtcggatctccctttgggccgcct ccccgcc |
| 3 | mutant WPRE | gagcatcttaccgccatttatacccatatt tgttctgttttcttgatttgggtatacat ttaaatgttaataaaacaaaatggtggggc aatcatttacattttttgggatatgtaatt actagttcaggtgtattgccacaagacaaa cttgttaagaaactttcccgttatttacgc tctgttcctgttaatcaacctctggattac aaaatttgtgaaagattgactgatattctt aactttgttgctccttttacgctgtgtgga tttgctgctttattgcctctgtatcttgct attgcttcccgtacggctttcgttttctcc tccttgtataaatcctggttgctgtctctt tttgaggagttgtggcccgttgtccgtcaa cgtggcgtggtgtgctctgtgtttgctgac gcaaccccactggctggggcattgccacc acctgtcaactcctttctgggactttcgct ttccccctcccgatcgccacggcagaactc atcgccgcctgccttgcccgctgctggaca ggggctaggttgctgggcactgataattcc gtggtgttgtc |
| 4 | mutant WPRE | cagtctgacgtacgcgtaatcaacctctgg attacaaaatttgtgaaagattgactggta ttcttaactatgttgctccttttacgctat gtggatacgctgctttaatgcctttgtatc atgctattgcttcccgtatggctttcattt tctcctccttgtataaatcctggttgctgt ctctttatgaggagttgtggcccgttgtca ggcaacgtggcgtggtgtgcactgtgtttg |

TABLE 3-continued

DNA and protein sequences

| SEQ ID NO: | Description | Sequence |
|---|---|---|
| | | ctgacgcaaccccactggttggggcattg ccaccacctgtcagctccttccgggactt tcgcttttccccctcccctattgccacggcgg aactcatcgccgcctgccttgcccgctgct ggacaggggctcggctgttgggcactgaca attccgtggtgttgtcggggaaatcatcgt cctttccttggctgctcgcctgtgttgcca cctggattctgcgcgggacgtccttctgct acgtcccttcggccctcaatccagcggacc ttccttcccgcggcctgctgccggctctgc ggcctcttccgcgtcttcgccttcgccctc agacgagtcggatctcccctttgggccgcct ccccgcc |
| 5 | Linker | SGSG |
| 6 | P2A | ATNFSLLKQAGDVEENPGP |
| 7 | T2A | EGRGSLLTCGDVEENPGP |
| 8 | E2A | QCTNYALLKLAGDVESNPGP |
| 9 | F2A | VKQTLNFDLLKLAGDVESNPGP |
| 10 | Furin | RAKR |
| 11 | CD8 alpha chain | MALPVTALLLPLALLLHAARPSQFRVSPLD RTWNLGETVELKCQVLLSNPTSGCSWLFQP RGAAASPTFLLYLSQNKPKAAEGLDTQRFS GKRLGDTFVLTLSDFRRENEGYYFCSALSN SIMYFSHFVPVFLPAKPTTTPAPRPPTPAP TIASQPLSLRPEACRPAAGGAVHTRGLDFA CDIYIWAPLAGTCGVLLLSLVITLYCNHRN RRRVCKCPRPVVKSGDKPSLSARYV |
| 12 | CD8 beta chain | MRPRLWLLLAAQLTVLHGNSVLQQTPAYIK VQTNKMVMLSCEAKISLSNMRIYWLRQRQA PSSDSHHEFLALWDSAKGTIHGEEVEQEKI AVFRDASRFILNLTSVKPEDSGIYFCMIVG SPELTFGKGTQLSVVDFLPTTAQPTKKSTL KKRVCRLPRPETQKGPLCSPITLGLLVAGV LVLLVSLGVAIHLCCRRRRARLRFMKQPGQ EGISGTFVPQCLHGYYSNTTTSQKLLNPWI LKT |
| 13 | R11KEA alpha chain | MEKNPLAAPLLILWFHLDCVSSILNVEQSP QSLHVQEGDSTNFTCSFPSSNFYALHWYRK ETAKSPEALFVMTLNGDEKKKGRISATLNT KEGYSYLYIKGSQPEDSATYLCALYNNNDM RFGAGTRLTVKPNIQNPDPAVYQLRDSKSS DKSVCLFTDFDSQTNVSQSKDSDVYITDKT VLDMRSMDFKSNSAVAWSNKSDFACANAFN NSIIPEDTFFPSPESSCDVKLVEKSFETDT NLNFQNLSVIGFRILLLKVAGFNLLMTLRL WSS |
| 14 | R11KE beta chain | MDSWTFCCVSLCILVAKHTDAGVIQSPRHE VTEMGQEVTLRCKPISGHNSLFWYRETMMR GLELLIYFNNNVPIDDSGMPEDRFSAKMPN ASFSTLKIQPSEPRDSAVYFCASSPGSTDT QYFGPGTRLTVEDLKNVFPPEVAVFEPSE AEISHTQKATLVCLATGFYPDHVELSWWWN GKEVHSGVSTDPQPLKEQPALNDSRYCLSS RLRVSATFWQNPRNHFRCQVQFYGLSENDE WTQDRAKPVTQIVSAEAWGRADCGFTSESY QQGVLSATILYEILLGKATLYAVLVSALVL MAMVKRKDSRG |
| 15 | R20P1H7 alpha chain | MEKMLECAFIVLWLQLGWLSGEDQVTQSPE ALRLQEGESSSLNCSYTVSGLRGLFWYRQD PGKGPEFLFTLYSAGEEKEKERLKATLTKK ESFLHITAPKPEDSATYLCAVQGENSGYST LTFGKGTMLLVSPDIQNPDPAVYQLRDSKS SDKSVCLFTDFDSQTNVSQSKDSDVYITDK TVLDMRSMDFKSNSAVAWSNKSDFACANAF NNSIIPEDTFFPSPESSCDVKLVEKSFETD TNLNFQNLSVIGFRILLLLKVAGFNLLMTLR LWSS |
| 16 | R20P1H7 beta chain | MGPQLLGYVVLCLLGAGPLEAQVTQNPRYL ITVTGKKLTVTCSQNMNHEYMSWYRQDPGL GLRQIYYSMNVEVTDKGDVPEGYKVSRKEK RNFPLILESPSPNQTSLYFCASSLGPGLAA YNEQFFGPGTRLTVLEDLKNVFPPEVAVFE PSEAEISHTQKATLVCLATGFYPDHVELSW WVNGKEVHSGVSTDPQPLKEQPALNDSRY CLSSRLRVSATFWQNPRNHFRCQVQFYGLS ENDEWTQDRAKPVTQIVSAEAWGRADCGFT SESYQQGVLSATILYEILLGKATLYAVLVS ALVLMAMVKRKDSRG |
| 17 | R7P1D5 alpha chain | MKTFAGFSFLFLWLQLDCMSRGEDVEQSLF LSVREGDSSVINCTYTDSSSTYLYWYKQEP GAGLQLLTYIFSNMDMKQDQRLTVLLNKKD KHLSLRIADTQTGDSAIYFCAEYSSASKII FGSGTRLSIRPNIQNPDPAVYQLRDSKSSD KSVCLFTDFDSQTNVSQSKDSDVYITDKTV LDMRSMDFKSNSAVAWSNKSDFACANAFNN SIIPEDTFFPSPESSCDVKLVEKSFETDTN LNFQNLSVIGFRILLLKVAGFNLLMTLRLW SS |
| 18 | R7P1D5 beta chain | MGSWTLCCVSLCILVAKHTDAGVIQSPRHE VTEMGQEVTLRCKPISGHDYLFWYRQTMMR GLELLIYFNNNVPIDDSGMPEDRFSAKMPN ASFSTLKIQPSEPRDSAVYFCASRANTGEL FFGEGSRLTVEDLKNVFPPEVAVFEPSEA EISHTQKATLVCLATGFYPDHVELSWWWNG KEVHSGVSTDPQPLKEQPALNDSRYCLSSR LRVSATFWQNPRNHFRCQVQFYGLSENDEW TQDRAKPVTQIVSAEAWGRADCGFTSESYQ QGVLSATILYEILLGKATLYAVLVSALVLM AMVKRKDSRG |
| 19 | R10P2G12 alpha chain | MLTASLLRAVIASICVVSSMAQKVTQAQTE ISVVEKEDVTLDCVYETRDTTYYLFWYKQP PSGELVFLIRRNSFDEQNEISGRYSWNFQK STSSFNFTITASQVVDSAVYFCALSEGNSG NTPLVFGKGTRLSVIANIQNPDPAVYQLRD SKSSDKSVCLFTDFDSQTNVSQSKDSDVYI TDKTVLDMRSMDFKSNSAVAWSNKSDFACA NAFNNSIIPEDTFFPSPESSCDVKLVEKSF ETDTNLNFQNLSVIGFRILLLKVAGFNLLM TLRLWSS |
| 20 | R10P2G12 beta chain | MGIRLLCRVAFCFLAVGLVDVKVTQSSRYL VKRTGEKVFLECVQDMDHENMFWYRQDPGL GLRLIYFSYDVKMKEKGDIPEGYSVSREKK ERFSLILESASTNQTSMYLCASSLSSGSHQ ETQYFGPGTRLLVLEDLKNVFPPEVAVFEP SEAEISHTQKATLVCLATGFYPDHVELSWW WNGKEVHSGVSTDPQPLKEQPALNDSRYCL SSRLRVSATFWQNPRNHFRCQVQFYGLSEN DEWTQDRAKPVTQIVSAEAWGRADCGFTSE SYQQGVLSATILYEILLGKATLYAVLVSAL VLMAMVKRKDSRG |
| 21 | R10P1A7 alpha chain | MKTFAGFSFLFLWLQLDCMSRGEDVEQSLF LSVREGDSSVINCTYTDSSSTYLYWYKQEP GAGLQLLTYIFSNMDMKQDQRLTVLLNKKD KHLSLRIADTQTGDSAIYFCAESKETRLMF GDGTQLVVKPNIQNPDPAVYQLRDSKSSDK SVCLFTDFDSQTNVSQSKDSDVYITDKTVL DMRSMDFKSNSAVAWSNKSDFACANAFNNS IIPEDTFFPSPESSCDVKLVEKSFETDTNL NFQNLSVIGFRILLLKVAGFNLLMTLRLWS S |

TABLE 3-continued

DNA and protein sequences

| SEQ ID NO: | Description | Sequence |
|---|---|---|
| 22 | R10P1A7 beta chain | MLLLLLLLGPGISLLLPGSLAGSGLGAWSQHPSVWICKSGTSVKIECRSLDFQATTMFWYRQFPKQSLMLMATSNEGSKATYEQGVEKDKFLINHASLTLSTLTVTSAHPEDSSFYICSARAGGHEQFFGPGTRLTVLEDLKNVFPPEVAVFEPSEAEISHTQKATLVCLATGFYPDHVELSWWNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 23 | R4P1D10 alpha chain | MKSLRVLLVILWLQLSWWWSQQKEVEQNSGPLSVPEGAIASLNCTYSDRGSQSFFWYRQYSGKSPELIMFIYSNGDKEDGRFTAQLNKASQYVSLLIRDSQPSDSATYLCAVNFHDKIIFGKGTRLHILPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 24 | R4P1D10 beta chain | MGFRLLCCVAFCLLGAGPVDSGVTQTPKHLITATGQRVTLRCSPRSGDLSVYWYQQSLDQGLQFLIHYYNGEERAKGNILERFSAQQFPDLHSELNLSSLELGDSALYFCASSVASAYGYTFGSGTRLTVVEDLKNVFPPEVAVFEPSEAEISHTQKATLVCLATGFFPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF |
| 25 | R4P3F9 alpha chain | MKSLRVLLVILWLQLSWWWSQQKEVEQNSGPLSVPEGAIASLNCTYSDRGSQSFFWYRQYSGKSPELIMFIYSNGDKEDGRFTAQLNKASQYVSLLIRDSQPSDSATYLCAAYSGAGSYQLTFGKGTKLSVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 26 | R4P3F9 beta chain | MGFRLLCCVAFCLLGAGPVDSGVTQTPKHLITATGQRVTLRCSPRSGDLSVYWYQQSLDQGLQFLIQYYNGEERAKGNILERFSAQQFPDLHSELNLSSLELGDSALYFCASSVESSYGYTFGSGTRLTVVEDLKNVFPPEVAVFEPSEAEISHTQKATLVCLATGFFPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF |
| 27 | R4P3H3 alpha chain | MKSLRVLLVILWLQLSWWWSQQKEVEQNSGPLSVPEGAIASLNCTYSDRGSQSFFWYRQYSGKSPELIMFIYSNGDKEDGRFTAQLNKASQYVSLLIRDSQPSDSATYLCAVKAGNQFYFGTGTSLTVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 28 | R4P3H3 beta chain | MGTRLLCWWVLGFLGTDHTGAGVSQSPRYKVAKRGQDVALRCDPISGHVSLFWYQQALGQGPEFLTYFQNEAQLDKSGLPSDRFFAERPEGSVSTLKIQRTQQEDSAVYLCASSLLTSGGDNEQFFGPGTRLTVLEDLKNVFPPEVAVFEPSEAEISHTQKATLVCLATGFYPDHVELSWWNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 29 | R36P3F9 alpha chain | METLLGVSLVILWLQLARVNSQQGEEDPQALSIQEGENATMNCSYKTSINNLQWYRQNSGRGLVHLILIRSNEREKHSGRLRVTLDTSKKSSSLLITASRAADTASYFCATVSNYQLIWGAGTKLIIKPDIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLFQNLSVIGFRILLLKVAGFNLLMTLRLWSS |
| 30 | R36P3F9 beta chain | MGPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASSSTGGLSGETQYFGPGTRLLVLEDLKNVFPPEVAVFEPSEAEISHTQKATLVCLATGFYPDHVELSWWNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 31 | R52P2G11 alpha chain | MKKHLTTFLVILWLYFYRGNGKNQVEQSPQSLIILEGKNCTLQCNYTVSPFSNLRWYKQDTGRGPVSLTIMTFSENTKSNGRYTATLDADTKQSSLHITASQLSDSASYICVVSAYGKLQFGAGTQVVVTPDIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 32 | R52P2G11 beta chain | MDSWTFCCVSLCILVAKHTDAGVIQSPRHEVTEMGQEVTLRCKPISGHNSLFWYRQTMMRGLELLIYFNNNVPIDDSGMPEDRFSAKMPNASFSTLKIQPSEPRDSAVYFCASSLGSPDGNQPQHFGDGTRLSILEDLNKVFPPEVAVFEPSEAEISHTQKATLVCLATGFFPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF |
| 33 | R53P2A9 alpha chain | MACPGFLWALVISTCLEFSMAQTVTQSQPEMSVQEAETVTLSCTYDTSESDYYLFWYKQPPSRQMILVIRQEAYKQQNATENRFSVNFQKAAKSFSLKISDSQLGDAAMYFCAYNSYAGGTSYGKLTFGQGTILTVHPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 34 | R53P2A9 beta chain | MGPGLLCWWLLCLLGAGPVDAGVTQSPTHLIKTRGQQVTLRCSPISGHKSVSWYQQVLGQGPQFIFQYYEEKEERGRGNFPDRFSARQFPNYSSELNVNALLLGDSALYLCASSLDGTSEQYFGPGTRLTVTEDLKNVFPPEVAVFEPSEAEISHTQKATLVCLATGFYPDHVELSWWNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |

TABLE 3-continued

DNA and protein sequences

| SEQ ID NO: | Description | Sequence |
|---|---|---|
| 35 | R26P1A9 alpha chain | METLLGVSLVILWLQLARVNSQQGEEDPQALSIQEGENATMNCSYKTSINNLQWYRQNSGRGLVHLILIRSNEREKHSGRLRVTLDTSKKSSSLLITASRAADTASYFCLIGASGSRLTFGEGTQLTVNPDIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 36 | R26P1A9 beta chain | MGSWTLCCVSLCILVAKHTDAGVIQSPRHEVTEMGQEVTLRCKPISGHDYLFWYRQTMMRGLELLIYFNNNVPIDDSGMPEDRFSAKMPNASFSTLKIQPSEPRDSAVYFCASSYFGWNEKLFFGSGTQLSVLEDLNKVFPPEVAVFEPSEAEISHTQKATLVCLATGFFPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF |
| 37 | R26P2A6 alpha chain | MMKSLRVLLVILWLQLSWVWSQQKEVEQDPGPLSVPEGAIVSLNCTYSNSAFQYFMWYRQYSRKGPELLMYTYSSGNKEDGRFTAQVDKSSKYISLFIRDSQPSDSATYLCAMSDVSGGYNKLIFGAGTRLAVHPYIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 38 | R26P2A6 beta chain | MGPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASTTPDGTDEQFFGPGTRLTVLEDLNKVFPPEVAVFEPSEAEISHTQKATLVCLATGFYPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 39 | R26P3H1 alpha chain | MASAPISMLAMLFTLSGLRAQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDMNRDDKIIFGKGTRLHILPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 40 | R26P3H1 beta chain | MSNQVLCCVVLCFLGANTVDGGITQSPKYLFRKEGQNVTLSCEQNLNHDAMYWYRQDPGQGLRLIYYSQIVRDKGDIAEGYSVSREKKESFPLTVTSAQKNPTAFYLCASSRAEGGEQYFGPGTRLTVTEDLKNVFPPEVAVFEPSEAEISHTQKATLVCLATGFYPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 41 | R35P3A4 alpha chain | MTSIRAVFIFLWLQLDLVNGENVEQHPSTLSVQEGDSAVIKCTYSDSASNYFPWYKQELGKRPQLIIDIRSNVGEKKDQRIAVTLNKTAKHFSLHITETQPEDSAVYFCAASPTGGYNKLIFGAGTRLAVHPYIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 42 | R35P3A4 beta chain | MSIGLLCCAALSLLWAGPVNAGVTQTPKFQVLKTGQSMTLQCAQDMNHEYMSWYRQDPGMGLRLIHYSVGAGITDQGEVPNGYNVSRTTEDFPLRLLSAAPSQTSVYFCASSLGGASQEQYFGPGTRLTVTEDLKNVFPPEVAVFEPSEAEISHTQKATLVCLATGFYPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 43 | R37P1C9 alpha chain | MKLVTSITVLLSLGIMGDAKTTQPNSMESNEEEPVHLPCNHSTISGTDYIHWYRQLPSQGPEYVIHGLTSNVNNRMASLAIAEDRKSSTLILHRATLRDAAVYYCILFNFNKFYFGSGTKLNVKPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 44 | R37P1C9 beta chain | MGPGLLHWMALCLLGTGHGDAMVIQNPRYQVTQFGKPVTLSCSQTLNHNVMYWYQQKSSQAPKLLFHYYDKDFNNEADTPDNFQSRRPNTSFCFLDIRSPGLGDAAMYLCATSSGETNEKLFFGSGTQLSVLEDLNKVFPPEVAVFEPSEAEISHTQKATLVCLATGFFPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF |
| 45 | R37P1H1 alpha chain | MTRVSLLWAVVVSTCLESGMAQTVTQSQPEMSVQEAETVTLSCTYDTSESNYYLFWYKQPPSRQMILVIRQEAYKQQNATENRFSVNFQKAAKSFSLKISDSQLGDTAMYFCAFGYSGGGADGLTFGKGTHLIIQPYIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 46 | R37P1H1 beta chain | MGPGLLCWALLCLLGAGLVDAGVTQSPTHLIKTRGQQVTLRCSPKSGHDTVSWYQQALGQGPQFIFQYYEEEERQRGNFPDRFSGHQFPNYSSELNVNALLLGDSALYLCASSNEGQGWEAEAFFGQGTRLTVVEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF |
| 47 | R42P3A9 alpha chain | MKRILGALLGLLSAQVCCVRGIQVEQSPPDLILQEGANSTLRCNFSDSVNNLQWFHQNPWGQLINLFYIPSGTKQNGRLSATTVATERYSLLYISSSQTTDSGVYFCAVHNFNKFYFGSGTKLNVKPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |

TABLE 3-continued

DNA and protein sequences

| SEQ ID NO: | Description | Sequence |
|---|---|---|
| 48 | R42P3A9 beta chain | MLSPDLPDSAWNTRLLCHVMLCLLGAVSAAGVIQSPRHLIKEKRETATLKCYPIPRHDTVYWYQQGPGQDPQFLISFYEKMQSDKGSIPDRFSAQQFSDYHSELNMSSLELGDSALYFCASSLLGQGYNEQFFGPGTRLTVLEDLKNVFPPEVAVFEPSEAEISHTQKATLVCLATGFYPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 49 | R43P3F2 alpha chain | MLTASLLRAVIASICVVSSMAQKVTQAQTEISVVEKEDVTLDCVYETRDTTYYLFWYKQPPSGELVFLIRRNSFDEQNEISGRYSWNFQKSTSSFNFTITASQVVDSAVYFCALSNNNAGNMLTFGGGTRLMVKPHIQNPDDAVYQLRDSKSSDKSVCLFTDFDSQTNVSQSKDSDVYITDKTVLDMRSMDFKSNSAVAWSNKSDFACANAAFNNSIIPEDTFFPSPESSCDVKLVEKSFETDTNLNFQNLSVIGFRILLLKVAGFNLLMTLRLWSS |
| 50 | R43P3F2 beta chain | MLSPDLPDSAWNTRLLCHVMLCLLGAVSAAGVIQSPRHLIKEKRETATLKCYPIPRHDTVYWYQQGPGQDPQFLISFYEKMQSDKGSIPDRFSAQQFSDYHSELNMSSLELGDSALYFCASSPTGTSYNEQFFGPGTRLTVLEDLKNVFPPEVAVFEPSEAEISHTQKATLVCLATGFYPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 51 | R43P3G5 alpha chain | MEKNPLAAPLLILWFHLDCVSSILNVEQSPQSLHVQEGDSTNFTCSFPSSNFYALHWYRWETAKSPEALFVMTLNGDEKKKGRISATLNTKEGYSYLYIKGSQPEDSATYLCALNRDDKIIFGKGTRLHILPNIQNPDDAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 52 | R43P3G5 beta chain | MGIRLLCRVAFCFLAVGLVDVKVTQSSRYLVKRTGEKVFLECVQDMDHENMFWYRQDPGLGLRLIYFSYDVKMKEKGDIPEGYSVSREKKERFSLILESASTNQTSMYLCASRLPSRTYEQYFGPGTRLTVTEDLKNVFPPEVAVFEPSEAEISHTQKATLVCLATGFYPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 53 | R59P2E7 alpha chain | METLLGLLILWLQLQWWSSKQEVTQIPAALSVPEGENLVLNCSFTDSAIYNLQWFRQDPGKGLTSLLLIQSSQREQTSGRLNASLDKSSGRSTLYIAASQPGDSATYLCAVNSDYKLSFGAGTTVTVRANIQNPDDAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 54 | R59P2E7 beta chain | MLSPDLPDSAWNTRLLCHVMLCLLGAVSAAGVIQSPRHLIKEKRETATLKCYPIPRHDTVYWYQQGPGQDPQFLISFYEKMQSDKGSIPDRFSAQQFSDYHSELNMSSLELGDSALYFCASSLGLGTGDYGYTFGSGTRLTVVEDLKNVFPPEVAVFEPSEAEISHTQKATLVCLATGFFPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF |
| 55 | R11P3D3 alpha chain | MEKNPLAAPLLILWFHLDCVSSILNVEQSPQSLHVQEGDSTNFTCSFPSSNFYALHWYRWETAKSPEALFVMTLNGDEKKKGRISATLNTKEGYSYLYIKGSQPEDSATYLCALYNNNDMRFGAGTRLTVKPNIQNPDDAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 56 | R11P3D3 beta chain | MDSWTFCCVSLCILVAKHTDAGVIQSPRHEVTEMGQEVTLRCKPISGHNSLFWYRQTMMRGLELLIYFNNNVPIDDSGMPEDRFSAKMPNASFSTLKIQPSEPRDSAVYFCASSPGSTDTQYFGPGTRLTVLEDLKNVFPPEVAVFEPSEAEISHTQKATLVCLATGFYPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 57 | R16P1C10 alpha chain | MKSLRVLLVILWLQLSWWSQQKEVEQNSGPLSVPEGAIASLNCTYSDRGSQSFFWYRQYSGKSPELIMFIYSNGDKEDGRFTAQLNKASQYVSLLIRDSQPSDSATYLCAAVISNFGNEKLTFGTGTRLTIIPNIQNPDDAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 58 | R16P1C10 beta chain | MGSRLLCWLLCLLGAGPVKAGVTQTPRYLIKTRGQQVTLSCSPISGHRSVSWYQQTPGQGLQFLFEYFSETQRNKGNFPGRFSGRQFSNSRSEMNVSTLELGDSALYLCASSPWDSPNEQYFGPGTRLTVTEDLKNVFPPEVAVFEPSEAEISHTQKATLVCLATGFYPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 59 | R16P1E8 alpha chain | MMKSLRVLLVILWLQLSWVWSQQKEVEQDPGPLSVPEGAIVSLNCTYSNSAFQYFMWYRQYSRKGPELLMYTYSSGNKEDGRFTAQVDKSSKYISLFIRDSQPSDSATYLCAMSEAAGNKLTFGGGTRVLVKPNIQNPDDAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 60 | R16P1E8 beta chain | MGTRLLCWAALCLLGAELTEAGVAQSPRYKIIEKRQSVAFWCNPISGHATLYWYQQILGQGPKLLIQFQNNGVVDDSQLPKDRFSAERLKGVDSTLKIQPAKLEDSAVYLCASSYTNQGEAFFGQGTRLTVVEDLKNVFPPEVAVFEPSEAEISHTQKATLVCLATGFPDHVELSWWWNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF |

TABLE 3-continued

DNA and protein sequences

| SEQ ID NO: | Description | Sequence |
|---|---|---|
| 61 | R17P1A9 alpha chain | MKSLRVLLVILWLQLSWWWSQQKEVEQNSG PLSVPEGAIASLNCTYSDRGSQSFFWYRQY SGKSPELIMSIYSNGDKEDGRFTAQLNKAS QYVSLLIRDSQPSDSATYLCAVLNQAGTAL IFGKGTTLSVSSNIQNPDDAVYQLRDSKSS DKSVCLFTDFDSQTNVSQKDSDVYITDKT VLDMRSMDFKSNSAVAWSNKSDFACANAFN NSIIPEDTFFPSPESSCDVKLVEKSFETDT NLNFQNLSVIGFRILLLKVAGFNLLMTLRL WSS |
| 62 | R17P1A9 beta chain | MGFRLLCCVAFCLLGAGPVDSGVTQTPKHL ITATGQRVTLRCSPRSGDLSVYWYQQSLDQ GLQFLIQYYNGEERAKGNILERFSAQQFPD LHSELNLSSLELGDSALYFCASSAETGPWL GNEQFFGPGTRLTVLEDLKNVFPPEVAVFE PSEAEISHTQKATLVCLATGFYPDHVELSW WWNGKEVHSGVSTDPQPLKEQPALNDSRYC LSSRLRVSATFWQNPRNHFRCQVQFYGLSE NDEWTQDRAKPVTQIVSAEAWGRADCGFTS ESYQQGVLSATILYEILLGKATLYAVLVSA LVLMAMVKRKDSRG |
| 63 | R17P1D7 alpha chain | MACPGFLWALVISTCLEFSMAQTVTQSQPE MSVQEAETVTLSCTYDTSESDYYLFWYKQP PSRQMILVIRQEAYKQQNATENRFSVNFQK AAKSFSLKISDSQLGDAAMYFCAYRWAQGG SEKLVFGKGTKLTVNPYIQKPDDAVYQLRD SKSSDKSVCLFTDFDSQTNVSQSKDSDVYI TDKTVLDMRSMDFKSNSAVAWSNKSDFACA NAFNNSIIPEDTFFPSPESSCDVKLVEKSF ETDTNLNFQNLSVIGFRILLLKVAGFNLLM TLRLWSS |
| 64 | R17P1D7 beta chain | MTIRLLCYMGFYFLGAGLMEADIYQTPRYL VIGTGKKITLECSQTMGHDKMYWYQQDPGM ELHLIHYSYGVNSTEKGDLSSESTVSRIRT EHFPLTLESARPSHTSQYLCATELWSSGGT GELFFGEGSRLTVLEDLKNVFPPEVAVFEP SEAEISHTQKATLVCLATGFYPDHVELSWW WVNGKEVHSGVSTDPQPLKEQPALNDSRYC LSSRLRVSATFWQNPRNHFRCQVQFYGLSE NDEWTQDRAKPVTQIVSAEAWGRADCGFTS ESYQQGVLSATILYEILLGKATLYAVLVSA LVLMAMVKRKDSRG |
| 65 | R17P1G3 alpha chain | IMSIYSNGDKEDGRFTAQLNKASQYVSLLI RDSQPSDSATYLCAVGPSGTYKYIFGTGTR LKVLANIQNPDDAVYQLRDSKSSDKSVCLF TDFDSQTNVSQSKDSDVYITDKTVLDMRSM DFKSNSAVAWSNKSDFACANAFNNSIIPED TFFPSPESSCDVKLVEKSFETDTNLNFQNL SVIGFRILLLKVAGFNLLMTLRLWSS |
| 66 | R17P1G3 beta chain | MGPQLLGYVVLCLLGAGPLEAQVTQNPRYL ITVTGKKLTVTCSQNMNHEYMSWYRQDPGL GLRQIYYSMNVEVTDKGDVPEGYKVSRKEK RNFPLILESPSPNQTSLYFCASSPGGSGNE QFFGPGTRLTVLEDLKNVFPPEVAVFEPSE AEISHTQKATLVCLATGFYPDHVELSWWWN GKEVHSGVSTDPQPLKEQPALNDSRYCLSS RLRVSATFWQNPRNHFRCQVQFYGLSENDE WTQDRAKPVTQIVSAEAWGRADCGFTSESY QQGVLSATILYEILLGKATLYAVLVSALVL MAMVKRKDSRG |
| 67 | R17P2B6 alpha chain | MKSLRVLLVILWLQLSWWWSQQKEVEQNSG PLSVPEGAIASLNCTYSDRGSQSFFWYRQY SGKSPELIMFIYSNGDKEDGRFTAQLNKAS QYVSLLIRDSQPSDSATYLCAVVSGGGADG LTFGKGTHLIIQPYIQKPDDAVYQLRDSKS SDKSVCLFTDFDSQTNVSQSKDSDVYITDK TVLDMRSMDFKSNSAVAWSNKSDFACANAF NNSIIPEDTFFPSPESSCDVKLVEKSFETD TNLNFQNLSVIGFRILLLKVAGFNLLMTLR LWSS |
| 68 | R17P2B6 beta chain | MLSPDLPDSAWNTRLLCHVMLCLLGAVSVA AGVIQSPRHLIKEKRETATLKCYPIPRHDT VYWYQQGPGQDPQFLISFYEKMQSDKGSIP DRFSAQQFSDYHSELNMSSLELGDSALYFC ASSLGRGGQPHFGDGTRLSILEDLNKVFP PEVAVFEPSEAEISHTQKATLVCLATGFFP DHVELSWWWVNGKEVHSGVSTDPQPLKEQP ALNDSRYCLSSRLRVSATFWQNPRNHFRCQ VQFYGLSENDEWTQDRAKPVTQIVSAEAWG RADCGFTSVSYQQGVLSATILYEILLGKAT LYAVLVSALVLMAMVKRKDF |
| 69 | R11P3D3KE alpha chain | MEKNPLAAPLLILWFHLDCVSSILNVEQSP QSLHVQEGDSTNFTCSFPSSNFYALHWYRK ETAKSPEALFVMTLNGDEKKKGRISATLNT KEGYSYLYIKGSQPEDSATYLCALYNNNDM RFGAGTRLTVKPNIQNPDDAVYQLRDSKSS DKSVCLFTDFDSQTNVSQKDSDVYITDKT VLDMRSMDFKSNSAVAWSNKSDFACANAFN NSIIPEDTFFPSPESSCDVKLVEKSFETDT NLNFQNLSVIGFRILLLKVAGFNLLMTLRL WSS |
| 70 | R11P3D3KE beta chain | NNNVPIDDSGMPEDRFSAKMPNASFSTLKI QPSEPRDSAVYFCASSPGSTDTQYFGPGTR LTVLEDLKNVFPPEVAVFEPSEAEISHTQK ATLVCLATGFYPDHVELSWWWNGKEVHSGV STDPQPLKEQPALNDSRYCLSSRLRVSATF WQNPRNHFRCQVQFYGLSENDEWTQDRAKP VTQIVSAEAWGRADCGFTSESYQQGVLSAT ILYEILLGKATLYAVLVSALVLMAMVKRKD SRG |
| 71 | R39P1C12 alpha chain | TYLYWYKQEPGAGLQLLTYIFSNMDMKQDQ RLTVLLNKKDKHLSLRIADTQTGDSAIYFC AEIDNQGGKLIFGQGTELSVKPNIQNPDPA VYQLRDSKSSDKSVCLFTDFDSQTNVSQSK DSDVYITDKTVLDMRSMDFKSNSAVAWSNK SDFACANAFNNSIIPEDTFFPSPESSCDVK LVEKSFETDTNLNFQNLSVIGFRILLLKVA GFNLLMTLRLWSS |
| 72 | R39P1C12 beta chain | MGPGLLCWALLCLLGAGLVDAGVTQSPTHL IKTRGQQVTLRCSPKSGHDTVSWYQQGLG GPQFIFQYYEEEERQRGNFPDRFSGHQFPN YSSELNVNALLLGDSALYCASSQLNTEAF FGQGTRLTVVEDLKNVFPPEVAVFEPSEAE ISHTQKATLVCLATGFFPDHVELSWWWVNG KEVHSGVSTDPQPLKEQPALNDSRYCLSSR LRVSATFWQNPRNHFRCQVQFYGLSENDEW TQDRAKPVTQIVSAEAWGRADCGFTSVSYQ QGVLSATILYEILLGKATLYAVLVSALVLM AMVKRKDF |
| 73 | R39P1F5 alpha chain | MKSLRVLLVILWLQLSWWWSQQKEVEQNSGP LSVPEGAIASLNCTYSDRGSQSFFWYRQYS GKSPELIMFIYSNGDKEDGRFTAQLNKASQ YVSLLIRDSQPSDSATYLCAVNNARLMFGD GTQLWVKPNIQNPDDAVYQLRDSKSSDKSV CLFTDFDSQTNVSQSKDSDVYITDKTVLDM RSMDFKSNSAVAWSNKSDFACANAFNNSII PEDTFFPSPESSCDVKLVEKSFETDTNLNF QNLSVIGFRILLLKVAGFNLLMTLRLWSS |
| 74 | R39P1F5 beta chain | MDTWLVCWAIFSLLKAGLTEPEVTQTPSHQ VTQMGQEVILRCVPISNHLYFYWYRQILGQ KVEFLVSFYNNEISEKSEIFDDQFSVERPD GSNFTLKIRSTKLEDSAMYFCASSGQGANE QYFGPGTRLTVTEDLKNVFPPEVAVFEPSE AEISHTQKATLVCLATGFYPDHVELSWWWN |

TABLE 3-continued

DNA and protein sequences

| SEQ ID NO: | Description | Sequence |
|---|---|---|
| | | GKEVHSGVSTDPQPLKEQPALNDSRYCLSS RLRVSATFWQNPRNHFRCQVQFYGLSENDE WTQDRAKPVTQIVSAEAWGRADCGFTSESY QQGVLSATILYEILLGKATLYAVLVSALVL MAMVKRKDSRG |
| 75 | R40P1C2 alpha chain | MACPGFLWALVISTCLEFSMAQTVTQSPE MSVQEAETVTLSCTYDTSESDYYLFWYKQP PSRQMILVIRQEAYKQQNATENRFSVNFQK AAKSFSLKISDSQLGDAAMYFCAYLNYQLI WGAGTKLIIKPDIQNPDPAVYQLRDSKSSD KSVCLFTDFDSQTNVSQSKDSDVYITDKTV LDMRSMDFKSNSAVAWSNKSDFACANAFNN SIIPEDTFFPSPESSCDVKLVEKSFETDTN LNFQNLSVIGFRILLLKVAGFNLLMTLRLW SS |
| 76 | R40P1C2 beta chain | MDTWLVCWAIFSLLKAGLTEPEVTQTPSHQ VTQMGQEVILRCVPISNHLYFYWYRQILGQ KVEFLVSFYNNEISEKSEIFDDQFSVERPD GSNFTLKIRSTKLEDSAMYFCASSEMTAVG QYFGPGTRLTVTEDLKNVFPPEVAVFEPSE AEISHTQKATLVCLATGFYPDHVELSWWWN GKEVHSGVSTDPQPLKEQPALNDSRYCLSS RLRVSATFWQNPRNHFRCQVQFYGLSENDE WTQDRAKPVTQIVSAEAWGRADCGFTSESY QQGVLSATILYEILLGKATLYAVLVSALVL MAMVKRKDSRG |
| 77 | R41P3E6 alpha chain | MKSLRVLLVILWLQLSWWWSQQKEVEQNSG PLSVPEGAIASLNCTYSDRGSQSFFWYRQY SGKSPELIMFIYSNGDKEDGRFTAQLNKAS QYVSLLIRDSQPSDSATYLCAAFSGYALNF GKGTSLLVTPHIQNPDPAVYQLRDSKSSDK SVCLFTDFDSQTNVSQSKDSDVYITDKTVL DMRSMDFKSNSAVAWSNKSDFACANAFNNS IIPEDTFFPSPESSCDVKLVEKSFETDTNL NFQNLSVIGFRILLLKVAGFNLLMTLRLWS S |
| 78 | R41P3E6 beta chain | MDTWLVCWAIFSLLKAGLTEPEVTQTPSHQ VTQMGQEVILRCVPISNHLYFYWYRQILGQ KVEFLVSFYNNEISEKSEIFDDQFSVERPD GSNFTLKIRSTKLEDSAMYFCASSQYTGEL FFGEGSRLTVLEDLKNVFPPEVAVFEPSEA EISHTQKATLVCLATGFYPDHVELSWVNG KEVHSGVSTDPQPLKEQPALNDSRYCLSSR LRVSATFWQNPRNHFRCQVQFYGLSENDEW TQDRAKPVTQIVSAEAWGRADCGFTSESYQ QGVLSATILYEILLGKATLYAVLVSALVLM AMVKRKDSRG |
| 79 | R43P3G4 alpha chain | MKSLRVLLVILWLQLSWWSQQKEVEQNSGP LSVPEGAIASLNCTYSDRGSQSFFWYRQYS GKSPELIMFIYSNGDKEDGRFTAQLNKASQ YVSLLIRDSQPSDSATYLCAVNGGDMRFGA GTRLTVKPNIQNPDPAVYQLRDSKSSDKSV CLFTDFDSQTNVSQSKDSDVYITDKTVLDM RSMDFKSNSAVAWSNKSDFACANAFNNSII PEDTFFPSPESSCDVKLVEKSFETDTNLNF QNLSVIGFRILLLKVAGFNLLMTLRLWSS |
| 80 | R43P3G4 beta chain | MDTWLVCWAIFSLLKAGLTEPEVTQTPSHQ VTQMGQEVILRCVPISNHLYFYWYRQILGQ KVEFLVSFYNNEISEKSEIFDDQFSVERPD GSNFTLKIRSTKLEDSAMYFCASSGQALE QYFGPGTRLTVTEDLKNVFPPEVAVFEPSE AEISHTQKATLVCLATGFYPDHVELSWWWN GKEVHSGVSTDPQPLKEQPALNDSRYCLSS RLRVSATFWQNPRNHFRCQVQFYGLSENDE WTQDRAKPVTQIVSAEAWGRADCGFTSESY QQGVLSATILYEILLGKATLYAVLVSALVL MAMVKRKDSRG |
| 81 | R44P3B3 alpha chain | MAMLLGASVLILWLQPDWNSQQKNDDQQVK QNSPSLSVQEGRISILNCDYTNSMFDYFLW YKKYPAEGPTFLISISSIKDKNEDGRFTVF LNKSAKHLSLHIVPSQPGDSAVYFCAASGL YNQGGKLIFGQGTELSVKPNIQNPDPAVYQ LRDSKSSDKSVCLFTDFDSQTNVSQSKDSD VYITDKTVLDMRSMDFKSNSAVAWSNKSDF ACANAFNNSIIPEDTFFPSPESSCDVKLVE KSFETDTNLNFQNLSVIGFRILLLKVAGFN LLMTLRLWSS |
| 82 | R44P3B3 beta chain | MGCRLLCCVVFCLLQAGPLDTAVSQTPKYL VTQMGNDKSIKCEQNLGHDTMYWYKQDSKK FLKIMFSYNNKELIINETVPNRFSPKSPDK AHLNLHINSLELGDSAVYFCASSLGDRGYE QYFGPGTRLTVTEDLKNVFPPEVAVFEPSE AEISHTQKATLVCLATGFYPDHVELSWWWN GKEVHSGVSTDPQPLKEQPALNDSRYCLSS RLRVSATFWQNPRNHFRCQVQFYGLSENDE WTQDRAKPVTQIVSAEAWGRADCGFTSESY QQGVLSATILYEILLGKATLYAVLVSALVL MAMVKRKDSRG |
| 83 | R44P3E7 alpha chain | MKTFAGFSFLFLWLQLDCMSRGEDVEQSLF LSVREGDSSVINCTYTDSSSTYLYWYKQEP GAGLQLLTYIFSNMDMKQDQRLTVLLNKKD KHLSLRIADTQTGDSAIYFCAEINNNARLM FGDGTQLVVKPNIQNPDPAVYQLRDSKSSD KSVCLFTDFDSQTNVSQSKDSDVYITDKTV LDMRSMDFKSNSAVAWSNKSDFACANAFNN SIIPEDTFFPSPESSCDVKLVEKSFETDTN LNFQNLSVIGFRILLLKVAGFNLLMTLRLW SS |
| 84 | R44P3E7 beta chain | MLSPDLPDSAWNTRLLCHVMLCLLGAVSVA AGVIQSPRHLIKEKRETATLKCYPIPRHDT VYWYQQGPGQDPQFLISFYEKMQSDKGSIP DRFSAQQFSDYHSELNMSSLELGDSALYFC ASSPPDQNTQYFGPGTRLTVEDLKNVFPP EVAVFEPSEAEISHTQKATLVCLATGFYPD HVELSWWWNGKEVHSGVSTDPQPLKEQPAL NDSRYCLSSRLRVSATFWQNPRNHFRCQVQ FYGLSENDEWTQDRAKPVTQIVSAEAWGRA DCGFTSESYQQGVLSATILYEILLGKATLY AVLVSALVLMAMVKRKDSRG |
| 85 | R49P2B7 alpha chain | MLLLLVPVLEVIFTLGGTRAQSVTQLGSHV SVSEGALVLLRCNYSSSVPPYLFWYVQYPN QGLQLLLKYTTGATLVKGINGFEAEFKKSE TSFHLTKPSAHMSDAAEYFCAVRIFGNEKL TFGTGTRLTIIPNIQNPDPAVYQLRDSKSS DKSVCLFTDFDSQTNVSQSKDSDVYITDKT VLDMRSMDFKSNSAVAWSNKSDFACANAFN NSIIPEDTFFPSPESSCDVKLVEKSFETDT NLNFQNLSVIGFRILLLKVAGFNLLMTLRL WSS |
| 86 | R49P2B7 beta chain | MGIRLLCRVAFCFLAVGLVDVKVTQSSRYL VKRTGEKVFLECVQDMDHENMFWYRQDPGL GLRLIYFSYDVKMKEKGDIPEGYSVSREKK ERFSLILESASTNQTSMYLCASSLMGELTG ELFFGEGSRLTVLEDLKNVFPPEVAVFEPS EAEISHTQKATLVCLATGFYPDHVELSWWW NGKEVHSGVSTDPQPLKEQPALNDSRYCLS SRLRVSATFWQNPRNHFRCQVQFYGLSEND EWTQDRAKPVTQIVSAEAWGRADCGFTSES YQQGVLSATILYEILLGKATLYAVLVSALV LMAMVKRKDSRG |
| 87 | R55P1G7 alpha chain | MMKSLRVLLVILWLQLSWWSQQKEVEQDPG PLSVPEGAIVSLNCTYSNSAFQYFMWYRQ YSRKGPELLMYTYSSGNKEDGRFTAQVDKS SKYISLFIRDSQPSDSATYLCAMMGDTGTA SKLTFGTGTRLQVTLDIQNPDPAVYQLRDS |

TABLE 3-continued

DNA and protein sequences

| SEQ ID NO: | Description | Sequence |
|---|---|---|
|  |  | KSSDKSVCLFTDFDSQTNVSQSKDSDVYIT DKTVLDMRSMDFKSNSAVAWSNKSDFACAN AFNNSIIPEDTFFPSPESSCDVKLVEKSFE TDTNLNFQNLSVIGFRILLLKVAGFNLLMT LRLWSS |
| 88 | R55P1G7 beta chain | MGIRLLCRVAFCFLAVGLVDVKVTQSSRYL VKRTGEKVFLECVQDMHENMFWYRQDPGL GLRLRLIYSYDVKMKEKGDIPEGYSVSREKK ERFSLILESASTNQTSMYLCASSFGGYEQY FGPGTRLTVTEDLKNVFPPEVAVFEPSEAE ISHTQKATLVCLATGFYPDHVELSWWWNGK EVHSGVSTDPQPLKEQPALNDSRYCLSSRL RVSATFWQNPRNHFRCQVQFYGLSENDEWT QDRAKPVTQIVSAEAWGRADCGFTSESYQQ GVLSATILYEILLGKATLYAVLVSALVLMA MVKRKDSRG |
| 89 | R59P2A7 alpha chain | VKPNIQNPDPAVYQLRDSKSSDKSVCLFTD FDSQTNVSQSKDSDVYITDKTVLDMRSMDF KSNSAVAWSNKSDFACANAFNNSIIPEDTF FPSPESSCDVKLVEKSFETDTNLNFQNLSV IGFRILLLKVAGFNLLMTLRLWSS |
| 90 | R59P2A7 beta chain | MLCSLLALLLGTFFGVRSQTIHQWPATLVQ PVGSPLSLECTVEGTSNPNLYWYRQAAGRG LQLLFYSVGIGQISSEVPQNLSASRPQDRQ FILSSKKLLLSDSGFYLCAWSGLVAEQFFG PGTRLTVLEDLKNVFPPEVAVFEPSEAEIS HTQKATLVCLATGFYPDHVELSWWWNGKEV HSGVSTDPQPLKEQPALNDSRYCLSSRLRV SATFWQNPRNHFRCQVQFYGLSENDEWTQD RAKPVTQIVSAEAWGRADCGFTSESYQQGV LSATILYEILLGKATLYAVLVSALVLMAMV KRKDSRG |
| 91 | Variant R4P3F9 alpha chain | MKSLRVLLVILWLQLSWVWSQQKEVEQNSGP LSVPEGAIASLNCTYSDRRSQSFFWYRQYS GKSPELIMFIYSNGDKEDGRFTAQLNKASQ YVSLLIRDSQPSDSATYLCAAYSGAGSYQL TFGKGTKLSVIPNIQNPDPAVYQLRDSKSS DKSVCLFTDFDSQTNVSQSKDSDVYITDKT VLDMRSMDFKSNSAVAWSNKSDFACANAFN NSIIPEDTFFPSPESSCDVKLVEKSFETDT NLNFQNLSVIGFRILLLKVAGFNLLMTLRL WSS |
| 92 | Variant R4P3F9 beta chain | MGFRLLCCVAFCLLGAGPVDSGVTQTPKHL ITATGQRVTLRCSPAMDHPYVYWYQQSLDQ GLQFLIQYYNGEERAKGNILERFSAQQFPD LHSELNLSSLELGDSALYFCASSVESSYGY TFGSGTRLTVVEDLNKVFPPEVAVFEPSEA EISHTQKATLVCLATGFFPDHVELSWWWNG KEVHSGVSTDPQPLKEQPALNDSRYCLSSR LRVSATFWQNPRNHFRCQVQFYGLSENDEW TQDRAKPVTQIVSAEAWGRADCGFTSVSYQ QGVLSATILYEILLGKATLYAVLVSALVLM AMVKRKDF |
| 93 | Furin consensus | RXXR |
| 94 | MSCV promoter | tgaaagaccccacctgtaggtttggcaagc tagcttaagtaacgccattttgcaaggcat ggaaaatacataactgagaatagagaagtt cagatcaaggttaggaacagagagacagca gaatatgggccaaacaggatatctgtggta agcagttcctgccccggctcagggccaaga acagatggtccccagatgcggtcccgccct cagcagtttctagagaaccatcagatgttt ccagggtgccccaaggacctgaaaatgacc ctgtgccttatttgaactaaccaatcagtt cgcttctcgcttctgttcgcgcgcttctgc tccccgagctcaataaaagagcccacaacc cctcact |
| 95 | RD114TR | MKLPTGMVILCSLIIVRAGFDDPRKAIALV QKQHGKPCECSGGQVSEAPPNSIQQVTCPG KTAYLMTNQKWKCRVTPKISPSGGELQNCP CNTFQDSMHSSCYTEYRQCRRINKTYYTAT LLKIRSGSLNEVQILQNPNQLLQSPCRGSI NQPVCWSATAPIHISDGGGPLDTKRVWTVQ KRLEQIHKAMTPELQYHPLALPKVRDDLSL DARTFDILNTTFRLLQMSNFSLAQDCWLCL KLGTPTPLAIPTPSLTYSLADSLANASCQI IPPLLVQPMQFSNSSCLSSPFINDTEQIDL GAVTFTNCTSVANVSSPLCALNGSVFLCGN NMAYTYLPQNWTRLCVQASLLPDIDINPGD EPVPIPAIDHYIHRPKRAVQFIPLLAGLGI TAAFTTGATGLGVSVTQYTKLSHQLISDVQ VLSGTIQDLQDQVDSLAEVVLQNRRGLDLL TAEQGGICLALQEKCCFYANKSGIVRNKIR TLQEELQKRRESLASNPLWTGLQGFLPYLL PLLGPLLTLLLILTIGPCVFNRLVQFVKDR ISVVQALVLTQQYHQLKPL |

TABLE 4

TAA Peptide sequences

| SEQ ID NO: | Amino Acid Sequence |
|---|---|
| 99 | YLYDSETKNA |
| 100 | HLMDQPLSV |
| 101 | GLLKKINSV |
| 102 | FLVDGSSAL |
| 103 | FLFDGSANLV |
| 104 | FLYKIIDEL |
| 105 | FILDSAETTTL |
| 106 | SVDVSPPKV |
| 107 | VADKIHSV |
| 108 | IVDDLTINL |
| 109 | GLLEELVTV |
| 110 | TLDGAAVNQV |
| 111 | SVLEKEIYSI |
| 112 | LLDPKTIFL |
| 113 | YTFSGDVQL |
| 114 | YLMDDFSSL |
| 115 | KVWSDVTPL |
| 116 | LLWGHPRVALA |
| 117 | KIWEELSVLEV |
| 118 | LLIPFTIFM |
| 119 | FLIENLLAA |

TABLE 4-continued

TAA Peptide sequences

| SEQ ID NO: | Amino Acid Sequence |
| --- | --- |
| 120 | LLWGHPRVALA |
| 121 | FLLEREQLL |
| 122 | SLAETIFIV |
| 123 | TLLEGISRA |
| 124 | KIQEILTQV |
| 125 | VIFEGEPMYL |
| 126 | SLFESLEYL |
| 127 | SLLNQPKAV |
| 128 | GLAEFQENV |
| 129 | KLLAVIHEL |
| 130 | TLHDQVHLL |
| 131 | TLYNPERTITV |
| 132 | KLQEKIQEL |
| 133 | SVLEKEIYSI |
| 134 | RVIDDSLVVGV |
| 135 | VLFGELPAL |
| 136 | GLVDIMVHL |
| 137 | FLNAIETAL |
| 138 | ALLQALMEL |
| 139 | ALSSSQAEV |
| 140 | SLITGQDLLSV |
| 141 | QLIEKNWLL |
| 142 | LLDPKTIFL |
| 143 | RLHDENILL |
| 144 | YTFSGDVQL |
| 145 | GLPSATTTV |
| 146 | GLLPSAESIKL |
| 147 | KTASINQNV |
| 148 | SLLQHLIGL |
| 149 | YLMDDFSSL |
| 150 | LMYPYIYHV |
| 151 | KVWSDVTPL |
| 152 | LLWGHPRVALA |
| 153 | VLDGKVAVV |
| 154 | GLLGKVTSV |
| 155 | KMISAIPTL |
| 156 | GLLETTGLLAT |
| 157 | TLNTLDINL |

TABLE 4-continued

TAA Peptide sequences

| SEQ ID NO: | Amino Acid Sequence |
| --- | --- |
| 158 | VIIKGLEEI |
| 159 | YLEDGFAYV |
| 160 | KIWEELSVLEV |
| 161 | LLIPFTIFM |
| 162 | ISLDEVAVSL |
| 163 | KISDFGLATV |
| 164 | KLIGNIHGNEV |
| 165 | ILLSVLHQL |
| 166 | LDSEALLTL |
| 167 | VLQENSSDYQSNL |
| 168 | HLLGEGAFAQV |
| 169 | SLVENIHVL |
| 170 | YTFSGDVQL |
| 171 | SLSEKSPEV |
| 172 | AMFPDTIPRV |
| 173 | FLIENLLAA |
| 174 | FTAEFLEKV |
| 175 | ALYGNVQQV |
| 176 | LFQSRIAGV |
| 177 | ILAEEPIYIRV |
| 178 | FLLEREQLL |
| 179 | LLLPLELSLA |
| 180 | SLAETIFIV |
| 181 | AILNVDEKNQV |
| 182 | RLFEEVLGV |
| 183 | YLDEVAFML |
| 184 | KLIDEDEPLFL |
| 185 | KLFEKSTGL |
| 186 | SLLEVNEASSV |
| 187 | GVYDGREHTV |
| 188 | GLYPVTLVGV |
| 189 | ALLSSVAEA |
| 190 | TLLEGISRA |
| 191 | SLIEESEEL |
| 192 | ALYVQAPTV |
| 193 | KLIYKDLVSV |
| 194 | ILQDGQFLV |
| 195 | SLLDYEVSI |

TABLE 4-continued

TAA Peptide sequences

| SEQ ID NO: | Amino Acid Sequence |
|---|---|
| 196 | LLGDSSFFL |
| 197 | VIFEGEPMYL |
| 198 | ALSYILPYL |
| 199 | FLFVDPELV |
| 200 | SEWGSPHAAVP |
| 201 | ALSELERVL |
| 202 | SLFESLEYL |
| 203 | KVLEYVIKV |
| 204 | VLLNEILEQV |
| 205 | SLLNQPKAV |
| 206 | KMSELQTYV |
| 207 | ALLEQTGDMSL |
| 208 | VIIKGLEEITV |
| 209 | KQFEGTVEI |
| 210 | KLQEEIPVL |
| 211 | GLAEFQENV |
| 212 | NVAEIVIHI |
| 213 | ALAGIVTNV |
| 214 | NLLIDDKGTIKL |
| 215 | VLMQDSRLYL |
| 216 | KVLEHVVRV |
| 217 | LLWGNLPEI |
| 218 | SLMEKNQSL |
| 219 | KLLAVIHEL |
| 220 | ALGDKFLLRV |
| 221 | FLMKNSDLYGA |
| 222 | KLIDHQGLYL |
| 223 | GPGIFPPPPPQP |
| 224 | ALNESLVEC |
| 225 | GLAALAVHL |
| 226 | LLLEAVWHL |
| 227 | SIIEYLPTL |
| 228 | TLHDQVHLL |
| 229 | SLLMWITQC |
| 230 | FLLDKPQDLSI |
| 231 | YLLDMPLWYL |
| 232 | GLLDCPIFL |
| 233 | VLIEYNFSI |

TABLE 4-continued

TAA Peptide sequences

| SEQ ID NO: | Amino Acid Sequence |
|---|---|
| 234 | TLYNPERTITV |
| 235 | AVPPPPSSV |
| 236 | KLQEELNKV |
| 237 | KLMDPGSLPPL |
| 238 | ALIVSLPYL |
| 239 | FLLDGSANV |
| 240 | ALDPSGNQLI |
| 241 | ILIKHLVKV |
| 242 | VLLDTILQL |
| 243 | HLIAEIHTA |
| 244 | SMNGGVFAV |
| 245 | MLAEKLLQA |
| 246 | YMLDIFHEV |
| 247 | ALWLPTDSATV |
| 248 | GLASRILDA |
| 249 | ALSVLRLAL |
| 250 | SYVKVLHHL |
| 251 | VYLPKIPSW |
| 252 | NYEDHFPLL |
| 253 | VYIAELEKI |
| 254 | VHFEDTGKTLLF |
| 255 | VLSPFILTL |
| 256 | HLLEGSVGV |

Example 2

Generation of WPRE Mutants

Wild-type WPRE sequences are used in lentiviral constructs to stabilize and enhance transcription of genes. Due to some reports that conclude that a protein (X protein) within the WPRE can cause oncogenesis, the US FDA has recommended that lentiviral constructs used in clinical trials for gene and cellular therapy find alternatives to using wild type WPRE. We believe that fulfilling FDA requirements will enable our T cell products to be used in clinical trials and potentially avoid safety concerns with some aspects of lentiviral vector design.

Two separate WPRE mutation strategies were explored in an attempt to develop WPRE mutants which do not express a functional X protein, while maintaining the post-transcriptional enhancement by WPRE on gene expression.

One variant was developed in which both the promoter region of X protein and the start codon of the X protein were mutated (SEQ ID NO: 4).

Another variant was developed in which the X protein promoter and full putative sequence have been deleted along with mutating start codons of any ORFs larger than 25aa within the WPRE (SEQ ID NO: 3).

Example 3

Lentiviral Constructs

A schematic of an expression cassette as used herein is provided in FIG. 3.

FIG. 4 provides a description of the cassettes used in the lentiviral constructs used in the experiments detailed below to examine the efficacy of WPRE mutants.

The lentiviral vectors used herein contain several elements previously shown to enhance vector function, including a central polypurine tract (cPPT) for improved replication and nuclear import, a promoter from the murine stem cell virus (MSCV) (SEQ ID NO: 94), which has been shown to lessen vector silencing in some cell types, and the backbone has a deleted 3'-LTR self-inactivating (SIN) vector design that may have improved safety, sustained gene expression and anti-silencing properties (Yang et al. *Gene Therapy* (2008) 15, 1411-1423, the content of which is incorporated by reference in its entirety).

The lentiviral vectors used herein encode both a TCRα chain and a TCRβ chain. In particular, the vectors used herein encode R4P3F9a and 13 chains (SEQ ID NO: 25 and 26) and variants thereof. Vectors described herein beginning with the abbreviation "R4" encode wild-type R4P3F9α and β chains (SEQ ID NO: 25 and 26); vectors beginning with the abbreviation "R4-B4" encode a wild-type R4P3F9α chain (SEQ ID NO: 25) and a variant R4P3F9 β chain (SEQ ID NO: 92); and vectors beginning with the abbreviation "R4-A1B4" encode a variant R4P3F9α chain (SEQ ID NO: 91) and a variant R4P3F9 β chain (SEQ ID NO: 92) (FIG. 4).

For each TCRαβ dimer described above, four separate WPRE variations were tested. "Variant A" is the wild-type WPRE according to SEQ ID NO: 2 (positive control); "variant B" contains no WPRE (negative control); "variant C" contains the mutant WPRE according to SEQ ID NO: 4 in which the X protein promoter and start codon have been mutated; and "variant D" contains the mutant WPRE according to SEQ ID NO: 3 in which start codons located throughout the WPRE sequence have been mutated and the X protein promoter and ORF have been deleted.

Example 4

Effect of WPRE Mutation on Lentiviral Construct Efficacy in T Cells

T cells were obtained from donors on Day 0, activated on Day 1, transduced with the various lentiviral vectors described above in Example 3 on Day 2 and harvested on Day 6 for testing. TCR surface expression was determined by flow cytometry and vector copy number was determined by qPCR.

Figure 5:
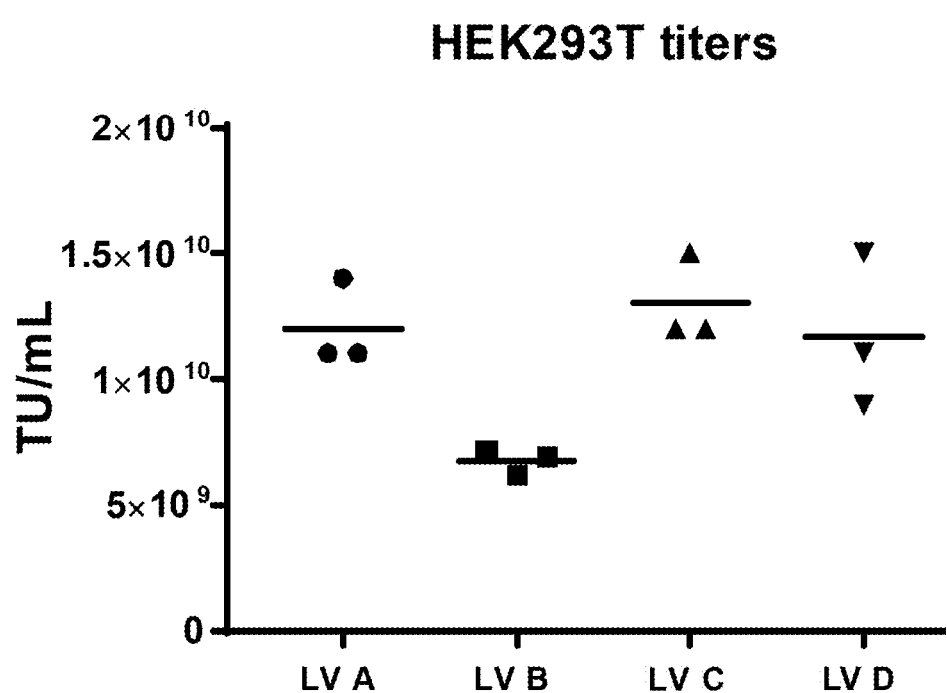
FIG. 5 shows HEK-293 T titers obtained following transduction with lentiviral constructs in accordance with some embodiments of the present disclosure. Variant A contains wild-type (WT) WPRE (positive control); variant B contains no WPRE (negative control); variant C contains a mutant WPRE in which the X protein promoter and start codon are mutated (SEQ ID NO: 4); and variant D contains a mutant WPRE in which start codons are mutated and both the X protein promoter and ORF are deleted (SEQ ID NO: 3).

FIG. 5 shows HEK-293 T titers obtained following transduction with lentiviral constructs in accordance with some embodiments of the present disclosure. The titers obtained using lentiviral constructs containing mutant WPREs (LV-C & LV-D) were similar to those obtained using lentiviral constructs containing wild-type (WT) WPRE (LV-A).

Figure 6:
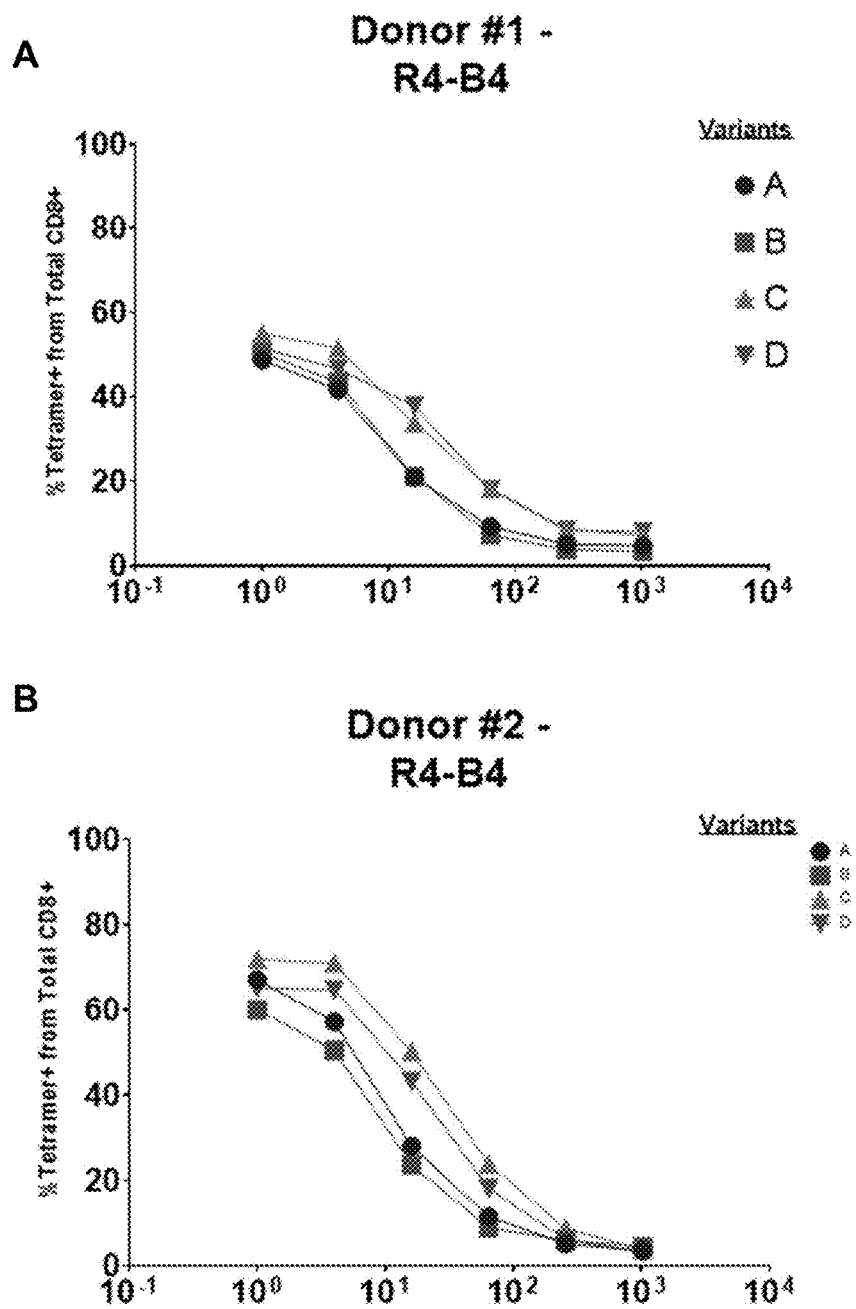
FIG. 6 shows expression of TCRs on the surface of CD8+ cells six days after transduction with R4-B4 lentiviral constructs in accordance with some embodiments of the present disclosure. Expression was detected by tetramer using lentiviral titration in two separate donors: Donor #1 in panel A and donor #2 in panel B. Log viral dilution factor is presented along the X-axis. Variant A contains wild-type (WT) WPRE (positive control); variant B contains no WPRE (negative control); variant C contains a mutant WPRE in which the X protein promoter and start codon are mutated (SEQ ID NO: 4); and variant D contains a mutant WPRE in which start codons are mutated and both the X protein promoter and ORF are deleted (SEQ ID NO: 3).

FIG. 6 shows expression of TCRs on the surface of CD8+ cells six days after transduction with R4-B4 lentiviral constructs in accordance with some embodiments of the present disclosure. Expression was detected by tetramer using lentiviral titration in two separate donors: Donor #1 in panel A and donor #2 in panel B. Log viral dilution factor is presented along the X-axis. Surprisingly, TCR expression was higher in CD8+ cells transduced with lentiviral constructs containing mutant WPREs (variants C & D) compared those transduced with lentiviral constructs containing either WT WPRE (variant A) or no WPRE (variant B).

Figure 7:
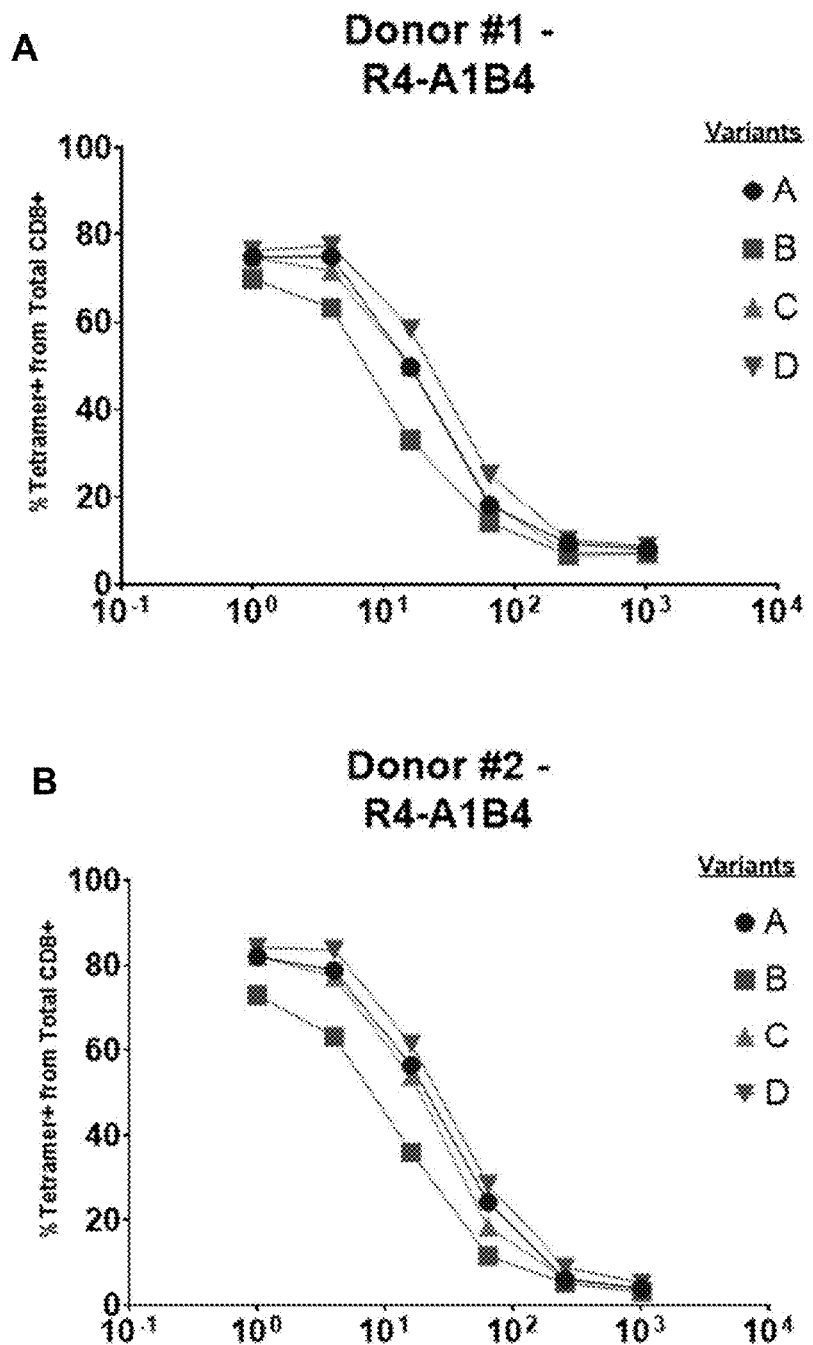
FIG. 7 shows expression of TCRs on the surface of CD8+ cells six days after transduction with R4-A1B4 lentiviral constructs in accordance with some embodiments of the present disclosure. Expression was detected by tetramer using lentiviral titration in two separate donors: Donor #1 in panel A and donor #2 in panel B. Log viral dilution factor is presented along the X-axis. Variant A contains wild-type (WT) WPRE (positive control); variant B contains no WPRE (negative control); variant C contains a mutant WPRE in which the X protein promoter and start codon are mutated (SEQ ID NO: 4); and variant D contains a mutant WPRE in which start codons are mutated and both the X protein promoter and ORF are deleted (SEQ ID NO: 3).

FIG. 7 shows expression of TCRs on the surface of CD8+ cells six days after transduction with R4-A1B4 lentiviral constructs in accordance with some embodiments of the present disclosure. Expression was detected by tetramer using lentiviral titration in two separate donors: Donor #1 in panel A and donor #2 in panel B. Log viral dilution factor is presented along the X-axis. Similar to the results from R4-B4 vectors shown in FIG. 6, TCR expression was highest in CD8+ cells transduced with lentiviral constructs containing variant D (mutant WPRE according to SEQ ID NO: 3).

Figure 8:
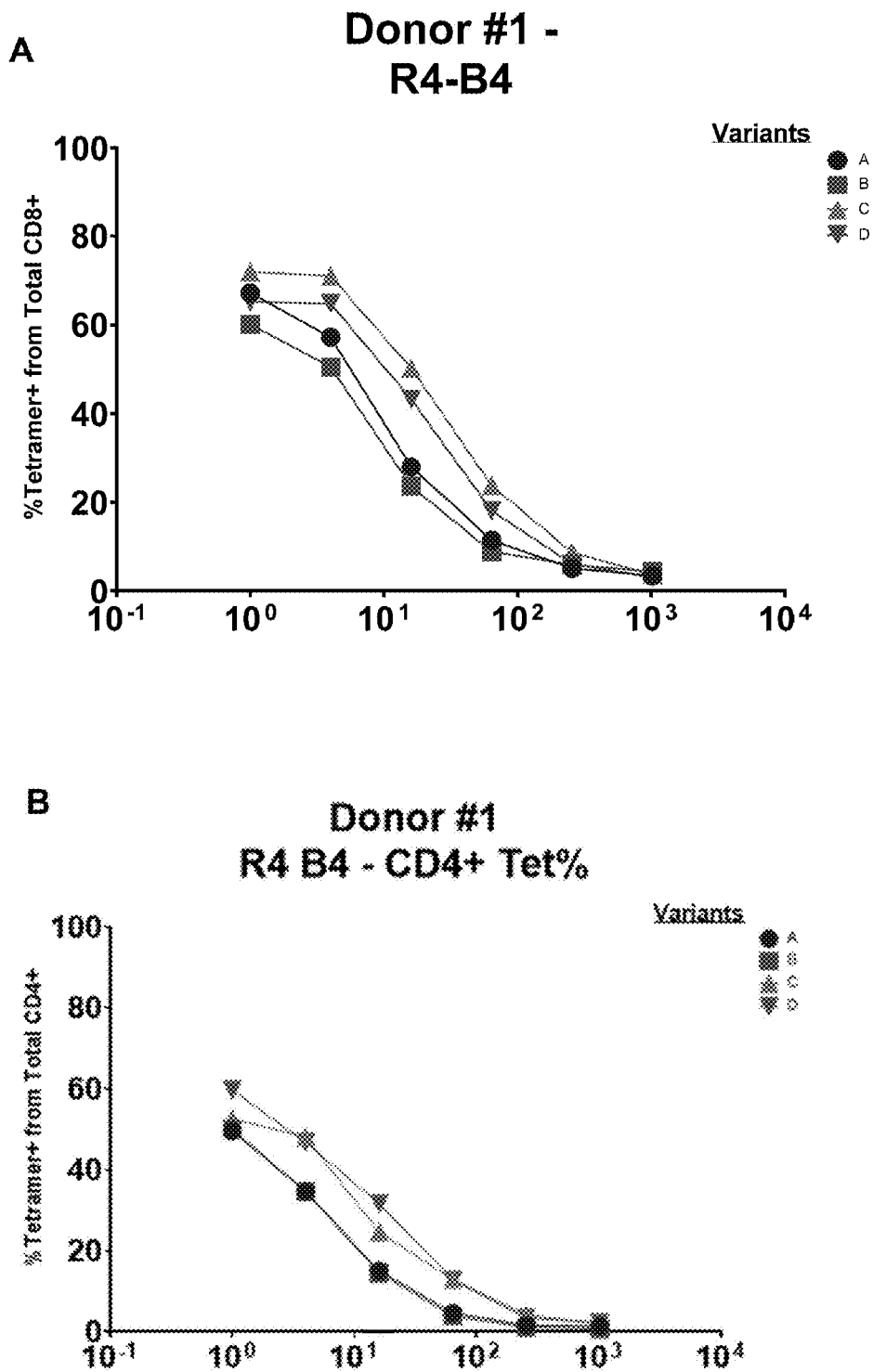
FIG. 8 shows expression of TCRs on the surface of CD8+ cells (A) or CD4+ cells (B) six days after transduction with R4-B4 lentiviral constructs in accordance with some embodiments of the present disclosure. Expression was detected by tetramer using lentiviral titration. Log viral dilution factor is presented along the X-axis. Variant A contains wild-type (WT) WPRE (positive control); variant B contains no WPRE (negative control); variant C contains a mutant WPRE in which the X protein promoter and start codon are mutated (SEQ ID NO: 4); and variant D contains a mutant WPRE in which start codons are mutated and both the X protein promoter and ORF are deleted (SEQ ID NO: 3).

FIG. 8 shows expression of TCRs on the surface of CD8+ cells (A) or CD4+ cells (B) six days after transduction with R4-B4 lentiviral constructs in accordance with some embodiments of the present disclosure. Expression was detected by tetramer using lentiviral titration. Log viral dilution factor is presented along the X-axis. These results further illustrate that TCR expression was higher in both CD8+ cells and CD4+ cells transduced with lentiviral constructs containing mutant WPREs (variants C & D) compared those transduced with lentiviral constructs containing either WT WPRE (variant A) or no WPRE (variant B).

Figure 9:
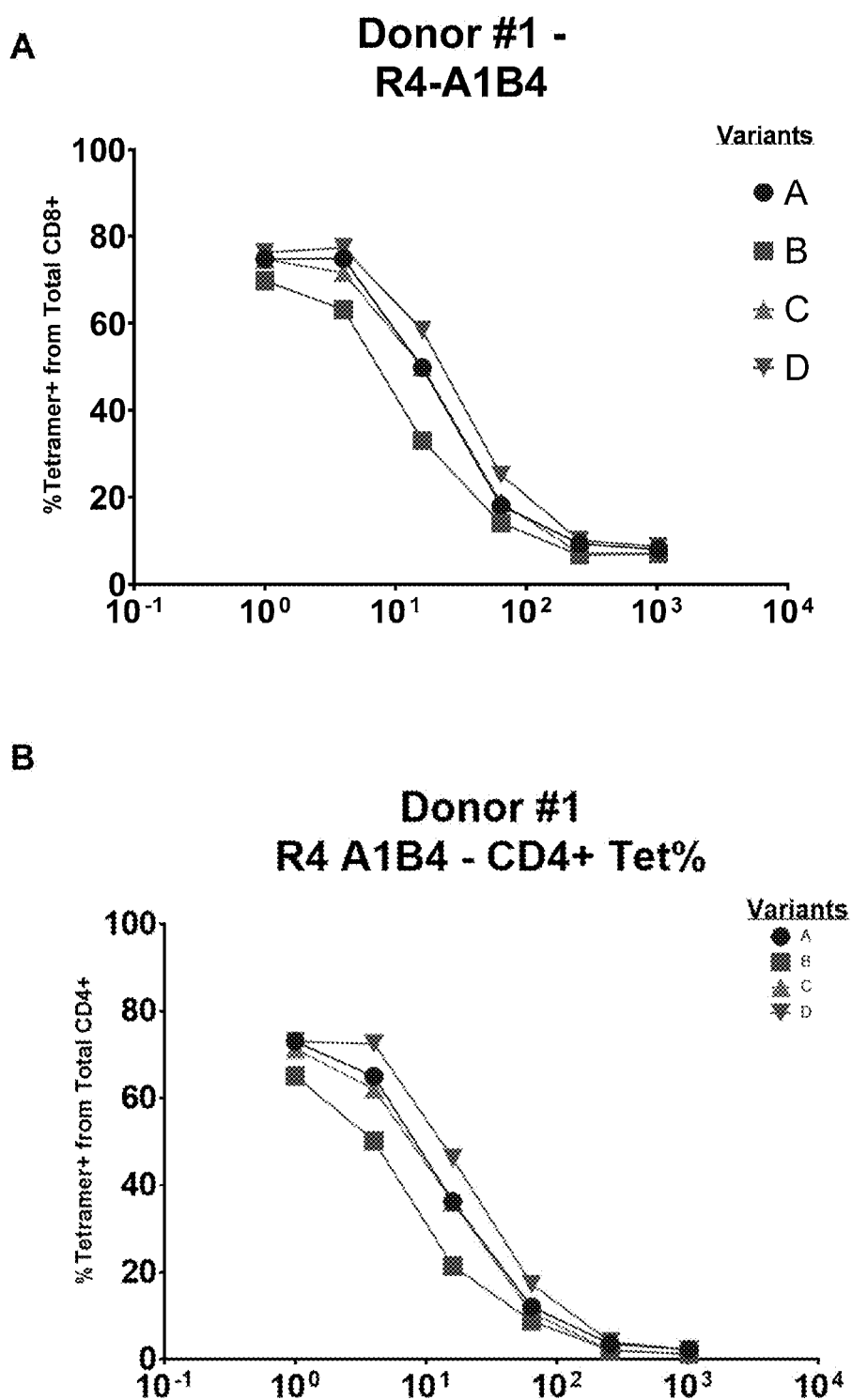
FIG. 9 shows expression of TCRs on the surface of CD8+ cells (A) or CD4+ cells (B) six days after transduction with R4-A1B4 lentiviral constructs in accordance with some embodiments of the present disclosure. Expression was detected by tetramer using lentiviral titration. Log viral dilution factor is presented along the X-axis. Variant A contains wild-type (WT) WPRE (positive control); variant B contains no WPRE (negative control); variant C contains a mutant WPRE in which the X protein promoter and start codon are mutated (SEQ ID NO: 4); and variant D contains a mutant WPRE in which start codons are mutated and both the X protein promoter and ORF are deleted (SEQ ID NO: 3).

FIG. 9 shows expression of TCRs on the surface of CD8+ cells (A) or CD4+ cells (B) six days after transduction with R4-A1B4 lentiviral constructs in accordance with some embodiments of the present disclosure. Expression was detected by tetramer using lentiviral titration. Log viral dilution factor is presented along the X-axis. Similar to the results shown in FIGS. 6-8, TCR expression was highest in CD8+ and CD4+ cells transduced with lentiviral constructs containing variant D (mutant WPRE according to SEQ ID NO: 3). IMA203 is a lentiviral construct expressing R11KE TCR and containing WT WPRE used as a negative control.

Figure 10:
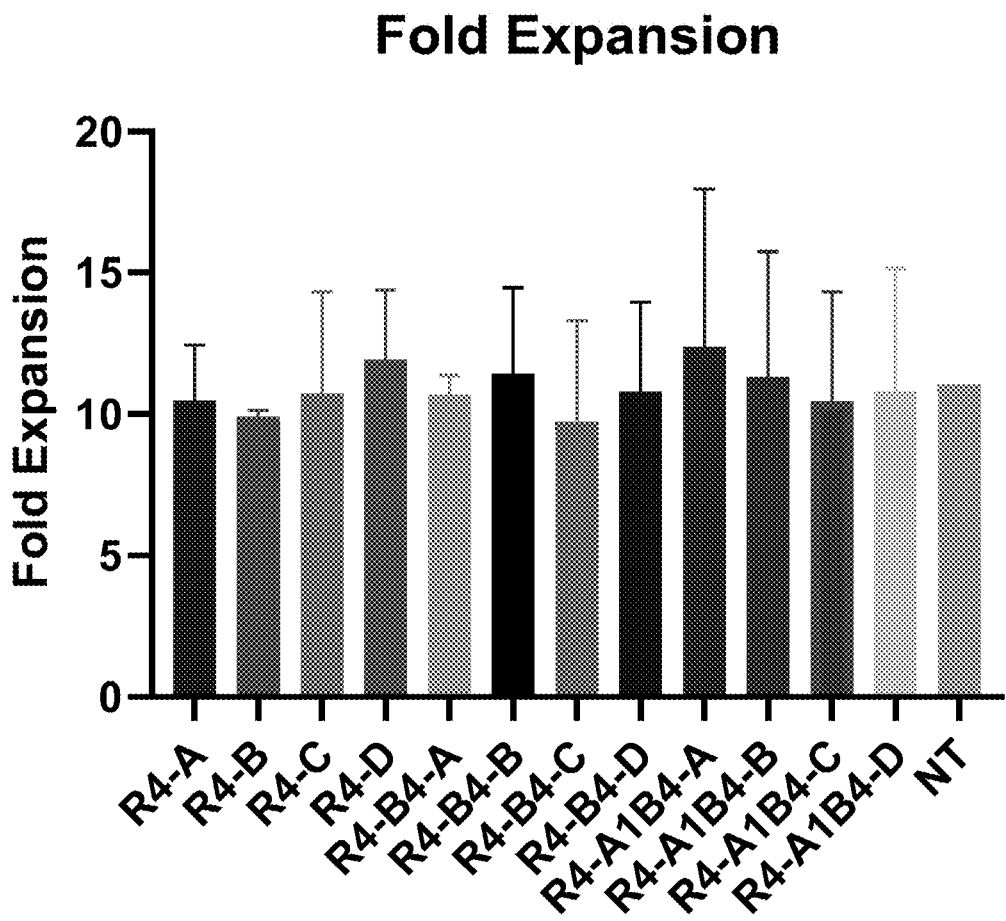
FIG. 10 shows fold expansion is not affected by WPRE mutations. Cell viability was higher than 90% for all lentiviral constructs tested at optimal MOI (data not shown). Description of the lentiviral abbreviations presented along the X-axis can be found in FIG. 4. Briefly, the last letter in each construct abbreviation corresponds to the WPRE used. Variant A contains wild-type (WT) WPRE (positive control); variant B contains no WPRE (negative control); variant C contains a mutant WPRE in which the X protein promoter and start codon are mutated (SEQ ID NO: 4); and variant D contains a mutant WPRE in which start codons are mutated and both the X protein promoter and ORF are deleted (SEQ ID NO: 3).

Fold expansion was not affected by WPRE mutations (FIG. 10). Cell viability was higher than 90% for all lentiviral constructs tested at optimal MOI (data not shown).

Figure 11:
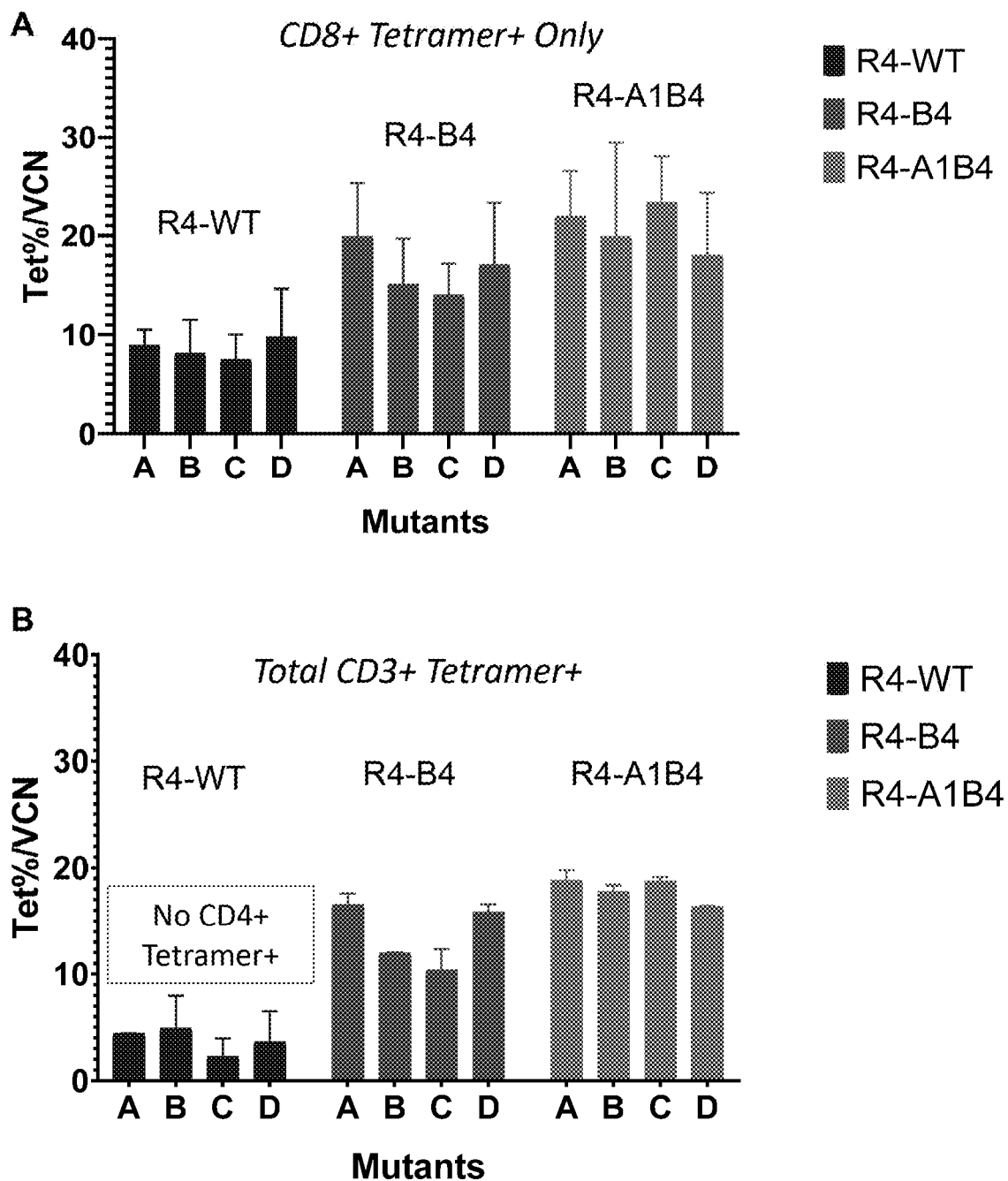
FIG. 11 shows that WPRE mutants do not alter TCR tetramer expression normalized to vector copy number. Data presented is the mean of all donors+/−standard deviation (SD). Panel A shows results for CD8+ Tetramer+ only. Panel B shows results for total CD3+ Tetramer+. A=wild-type (WT) WPRE (positive control); B=no WPRE (negative control); C=mutant WPRE in which the X protein promoter and start codon are mutated (SEQ ID NO: 4); and D=mutant WPRE in which start codons are mutated and both the X protein promoter and ORF are deleted (SEQ ID NO: 3).
Figure 12:
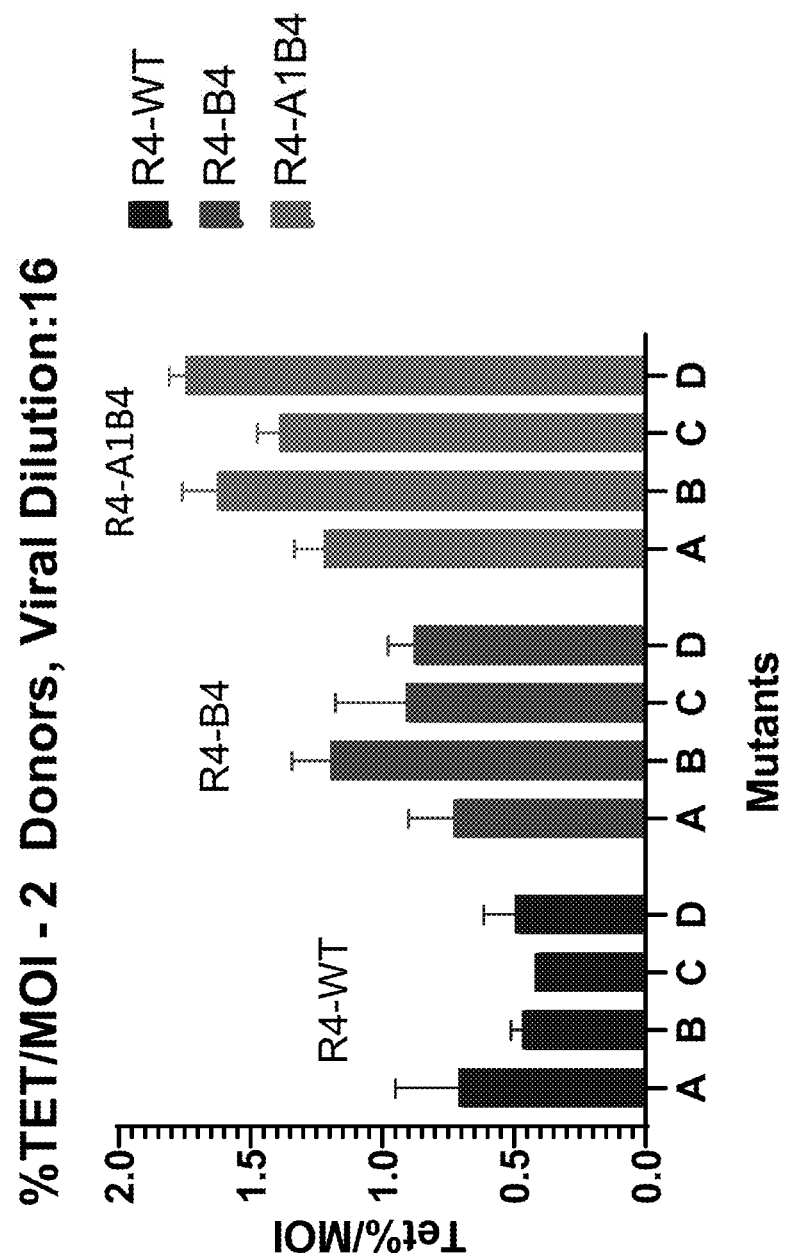
FIG. 12 shows that WPRE mutants demonstrate comparable TCR tetramer expression normalized to viral titer. Data presented is the mean of all donors+/−standard deviation (SD). A=wild-type (WT) WPRE (positive control); B=no WPRE (negative control); C=mutant WPRE in which the X protein promoter and start codon are mutated (SEQ ID NO: 4); and D=mutant WPRE in which start codons are mutated and both the X protein promoter and ORF are deleted (SEQ ID NO: 3).

WPRE mutants demonstrate comparable TCR tetramer surface expression normalized to vector copy number (FIG. 11) or normalized to viral titer (FIG. 12).

Figure 13:
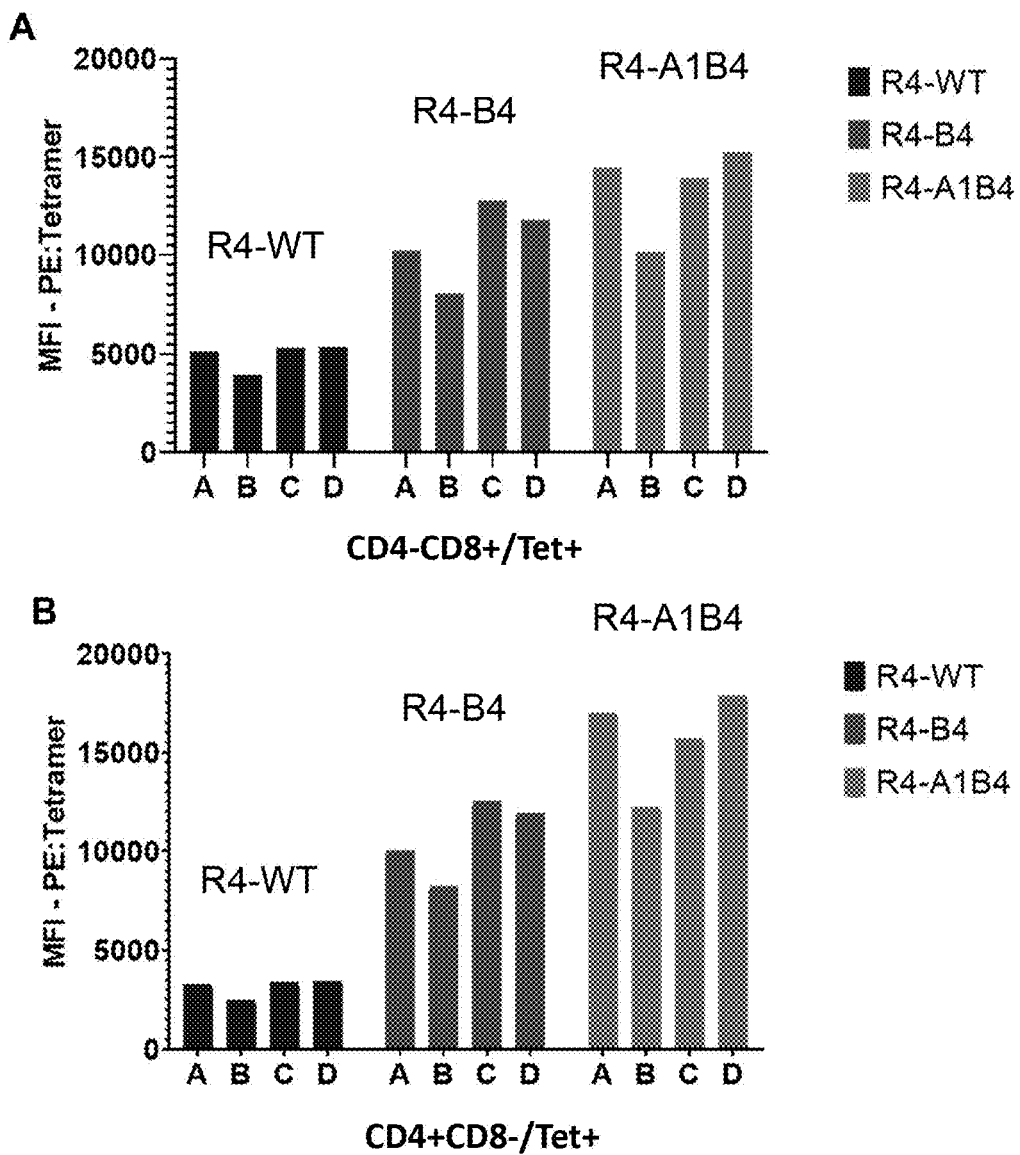
FIG. 13 shows that WPRE mutants demonstrate comparable TCR tetramer surface expression as determined by flow cytometry. Panel A presents CD4−CD8+/tetramer+ data. Panel B presents CD4+CD8−/tetramer+ data. A=wild-type (WT) WPRE (positive control); B=no WPRE (negative control); C=mutant WPRE in which the X protein promoter and start codon are mutated (SEQ ID NO: 4); and D=mutant WPRE in which start codons are mutated and both the X protein promoter and ORF are deleted (SEQ ID NO: 3).
Figure 14B:
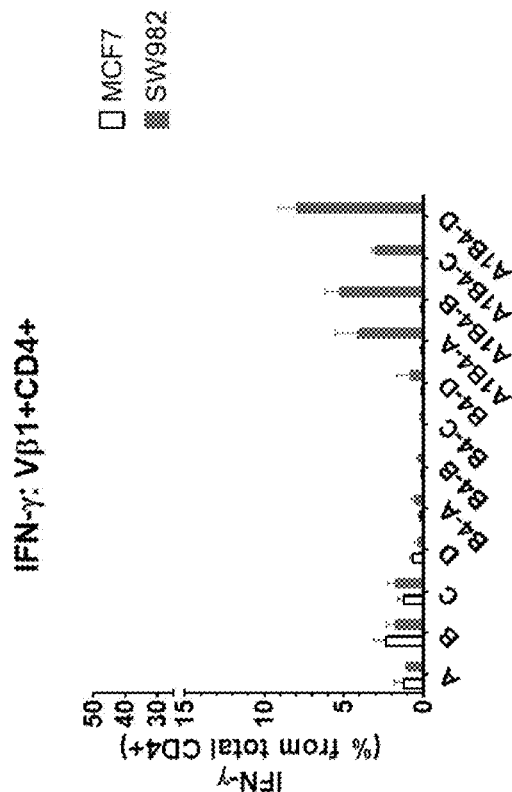
FIG. 14 shows cytokine production of CD4+ or CD8+ T cells in the presence of target-positive tumor cells. Panel A presents interferon-γ (IFN-γ) production in CD8+ T cells. Panel B presents IFN-γ production in CD4+ T cells. Panel C presents tumor necrosis factor-α (TNF-α) production in C8+ T cells. Panel D presents TNF-α production in CD4+ T cells. MCF7=negative; SW982=460 CpC. Description of the lentiviral abbreviations presented along the X-axis can be found in FIG. 4. Briefly, the last letter in each construct abbreviation corresponds to the WPRE used. Variant A contains wild-type (WT) WPRE (positive control); variant B contains no WPRE (negative control); variant C contains a mutant WPRE in which the X protein promoter and start codon are mutated (SEQ ID NO: 4); and variant D contains a mutant WPRE in which start codons are mutated and both the X protein promoter and ORF are deleted (SEQ ID NO: 3).
Figure 14A:
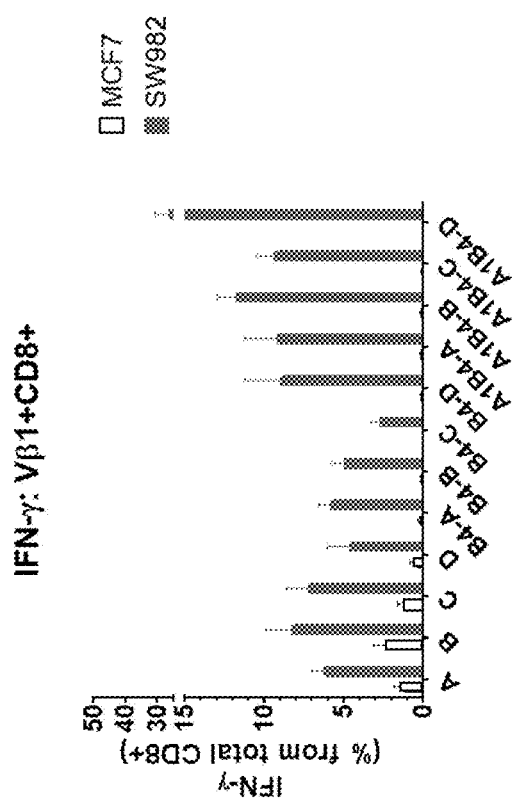
Figure 14D:
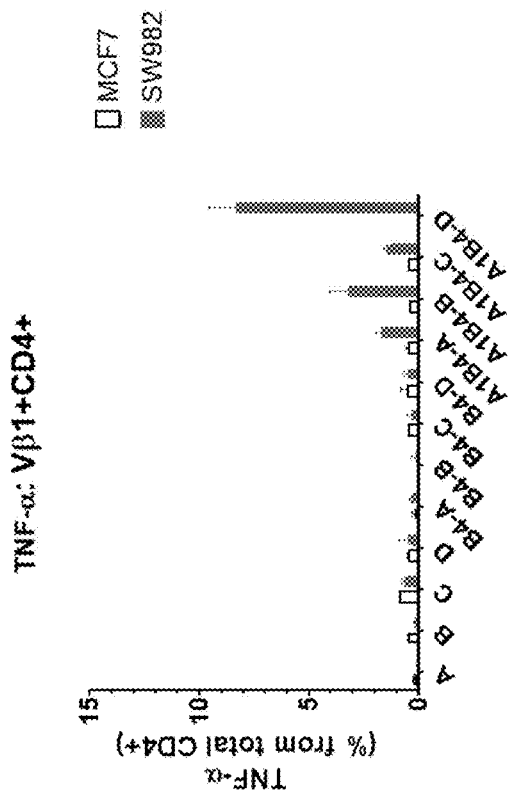
Figure 14C:
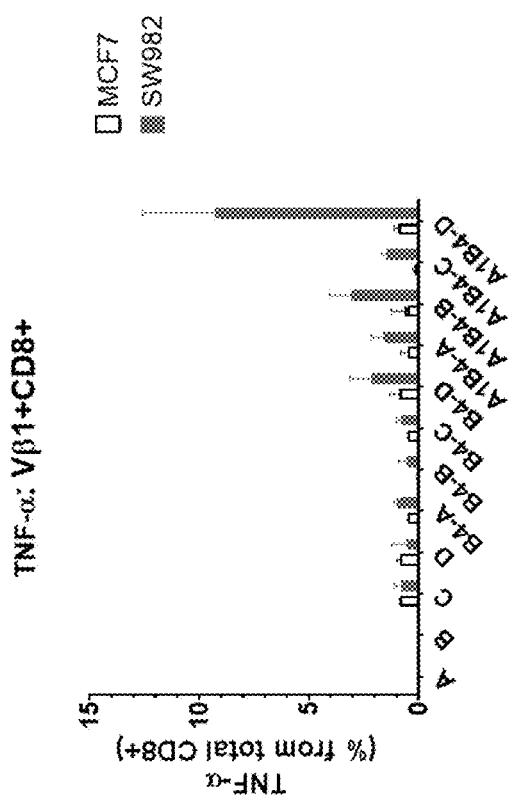

Similarly, FIG. 13 shows that WPRE mutants demonstrate comparable TCR tetramer surface expression as determined by flow cytometry. Panel A presents CD4-CD8+/tetramer+ data. Panel B presents CD4+CD8-/tetramer+ data.

FIG. 14 shows cytokine production of CD4+ or CD8+ T cells in the presence of target-positive tumor cells. Panel A presents interferon-γ (IFN-γ) production in CD8+ T cells. Panel B presents IFN-γ production in CD4+ T cells. Panel C presents tumor necrosis factor-α (TNF-α) production in C8+ T cells. Panel D presents TNF-α production in CD4+ T cells. MCF7=negative; SW982=460 CpC.

Example 5

γδ T Cell Manufacturing

To isolate γδ T cells, in an aspect, γδ T cells may be isolated from a subject or from a complex sample of a subject. In an aspect, a complex sample may be a peripheral blood sample, a cord blood sample, a tumor, a stem cell precursor, a tumor biopsy, a tissue, a lymph, or from epithelial sites of a subject directly contacting the external milieu or derived from stem precursor cells. γδ T cells may be directly isolated from a complex sample of a subject, for example, by sorting γδ T cells that express one or more cell surface markers with flow cytometry techniques. Wild-type γδ T cells may exhibit numerous antigen recognition, antigen-presentation, co-stimulation, and adhesion molecules that can be associated with a γδ T cells. One or more cell surface markers, such as specific γδ TCRs, antigen recognition, antigen-presentation, ligands, adhesion molecules, or co-stimulatory molecules may be used to isolate wild-type γδ T cells from a complex sample. Various molecules associated with or expressed by γδ T-cells may be used to isolate γδ T cells from a complex sample, e.g., isolation of mixed population of Vδ1+, Vδ2+, Vδ3+ cells or any combination thereof.

For example, peripheral blood mononuclear cells can be collected from a subject, for example, with an apheresis machine, including the Ficoll-Paque™ PLUS (GE Healthcare) system, or another suitable device/system. γδ T-cell(s), or a desired subpopulation of γδ T-cell(s), can be purified from the collected sample with, for example, with flow cytometry techniques. Cord blood cells can also be obtained from cord blood during the birth of a subject.

Positive and/or negative selection of cell surface markers expressed on the collected γδ T cells can be used to directly isolate γδ T cells, or a population of γδ T cells expressing similar cell surface markers from a peripheral blood sample, a cord blood sample, a tumor, a tumor biopsy, a tissue, a lymph, or from an epithelial sample of a subject. For instance, γδ T cells can be isolated from a complex sample based on positive or negative expression of CD2, CD3, CD4, CD8, CD24, CD25, CD44, Kit, TCR α, TCR β, TCR α, TCR δ, NKG2D, CD70, CD27, CD30, CD16, CD337 (NKp30), CD336 (NKp46), OX40, CD46, CCR7, and other suitable cell surface markers.

Figure 15:
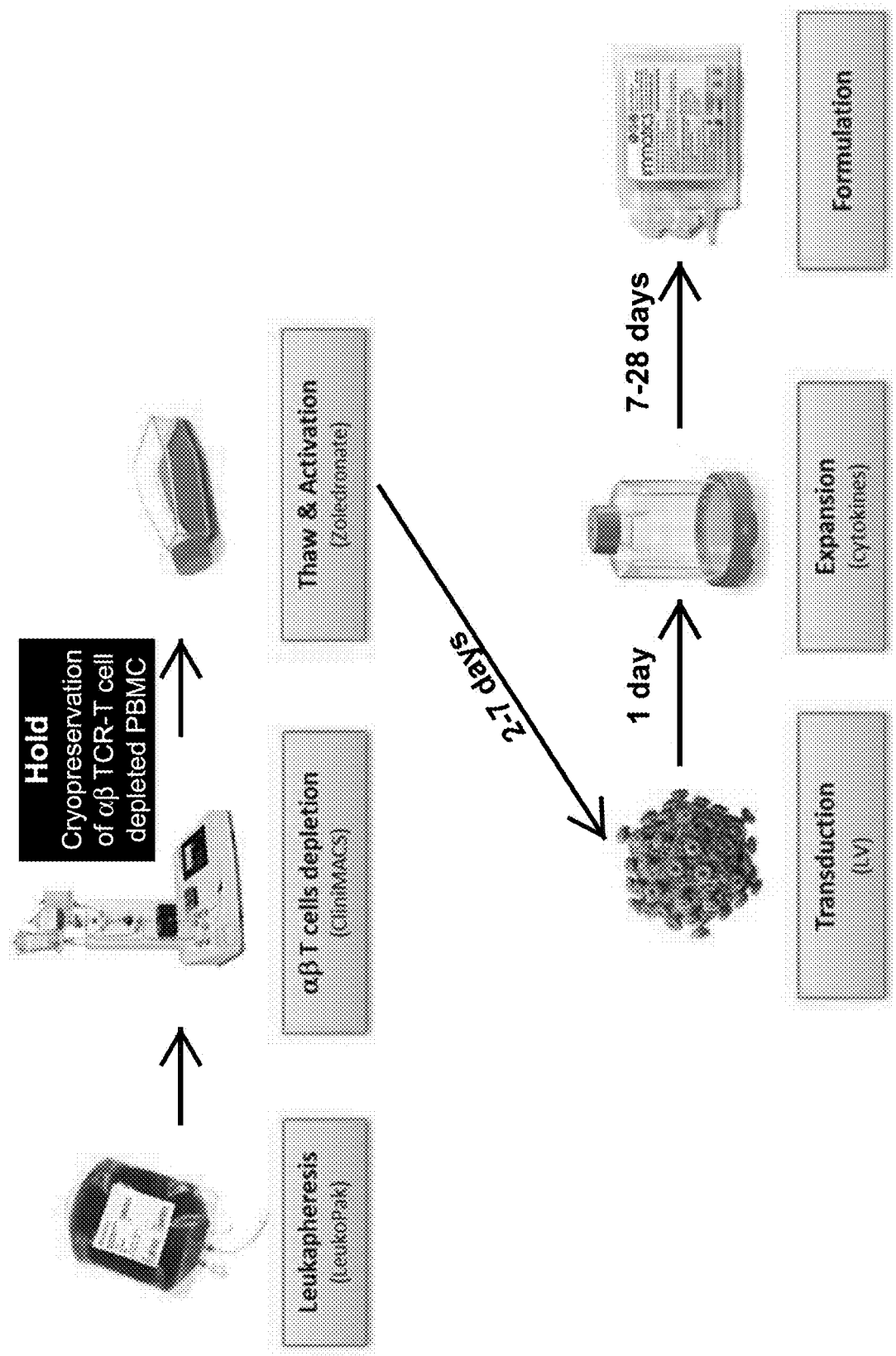
FIG. 15 shows a γδ T cell manufacturing process according to one embodiment of the present disclosure. γδ T cell manufacturing may include collecting or obtaining white blood cells or PBMC, e.g., leukapheresis product, depleting αβ T cells from PBMC or leukapheresis product, followed by activation, transduction, and expansion of γδ T cells.

FIG. 15 shows γδ T cell manufacturing according to an embodiment of the present disclosure. This process may include collecting or obtaining white blood cells or PBMC from leukapheresis products. Leukapheresis may include collecting whole blood from a donor and separating the components using an apheresis machine. An apheresis machine separates out desired blood components and returns the rest to the donor's circulation. For instance, white blood cells, plasma, and platelets can be collected using apheresis equipment, and the red blood cells and neutrophils are returned to the donor's circulation. Commercially available leukapheresis products may be used in this process. Another way to obtain white blood cells is to obtain them from the buffy coat. To isolate the buffy coat, whole anticoagulated blood is obtained from a donor and centrifuged. After centrifugation, the blood is separated into plasma, red blood cells, and buffy coat. The buffy coat is the layer located between the plasma and red blood cell layers. Leukapheresis collections may result in higher purity and considerably increased mononuclear cell content than that achieved by buffy coat collection. The mononuclear cell content possible with leukapheresis may typically be 20 times higher than that obtained from the buffy coat. In order to enrich for mononuclear cells, the use of a Ficoll gradient may be needed for further separation.

To deplete αβ T cells from PBMC, TCR-expressing cells may be separated from the PBMC by magnetic separation, e.g., using CliniMACS® magnetic beads coated with anti-αβ TCR antibodies, followed by cryopreserving TCR-T cells depleted PBMC. To manufacture "off-the-shelf" T-cell products, cryopreserved TCR-T cells depleted PBMC may be thawed and activated in small/mid-scale, e.g., 24 to 4-6 well plates or T75/T175 flasks, or in large scale, e.g., 50 ml-100 liter bags, in the presence of aminobisphosphonate, e.g., zoledronate, and/or isopentenylpyrophosphate (IPP) and/or cytokines, e.g., interleukin 2 (IL-2), interleukin 15 (IL-15), and/or interleukin 18 (IL-18), and/or other activators, e.g., Toll-like receptor 2 (TLR2) ligand, for 1-10 days, e.g., 2-7 days.

FIG. 15 shows the activated T cells may be engineered by transducing with a viral vector, such as lentiviral vector, expressing exogenous genes of interest, such as αβ TCRs against specific cancer antigen and CD8, into isolated γδ T cells. Transduction may be carried out once or multiple times to achieve stable transgene expression in small scale, e.g., 24 to 4-6 well plates, or mid/large scale for 1/2-5 days, e.g., 1 day.

Figure 16:
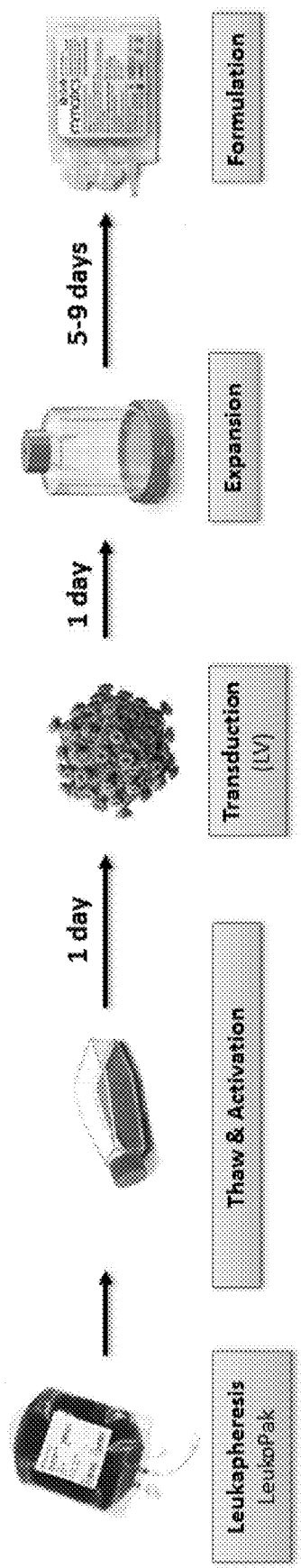
FIG. 16 shows a T cell manufacturing process according to another embodiment of the present disclosure. T cell manufacturing may include collecting or obtaining white blood cells or PMBC, e.g., leukapheresis product followed by activation, transduction, and expansion of T cells.

FIG. 16 further shows expansion of the transduced or engineered γδ T cells may be carried out in the presence of cytokines, e.g., IL-2, IL-15, IL-18, and others, in small/mid-scale, e.g., flasks/G-Rex, or in large scale, e.g., 50 ml-100-liter bags, for 7-35 days, e.g., 7-28 days. The expanded transduced T cell products may then be cryopreserved as "off-the-shelf" T-cell products for infusion into patients.

Example 6

Figure 17:
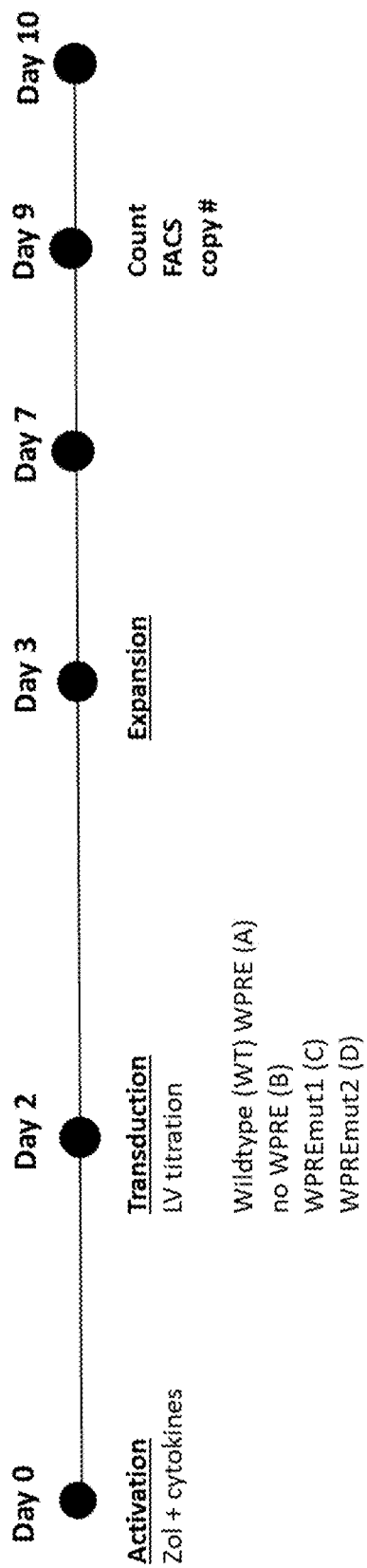
FIG. 17 shows γδ T cell manufacturing process in accordance with one embodiment of the present disclosure.

Comparison of γδ T Cells Transduced with Lentiviral Vectors (LV) with Different WPRE FIG. 17 shows an example of γδ T cell manufacturing process, in which γδ T cells transduced with LV expressing TCR (binding to SLLQHLIGL (SEQ ID NO: 148)/MHC complex) and CD8 having different WPRE were compared. Briefly, on Day 0, γδ T cells were activated in the presence of zoledronate and cytokines and then transduced on Day 2 with a LV expressing TCR and CD8 having the wild type (WT) WPRE (SEQ ID NO: 2) (A), no WPRE (B), WPREmut1 (SEQ ID NO: 4) (C), or WPREmut2 (SEQ ID NO: 3) (D) at 3.75 µl, 7.50 µl, 15 µl, 30 µl, 60 µl, or 120 µl of LV per 1×10$^6$ cells. The LV titers of Batch #1 and Batch #2 are shown in Table 5.

TABLE 5

| LV | Batch #1 Titer | Batch #2 Titer |
| --- | --- | --- |
| WT WPRE | 1.8 × 10$^8$ IU/ml | 7.56 × 10$^7$ IU/ml |
| WPREmut1 | 1.4 × 10$^8$ IU/ml | 6.47 × 10$^7$ IU/ml |
| WPREmut2 | 1.5 × 10$^8$ IU/ml | 5.11 × 10$^7$ IU/ml |
| No WPRE | 2.3 × 10$^8$ IU/ml | 5.85 × 10$^7$ IU/ml |

Table 5 shows that LV from Batch #1 have about 10-fold higher titers than that from Batch #2. On Day 3, the transduced cells were expanded. On day 9, cells were counted and analyzed by FACS to measure TCR/CD8-expressing γδ T cells and copy number of integrated transgenes.

LV from Batch #1

Figure 18A:
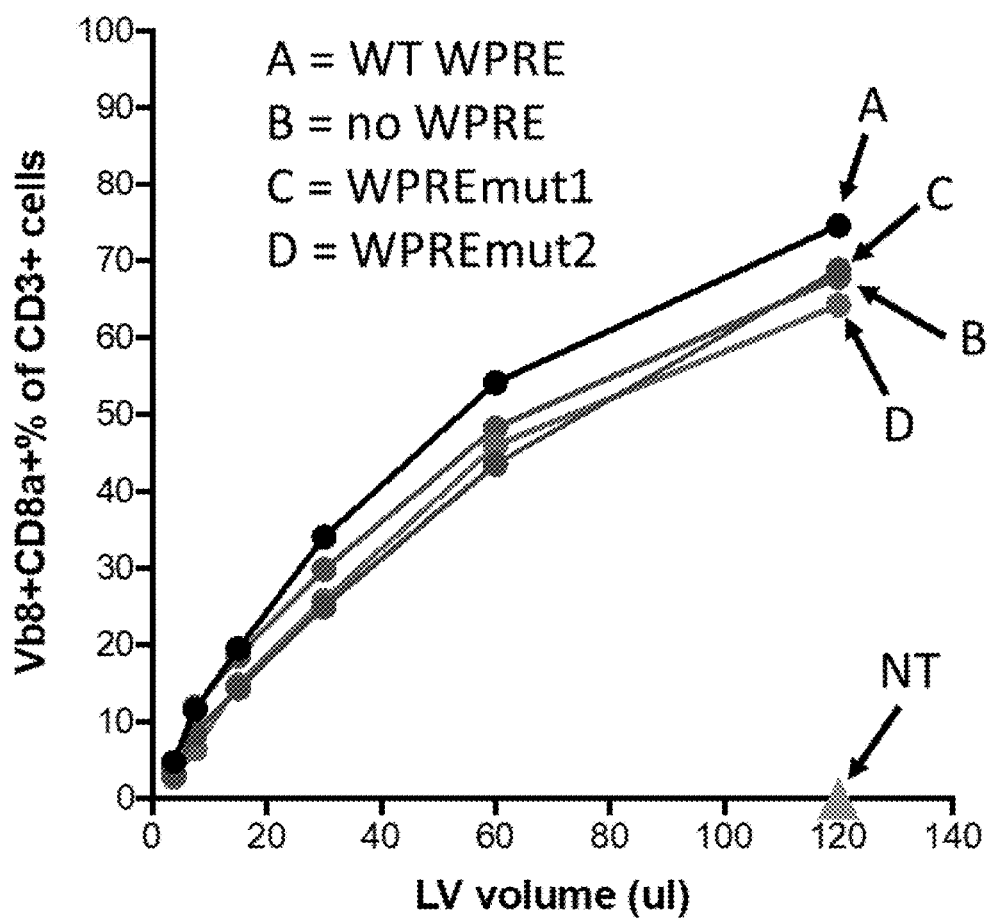
FIG. 18A shows the effect of WPRE on transgene expression in γδ T cells in accordance with one embodiment of the present disclosure.
Figure 18B:
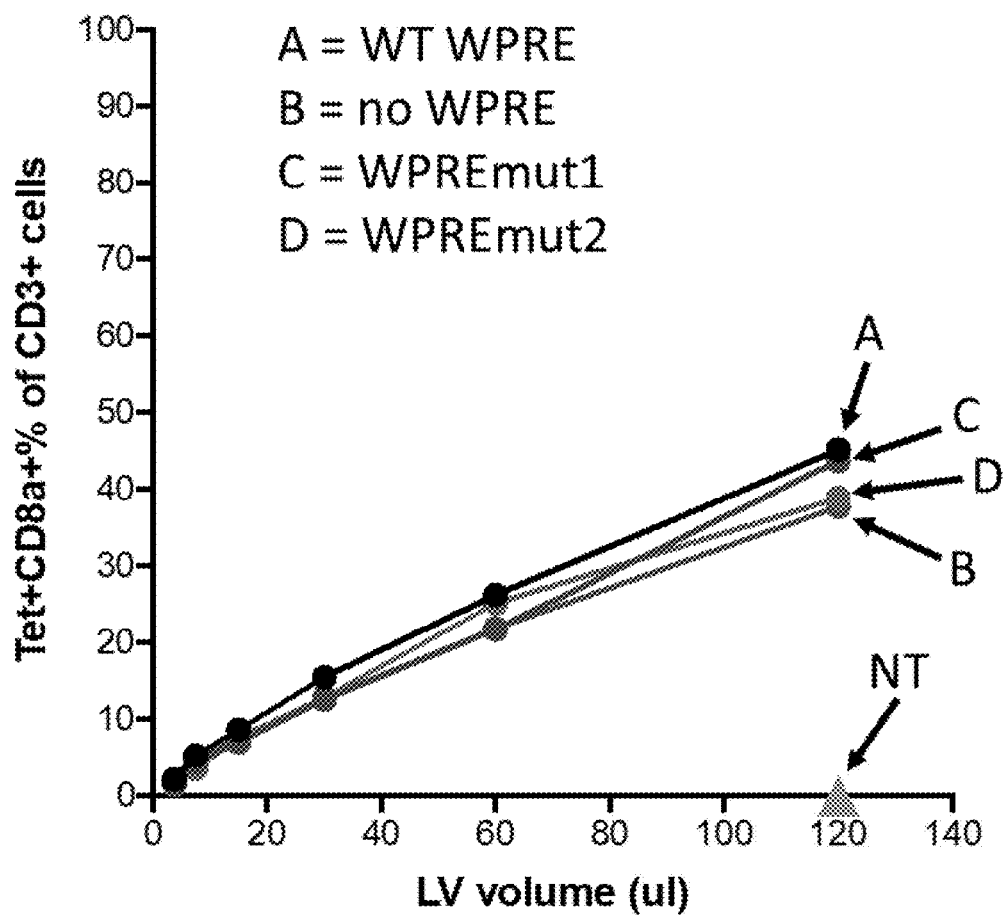
FIG. 18B shows the effect of WPRE on transgene expression in γδ T cells in accordance with another embodiment of the present disclosure.

Anti-Vβ8 antibody and anti-CD8α antibody were used to stain TCR+CD8α+ γδ T cells in FACS analysis. FIG. 18A shows % Vβ8+CD8α+ γδ T cells increases with increasing amount of LV used in transduction. There is no significant difference in transduction efficiency between γδ T cells transduced with LV having the wild type (WT) WPRE (A), no WPRE (B), WPREmut1 (C), and WPREmut2 (D). The non-transduced (NT) cells serve as negative control. SLLQHLIGL (SEQ ID NO: 148)/MHC tetramer and anti-CD8α antibody were used to stain TCR+CD8α+ γδ T cells. FIG. 18B shows % tetramer+CD8α+ γδ T cells increases with increasing amount of LV used in transduction. There is no significant difference in transduction efficiency between γδ T cells transduced with LV having the wild type (WT)

Figure 19A:
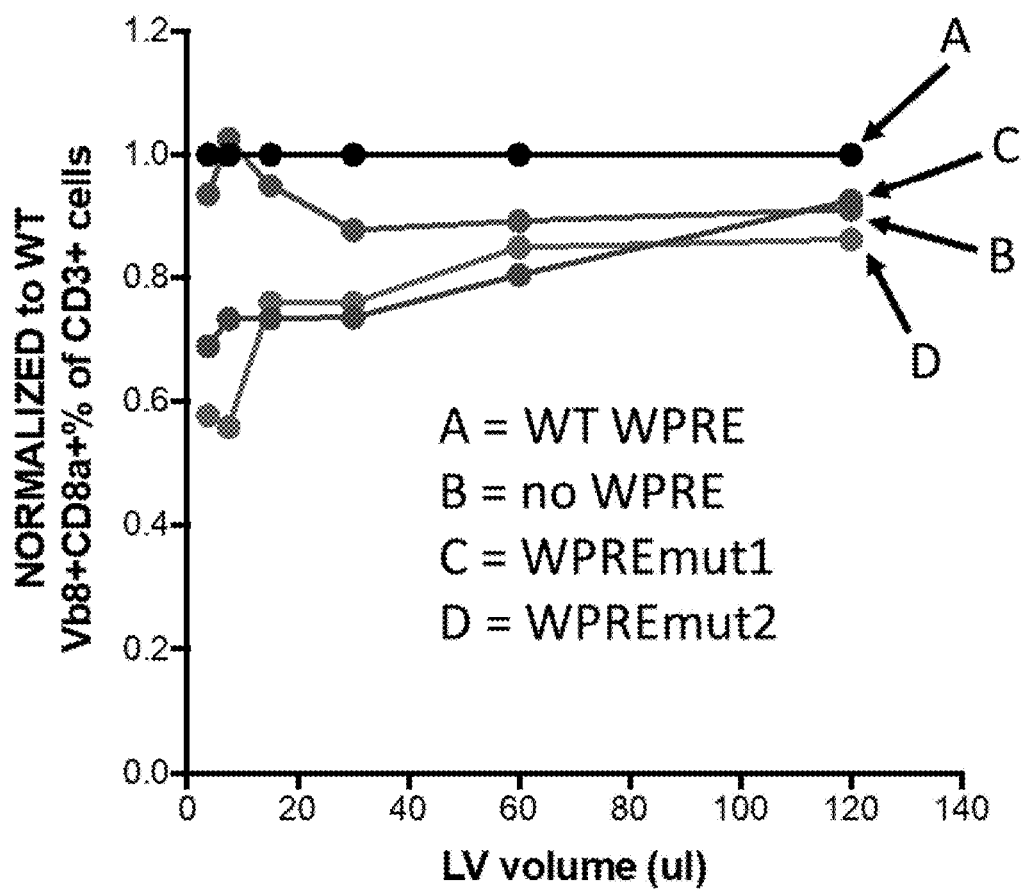
FIG. 19A shows the effect of WPRE on transgene expression in γδ T cells in accordance with another embodiment of the present disclosure.
Figure 19B:
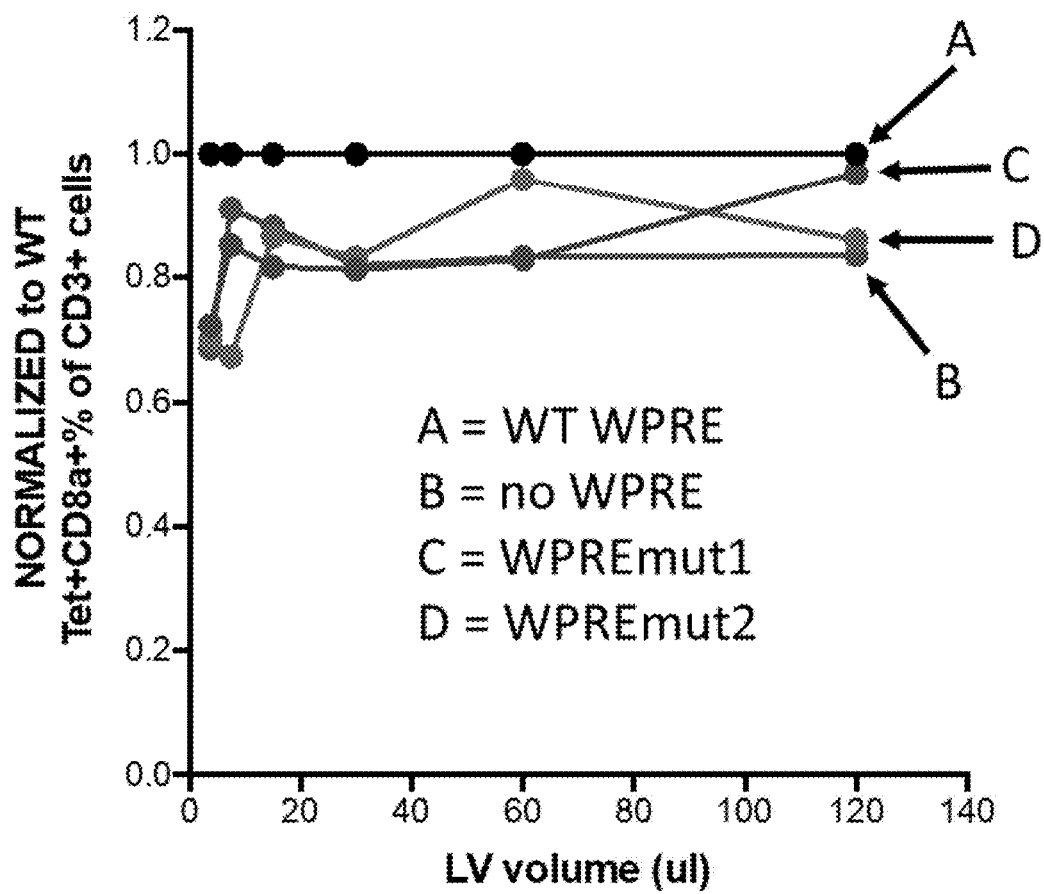
FIG. 19B shows the effect of WPRE on transgene expression in γδ T cells in accordance with another embodiment of the present disclosure.

WPRE (A), no WPRE (B), WPREmut1 (C), and WPREmut2 (D). The non-transduced (NT) cells serve as negative control. Transduction efficiencies were then normalized to that of WT WPRE. There is no significant difference in normalized transduction efficiency between γδ T cells transduced with LV having the wild type (WT) WPRE (A), no WPRE (B), WPREmut1 (C), and WPREmut2 (D) with respect to % Vβ8+CD8α+ γδ T cells (FIG. 19A) and % tetramer+CD8α+ γδ T cells (FIG. 19B). These results show transduction efficiencies are comparable among γδ T cells transduced with LV having WT WPRE, WPREmut1, WPREmut2, and no WPRE.

Figure 20:
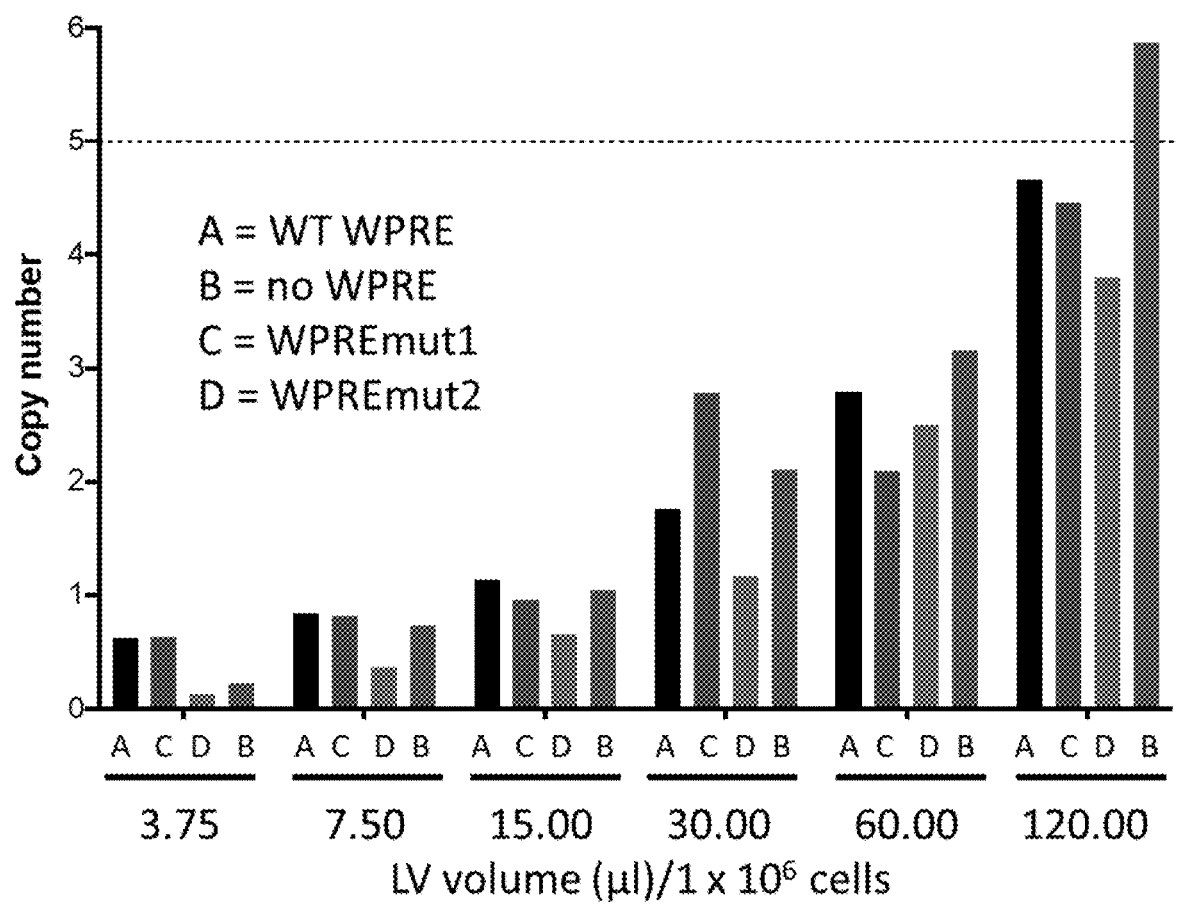
FIG. 20 shows the effect of WPRE on copy numbers of integrated transgene in γδ T cells in accordance with one embodiment of the present disclosure.
Figure 21:
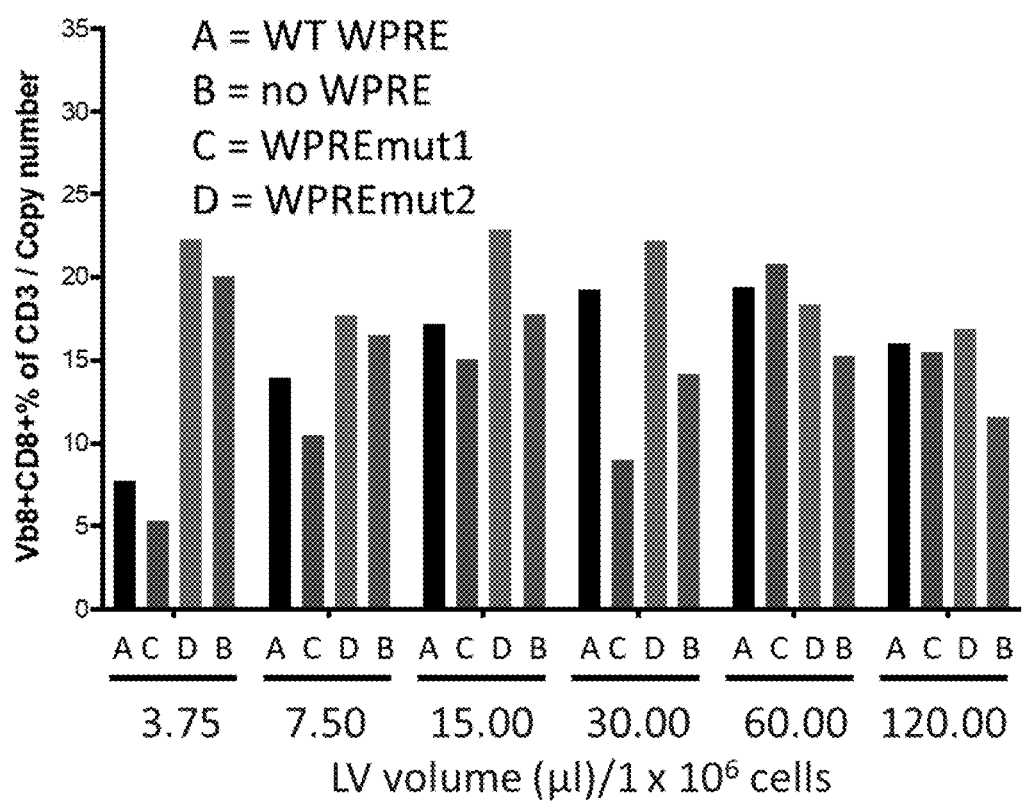
FIG. 21 shows the effect of WPRE on transgene expression/copy number of integrated transgene ratios in γδ T cells in accordance with one embodiment of the present disclosure.
Figure 22:
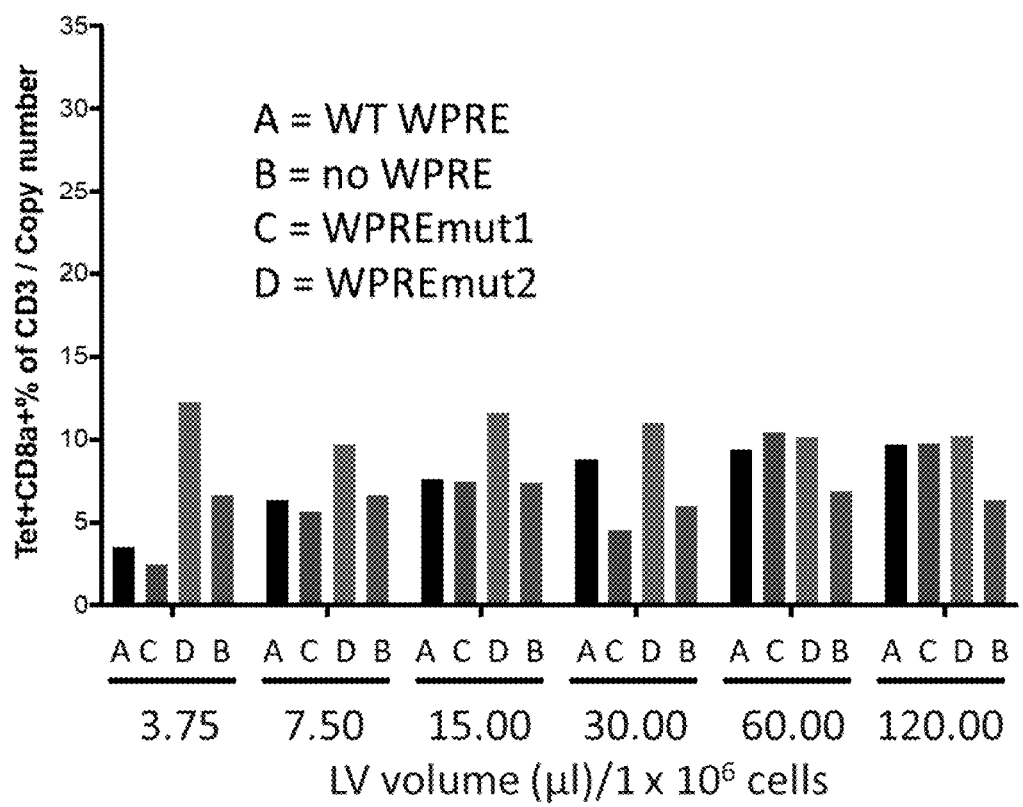
FIG. 22 shows the effect of WPRE on transgene expression/copy number of integrated transgene ratios in γδ T cells in accordance with another embodiment of the present disclosure.

FIG. 20 shows copy number of integrated transgenes in γδ T cells generally increases with increasing amount of LV used in transduction. There is no significant difference in copy numbers of integrated transgenes between γδ T cells transduced with LV having the wild type (WT) WPRE (A), no WPRE (B), WPREmut1 (C), and WPREmut2 (D). γδ T cells transduced with LV with no WPRE (B) at 120 μl/1×10$^6$ cells appears to have slightly higher copy number of integrated transgenes than that transduced with LV having different WPRE. Transduction efficiency/copy number ratios were then determined. FIG. 21 shows that % Vβ8+CD8α+/copy number ratios are comparable among γδ T cells transduced with LV having WT WPRE, WPREmut1, WPREmut2, and no WPRE. Similarly, FIG. 22 shows that % tetramer+CD8α+/copy number ratios are comparable among γδ T cells transduced with LV having WT WPRE, WPREmut1, WPREmut2, and no WPRE.

LV from Batch #2

Figure 23:
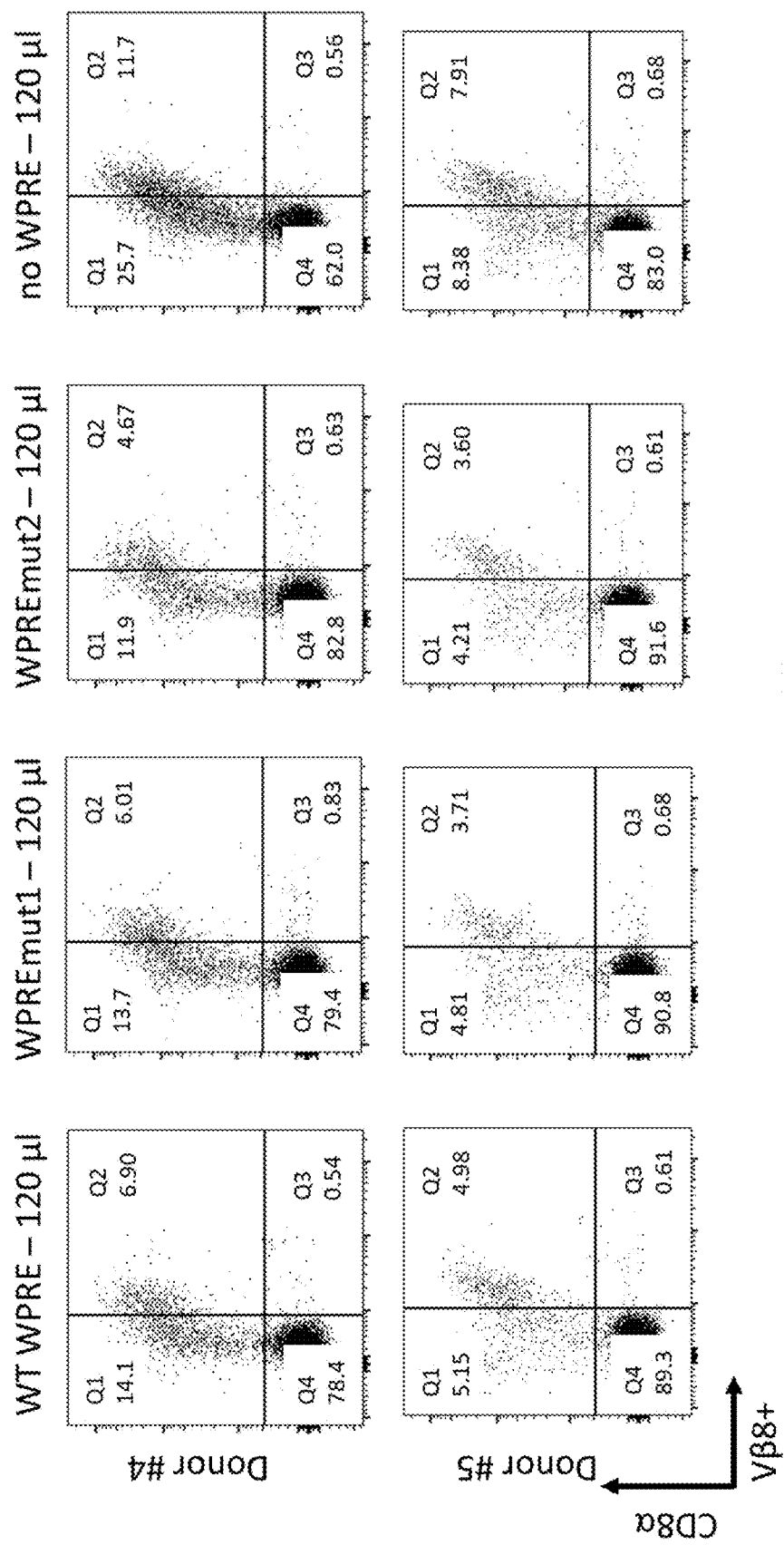
FIG. 23 shows the effect of WPRE on transgene expression in γδ T cells in accordance with another embodiment of the present disclosure.

As shown in Table 5, LV from Batch #1 have about 10-fold higher titers than that from Batch #2. In general, transduction with LV from Batch #2 resulted in lower transduction efficiency than that with LV from Batch #1 due to lower LV titers. FIG. 23 shows, at 120 μl LV/1×10$^6$ cells, γδ T cells obtained from Donors #4 and #5 transduced with LV having no WPRE resulted in higher % Vβ8+CD8α+ γδ T cells (11.7% and 7.91%, respectively) than that transduced with WT WPRE (6.90% and 4.98%, respectively), WPREmut1 (6.01% and 3.71%, respectively), and WPREmut2 (4.67% and 3.60%, respectively).

Table 6 shows the copy numbers of integrated transgenes of γδ T cells obtained from Donors #4 and #5 transduced with LV having WT WPRE, no WPRE, WPREmut1, and WPREmut2. Overall, copy numbers of integrated transgenes are lower than that of Batch #1 due to low LV titers.

TABLE 6

| LV contains | Volume μl/1 × 10$^6$ cells | Copy Number |
|---|---|---|
| Donor #4 | | |
| WT WPRE | 120 | 0.73 |
| | 60 | 0.50 |
| | 30 | 0.10 |
| | 15 | 0.06 |
| | 7.5 | 0.15 |
| | 3.25 | 0.05 |
| WPREmut1 | 120 | 1.11 |
| | 60 | 0.78 |
| | 30 | 0.42 |
| | 15 | 0.18 |
| | 7.5 | 0.09 |
| | 3.25 | 0.05 |
| WPREmut2 | 120 | 0.85 |
| | 60 | 0.74 |
| | 30 | 0.35 |
| | 15 | 0.16 |
| | 7.5 | 0.11 |
| | 3.25 | 0.06 |
| no WPRE | 120 | 1.42 |
| | 60 | 0.58 |
| | 30 | 0.26 |
| | 15 | 0.14 |
| | 7.5 | 0.11 |
| | 3.25 | 0.04 |
| Non transduced | N/A | 0 |
| Donor #5 | | |
| WT WPRE | 120 | 1.22 |
| | 60 | 0.43 |
| | 30 | 0.18 |
| | 15 | 0.10 |
| | 7.5 | 0.04 |
| | 3.25 | 0.02 |
| WPREmut1 | 120 | 0.46 |
| | 60 | 0.33 |
| | 30 | 0.34 |
| | 15 | 0.13 |
| | 7.5 | 0.06 |
| | 3.25 | 0.04 |
| WPREmut2 | 120 | 0.69 |
| | 60 | 0.57 |
| | 30 | 0.29 |
| | 15 | 0.14 |
| | 7.5 | 0.12 |
| | 3.25 | 0.04 |
| no WPRE | 120 | 0.68 |
| | 60 | 0.55 |
| | 30 | 0.27 |
| | 15 | 0.32 |
| | 15 | 0.20 |
| | 7.5 | 0.00 |
| Non transduced | N/A | 0 |

Figure 24:
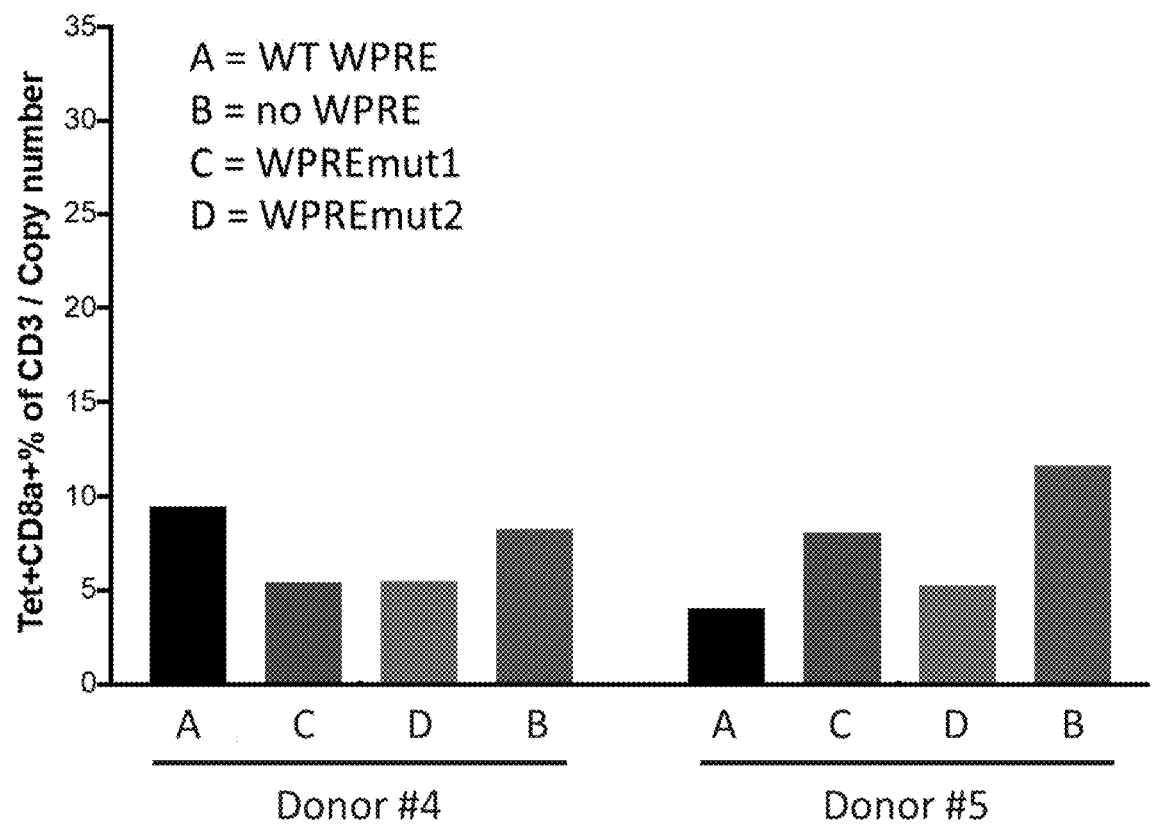
FIG. 24 shows the effect of WPRE on transgene expression/copy number of integrated transgene ratios in γδ T cells in accordance with another embodiment of the present disclosure.
Figure 25:
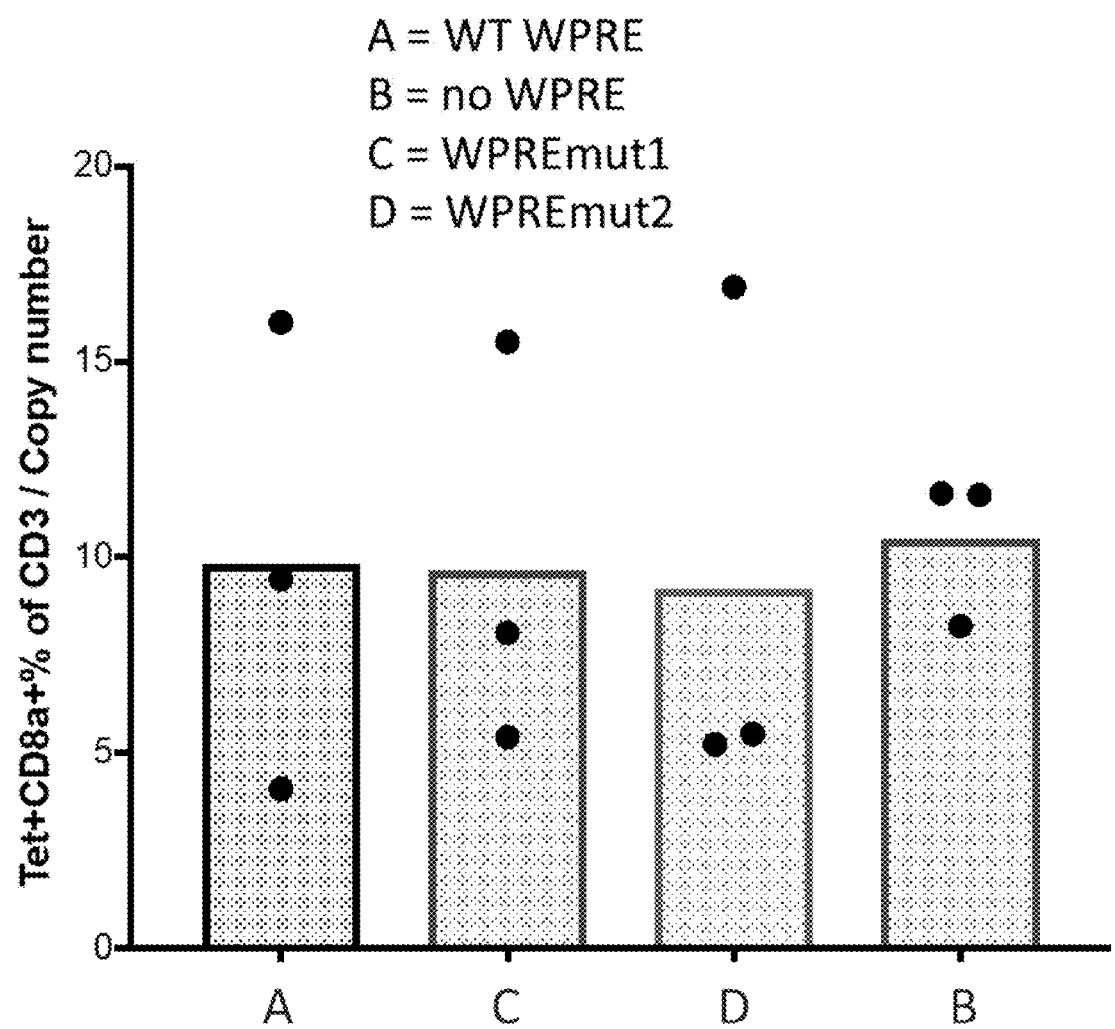
FIG. 25 shows the effect of WPRE on transgene expression/copy number of integrated transgene ratios in γδ T cells in accordance with another embodiment of the present disclosure.

FIG. 24 shows, at 120 μl LV/1×10$^6$ cells, % tetramer+CD8α+/copy number ratios are comparable among γδ T cells obtained from Donors #4 and #5 transduced with LV having WT WPRE (A), WPREmut1 (C), WPREmut2 (D), and no WPRE (B). FIG. 25 shows combined data, at 120 μl LV/1×10$^6$ cells, obtained from Donors #3, #4, and #5. These combined results show % tetramer+CD8α+/copy number ratios are comparable among γδ T cells transduced with LV having WT WPRE (A), WPREmut1 (C), WPREmut2 (D), and no WPRE (B). γδ T cells transduced with LV having no WPRE appear to have less variation in % tetramer+CD8α+/copy number ratios than that transduced with LV having different WPRE.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A vector comprising a mutant woodchuck post-transcriptional regulatory element (WPRE) of SEQ ID NO: 1,
wherein the mutant WPRE comprises mutations in five or six start codons at positions selected from the group consisting of 106-108, 152-154, 245-247, 272-274, 283-285, and 362-364 of SEQ ID NO: 1,
wherein the mutant WPRE does not comprise an X protein promoter and
wherein the mutant WPRE does not comprise an X protein open reading frame (ORF).

2. The vector of claim 1, wherein the five or six start codons are mutated at one, two, or all three positions within the start codon.

3. The vector of claim 1, wherein the five or six start codons are mutated from ATG to TTG.

4. The vector of claim 1, further comprising a nucleotide sequence encoding a protein selected from the group of consisting of enzymes, cytokines, chemokines, antibodies, engineered immunoglobulin-like molecules, a single chain antibody, fusion proteins, immune co-stimulatory molecules, immunomodulatory molecules, a trans dominant negative mutant of a target protein, a toxin, a conditional toxin, an antigenic peptide, an antigen receptor, a chimeric antigen receptor, a T-cell receptor (TCR), a tumor suppressor protein, growth factors, membrane proteins, pro- and anti-angiogenic proteins and peptides, vasoactive proteins and peptides, antiviral proteins, and derivatives thereof.

5. The vector of claim 1, comprising a first nucleotide sequence S1 encoding a protein Z1 and a second nucleotide sequence S2 encoding a protein Z2, wherein Z1 and Z2 form a first dimer.

6. The vector of claim 5, wherein the first dimer Z1Z2 is a T cell dimeric signaling module, a TCR, an antibody, an antigen receptor, or a chimeric antigen receptor.

7. The vector of claim 5, wherein the first dimer Z1Z2 is a TCR that binds to a target antigenic (TA) peptide, and wherein the target antigenic (TA) peptide is a viral peptide, a bacterial peptide or a tumor associated antigen (TAA) antigenic peptide.

8. The vector of claim 5, wherein the first dimer Z1Z2 is selected from SEQ ID NO: 13 and 14, 15 and 16, 17 and 18, 19 and 20, 21 and 22, 23 and 24, 25 and 26, 25 and 92, 91 and 92, 27 and 28, 29 and 30, 31 and 32, 33 and 34, 35 and 36, 37 and 38, 39 and 40, 41 and 42, 43 and 44, 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, or 89 and 90.

9. The vector of claim 5, further comprising a third nucleotide sequence S3 encoding a protein Y1 and a fourth nucleotide sequence S4 encoding a protein Y2, wherein Y1 and Y2 form a second dimer, wherein the first dimer Z1Z2 is structurally different from the second dimer Y1Y2.

10. The vector of claim 9, wherein the second dimer Y1Y2 is a TCR co-receptor.

11. The vector of claim 9, wherein the second dimer Y1Y2 is SEQ ID NO: 11 and 12.

12. The vector of claim 1, further comprising a nucleotide sequence encoding a 2A peptide and a nucleotide sequence encoding a linker peptide.

13. The vector of claim 1, further comprising a nucleotide sequence encoding a furin cleavage site (SEQ ID NO: 10).

14. The vector of claim 1, further comprising a promoter sequence selected from cytomegalovirus (CMV) promoter, phosphoglycerate kinase (PGK) promoter, myelin basic protein (MBP) promoter, glial fibrillary acidic protein (GFAP) promoter, modified MoMuLV LTR containing myeloproliferative sarcoma virus enhancer (MNDU3), Ubiqitin C promoter, EF-1 alpha promoter, or Murine Stem Cell Virus (MSCV) promoter.

15. The vector of claim 1, wherein the vector is a viral vector selected from adenoviruses, poxviruses, alphaviruses, arenaviruses, flaviruses, rhabdoviruses, retroviruses, lentiviruses, herpesviruses, paramyxoviruses, or picornaviruses.

16. The vector of claim 15, wherein the vector is pseudotyped with an envelope protein of a virus selected from the native feline endogenous virus (RD114), a chimeric version of RD114 (RD114TR), gibbon ape leukemia virus (GALV), a chimeric version of GALV (GALV-TR), amphotropic murine leukemia virus (MLV 4070A), baculovirus (GP64), vesicular stomatitis virus (VSV-G), fowl plague virus (FPV), Ebola virus (EboV), or baboon retroviral envelope glycoprotein (BaEV), lymphocytic choriomeningitis virus (LCMV).

17. The vector of claim 1, wherein the mutant WPRE comprises the nucleotide sequence at least 80% identity to SEQ ID NO: 3.

18. The vector of claim 1, further comprising a nucleotide sequence encoding an RNA selected from the group consisting of anti-sense RNA, small interfering RNA (siRNA), microRNA, shRNA, RNAi, and ribozyme.

19. The vector of claim 1, wherein the mutant WPRE comprises mutations in five start codons at positions selected from the group consisting of 106-108, 152-154, 245-247, 272-274, 283-285, and 362-364 of SEQ ID NO: 1.

20. The vector of claim 1, wherein the mutant WPRE comprises mutations in start codons at positions 106-108, 152-154, 245-247, 272-274, 283-285, and 362-364 of SEQ ID NO: 1.

* * * * *